United States Patent
Leong et al.

(10) Patent No.: US 12,351,617 B2
(45) Date of Patent: *Jul. 8, 2025

(54) IMMUNE CELLS COMPRISING TRUNCATED NKG2D CHIMERIC RECEPTORS

(71) Applicants: National University of Singapore, Singapore (SG); Nkarta, Inc., South San Francisco, CA (US)

(72) Inventors: Jun Hao Leong, Singapore (SG); Noriko Shimasaki, Singapore (SG); See Voon Seow, Singapore (SG); Dario Campana, Singapore (SG); James Barnaby Trager, Albany, CA (US); Alexandra Leida Liana Lazetic, San Jose, CA (US); Chao Guo, San Francisco, CA (US); Luxuan Guo Buren, San Francisco, CA (US); Shyam Sashikant Masrani, London (GB)

(73) Assignees: National University of Singapore, Singapore (SG); Nkarta, Inc., South San Francisco, CA (US)

( * ) Notice: Subject to any disclaimer, the term of this patent is extended or adjusted under 35 U.S.C. 154(b) by 129 days.

This patent is subject to a terminal disclaimer.

(21) Appl. No.: 17/740,899

(22) Filed: May 10, 2022

(65) Prior Publication Data

US 2023/0002471 A1   Jan. 5, 2023

Related U.S. Application Data

(63) Continuation of application No. 16/497,678, filed as application No. PCT/US2018/024650 on Mar. 27, 2018, now Pat. No. 11,365,236.

(Continued)

(51) Int. Cl.
*C07K 14/705* (2006.01)
*C07K 14/52* (2006.01)
(Continued)

(52) U.S. Cl.
CPC ...... *C07K 14/7056* (2013.01); *C07K 14/5443* (2013.01); *C07K 14/7051* (2013.01);
(Continued)

(58) Field of Classification Search
None
See application file for complete search history.

(56) References Cited

U.S. PATENT DOCUMENTS 4,650,764 A    3/1987 Temin et al.
4,690,915 A    9/1987 Rosenberg
(Continued)

FOREIGN PATENT DOCUMENTS

CN    101684456 A    3/2010
CN    103113470 A    5/2013
(Continued)

OTHER PUBLICATIONS

U.S. Appl. No. 60/383,872, filed May 28, 2002, Sadelain et al.
(Continued)

*Primary Examiner* — Claire Kaufman
(74) *Attorney, Agent, or Firm* — Hamilton, Brook, Smith & Reynolds, P.C.

(57) ABSTRACT

Several embodiments disclosed herein relate to the compositions comprising engineered Natural Killer (NK) cells that express a chimeric receptor, the chimeric receptor imparting to the NK cells an enhanced ability to target specific cells, such as cancerous cells or those affected by an infectious disease. Several embodiments relate to NK cells that target cells expressing natural ligands of NKG2D, where the NK cells comprise transmembrane and/or signaling domains that
(Continued)

lead to cytotoxic and/or cytolytic effects when the NK cells bind a target cell. Uses of NK cell compositions to treat diseases are also provided for in several embodiments.

8 Claims, 42 Drawing Sheets

Specification includes a Sequence Listing.

Related U.S. Application Data

(60) Provisional application No. 62/628,774, filed on Feb. 9, 2018, provisional application No. 62/477,335, filed on Mar. 27, 2017.

(51) Int. Cl.
  *C07K 14/54* (2006.01)
  *C07K 14/725* (2006.01)
  *C12N 5/10* (2006.01)
  *C12N 15/62* (2006.01)

(52) U.S. Cl.
  CPC ...... *C07K 14/70517* (2013.01); *C12N 15/625* (2013.01); *C07K 14/70578* (2013.01); *C07K 2317/24* (2013.01); *C07K 2317/53* (2013.01); *C07K 2319/02* (2013.01); *C07K 2319/03* (2013.01); *C07K 2319/33* (2013.01)

(56) References Cited

U.S. PATENT DOCUMENTS

| | | | |
|---|---|---|---|
| 4,844,893 A | 7/1989 | Honsik et al. |
| 4,980,289 A | 12/1990 | Temin et al. |
| 5,124,263 A | 6/1992 | Temin et al. |
| 5,359,046 A | 10/1994 | Capon |
| 5,399,346 A | 3/1995 | Anderson et al. |
| 5,595,756 A | 1/1997 | Bally et al. |
| 5,653,977 A | 8/1997 | Saleh |
| 5,674,704 A | 10/1997 | Goodwin et al. |
| 5,686,281 A | 11/1997 | Roberts |
| 5,712,149 A | 1/1998 | Roberts |
| 6,103,521 A | 8/2000 | Capon et al. |
| 6,303,121 B1 | 10/2001 | Kwon |
| 6,319,494 B1 | 11/2001 | Capon et al. |
| 6,355,476 B1 | 3/2002 | Kwon |
| 6,361,998 B1 | 3/2002 | Bell et al. |
| 6,410,319 B1 | 6/2002 | Raubitschek et al. |
| 6,797,514 B2 | 9/2004 | Berenson et al. |
| 7,052,906 B1 | 5/2006 | Lawson et al. |
| 7,070,995 B2 | 7/2006 | Jensen |
| 7,435,596 B2 | 10/2008 | Campana et al. |
| 7,446,179 B2 | 11/2008 | Jensen et al. |
| 7,446,190 B2 | 11/2008 | Sadelain et al. |
| 7,763,243 B2 | 7/2010 | Lum et al. |
| 7,932,055 B2 | 4/2011 | Spee et al. |
| 7,994,298 B2 | 8/2011 | Zhang et al. |
| 8,026,097 B2 | 9/2011 | Campana et al. |
| 8,399,645 B2 | 3/2013 | Campana et al. |
| 9,487,800 B2 | 11/2016 | Schonfeld et al. |
| 9,511,092 B2 | 12/2016 | Campana et al. |
| 9,605,049 B2 | 3/2017 | Campana et al. |
| 9,834,590 B2 | 12/2017 | Campana et al. |
| 9,856,322 B2 | 1/2018 | Campana et al. |
| 10,391,126 B2 | 8/2019 | Cooper et al. |
| 10,428,305 B2 | 10/2019 | Campana et al. |
| 10,538,739 B2 | 1/2020 | Campana et al. |
| 10,774,309 B2 | 9/2020 | Campana et al. |
| 10,774,311 B2 | 9/2020 | Campana et al. |
| 10,801,012 B2 | 10/2020 | Campana et al. |
| 10,829,737 B2 | 11/2020 | Campana et al. |
| 10,836,999 B2 | 11/2020 | Campana et al. |
| 11,141,436 B2 | 10/2021 | Trager et al. |
| 11,154,575 B2 | 10/2021 | Trager et al. |
| 11,253,547 B2 | 2/2022 | Trager et al. |
| 11,365,236 B2 | 6/2022 | Leong et al. |
| 11,560,548 B2 | 1/2023 | Campana et al. |
| 11,673,937 B2 | 6/2023 | Campana et al. |
| 11,873,512 B2 | 1/2024 | Campana et al. |
| 11,896,616 B2 | 2/2024 | Kamiya et al. |
| 2002/0018783 A1 | 2/2002 | Sadelain et al. |
| 2003/0129649 A1 | 7/2003 | Kobilka et al. |
| 2003/0147869 A1 | 8/2003 | Riley |
| 2003/0215427 A1 | 11/2003 | Jensen |
| 2004/0038886 A1 | 2/2004 | Finney et al. |
| 2004/0043401 A1 | 3/2004 | Sadelain et al. |
| 2004/0126363 A1 | 7/2004 | Jensen et al. |
| 2005/0042208 A1 | 2/2005 | Sagawa et al. |
| 2005/0048549 A1 | 3/2005 | Cao et al. |
| 2005/0113564 A1 | 5/2005 | Campana et al. |
| 2006/0093605 A1 | 5/2006 | Campana et al. |
| 2006/0247191 A1 | 11/2006 | Finney et al. |
| 2007/0160578 A1 | 7/2007 | Waldmann et al. |
| 2007/0166327 A1 | 7/2007 | Cooper et al. |
| 2008/0247990 A1 | 10/2008 | Campbell |
| 2008/0299137 A1 | 12/2008 | Svendsen |
| 2009/0281035 A1 | 11/2009 | Spee et al. |
| 2010/0029749 A1 | 2/2010 | Zhang et al. |
| 2012/0015434 A1 | 1/2012 | Campana et al. |
| 2012/0148552 A1 | 6/2012 | Jensen |
| 2012/0282256 A1 | 11/2012 | Campana et al. |
| 2012/0321666 A1 | 12/2012 | Copper et al. |
| 2013/0072401 A1 | 3/2013 | Ye et al. |
| 2013/0266551 A1 | 10/2013 | Campana et al. |
| 2013/0280221 A1 | 10/2013 | Schonfeld et al. |
| 2013/0288368 A1 | 10/2013 | June et al. |
| 2014/0023626 A1 | 1/2014 | Peled et al. |
| 2014/0271635 A1 | 9/2014 | Brogdon et al. |
| 2014/0286973 A1 | 9/2014 | Powell, Jr. |
| 2014/0302608 A1 | 10/2014 | Dominici et al. |
| 2014/0349402 A1 | 11/2014 | Cooper |
| 2015/0139943 A1 | 5/2015 | Campana et al. |
| 2015/0190471 A1 | 7/2015 | Copik et al. |
| 2015/0218649 A1 | 8/2015 | Saenger et al. |
| 2016/0000828 A1 | 1/2016 | Campana et al. |
| 2016/0152723 A1 | 6/2016 | Chen et al. |
| 2016/0158285 A1 | 6/2016 | Cooper et al. |
| 2017/0044227 A1 | 2/2017 | Schonfeld |
| 2017/0073423 A1 | 3/2017 | Juillerat et al. |
| 2017/0073638 A1 | 3/2017 | Campana et al. |
| 2017/0129967 A1 | 5/2017 | Wels et al. |
| 2017/0283482 A1 | 10/2017 | Campana et al. |
| 2017/0355957 A1 | 12/2017 | Biondi et al. |
| 2018/0002397 A1 | 1/2018 | Shah et al. |
| 2018/0044391 A1 | 2/2018 | Gundram et al. |
| 2018/0086831 A1 | 3/2018 | Pule et al. |
| 2018/0104278 A1 | 4/2018 | Zhang et al. |
| 2018/0117146 A1 | 5/2018 | Yu et al. |
| 2018/0134765 A1 | 5/2018 | Landgraf et al. |
| 2019/0038733 A1 | 2/2019 | Campana et al. |
| 2019/0046571 A1 | 2/2019 | Campana et al. |
| 2019/0290693 A1 | 9/2019 | Qi et al. |
| 2019/0336533 A1 | 11/2019 | Hwang et al. |
| 2019/0376037 A1 | 12/2019 | Campana et al. |
| 2020/0016208 A1 | 1/2020 | Kamiya et al. |
| 2020/0131244 A1 | 4/2020 | Leong et al. |
| 2020/0255803 A1 | 8/2020 | Zhang et al. |
| 2020/0407686 A1 | 12/2020 | Campana et al. |
| 2021/0009951 A1 | 1/2021 | Hu et al. |
| 2021/0017271 A1 | 1/2021 | Tan et al. |
| 2021/0046115 A1 | 2/2021 | Seow et al. |
| 2021/0054409 A1 | 2/2021 | Zhu et al. |
| 2021/0324388 A1 | 10/2021 | Vinanica et al. |
| 2021/0338727 A1 | 11/2021 | Trager et al. |
| 2021/0363218 A1 | 11/2021 | Fan et al. |
| 2022/0002424 A1 | 1/2022 | Trager et al. |
| 2022/0047635 A1 | 2/2022 | Liu et al. |
| 2022/0233590 A1 | 7/2022 | Trager et al. |
| 2022/0233593 A1 | 7/2022 | Trager et al. |
| 2022/0411754 A1 | 12/2022 | Trager et al. |
| 2023/0028399 A1 | 1/2023 | Rajangam et al. |
| 2023/0220343 A1 | 7/2023 | Campana et al. |

(56) References Cited

U.S. PATENT DOCUMENTS

| | | | |
|---|---|---|---|
| 2023/0265390 A1 | 8/2023 | Trager et al. | |
| 2023/0390392 A1 | 12/2023 | Trager et al. | |
| 2024/0335536 A1 | 10/2024 | Trager et al. | |

FOREIGN PATENT DOCUMENTS

| | | |
|---|---|---|
| CN | 105838677 A | 8/2016 |
| CN | 105985931 A | 10/2016 |
| CN | 107109363 A | 8/2017 |
| CN | 107827990 A | 3/2018 |
| EP | 0 952 213 A2 | 3/1999 |
| EP | 0 830 599 B1 | 4/2000 |
| EP | 1 231 262 A1 | 8/2002 |
| EP | 1 306 427 A1 | 5/2003 |
| EP | 1 053 301 B1 | 4/2004 |
| EP | 1 820 017 | 6/2006 |
| EP | 1 233 058 B1 | 12/2006 |
| EP | 1 036 327 B1 | 7/2009 |
| EP | 2 411 507 A0 | 9/2010 |
| EP | 2 493 485 | 5/2011 |
| EP | 2 493 486 | 5/2011 |
| EP | 2 593 542 | 1/2012 |
| EP | 2 141 997 B1 | 10/2012 |
| EP | 2 614 151 | 10/2012 |
| EP | 2 756 521 | 3/2013 |
| EP | 2 866 834 A0 | 1/2014 |
| EP | 2 903 637 | 4/2014 |
| EP | 2 904 106 | 4/2014 |
| EP | 2 948 544 | 7/2014 |
| EP | 2 956 175 | 8/2014 |
| EP | 2 961 831 | 9/2014 |
| EP | 2 964 753 | 9/2014 |
| EP | 2 970 426 | 9/2014 |
| EP | 2 968 601 | 10/2014 |
| EP | 2 986 636 | 10/2014 |
| EP | 2 537 416 B1 | 11/2014 |
| EP | 3 008 173 | 12/2014 |
| EP | 2 856 876 A1 | 4/2015 |
| EP | 3 057 986 | 4/2015 |
| EP | 3 063 175 | 5/2015 |
| EP | 3 071 221 | 5/2015 |
| EP | 3 071 222 | 5/2015 |
| EP | 3 071 223 | 5/2015 |
| EP | 3 083 671 | 6/2015 |
| EP | 3 083 691 | 6/2015 |
| EP | 3 094 653 | 7/2015 |
| EP | 3 105 318 | 8/2015 |
| EP | 3 105 335 | 8/2015 |
| EP | 2 968 492 | 9/2015 |
| EP | 3 119 425 | 9/2015 |
| EP | 3 126 380 | 10/2015 |
| EP | 3 134 432 | 10/2015 |
| EP | 3 180 359 | 2/2016 |
| EP | 3 189 132 | 3/2016 |
| EP | 3 012 268 A1 | 4/2016 |
| EP | 2 614 077 B1 | 8/2016 |
| EP | 3 115 373 A1 | 1/2017 |
| EP | 3 567 049 A2 | 11/2019 |
| JP | 2017-112982 A | 6/2017 |
| KR | 10-2660336 B1 | 4/2024 |
| WO | WO 92/17198 A1 | 10/1992 |
| WO | WO 95/007358 A1 | 3/1995 |
| WO | WO 96/023814 A1 | 8/1996 |
| WO | WO 96/024671 A1 | 8/1996 |
| WO | WO 96/41163 A1 | 12/1996 |
| WO | WO 97/023613 A2 | 7/1997 |
| WO | WO 98/026061 A2 | 6/1998 |
| WO | WO 99/000494 A2 | 1/1999 |
| WO | WO 99/06557 A2 | 2/1999 |
| WO | WO 99/38954 A1 | 8/1999 |
| WO | WO 99/057268 A1 | 11/1999 |
| WO | WO 2000/014257 A1 | 3/2000 |
| WO | WO 00/23573 A2 | 4/2000 |
| WO | WO 01/29191 A1 | 4/2001 |
| WO | WO 01/38494 A1 | 5/2001 |
| WO | WO 02/10350 A1 | 2/2002 |
| WO | WO 02/033101 A1 | 4/2002 |
| WO | WO 02/077029 A2 | 10/2002 |
| WO | WO 03/089616 A2 | 10/2003 |
| WO | WO 2004/027036 A2 | 4/2004 |
| WO | WO 2004/039840 A1 | 5/2004 |
| WO | 2005000890 A1 | 1/2005 |
| WO | WO 2005/044996 A2 | 5/2005 |
| WO | WO 2005/118788 A2 | 12/2005 |
| WO | WO 2006/036445 A2 | 4/2006 |
| WO | WO 2006/052534 A2 | 5/2006 |
| WO | WO 2006/061626 A2 | 6/2006 |
| WO | 2006119115 A2 | 11/2006 |
| WO | WO 2007/046006 A2 | 4/2007 |
| WO | WO 2008/121420 A1 | 10/2008 |
| WO | WO 2009/117566 A1 | 9/2009 |
| WO | WO 2010/071836 A1 | 6/2010 |
| WO | WO 2010/110734 A1 | 9/2010 |
| WO | WO 2011/020047 A1 | 2/2011 |
| WO | WO 2011/053321 A1 | 5/2011 |
| WO | WO 2011/053322 A1 | 5/2011 |
| WO | WO 2011/069019 A2 | 6/2011 |
| WO | WO 2011/080740 A1 | 7/2011 |
| WO | WO 2011/150976 A1 | 12/2011 |
| WO | WO 2012/009422 A1 | 1/2012 |
| WO | WO 2012/031744 A1 | 3/2012 |
| WO | WO 2012/040323 A2 | 3/2012 |
| WO | WO 2012/071411 A2 | 5/2012 |
| WO | WO 2012/079000 A1 | 6/2012 |
| WO | WO 2012/136231 A1 | 10/2012 |
| WO | 2013043196 A1 | 3/2013 |
| WO | WO 2013/040371 A2 | 3/2013 |
| WO | WO 2013/040557 A2 | 3/2013 |
| WO | WO 2013/123720 A2 | 8/2013 |
| WO | WO 2013/123726 A1 | 8/2013 |
| WO | WO 2014/005072 A1 | 1/2014 |
| WO | WO 2014/011993 A2 | 1/2014 |
| WO | 2017/029512 A1 | 2/2014 |
| WO | WO 2014/055413 A2 | 4/2014 |
| WO | WO 2014/055442 A2 | 4/2014 |
| WO | WO 2014/055657 A1 | 4/2014 |
| WO | WO 2014/055668 A1 | 4/2014 |
| WO | WO 2014/099671 A1 | 6/2014 |
| WO | WO 2014/117121 A1 | 7/2014 |
| WO | WO 2014/127261 A1 | 8/2014 |
| WO | WO 2014/134165 A1 | 9/2014 |
| WO | WO 2014/138704 A1 | 9/2014 |
| WO | WO 2014/145252 A2 | 9/2014 |
| WO | WO 2014/164554 A1 | 10/2014 |
| WO | WO 2014/172584 A1 | 10/2014 |
| WO | WO 2014/186469 A2 | 11/2014 |
| WO | WO 2014/201021 A2 | 12/2014 |
| WO | WO 2015/058018 A1 | 4/2015 |
| WO | WO 2015/066551 A2 | 5/2015 |
| WO | WO 2015/075468 A1 | 5/2015 |
| WO | WO 2015/075469 A1 | 5/2015 |
| WO | WO 2015/075470 A1 | 5/2015 |
| WO | WO 2015/092024 A2 | 6/2015 |
| WO | WO 2015/095895 A1 | 6/2015 |
| WO | WO 2015/105522 A1 | 7/2015 |
| WO | WO 2015/120421 A1 | 8/2015 |
| WO | WO 2015/123642 A1 | 8/2015 |
| WO | WO 2015/142314 A1 | 9/2015 |
| WO | WO 2015/142661 A1 | 9/2015 |
| WO | 2015/15791 A1 | 10/2015 |
| WO | WO 2015/150771 A1 | 10/2015 |
| WO | WO 2015/154012 A1 | 10/2015 |
| WO | WO 2015/154012 A8 | 10/2015 |
| WO | WO 2015/164759 A2 | 10/2015 |
| WO | WO 2015/174928 A1 | 11/2015 |
| WO | 2015188119 A1 | 12/2015 |
| WO | WO 2015/193411 A1 | 12/2015 |
| WO | WO 2016/011210 A2 | 1/2016 |
| WO | WO 2016/030691 A1 | 3/2016 |
| WO | WO 2016/033331 A1 | 3/2016 |
| WO | WO 2016/040441 A1 | 3/2016 |
| WO | WO 2016/042041 A1 | 3/2016 |
| WO | WO 2016/042461 A1 | 3/2016 |
| WO | WO 2016/061574 A1 | 4/2016 |

(56) References Cited

FOREIGN PATENT DOCUMENTS

| | | |
|---|---|---|
| WO | WO 2016/069607 A1 | 5/2016 |
| WO | WO 2016/073602 A2 | 5/2016 |
| WO | WO 2016/073629 A1 | 5/2016 |
| WO | WO 2016/073755 A2 | 5/2016 |
| WO | WO 2016/075612 A1 | 5/2016 |
| WO | WO 2016/100985 A2 | 6/2016 |
| WO | 2016118857 A1 | 7/2016 |
| WO | WO 2016/109661 A1 | 7/2016 |
| WO | WO 2016/109668 A1 | 7/2016 |
| WO | WO 2016/115482 A1 | 7/2016 |
| WO | WO 2016/123122 A1 | 8/2016 |
| WO | WO 2016/123333 A1 | 8/2016 |
| WO | WO 2016/124765 A1 | 8/2016 |
| WO | WO 2016/124930 A1 | 8/2016 |
| WO | WO 2016/126213 A1 | 8/2016 |
| WO | WO 2016/126608 A1 | 8/2016 |
| WO | WO 2016/139487 A1 | 9/2016 |
| WO | WO 2016/141357 A1 | 9/2016 |
| WO | WO 2016/142314 A1 | 9/2016 |
| WO | WO 2016/149254 A1 | 9/2016 |
| WO | WO 2016/151315 A1 | 9/2016 |
| WO | WO 2016/154055 A1 | 9/2016 |
| WO | WO 2016/154585 A1 | 9/2016 |
| WO | 2016/168773 A1 | 10/2016 |
| WO | WO 2016/172537 A1 | 10/2016 |
| WO | WO 2016/172583 A1 | 10/2016 |
| WO | WO 2016/174405 A1 | 11/2016 |
| WO | WO 2016/174406 A1 | 11/2016 |
| WO | WO 2016/174407 A1 | 11/2016 |
| WO | WO 2016/174408 A1 | 11/2016 |
| WO | WO 2016/174409 A1 | 11/2016 |
| WO | WO 2016/174461 A1 | 11/2016 |
| WO | WO 2016/174652 A1 | 11/2016 |
| WO | WO 2016/179684 A1 | 11/2016 |
| WO | WO 2016/191587 A1 | 12/2016 |
| WO | WO 2016/191755 A1 | 12/2016 |
| WO | WO 2016/196388 A1 | 12/2016 |
| WO | WO 2016/197108 A1 | 12/2016 |
| WO | WO 2016/201304 A1 | 12/2016 |
| WO | WO 2016/210293 A1 | 12/2016 |
| WO | WO 2017/004150 A1 | 1/2017 |
| WO | WO 2017/011804 A1 | 1/2017 |
| WO | WO 2017/021701 A1 | 2/2017 |
| WO | WO 2017/023859 A1 | 2/2017 |
| WO | WO 2017/024131 A1 | 2/2017 |
| WO | WO 2017/027325 A1 | 2/2017 |
| WO | WO 2017/029511 A1 | 2/2017 |
| WO | WO 2017/032777 A1 | 3/2017 |
| WO | WO 2017/034615 A1 | 3/2017 |
| WO | WO 2017/037083 A1 | 3/2017 |
| WO | WO 2017/058752 A1 | 4/2017 |
| WO | WO 2017/058753 A1 | 4/2017 |
| WO | WO 2017/079694 A2 | 5/2017 |
| WO | WO 2017/079705 A1 | 5/2017 |
| WO | WO 2017/079881 A1 | 5/2017 |
| WO | WO 2017/096329 A1 | 6/2017 |
| WO | WO 2017/127729 A1 | 7/2017 |
| WO | WO 2017/172981 A2 | 10/2017 |
| WO | 2017/186928 A1 | 11/2017 |
| WO | WO 2018/022646 A1 | 2/2018 |
| WO | 2018/106732 A1 | 6/2018 |
| WO | WO 2018/103503 A1 | 6/2018 |
| WO | 2018124766 A2 | 7/2018 |
| WO | WO 2018/182511 A1 | 10/2018 |
| WO | WO 2018/183385 A1 | 10/2018 |
| WO | WO 2019/062817 A1 | 4/2019 |
| WO | WO 2019/077037 A1 | 4/2019 |
| WO | 2019/091478 A1 | 5/2019 |
| WO | 2019/129220 A1 | 7/2019 |
| WO | WO 2019/129002 A1 | 7/2019 |
| WO | WO 2019/155286 A2 | 8/2019 |
| WO | WO 2019/155288 A1 | 8/2019 |
| WO | 2019/169290 A1 | 9/2019 |
| WO | WO 2019/193476 A1 | 10/2019 |
| WO | WO 2020/044239 A1 | 3/2020 |
| WO | WO 2020/083282 A1 | 4/2020 |
| WO | WO 2021/009694 A1 | 1/2021 |

OTHER PUBLICATIONS

Abken et al., "Chimeric T-cell receptors: highly specific tools to target cytotoxic T-lymphocytes to tumour cells," Cancer Treat Rev., 23(2):97-112, Mar. 1997.

Abken, H., et al., "Tuning tumor-specific T-cell activation: a matter of costimulation?" TRENDS in Immunol. 23: 240-245 (2002).

Aguera-Gonzalez et al., "Palmitoylation of MICA, a ligand for NKG2D, mediates its recruitment to membrane microdomains and promotes its shedding," Eur. J. Immunol. Vol. 41, pp. 3667-3676 (2011).

Alderson et al., "Molecular and Biological Characterization of Human 4-1BB and its Ligand," Eur. J. Immunol., 1994, 24: 2219-2227.

Allison and Lanier, "Structure, function, and serology of the T-cell antigen receptor complex," Annu Rev Immunol, 1987, 5:503-40.

Alvarez-Vallina, L. and Hawkins, R.E., "Antigen-specific targeting of CD28-mediated T cell co-stimulation using chimeric single-chain antibody variable fragment-CD28 receptors," Eur. J. Immunol. 26: 2304-2309 (1996).

Annenkov, A., et al., "Engineering mouse T lymphocytes specific to type II collagen by transduction with a chimeric receptor consisting of a single chain Fv and TCR zeta," Gene Therapy 7: 714-722 (2000).

Antony, G.K., et al., "Interleukin 2 in cancer therapy," Curr Med Chem., 17(29): 3297-3302 (2010).

Aoudjit and Vuori., "Integrin Signaling in Cancer Cell Survival and Chemoresistance," Chemotherapy Research and Practice., 2012(Article ID 283181), 16 pages, 2012.

Appelbaum, "Haematopoietic cell transplantation as immunotherapy," Nature, 2001, 411(6835): 385-389.

Aruffo, A., et al., "Molecular cloning of a CD28 cDNA by a high-efficiency COS cell expression system," Proc. Natl. Acad. Sci., 1987, 84:8573-8577.

ATCC No. CCL-243, 1975.

Azuma, M, et al., "Functional Expression of B7/BB1 on Activated T Lymphocytes," J. Exp. Med. 177: 845-850 (1993).

Baek, H.J et al., "Ex vivo expansion of natural killer cells using cryopreserved irradiated feeder cells," *Anticancer Research*, 33: 2011-2020 (2013).

Barber et al., "Chimeric NKG2D Expressing T Cells Eliminate Immunosuppression and Activate Immunity within the Ovarian Tumor Microenvironment," J. Immunol, vol. 183, pp. 6939-6947 (2009).

Barber et al., "Chimeric NKG2D Receptor-Bearing T Cells as Immunotherapy for Ovarian Cancer," American Association for Cancer, vol. 67, No. 10, pp. 5003-5008, (May 15, 2007).

Barber et al., "Chimeric NKG2D receptor-expressing T cells as an immunotherapy for multiple myeloma," Experimental Hematology, vol. 36, pp. 1318-1328, (2008).

Barber et al., "Chimeric NKG2D T Cells Require Both T Cell- and Host-Derived Cytokine Secretion and Perforin Expression to Increase Tumor Antigen Presentation and Systemic Immunity," J. Immunol, vol. 183, pp. 2365-2372 (2009).

Barber et al., "Immunotherapy with Chimeric NKG2D Receptors Leads to Long-Term Tumor-Free Survival and Development of Host Antitumor Immunity in Murine Ovarian Cancer," J. Immunol., vol. 180, pp. 72-78, (2008).

Barber et al., "Treatment of multiple myeloma with adoptively transferred chimeric NKG2D receptor-expressing T cells," Gene Therapy, vol. 18, pp. 509-516, (2011).

Barrett, D.M., et al., "Chimeric Antigen Receptor Therapy for Cancer," Annu Rev. Med. 65: 333-347 (2014).

Bartholomew et al., "Mesenchymal stem cells suppress lymphocyte proliferation in vitro and prolong skin graft survival in vivo," Exp Hematol, Jan. 2002, 30(1): 42-8.

Batlevi, C.L., et al. "Novel immunotherapies in lymphoid malignancies," Nature Rev. Clin. Oncol.13:25-40 (2016).

(56) References Cited

OTHER PUBLICATIONS

Baum et al., "Side effects of retroviral gene transfer into hematopoietic stem cells," Blood, Mar. 2003, 101(6): 2099-114.
Bejcek et al., "Development and Characterization of Three Recombinant Single Chain Antibody Fragments (scFvs) Directed against the CD19 Antigen," Cancer Res., 1995, 55:2346-2351.
Berger, C. et al., "Safety and immunologic effects of IL-15 administration in nonhuman primates," *Blood*, 114(12): 2417-2426 (2009).
Besser, M.J., et al., "Adoptive Transfer of Tumor-Infiltrating Lymphocytes in Patients with Metastatic Melanoma: Intent-to-Treat Analysis and Efficacy after Failure to Prior Immunotherapies," Clin. Cancer Res. 19: 4792-4800 (2013).
Better et al., "Manufacturing and Characterization of KTE-C19 in a Multicenter Trial of Subjects with Refractory Aggressive Non-Hodgkin Lymphoma (NHL) (ZUMA-1)," Poster session presented at the American Association for Cancer Research Annual Meeting, New Orleans, Louisiana (2016).
Billadeau et al., "NKG2D-DAP10 triggers human NK cell-mediated killing via a Syk-independent regulatory pathway," Nat Immunol, Jun. 2003, 4(6): 557-64.
Bischof et al., "Autonomous induction of proliferation, JNK and NF-xB activation in primary resting T cells by mobilized CD28," Eur J Immunol., 30(3):876-882, Mar. 2000.
Bork et al., "The immunoglobulin fold. Structural classification, sequence patterns and common core," J Mol Biol., 242(4):309-320, Sep. 30, 1994.
Boyman, O., et al., "The role of interleukin-2 during homeostasis and activation of the immune system," *Nat Rev Immunol.*, 12: 180-190 (2012).
Brentjens et al., "Eradication of Systemic B-Cell Tumors by Genetically Targeted Human T Lymphocytes Co-Stimulated By CD80 and Interleukin-15," Nature Medicine, 2003, 9: 279-286.
Brentjens, R.J., et al., "CD19-Targeted T Cells Rapidly Induce Molecular Remissions in Adults with Chemotherapy-Refractory Acute Lymphoblastic Leukemia," Sci. Trans. Med. 5: 1-9 (2013).
Brentjens, R.J., et al., "Safety and persistence of adoptively transferred autologous CD19-targeted T cells in patients with relapsed or chemotherapy refractory B-cell leukemias," Blood 119(18): 4817-4828 (2011).
Bridgeman, U.S., et al., "Building Better Chimeric Antigen Receptors for Adoptive T Cell Therapy," Current Gene Therapy 10: 77-90 (2010).
Brocker et al., "New simplified molecular design for functional T cell receptor," Eur J Immunol., 23(7):1435-1439, Jul. 1993.
Bromley et al., "The immunological synapse and CD28-CD80 interactions," Nat Immunol., 2(12):1159-1166, Dec. 2001.
Bronte, V., and Mocellin, S., "Suppressive Influences in the Immune Response to Cancer," J. Immunother . 32: 1-11 (2009).
Budagian, V. et al., "IL-15/IL-15 receptor biology: A guided tour through an expanding universe," *Cytokine & Growth Factor Reviews*, 17: 259-280 (2006).
Bukczynski et al., "Costimulation of Human CD28-T Cells by 4-1BB Ligand," Eur. J. Immunol., 2003, 33: 446-454.
Burkett, P.R. et al., "Coordinate expression and trans presentation of interleukin (IL)-15Ralpha and IL-15 supports natural killer cell and memory CD8+ T cell homeostasis," *J Exp Med.*, 200(7): 825-834 (2004).
Caligiuri et al., "Immunotherapeutic approaches for hematologic malignancies," Hematology Am Soc Hematol Educ Program, 2004, 37-53.
Campana et al., "Immunophenotyping of Leukemia," Journal of Immunol Methods, 2000, 243: 59-75.
Cardoso AA, et al. Pre-B acute lymphoblastic leukemia cells may induce T-cell anergy to alloantigen. Blood 88:41-48 (1996).
Carson, W.E. et al., "A potential role for interleukin-15 in the regulation of human natural killer cell survival," J Clin Invest., 99(5): 937-943 (1997).
Carter, P., et al., "Identification and validation of cell surface antigens for antibody targeting in oncology," Endocrine-Related Cancer 11: 659-687 (2004).
Cesano, A., et al. "Reversal of Acute Myelogenous Leukemia in Humanized SCID Mice Using a Novel Adoptive Transfer Approach," J. Clin. Invest. 94: 1076-1084 (1994).
Chambers, C.A., "The expanding world of co-stimulation: the two-signal model revisited," TRENDS in Immunol., 2001, 22(4):217-223.
Champlin R. "T-cell depletion to prevent graft-versus-host disease after bone marrow transplantation," Hematol Oncol Clin North Am. Jun. 1990;4(3):687-98.
Chang, Y.H. et al., "A chimeric receptor with NKG2D specificity enhances natural killer cell activation and killing of tumor cells," Cancer Res., 73(6): 1777-1786 (2013).
Chao, D.T. et al., "BCL-2 family: regulators of cell death," Annu Rev Immunol., 16: 395-419 (1998).
Cheresh et al., "Disialogangliosides GD2 and GD3 Are Involved in the Attachment of Human Melanoma and Neuroblastoma Cells to Extracellular Matrix Proteins," J Cell Biol. 1986, 102(3):688- 696.
Chertova, E. et al., "Characterization and favorable in vivo properties of heterodimeric soluble IL-15.IL-15Ralpha cytokine compared to IL-15 monomer," J Biol Chem., 288(25): 18093-18103 (2013).
Cheung et al., "Anti-Idiotypic Antibody Facilitates scFv Chimeric Immune Receptor-Gene Transduction and Clonal Expansion of Human Lymphocytes for Tumor Therapy," Hybridoma and Hybridomics, 2003, 24(4): 209-218.
Chiorean and Miller, "The biology of natural killer cells and implications for therapy of human disease," J Hematother Stem Cell Res, Aug. 2001, 10(4): 451-63.
Cho, D., and D. Campana, "Expansion and activation of natural killer cells for cancer immunotherapy," The Korean Journal of Laboratory Medicine, 29(2): 89-96 (2009).
Clarke et al., "Folding studies of immunoglobulin-like beta-sandwich proteins suggest that they share a common folding pathway," Structure, 7(9):1145-1153, Sep. 15, 1999.
ClinicalTrials.gov, "A Multi-Center Study Evaluating KTE-C19 in Pediatric and Adolescent Subjects With Relapsed/Refractory B-precursor Acute Lymphoblastic Leukemia (ZUMA-4)," available at https://clinicaltrials.gov/show/NCT02625480, NCT02625480 (Retrieved from the Internet on Jun. 21, 2016).
ClinicalTrials.gov, "A Phase 1-2 Multi-Center Study Evaluating KTE-C19 in Subjects With Refractory Aggressive Non-Hodgkin Lymphoma (ZUMA-1) (ZUMA-1)," available at https://clinicaltrials.gov/show/NCT02348216, NCT02348216 (Retrieved from the Internet on Jun. 21, 2016).
ClinicalTrials.gov, "A Phase 2 Multicenter Study Evaluating Subjects With Relapsed/Refractory Mantle Cell Lymphoma (ZUMA-2)," available at https://clinicaltrials.gov/show/NCT02601313, NCT02601313 (Retrieved from the Internet on Jun. 21, 2016).
ClinicalTrials.gov, "A Study Evaluating KTE-C19 in Adult Subjects With Relapsed/Refractory B-precursor Acute Lymphoblastic Leukemia (r/r All) (ZUMA-3) (ZUMA-3)," available at https://clinicaltrials.gov/show/NCT02614066, NCT02614066 (Retrieved from the Internet on Jun. 21, 2016).
ClinicalTrials.gov, "Administration of Anti-CD19-chimeric-antigen-receptor-transduced T Cells From the Original Transplant Donor to Patients With Recurrent or Persistent B-cell Malignancies After Allogenic Stem Cell Transplantation," available at https://clinicaltrials.gov/show/NCT01087294, NCT01087294 (Retrieved from the Internet on Jun. 21, 2016).
ClinicalTrials.gov, "Anti-CD19 White Blood Cells for Children and Young Adults With B Cell Leukemia or Lymphoma," available at https://clinicaltrials.gov/show/NCT01593696, NCT01593696 (Retrieved from the Internet on Jun. 21, 2016).
ClinicalTrials.gov, "Car T Cell Receptor Immunotherapy for Patients With B-cell Lymphoma," available at https://clinicaltrials.gov/show/NCT00924326, NCT00924326 (Retrieved from the Internet on Jun. 21, 2016).
ClinicalTrials.gov, "CD 19 Car T Cells for B Cell Malignancies After Allogeneic Transplant," available at https://clinicaltrials.gov/show/NCT01475058, NCT01475058 (Retrieved from the Internet on Jun. 21, 2016).
ClinicalTrials.gov, "CD19 Chimeric Receptor Expressing T Lymphocytes in B-Cell Non Hodgkin's Lymphoma, ALL & CLL

(56) References Cited

OTHER PUBLICATIONS (CRETI-NH)," available at https://clinicaltrials.gov/show/NCT00586391, NCT00586391 (Retrieved from the Internet on Jun. 21, 2016).
ClinicalTrials.gov, "CD19+ Car T Cells for Lymphoid Malignancies," available at https://clinicaltrials.gov/show/NCT02529813, NCT02529813 (Retrieved from the Internet on Jun. 21, 2016).
ClinicalTrials.gov, "Consolidation Therapy With Autologous T Cells Genetically Targeted to the B Cell Specific Antigen CD19 in Patients With Chronic Lymphocytic Leukemia Following Upfront Chemotherapy With Pentostatin, Cyclophosphamide and Rituximab," available at https://clinicaltrials.gov/show/NCT01416974, NCT01416974 (Retrieved from the Internet on Jun. 21, 2016).
ClinicalTrials.gov, "Genetically Engineered Lymphocyte Therapy in Treating Patients With B-Cell Leukemia or Lymphoma That is Resistant or Refractory to Chemotherapy," available at https://clinicaltrials.gov/show/NCT01029366, NCT01029366 (Retrieved from the Internet on Jun. 21, 2016).
ClinicalTrials.gov, "High Dose Therapy and Autologous Stem Cell Transplantation Followed by Infusion of Chimeric Antigen Receptor (CAR) Modified T-Cells Directed Against CD19+ B-Cells for Relapsed and Refractory Aggressive B Cell Non-Hodgkin Lymphoma," available at https://clinicaltrials.gov/show/NCT01840566, NCT01840566 (Retrieved from the Internet on Jun. 21, 2016).
ClinicalTrials.gov, "In Vitro Expanded Allogeneic Epstein-Barr Virus Specific Cytotoxic T- Lymphocytes (EBV-CTLs) Genetically Targeted to the CD19 Antigen in B-cell Malignancies," available at https://clinicaltrials.gov/show/NCT01430390, NCT01430390 (Retrieved from the Internet on Jun. 21, 2016).
ClinicalTrials.gov, "Precursor B Cell Acute Lymphoblastic Leukemia (B-ALL) Treated With Autologous T Cells Genetically Targeted to the B Cell Specific Antigen CD19," available at https://clinicaltrials.gov/show/NCT01044069, NCT01044069 (Retrieved from the Internet on Jun. 21, 2016).
ClinicalTrials.gov, "Study Evaluating the Efficacy and Safety of JCAR015 in Adult B-cell Acute Lymphoblastic Leukemia (B-All) (Rocket)," available at https://clinicaltrials.gov/show/NCT02535364, NCT02535364 (Retrieved from the Internet on Jun. 21, 2016).
ClinicalTrials.gov, "T Cells Expressing a Fully-human AntiCD19 Chimeric Antigen Receptor for Treating B-cell Malignancies," available at https://clinicaltrials.gov/show/NCT02659943, NCT02659943(Retrieved from the Internet on Jun. 21, 2016).
ClinicalTrials.gov, "T-Lymphocytes Genetically Targeted to the B-Cell Specific Antigen CD19 in Pediatric and Young Adult Patients With Relapsed B-Cell Acute Lymphoblastic Leukemia," available at https://clinicaltrials.gov/show/NCT01860937, NCT01860937(Retrieved from the Internet on Jun. 21, 2016).
ClinicalTrials.gov, "Treatment of Relapsed or Chemotherapy Refractory Chronic Lymphocytic Leukemia or Indolent B Cell Lymphoma Using Autologous T Cells Genetically Targeted to the B Cell Specific Antigen CD19", Available at: https://clinicaltrials.gov/show/NCT00466531, NCT00466531(Retrieved from the Internet on Jun. 21, 2016).
Cochran et al., "Receptor clustering and transmembrane signaling in T cells," Trends Biochem Sci., 26(5):304-310, May 2001.
Collins et al., "Donor leukocyte infusions in 140 patients with relapsed malignancy after allogencic bone marrow transplantation," J Clin Oncol, Feb. 1997, 15(2): 433-44.
Collins et al., "Donor leukocyte infusions in acute lymphocytic leukemia," Bone Marrow Transplantation, 2000, 26: 511-516.
Cooley, S. et al., "Donor selection for natural killer cell receptor genes leads to superior survival after unrelated transplantation for acute myelogenous leukemia," Blood, 116(14): 2411-2419 (2010).
Cooper, M.A. et al., "In vivo evidence for a dependence on interleukin 15 for survival of natural killer cells," Blood, 100(10): 3633-3638 (2002).
Cooper et al., "T-Cell Clones can be Rendered Specific for CD 19: Toward the Selective Augmentation of the Graft-Versus-B Lineage Leukemia Effect," Blood, 2003, pp. 1637-1644, vol. 101.
Cruz et al., "Infusion of donor-derived CD19-redirected virus-specific T cells for B-cell malignancies relapsed after allogeneic stem cell transplant: a phase 1 study," Blood 122(17):2965-2973 (2013).
Curti, A. et al., "Successful transfer of alloreactive haploidentical KIR ligand-mismatched natural killer cells after infusion in elderly high risk acute myeloid leukemia patients," Blood, 118(12):3273-3279 (2011).
Damle et al., "Differential regulatory signals delivered by antibody binding to the CD28 (Tp44) molecule during the activation of human T lymphocytes," J Immunol., 140(6):1753-1761, Mar. 15, 1988.
Darcy, P.K., et al., "Expression in cytotoxic T lymphocytes of a single-chain anti-carcinoembryonic antigen antibody. Redirected Fas ligand-mediated lysis of colon carcinoma," Eur. J. Immunol. 28: 1663-1672 (1998).
Davila, M.L., et al., "Efficacy and Toxicity Management of 19-28z Car T Cell Therapy in B Cell Acute Lymphoblastic Leukemia," Science Translat. Med. 6(24) (2014).
DeBenedette et al., "Role of 4-1BB ligand in costimulation of T lymphocyte growth and its upregulation on M12 B lymphomas by cAMP," J Exp Med, Mar. 1995, 181(3): 985-92.
DeBenedette, MA, et al.. "Costimulation of CD28- T Lymphocytes by 4-1 BB Ligand," J. Immunol., 1997, pp. 551-559, vol. 158.
Delahaye, N.F. et al., "Alternatively spliced NKp30 isoforms affect the prognosis of gastrointestinal stromal tumors," *Nat Med., 17*(6): 700-707 (2011).
Diefenbach et al., "Selective associations with signaling proteins determine stimulatory versus costimulatory activity of NKG2D," Nature Publishing Group, vol. 3, No. 12, pp. 1142-1149, (Dec. 2002).
Dotti et al., "Design and Development of Therapies using Chimeric Antigen Receptor-Expressing T cells," Immunol Rev., 257(1), 35 pages, Jan. 2014.
Doubrovian, et al., "Evasion from NK Cell Immunity by MHC Class I Chain-Related Molecules Expressing Colon Adenocarcinoma," Journal of Immunology, vol. 171, pp. 689-6899, (2003).
Dubois et al., "IL-15Rα recycles and presents IL-15 in trans to neighboring cells," Immunity, Nov. 2002, 17(5): 537-47.
Dubois, S., et al., "Preassociation of IL-15 with IL-15R alpha-IgG1-Fc enhances its activity on proliferation of NK and CD8+/CD44high T cells and its antitumor action," Journal of Immunology, 180(4):2099-2106 (2008).
Dudley, M.E., et al., "Adoptive Transfer of Cloned Melanoma—Reactive T Lymphocytes for the Treatment of Patients with Metastatic Melanoma," J. Immunother. 24: 363-373 (2001).
Ellis et al., "Interactions of CD80 and CD86 with CD28 and CTLA4," J Immunol., 156(8):2700-2709, Apr. 15, 1996.
Eshhar et al., "Specific activation and targeting of cytotoxic lymphocytes through chimeric single chains consisting of antibody-binding domains and the γ or ζ subunits of the immunoglobulin and T-cell receptors," Proc. Natl. Acad. Sci. USA, 1993, 90:720-724.
Eshhar, Z, et al. "Functional Expression of Chimeric Receptor Genes in Human T Cells," J. Immunol. Methods, 2001, 248(1-2):67-76.
Eshhar, Z., "Tumor-specific T-bodies: towards clinical application," Cancer Immunol. Immunother. 45: 131-136 (1997).
Fagan, E.A., and Eddleston, A.L.W.F., "Immunotherapy for cancer: the use of lymphokine activated killer (LAK) cells," Gut 28: 113-116 (1987).
Farag et al., "Natural killer cell receptors: new biology and insights into the Graft-versus-leukemia effect," Blood, 2002, 100(6):1935-1947.
Fehniger TA, et al.; "Ontogeny and expansion of human natural killer cells: clinical implications", Int Rev Immunol. Jun. 2001; 20(3-4):503-534.
Fehniger, T.A., et al., "Interleukin 15: biology and relevance to human disease," Blood, 97(1): 14-32 (2001).
Ferlazzo, G. et al., "Distinct roles of IL-12 and IL-15 in human natural killer cell activation by dendritic cells from secondary lymphoid organs," PNAS, 101(47): 16606-16611 (2004).

(56) References Cited

OTHER PUBLICATIONS

Fernandez-Messina et al., "Human NKG2D-ligands: cell biology strategies ensure immune recognition," Frontiers in Immunology, vol. 3, Article 299, 9 Pages, (Sep. 2012).
Ferris, R.L. et al., "Tumor antigen-targeted, monoclonal antibody-based immunotherapy: clinical response, cellular immunity, and immunoescape," J Clin Oncol, 28(28): 4390-4399 (2010).
Finney et al., "Activation of resting human primary T cells with chimeric receptors: costimulation from CD28, inducible costimulator, CD134, and CD137 in series with signals from the TCR zeta chain", J Immunol. Jan. 1, 2004; 172(1):104-113.
Finney et al., "Chimeric receptors providing both primary and costimulatory signaling in T cells from a single gene product," J Immunol. Sep. 15, 1998;161(6):2791-2797.
Foon et al., "Clinical and immune responses in advanced melanoma patients immunized with an anti-idiotype antibody mimicking disialoganglioside GD2," J Clin Oncol., 18(2):376-384, Jan. 2000.
Freshney, Animal Cell Culture, Cancer Research Campaign, IRL Press, 1986, 248 pages [Table of Contents Only].
Fujisaki, H. et al., "Expansion of highly cytotoxic human natural killer cells for cancer cell therapy," Cancer Res., 69(9): 4010-4017 (2009).
Fujisaki, H. et al., "Replicative potential of human natural killer cells," Br J Haematol,145: 606-613 (2009).
Gardner, R., et al., "Acquisition of a CD19 negative myeloid phenotype allows immune escape of MLL-rearranged B-ALL from CD19 Car-T cell therapy," Blood (forthcoming 2016).
Garrity et al., "The activating NKG2D receptor assembles in the membrane with two signaling dimers into a hexameric structure," PNAS, vol. 102, No. 21, pp. 7641-7646, May 24, 2005.
Geiger and Jyothi, "Development and application for receptor-modified T lymphocytes for adoptive immunotherapy," Transfus Med Rev, Jan. 2001, 15(1): 21-34.
Geiger et al., "Integrated src kinase and costimulatory activity enhances signal transduction through single-chain chimeric receptors in T lymphocytes", Blood. Oct. 15, 2001; 98(8):2364-2371.
GenBank Accession No. NM 007360 GI:315221123, *Homo sapiens* killer cell lectin like receptor K1 (KLRK1), mRNA, dated May 29, 2017, 4 pages.
GenBank Accession No. NM_000734 Gi: 37595563, *Homo sapiens* CD3Z antigen, zeta polypeptide (TiT3 complex) (CD3Z), transcript variant 2, mRNA, dated Oct. 27, 2004, 6 pages.
GenBank Accession No. NM_001768 GI: 27886640, *Homo sapiens* CD8 antigen, alpha polypeptide (p32) (CD8A), transcript variant 1, mRNA, dated Oct. 27, 2004, 5 pages.
GenBank Accession No. NM_011612 GI: 6755830, Mus musculus tumor necrosis factor receptor superfamily, member 9 (Tnfrsf9), mRNA, dated Oct. 26, 2004, 8 pages.
Germain et al., "T-cell signaling: the importance of receptor clustering," Curr Biol., 7(10):R640-R644, Oct. 1, 1997.
Ghobadi, et al., "Updated Phase 1 Results from ZUMA-1: A Phase 1-2 Multicenter StudyEvaluating the Safety and Efficacy of KTE-C19 (Anti-CD19 Car T Cells) in Subjects With Refractory Aggressive Non-Hodgkin Lymphoma," Slides accompanying oral presentation at the American Association for Cancer Research Annual Meeting, New Orleans, Louisiana (2016).
Ghorashian, S., et al., "CD19 chimeric antigen receptor T cell therapy for haematological malignancies," Br. J. Haematol. 169:463-478 (2015).
Giebel, S. et al., "Survival advantage with KIR ligand incompatibility in hematopoietic stem cell transplantation from unrelated donors," *Blood*, 102(3): 814-819 (2003).
Gilfillan et al., "NKG2D recruits two distinct adapters to trigger NK cell activation and costimulation," Nature Publishing Group, Nature Immunology, vol. 3, No. 12, pp. 1150-1155, Dec. 2002.
Gill, S., et al., "Chimeric antigen receptor T cell therapy: 25 years in the making," Blood Rev. (2015).
Ginaldi, L., et al., "Levels of expression of CD19 and CD20 in chronic B cell leukaemias," J. Clin. Pathol. 51: 364-369 (1998).

Giuliani, M. et al., "Generation of a novel regulatory NK cell subset from peripheral blood CD34+ progenitors promoted by membranc-bound IL-15," PLos One, 3(5): c2241 (2008).
Gong et al., "Cancer Patient T Cells Genetically Targeted to Prostate-Specific Membrane Antigen Specifically Lyse Prostate Cancer Cells and Release Cytokines in Response to Prostate-Specific Membrane Antigen," Neoplasia, 1999, 1(2): 123-127.
Goodier and Londei, "CD28 is not directly involved in the response of human CD3- CD56+ natural killer cells to lipopolysaccharide: a role for T cells," Immunology, Apr. 2004, 111(4): 384-90.
Goodwin et al., "Molecular cloning of a ligand for the inducible T cell gene 4-1 BB: a member of an emerging family of cytokines with homology to tumor necrosis factor", Eur J Immunol. Oct. 1993; 23(10):2631-2641.
Greene et al., "Covalent dimerization of CD28/CTLA-4 and oligomerization of CD80/CD86 regulate T cell costimulatory interactions," J Biol Chem., 271(43):26762-26771, Oct. 25, 1996.
Greenfield, E.A., et al., "CD28/B7 Costimulation: A Review," Crit. Rev. Immunol. 18: 389-418 (1998).
Greenwald et al., "The B7 Family Revisited," Annu. Rev. Immunol., 2005, 23: 515-548.
Grillo-López, A., "Rituximab: An Insider's Historical Perspective," Seminars in Oncology 27(6 Suppl 12): 9-16 (2012).
Gross and Eshhar, "Endowing T cells with antibody specificity using chimeric T cell receptors," FASEB J. Dec. 1992;6(15):3370-3378.
Grupp et al., "Chimeric antigen receptor-modified T cells for acute lymphoid leukemia," N Engl J Med. Apr. 18, 2013; 368 (16):1509-1518.
Handgretinger, R., et al., "A phase I study of neuroblastoma with the anti-ganglioside GD2 antibody 14.G2a," Cancer Immunol. Immunother. 35: 199-204 (1992).
Hara et al., "NKG2D gene polymorphisms are associated with disease control of chronic myeloid leukemia by dasatinib," Int. J. Hematol., 9 pages, Aug. 9, 2017.
Harada H, et al., "Selective expansion of human natural killer cells from peripheral blood mononuclear cells by the cell line, HFWT", Jpn J Cancer Res. Mar. 2002; 93(3):313-319.
Harada H, et al.; "A Wilms tumor cell line, HFWT, can greatly stimulate proliferation of CD56+ human natural killer cells and their novel precursors in blood mononuclear cells", Exp Hematol. Jul. 2004; 32(7):614-621.
Harding et al., "CD28-mediated signalling co-stimulates murine T cells and prevents induction of anergy in T-cell clones," Nature, 356(6370):607-609, Apr. 16, 1992.
Harmon et al., "Dexamethasone induces irreversible Gl arrest and death of a human lymphoid cell line," J Cell Physiol, Feb. 1979, 98(2): 267-78.
Haynes NM, et al., "Rejection of syngeneic colon carcinoma by CTLs expressing single-chain antibody receptors codelivering CD28 costimulation", J Immunol., Nov. 15, 2002; 169(10):5780-5786.
Haynes NM, et al., "Single-chain antigen recognition receptors that costimulate potent rejection of established experimental tumors", Blood, Nov. 1, 2002; 100(9):3155-3163.
Haynes, N.M., et al., "Redirecting Mouse CTL Against Colon Carcinoma: Superior Signaling Efficacy of Single-Chain Variable Domain Chimeras Containing TCR-ζ vs FcεRI-γ," J. Immunol. 166: 182-187 (2001).
Heuser, C., et al., "T-cell activation by recombinant immunoreceptors: Impact of the intracellular signalling domain on the stability of receptor expression and antigen-specific activation of grafted T cells," Gene Therapy 10: 1408-1419 (2003).
Hollyman, D., et al., "Manufacturing Validation of Biologically Functional T Cells Targeted to CD19 Antigen for Autologous Adoptive T cell Therapy," J. Immunother. 32: 169-180 (2009).
Hombach, et al., "Tumor-specific T cell activation by recombinant immunoreceptors: CD3 zeta signaling and CD28 costimulation are simultaneously required for efficient IL-2 secretion and can be integrated into one combined CD28/CD3 zeta signaling receptor molecule", J Immunol., Dec. 1, 2001; 167(11 ):6123-6131.
Hombach et al., "T-Cell Activation by Recombinant Receptors: CD28 Costimulation Is Required for Interleukin 2 Secretion and

(56) References Cited

OTHER PUBLICATIONS

Receptor-mediated T-Cell Proliferation but Does Not Affect Receptor-mediated Target Cell Lysis," Cancer Res., 2001, 61:1976-1982.
Hombach et al., "The recombinant T cell receptor strategy: insights into structure and function of recombinant immunoreceptors on the way towards an optimal receptor design for cellular irnrnunotherapy," Curr Gene Ther. 2002 2(2):211-226.
Hombach, A., et al., "Adoptive immunotherapy with genetically engineered T cells: modification of the IgG1 Fc 'spacer' domain in the extracellular moiety of chimeric antigen receptors avoids 'off-target' activation and unintended initiation of an innate immune response," Gene Therapy 17: 1206-1213 (2010).
Hombach, A., et al., "T cell activation by recombinant FcεRI γ-chain immune receptors: an extracellular spacer domain impairs antigendependent T cell activation but not antigen recognition," Gene Therapy 7: 1067-1075 (2000).
Horng et al., "NKG2D signaling is coupled to the interleukin 15 receptor signaling pathway," Nature Immunology, vol. 8, No. 12, pp. 1345-1352, Dec. 2007.
Hsu, C. et al., "Cytokine-independent growth and clonal expansion of a primary human CD8+ T-cell clone following retroviral transduction with the IL-15 gene," *Blood*, 109(12): 5168-5177 (2007).
Hsu, K.C. et al., "Improved outcome in HLA-identical sibling hematopoietic stem-cell transplantation for acute myelogenous leukemia predicted by KIR and HLA genotypes," Blood, 105(12): 4878-4884 (2005).
Hurtado et al., "Potential role of 4-1BB in T cell activation. Comparison with the costimulatory molecule CD28," J Immunol, Oct. 1995, 155(7): 3360-3367.
Imai C, et al., "Chimeric receptors with 4-1BB signaling capacity provoke potent cytotoxicity against acute lymphoblastic leukemia", Leukemia., Feb. 12, 2004; 18(4):676-684.
Imai C, et al., "T-cell immunotherapy for B-lineage acute lymphoblastic leukemia using chimeric antigen receptors that deliver 4-1 BB-mediated costimulatory signals", Blood. Nov. 16, 2003; 102(11):66a-67a. (Abstract #223).
Imai C et al. "Genetic modification of primary natural killer cells overcomes inhibitory signals and induces specific killing of leukemic cells," Blood. 2005; 106:376-383.
Imai et al. "Genetic Modification of T cells for cancer therapy," Journal of Biological Regulators and Homeostatic Agents, 18 (1): p. 62-71; Jan. 2004.
Imai, C., ct al; "A novel method for propagating primary natural killer (NK) cells allows highly Efficient expression of anti-CD19 chimeric receptors and generation of powerful cytotoxicity Against NK-resistent acute lymphoblastic leukemia cells." Abstract# 306 Blood 104 (Nov. 16, 2004).
Imamura, M et al., "Autonomous growth and increased cytotoxicity of natural killer cells expressing membrane-bound interleukin-15," *Blood*, 124(7): 1081-1088 (Jul. 8, 2014).
Inaguma et al., "Expression of neural cell adhesion molecule Li (CD171) in neuroectodermal and other tumors. An immunohistochemical study of 5155 tumors and critical evaluation of CD171 prognostic value in gastrointestinal stromal tumors," Oncotarge., 7(34):55276-55289, Jul. 11, 2016.
Ishii, H. et al., "Monocytes enhance cell proliferation and LMP1 expression of nasal natural killer/T-cell lymphoma cells by cell contact-dependent interaction through membrane-bound IL-15," International Journal of Cancer, 130: 48-58 (2012).
Ishiwata I, et al., "Carcinoembryonic proteins produced by Wilms' tumor cells in vitro and in vivo", Exp Pathol. 1991; 41(1):1-9.
Israeli, R.S., et al., "Expression of the Prostate-specific Membrane Antigen," Cancer Res., 1994, 54:1807-1811.
Ito et al., "Hyperdiploid acute lymphoblastic leukemia with 51 to 65 chromosomes: a distinct biological entity with a marked propensity to undergo apoptosis," Blood, Jan. 1999, 93(1): 315-20.
Jena et al., "Redirecting T-cell specificity by introducing a tumor-specific chimeric antigen receptor," Blood, 2010, 116(7):1035-1044.
Jenkins et al., "Inhibition of antigen-specific proliferation of type 1 murine T cell clones after stimulation with immobilized anti-CD3 monoclonal antibody," J Immunol., 144(1):16-22, Jan. 1, 1990.
Jensen, M., et al., "CD20 is a molecular target for scFvFc:ζ receptor redirected T cells: implications for cellular immunotherapy of CD20+ malignancy," Biol. Blood and Marrow Transplantation 4: 75- 83 (1998).
Jensen, M.C., et al., "Anti-transgene Rejection Responses Contribute to Attenuated Persistence of Adoptively Transferred CD20/CD19- Specific Chimeric Antigen Receptor Redirected T Cells in Humans," Biol. Blood Marrow Transplant 16: 1245-1256 (2010).
Jiang et al., "Functional characterization of interleukin-15 gene transduction into the human natural killer cell line N Kl," Cytother. 10(3):265-274, 2008.
Jiang, W. et al., "hIL-15 gene-modified human natural killer cells (NKL-IL15) augments the anti- human hepatocellular carcinoma effect in vivo," Immunobiology, 219: 547-553 (Mar. 12, 2014).
Johnson and Jenkins, "The role of anergy in peripheral T cell unresponsiveness," Life Sci, 1994, 55(23): 1767-1780.
June et al., "The B7 and CD28 receptor families," Immunol Today, Jul. 1994, 15(7): 321-31.
Kabalak et al., "Association of an NKG2D gene variant with systemic lupus erythematosus in two populations," Human Immunology, vol. 71, pp. 74-78, 2010.
Kalos et al., "T Cells with Chimeric Antigen Receptors Have Potent Antitumor Effects and Can Establish Memory in Patients with Advanced Leukemia," Sci Transl Med. Aug. 10, 2011;3(95):95ra73.
Kariv, I., et al., "Analysis of the Site of Interaction of CD28 with Its Counter-Receptors CD80 and CD86 and Correlation with Function," J. of Immunol. 157: 29-38 (1996).
Kershaw, M.H., et al., "A Phase I Study on Adoptive Immunotherapy Using Gene-Modified T Cells for Ovarian Cancer," Clin. Cancer Res. 12:6106-6115 (2006).
Khammari, A., et al., "Long-term follow-up of patients treated by adoptive transfer of melanoma tumor-infiltrating lymphocytes as adjuvant therapy for stage III melanoma," Cancer Immunol. Immunother. 56: 1853-1860 (2007).
Kim Y J, et al., "Human 4-1 BB regulates CD28 co-stimulation to promote Th1 cell responses. Eur J. Immunol", Mar. 1998; 28(3):881-890.
Kim Y J, et al., "Novel T cell antigen 4-1 BB associates with the protein tyrosine kinase p56lck1", J Immunol. Aug. 1, 1993; 151(3):1255-1262.
Kitaya, K. et al., "IL-15 expression at human endometrium and decidua," Biology of Reproduction, 63(3): 683-687 (2000).
Kitaya, K., et al., "Regulatory role of membrane-bound form interleukin-15 on human uterine microvascular endothelial cells in circulating CD16(-) natural killer cell extravasation into human endometrium," Biology of Reproduction, 89(3): 70 (2013).
Klein E, et al., "Properties of the K562 cell line, derived from a patient with chronic myeloid leukemia", Int J Cancer. Oct. 15, 1976; 18(4 ):421-431.
Klingemann HG, et al., "Ex vivo expansion of natural killer cells for clinical applications", Cytotherapy. 2004; 6(1 ):15-22.
Kobayashi et al., "Role of trans-cellular IL-15 presentation in the activation of NK cell-mediated killing, which leads to enhanced tumor immunosurveillance," Blood, Jan. 2005, 105(2): 721-727.
Kochenderfer, J.N. et al. "Construction and Pre-clinical Evaluation of an Anti-CD19 Chimeric Antigen Receptor," J. Immunother. 32(7):689-702 (2009).
Kochenderfer, J.N., et al. "Chemotherapy-Refractory Diffuse Large B-Cell Lymphoma and Indolent B-Cell Malignancies Can be Effectively Treated With Autologous T Cells Expressing an Anti-CD19 Chimeric Antigen Receptor," J. Clin. Oncol. 33:540-549 (2014).
Kochenderfer, J.N., et al. "Donor-derived CD19-targeted T cells cause regression of malignancy persisting after allogeneic hematopoietic stem cell transplantation," Blood 122(25): 4129-4139 (2013).
Kochenderfer, J.N., et al., "B-cell depletion and remissions of malignancy along with cytokine-associated toxicity in a clinical trial of anti-CD19 chimeric-antigen-receptor-transduced T cells," Blood 119(12):2709-2720 (2012).

(56) References Cited

OTHER PUBLICATIONS

Kochenderfer, J.N., et al., "Eradication of B-lineage cells and regression of lymphoma in a patient treated with autologous T cells genetically-engineered to recognize CD19," Blood 116(20):4099-4102 (2010).
Koeffler and Golde, "Acute myelogenous leukemia: a human cell line responsive to colony-stimulating activity," Science, Jun. 1978, 200(4337): 1153-1154.
Koehler et al. "Engineered T Cells for the Adoptive Therapy of B-Cell Chronic Lymphocytic Leukaemia," Advances in Hematology, vol. 2012, Article ID 595060, 13 pages; doi:10.1155/2012/595060 (2012).
Kohn et al., "CARs on track in the clinic," Mol Ther. Mar. 2011; 19(3):432-438.
Koka, R. et al., "Cutting edge: murine dendritic cells require IL-15R alpha to prime NK cells," *J Immunol.*, 173(6): 3594-3598 (2004).
Kolb HJ, et al., "Graft-Versus-Leukemia Effect of Donor Lymphocyte Transfusions in Marrow Grafted Patients," Blood, 1995, 86(5):2041-2050.
Kowolik, C.M., "CD28 Costimulation Provided through a CD19-Specific Chimeric Antigen Receptor Enhances In vivo Persistence and Antitumor Efficacy of Adoptively Transferred T Cells," Cancer Research 66(22): 10995-11004 (2006).
Krampera et al., "Bone marrow mesenchymal stem cells inhibit the respnose of naïve and memory antigen-specific T cells to their cognate peptide," Blood, May 2003, 101(9): 3722-9.
Krause et al., "Antigen-dependent CD28 Signaling Selectively Enhances Survival and Proliferation in Genetically Modified Activated Human Primary T Lymphocytes," J. Exp. Med., 1998, 188(4):619-626.
Krug, C., et al., "Stability and activity of MCSP-specific chimeric antigen receptors (CARs) depend on the scFv antigen-binding domain and the protein backbone," Cancer Immunol. Immunother. 64:1623- 1635 (2015).
Kuo et al., "Efficient gene transfer into primary murine lymphocytes obviating the need for drug selection," Blood, Aug. 1993, 82(3): 845-52.
Kurokawa, M. and S. Kornbluth, "Caspases and kinases in a death grip," *Cell, 138(5)*: 838-854 (2009).
Kwon BS, et al., "cDNA sequences of two inducible T-cell genes", Proc Natl Acad Sci U SA. Mar. 1989; 86(6):1963-1967.
Lafrenicrc, R. and Rosenberg, S.A., "Successful Immunotherapy of Murinc Experimental Hepatic Metastases with Lymphokine-activated Killer Cells and Recombinant Interleukin 2," Cancer Res. 45: 3735-3741 (1985).
Lamers, C.H.J., et al., "Treatment of Metastatic Renal Cell Carcinoma With Autologous T-Lymphocytes Genetically Retargeted Against Carbonic Anhydrase IX: First Clinical Experience," J. Clin. Oncol. 24: e20-e22 (2006).
Lang et al., "Absence of B7.1-CD28/CTLA-4-mediated co-stimulation in human NK cells," Eur. J. Immunol, Mar. 1998, 28: 780-786.
Langer et al., "Comparative Evaluation of Peripheral Blood T Cells and Resultant Engineered Anti- CD19 CAR T-Cell Products From Patients With Relapsed/Refractory Non-Hodgkin Lymphoma (NHL)," Abstract 2305, Proceedings: AACR 107th Annual Meeting 2016; Apr. 16-20, 2016, New Orleans, Louisiana.
Lanzavecchia et al., "Antigen decoding by T lymphocytes: from synapses to fate determination," Nat Immunol., 2(6):487-492, Jun. 2001.
Lapteva, N. et al., "Large-scale ex vivo expansion and characterization of natural killer cells for clinical applications," *Cytotherapy, 14(9)*: 1131-1143 (2012).
Le Blanc et al., "Mesenchymal stem cells inhibit and stimulate mixed lymphocyte cultures and mitogenic responses independently of the major histocompatability complex," Scand J Immunol, Jan. 2003, 57(1): 11-20.
Lee, D.W., et al., "T cells expressing CD19 chimeric antigen receptors for acute lymphoblastic leukaemia in children and young adults: a phase 1 dose-escalation trial," Lancet 385:517-528 (2015).
Lehner et al., "Redirecting T Cells to Ewing's Sarcoma Family of Tumors by a Chimeric NKG2D Receptor Expressed by Lentiviral Transduction of MRNA Transfection," PLoS One, vol. 7, Issue 2, Feb. 2012.
Leung, W. et al., "Determinants of antileukemia effects of allogeneic NK cells," J Immunol., 172(1): 644-650 (2004).
Li et al., "Costimulation by CD48 and B7-1 induces immunity against poorly immunogenic tumors," J Exp Med, Feb. 1996, 183(2): 639-44.
Li et al., "Polarization Effects of 4-1BB during CD28 Costimulation in Generating Tumor-reactive T Cells for Cancer Immunotherapy," Cancer Research vol. 63, pp. 2546-2552, May 15, 2003.
Liao, W. et al., "Interleukin-2 at the crossroads of effector responses, tolerance, and immunotherapy," Immunity, 38(1): 13-25 (2013).
Liebowitz et al., "Costimulatory approaches to adoptive immunotherapy," Curr Opin Oncol, Nov. 1998, 10(6): 533-41.
Linsley and Ledbetter, "The role of CD28 receptor during T cell responses to antigen," Annu Rev Immunol, 1993, 191-212.
Liu, H., et al., "Monoclonal Antibodies to the Extracellular Domain of Prostate-specific Membrane Antigen Also React with Tumor Vascular Endothelium," Cancer Res. 57: 3629-3634 (1997).
Liu, L, et al. "Novel CD4-Based Bispecific Chimeric Antigen Receptor Designed for Enhanced Anti-HIV Potency and Absence of HIV Entry Receptor Activity," J. Virol. 89(13):6685-6694 (2015).
Lozzio et al., "Properties and Usefulness of the Original K-562 Human Myelogenous Leukemia Cell Line," Leukemia Research, vol. 3, No. 6, pp. 363-370, 1979.
Lode et al., "Targeted cytokines for cancer immunotherapy," Immunol Res., 21(2-3):279-288, 2000.
López-Requena et al., "Gangliosides, Ab1 and Ab2 antibodies III. The idiotype of anti-ganglioside mAb P3 is immunogenic in a T cell-dependent manner," Mol Immunol., 2007, 44(11):2915-2922.
López-Requena et al., "Gangliosides, Ab1 and Ab2 antibodies IV. Dominance of VH domain in the induction of anti-idiotypic antibodies by Jene gun immunization," Mol Immunol. Apr. 2007;44(11):3070-3075. Epub Mar. 2, 2007.
Lozzio CB, et al., "Human chronic myelogenous leukemia cell-line with positive Philadelphia chromosome", Blood. Mar. 1975; 45(3):321-334.
Lugli, E. et al., "Transient and persistent effects of IL-15 on lymphocyte homeostasis in nonhuman primates," Blood, 116(17): 3238-3248 (2010).
Ma et al., "Chapter 15: Genetically engineered T cells as adoptive immunotherapy of cancer," Cancer Chemotherapy and Biological Response Modifiers Annual 20, Ch. 15, pp. 315-341, Giaccone et al. (Eds.), Elsevier, 2002.
Maher J., et al., "Human T-lymphocyte cytotoxicity and proliferation directed by a single chimeric TCRzeta /CD28 receptor", Nat Biotechnol. Jan. 2002; 20(1):70-75.
Maloney, D.G., "Newer Treatments for Non-Hodgkin's Lymphoma: Monoclonal Antibodies," Oncology 12(10): 63-76 (1998).
Manabe et al., "Interleukin-4 induces programmed cell death (apoptosis) in cases of high-risk acute lymphoblastic leukemia," Blood, Apr. 1994, 83(7): 1731-7.
Mann et al., "Construction of a retrovirus packaging mutant and its use to produce helper-free defective retrovirus," Cell, May 1983, 33(1): 153-159.
Manzke et al., "Immunotherapeutic strategies in neuroblastoma: antitumoral activity of deglycosylated Ricin A conjugated anti-GD2 antibodies and anti-CD3xanti-GD2 bispecific antibodies," Med Pediatr Oncol., 36(1):185-189, Jan. 2001.
Manzke et al., "Locoregional treatment of low-grade B-cell lymphoma with CD3xCD19 bispecific antibodies and CD28 costimulation. I. Clinical phase I evaluation," Int J Cancer., 91(4):508-515, Feb. 15, 2001.
Manzke et al., "Locoregional treatment of low-grade B-cell lymphoma with CD3xCD19 bispecific antibodies and CD28 costimulation. II. Assessment of cellular immune responses," Int J Cancer., 91(4):516-522, Feb. 15, 2001.
Marincola, F.M., et al., "Escape of Human Solid Tumors from T-Cell Recognition: Molecular Mechanisms and Functional Significance," Adv. Immunol. 74: 181-273 (2000).

(56) References Cited

OTHER PUBLICATIONS

Markowitz et al., "A safe packaging line for gene transfer: separating viral genes on two different plasmids," J Virol, Apr. 1988, 62(4): 1120-4.
Marktel et al., "Immunologic potential of donor lymphocytes expressing a suicide gene for early immune reconstitution after hematopoietic T-cell-depleted stem cell transplantation," Blood, Feb. 2003, 101(4): 1290-8.
Martinet O., et al., "T cell activation with systemic agonistic antibody versus local 4-1 BB ligand gene delivery combined with interleukin-12 eradicate liver metastases of breast cancer," Gene Ther. Jun. 2002; 9(12):786-792.
Martinez, E., et al., "Cutting Edge: NKG2D-Dependent Cytotoxicity Is Controlled by Ligand Distribution in the Target Cell Membrane", The Journal of Immunology, 2011, 186:5538-5542.
Maude et al., "Chimeric antigen receptor T cells for sustained remissions in leukemia," N Engl J Med., 371(16):1507-1517, Oct. 16, 2014.
Maus MV, et al., "Ex vivo expansion of polyclonal and antigen-specific cytotoxic T lymphocytes by artificial APCs expressing ligands for the T-cell receptor, CD28 and 4-1BB", Nat Biotechnol. Feb. 2002; 20(2): 143-148.
May KF, JR, et al., "Anti-4-1 BB monoclonal antibody enhances rejection of large tumor burden by promoting survival but not clonal expansion of tumor-specific CDS+ T cells," Cancer Res. 2002, 62(12):3459-3465.
McLaughlin et al., "Adoptive T-cell therapies for refractory/relapsed leukemia and lymphoma: current strategies and recent advances," Ther Adv Hematol., 6(6):295-307, Dec. 2015.
Melero, I. et al., "Monoclonal antibodies against the 4-1BB T-cell activation molecule eradicate established tumors," Nature Med., 1997, 3:682-685.
Melero I, et al., "Amplification of tumor immunity by gene transfer of the co-stimulatory 4-1 BB ligand: synergy with the CD2S co-stimulatory pathway," Eur J Immunol., 1998, 28(3):1116-1121.
Melero I, et al., "NK1.1 cells express 4-1BB (CDw137) costimulatory molecule and are required for tumor immunity elicited by anti-4-1 BB monoclonal antibodies," Cell Immunol., 1998, 190(2): 167-172.
Mihara et al., "Development and functional characterization of human bone marrow mesenchymal cells immortalized by enforced expression of telomerase," Br J Haematol, Mar. 2003, 120(5): 846-9.
Miller et al., "Role of monocytes in the expansion of human activated natural killer cells, " Blood, Nov. 1992, 80(9): 2221-9.
Miller et al., "Successful adoptive transfer and in vivo expansion of human haploidentical NK cells in patients with cancer," Blood, Apr. 2005, 105(8): 3051-7.
Miller, J.S., "Therapeutic applications: natural killer cells in the clinic," *Hematology Am Soc Hematol Educ Program* 2013: 247-253 (2013).
Milone MC, et al., "Chimeric receptors containing CD137 signal transduction domains mediate enhanced survival of T cells and increased anti leukemic efficacy in vivo", Mol Ther. Apr. 21, 2009; 17(8):1453-1464.
Mishra, A. et al., "Aberrant overexpression of IL-15 initiates large granular lymphocyte leukemia through chromosomal instability and DNA hypermethylation," *Cancer Cell, 22(5)*: 645-655 (2012).
Mogi et al., "Tumour rejection by gene transfer of 4-1BB ligand and into a CD80(+) murine squamous cell carcinoma and the requirements of co-stimulatory molecules on tumour and host cells," Immunology, Dec. 2000, 101(4): 541-7.
Mondino and Jenkins, "Surface proteins involved in T cell costimulation," J Leukoc Biol, Jun. 1994, 55(6): 805-15.
Mora, "Dinutuximab for the treatment of pediatric patients with high-risk neuroblastoma," Expert Rev Clin Pharmacol., 9(5):647-653, Epub Mar. 21, 2016.
Morandi, B. et al., "NK cells provide helper signal for CD8+ T cells by inducing the expression of membrane-bound IL-15 on DCs," International Immunology, 21(5): 599-606 (2009).
Moretta L, et al., "Unravelling natural killer cell function: triggering and inhibitory human NK receptors," EMBO J., 2004, 23(2):255-259.
MORITZ and Groner, "A spacer region between the single chain antibody- and the CD3 ζ-chain domain of chimeric T cell receptor components is required for efficient ligand binding and signaling activity," Gene Ther. Oct. 1995; 2(8):539-546.
Moritz, D., et al., "Cytotoxic T lymphocytes with a grafted recognition specificity for ERBB2-expressing tumor cells," Proc. Natl. Acad. Sci. USA 91:4318-4322 (1994).
Mortier, E., et al., "IL-15Ralpha chaperones IL-15 to stable dendritic cell membrane complexes that activate NK cells via trans presentation," *The Journal of Experimental Medicine, 205(5)*:1213-1225 (2008).
Musso, T. et al., "Human monocytes constitutively express membranc-bound, biologically active, and interferon-gamma-upregulated interleukin-15," *Blood, 93(10)*: 3531-3539 (1999).
Nadler et al., "B4, a human B lymphocyte-associated antigen expressed on normal, mitogen-activated, and malignant B lymphocytes," J Immunol, Jul. 1983, 131(1): 244-50.
Nagashima et al., "Stable transduction of the interleukin-2 gene into human natural killer cell lines and their phenotypic and functional characterization in vitro and in vivo," Blood, May 1998, 91(10): 3850-61.
Nakamura et al., "Chimeric anti-ganglioside GM2 antibody with antitumor activity," Cancer Res. Mar. 15, 1994; 54(6):1511-6.
Naume et al., "A comparative study of IL-12 (cytotoxic lymphocyte maturation factor)-, IL-2-, and IL-7-induced effects on immunomagnetically purified CD56+ NK cells," J Immunol, Apr. 1992, 148(8): 2429-36.
Neepalu et al., "Phase 1 Biomarker Analysis of the ZUMA-1 Study: A Phase 1-2 Multi-Center Study Evaluating the Safety and Efficacy of Anti-CD19 CAR T Cells (KTE-C19) in Subjects with Refractory Aggressive Non-Hodgkin Lymphoma," Poster session presented at the American Scoiety of Hematology Annual Meeting, Orlando, Florida (Dec. 5-8, 2015).
Negrini, S. et al., "Membrane-bound IL-15 stimulation of peripheral blood natural killer progenitors leads to the generation of an adherent subset co-expressing dendritic cells and natural killer functional markers," *Haematologica, 96(5)*: 762-766 (2011).
Nicholson et al., "Construction and characterisation of a functional CD19 specific single chain Fv fragment for immunotherapy of B lineage leukaemia and lymphoma," Mol Immunol., 34(16-17):1157-1165, Nov.-Dec., 1997.
Nishigaki et al., "Prevalence and growth characteristics of malignant stem cells in B-lineage acute lymphoblastic leukemia," Blood, May 1997, 89(10): 3735-44.
Nunès et al., "The role of p21ras in CD28 signal transduction: triggering of CD28 with antibodies, but not the ligand B7-1, activates p21ras," J Exp Med., 180(3):1067-1076, Sep. 1, 1994.
Oelke, M. et al., "Ex vivo induction and expansion of antigen-specific cytotoxic T cells by HLA-Ig-coated artificial antigen-presenting cells," Nat Med., 2003, 9(5):619-624.
Olsen, S.K. et al., "Crystal structure of the interleukin-15 interleukin-15 receptor a complex Insights into trans and cis presentation," The Journal of Biological Chemistry, 282(51): 37191-37204 (2007).
Ozkaynak, M.F. et al., "Phase I Study of Chimeric Human/Murine Anti-Ganglioside GD2 Monoclonal Antibody (ch14.18) With Granulocyte-Macrophage Colony-Stimulating Factor in Children With Nueroblastoma Immediately After Hematopoietic Stem-Cell Transplantation: A Children's Cancer Group Study," J. Clinical Oncol. 18: 4077-4085 (2000).
Pan et al., "Regulation of dendritic cell function by NK cells: mechanisms underlying the synergism in the combination therapy of IL-12 and 4-1BB activation," J Immunol, Apr. 2004, 172(8): 4779-4789.
Park, J.H., and Brentjens, R.J., "Are All Chimeric Antigen Receptors Created Equal?" J. Clin. Oncol. 33: 651-653 (2015).
Park, J.H., et al., "CD19-Targeted 19-28z CAR Modified Autologous T Cells Induce High Rates of Complete Remission and Durable Responses in Adult Patients with Relapsed, Refractory B-Cell ALL," Abstract presented at the American Society of Hematology

(56) References Cited

OTHER PUBLICATIONS

Annual Meeting, San Francisco, California, available at https://ash.confex.com/ash/2014/webprogram/Paper76573.html (Dec. 6-9, 2014).
Park, J.H., et al., Abstract, "682 Implications of Minimal Residual Disease Negative Complete Remission (MRD-CR) and Allogeneic Stem Cell Transplant on Safety and Clinical Outcome of CD19-Targeted 19-28z CAR Modified T cells in Adult Patients with Relapsed, Refractory B-Cell ALL," Am. Soc'y Hematol., available at https://ash.confex.com/ash/2015/webprogram/Paper86688.html (Dec. 5-8, 2015).
Park, Y.P., et al., "Complex Regulation of Human NKG2D-DAP10 Cell Surface Expression: Opposing Roles of the γc Cytokines and TGF-α1", Blood, Sep. 15, 2011, vol. 118, No. 11, pp. 3019-3027.
Parkhurst, M.R. et al., "Adoptive transfer of autologous natural killer cells leads to high levels of circulating natural killer cells but does not mediate tumor regression," Clin Cancer Res., 17(19): 6287-97 (2011).
Patel, S.D., et al., "Impact of chimeric immune receptor extracellular protein domains on T cell function," Gene Therapy 6: 412-419 (1999).
Paul, W.E., Fundamental Immunology, Third Edition, Chs. 1, 13 and 32 (pp. 1-20, 467-504, and 1143-1178), Raven Press, New York (1993).
Peach, R.J., et al., "Complementarity Determining Region 1 (CDR1)- and CDR3-analogous Regions in CTLA-4 and CD28 Determine the Binding to B7-1," J. Exp. Med. 180: 2049-2058 (1994).
Perussia et al., "Preferential proliferation of natural killer cells among peripheral blood mononuclear cells cocultured with B lymphoblastoid cell lines," Nat Immun Cell Growth Regul, 1987, 6(4): 171-88.
Pollok et al., "Regulation of 4-1BB expression by cell-cell interactions and the cytokines, interleukin-2 and interleukin-4," Eur J Immunol, Feb. 1995, 25(2): 488-94.
Pollok Ke, et al., "Inducible T cell antigen 4-1 BB Analysis of expression and function," J Immunol., 1993, 150(3):771-781.
Porter and Antin, "The graft-versus-leukemia of allogeneic cell therapy," Annu Rev Med, 1999, 50: 369-86.
Porter DL ct al., "Chimcric Antigen Receptor-Modified T Cells in Chronic Lymphoid Leukemia", N. Eng. J. Med. Aug. 25, 2011; 365(8):725-733.
Porter et al., "Induction of graft-versus-host disease as immunotherapy for relapsed chronic mycloid leukemia," N Engl J Med, Jan. 1994, 330(2): 100-6.
Pui et al., "Childhood acute lymphoblastic leukaemia—current status and future perspectives," Lancet Oncol, Oct. 2001, 2(10): 597-607.
Pule et al. "Virus-specific T cells engineered to coexpress tumor-specific receptors: persistence and antitumor activity in individuals with neuroblastoma," Nature Med., 2008, 14(11):1264-1270.
Qian, L et al., "Construction of a plasmid for co-expression of mouse membrane-bound form of IL-15 and RAE-18 and its biological activity," *Plasmid, 65(3)*: 239-245 (2011).
Rajagopalan et al., Found: a cellular activating ligand for N Kp44, Blood, 122(17):2921-2922, Oct. 2013.
Ramos, C.A., et al., "CD19-CAR Trials," The Cancer J. 20: 112-118 (2014).
Ramos and Dotti, "Chimeric antigen receptor (CAR)-engineered lymphocytes for cancer therapy," Expert Opin Biol Ther., 2011, 11(7):855-873.
Riddell, S.R., et al., "T-Cell Therapy of Leukemia," Cancer Control 9: 114-122 (2002).
Riley et al., "The CD28 family: a T-cell rheostat for therapeutic control of T-cell activation," Blood, 2005, 105:13-21.
Roberts et al., "Antigen-specific cytolysis by neutrophils and NK cells expressing chimeric immune receptors bearing zeta or gamma signaling domains," J Immunol, Jul. 1998, 161(1): 375-84.
Robertson MJ, et al.; "Costimulation of human natural killer cell proliferation: role of accessory cytokines and cell contact-dependent signals", Nat Immun. 1996-1997; 15(5):213-226.

Rooney et al., "Use of gene-modified virus-specific T lymphocytes to control Epstein-Barr-virus-related lymphoproliferation," Lancet, Jan. 1995, 345(8941): 9-13.
Rosenberg et al., "Special Report: Use of tumor-infiltrating lymphocytes and interleukin-2 in the immunotherapy of patients with metastatic melanoma," N. Engl. J. Med., 1988, 319:1676-1680.
Rosenberg, S.A., and Dudley, M.E., "Adoptive cell therapy for the treatment of patients with metastatic melanoma," Curr. Opin. Immunol. 21: 233-240 (2009).
Rosenfeld et al., "Phenotypic characterization of a unique non-T, non-B acute lymphoblastic leukaemia cell line," Nature, Jun. 1977, 267(5614): 843-3.
Rosenstein, M. et al., "Extravasation of intravascular fluid mediated by the systemic administration of recombinant interleukin 2," *J Immunol, 137(5)*: 1735-1742 (1986).
Ross et al., "Classification of pediatric acute lymphoblastic leukemia by gene expression profiling," Blood, Oct. 2003, 102(8): 2951-9.
Rossi, J.M., et al., "Phase 1 Biomarker Analysis of ZUMA-1 (KTEC19-101) Study: A Phase 1-2 Multi-Center Study Evaluating the Safety and Efficacy of Anti-CD19 CAR T cells (KTE-C19) in Subjects with Refractory Aggressive Non-Hodgkin Lymphoma (NHL)," Abstracted presented at the American Society of Hematology Annual Meeting, Orlando, Florida, available at https://ash.confex.com/ash/2015/webprogram/Paper80339.html. (Dec. 5-8, 2015).
Rossig C, et al., "Epstein-Barr virus-specific human T lymphocytes expressing antitumor chimeric T-cell receptors: potential for improved immunotherapy," Blood, 2002, 99:2009-2016.
Rossig et al., "Targeting of G(D2)-positive tumor cells by human T lymphocytes engineered to express chimeric T-cell receptor genes," Int J Cancer, Oct. 2001, 94(2): 228-36.
Rowley, J et al., "Expression of IL-15RA or an IL-15/IL-15RA fusion on CD8+ T cells modifies adoptively transferred T-cell function in cis," *European Journal of Immunology, 39*: 491-506 (2009).
Rubnitz, J.E. et al., "NKAML: a pilot study to determine the safety and feasibility of haploidentical natural killer cell transplantation in childhood acute myeloid leukemia," J Clin Oncol, 28(6): 955-959 (2010).
Ruggeri, L. et al., "Effectiveness of donor natural killer cell alloreactivity in mismatched hematopoietic transplants," Science, 295(5562): 2097-2100 (2002).
Sadelain et al., "The promise and potential pitfalls of chimeric antigen receptors," Curr Opin Immunol., 2009, 21(2):215-223.
Sadelain et al., "Targeting tumours with genetically enhanced T lymphocytes," Nat Rev Cancer. Jan. 2003;3(1):35-45.
Sadelain, M., "Car Therapy: the CD19 Paradigm," J. Clin. Investigation 125: 3392-3400 (2015).
Sahm et al., "Expression of IL-15 in N K cells results in rapid enrichment and selective cytotoxicity of gene-modified effectors that carry a tumor-specific antigen receptor," Cancer Immunol. Immunother., 61 (9): 1451-1461, Feb. 2012.
Salih, H.R., et al., "Cutting Edge: Down-Regulation of MICA on Human Tumors by Proteolytic Shedding, The Journal of Immunology", 2002, 169:4098-4102.
Salomon and Bluestone, "Complexities of CD28/B7: CTLA-4 costimulatory pathways in autoimmunity and transplantation," Annu Rev Immunol, 2001, 19: 225-52.
Sambrook et "Molecular Cloning: A Laboratory Manual," (1989) [Table of Contents and Preface Only].
Sankhla, S.K., et al., "Adoptive immunotherapy using lymphokineactivated killer (LAK) cells and interleukin-2 for recurrent malignant primary brain tumors," J Neurooncol. 27: 133-140 (1995).
Savoldo, B., et al., "CD28 costimulation improves expansion and persistence of chimeric antigen receptor modified T cells in lymphoma patients," J. Clin. Invest. 121(5):1822-1826 (2011).
Schmaltz et al., "T cells require TRAIL for optimal graft-versus-tumor activity," Nat Med, Dec. 2002, 8(12): 1433-7.
Schneider et al., "Characterization of EBV-genome negative "null" and "T" cell lines derived from children with acute lymphoblastic leukemia and leukemic transformed non-Hodgkin lymphoma," Int J Cancer, May 1977, 19(5): 621-6.

(56) References Cited

OTHER PUBLICATIONS

Schroers et al., "Gene transfer into human T lymphocytes and natural killer cells by Ad5/F35 chimeric adenoviral vectors," Exp Hematol, Jun. 2004, 32(6): 536-46.
Schulz, G., et al., "Detection of Ganglioside GD2 in Tumor Tissues and Sera of Neuroblastoma Patients," Cancer Research 44: 5914-5920 (1984).
Schumacher, "T-cell-receptor gene therapy," Nat Rev Immunol, Jul. 2002, 2(7): 512-9.
Schwartz et al., "Structural basis for co-stimulation by the human CTLA-4/B7-2 complex," Nature, 410(6828):604-608, Mar. 29, 2001.
Schwarz et al., "ILA, the human 4-1BB homologue, is inducible in lymphoid and other cell lineages," Blood, Feb. 1995, 85(4): 1043-52.
Scott, A.M et al., "Antibody therapy of cancer," *Nat Rev Cancer*, 12(4): 278-287 (2012).
Sentman, C.L., et al., "NK Cell Receptors as Tools in Cancer Immunotherapy", Advances in Cancer Research, 2006, pp. 249-292.
Sentman, C.L., et al., "NKG2D CARs as Cell Therapy for Cancer", The Cancer Journal, vol. 20, No. 2, Mar./Apr. 2014, pp. 156-159.
Sheard, M.A. et al., "Membrane-bound TRAIL supplements natural killer cell cytotoxicity against neuroblastoma cells," Journal of Immunotherapy, 36(5): 319-329 (2013).
Shimasaki, N. et al., "A clinically adaptable method to enhance the cytotoxicity of natural killer cells against B-cell malignancies," Cytotherapy, 14(7): 830-840 (2012).
Shook et al., "Natural Killer Cell Engineering for Cellular Therapy of Cancer," National Institutes of Health, Tissue Antigens, vol. 78, No. 6, pp. 409-415, Dec. 2011.
Shuford WW, et al., "4-1 BB costimulatory signals preferentially induce CDS+ T cell proliferation and lead to the amplification in vivo of cytotoxic T cell responses", J Exp Med. Jul. 7, 1997; 186(1):47-55.
Shum et al., "Conservation and Variation in Human and Common Chimpanzee CD($ and NKG2 Genes," The American Association of Immunologists, The Journal of Immunology, pp. 240-252, Downloaded on Jun. 18, 2017.
Sica G, Chen L. Modulation of the immune response through 4-1BB. In: Habib N, ed. Cancer gene therapy: past achievements and future challenges. New York: Kluwer Academic/Plenum Publishers; 355-362 (2000) [BOOK].
Slavik et al., "CD28/CTLA-4 and CD80/CD86 families: signaling and function," Immunol Res., 19(1):1-24, 1999.
Slavin ct al., "Allogencic cell therapy with donor peripheral blood cells and recombinant human interleukin-2 to treat leukemia relapse after allogeneic bone marrow transplantation," Blood, Mar. 1996, 87(6): 2195-204.
Sneller, M.C. et al., "IL-15 administered by continuous infusion to rhesus macaques induces massive expansion of CD8+ T effector memory population in peripheral blood," Blood, 118(26): 6845-6848 (2011).
Somanchi, S.S. et al., "Expansion, purification, and functional assessment of human peripheral blood NK cells," Journal of Visualized Experiments, 48A: 2540 (2011).
Song et al., "Chimeric NKG2D CAR-Expressing T Cell-Mediated Attack of Human Ovarian Cancer is Enhanced by Histone Deacetylase Inhibition," Human Gene Therapy, vol. 24, pp. 295-305, Mar. 2013.
Spear et al., "Chimeric Antigen Receptor T Cells Shape Myeloid Cell Function within the Tumor Microenvironment through IFN-γ and GM-CSF," The Journal of Immunology, pp. 6389-6399, 2014.
Spear et al., "Collaboration of chimeric antigen receptor (CAR)-expressing T cells and host T cells for optimal elimination of established ovarian tumors," Oncolmmunology, vol. 2, No. 2, 12 pages, Apr. 2013.
Spear et al., "NKG2D CAR T-cell therapy inhibits the growth of NKG2D ligand heterogeneous tumors," Immunology and Cell Biology, vol. 91, pp. 435-440, 2013.

Srinivasan et al., "A retro-inverso peptide mimic of CD28 encompassing the MYPPPY motif adopts a polyproline type II helix and inhibits encephalitogenic T cells in vitro," J Immunol., 167(1):578-585, Jul. 1, 2001.
Srivannaboon et al., "Interleukin-4 variant (BAY 36-1677) selectively induces apoptosis in acute lymphoblastic leukemia cells," Blood, Feb. 2001, 97(3): 752-8.
Stamper et al., "Crystal structure of the B7-1/CTLA-4 complex that inhibits human immune responses," Nature, 410(6828):608-611, Mar. 29, 2001.
Stein, P.H., et al., "The Cytoplasmic Domain of CD28 is both Necessary and Sufficient for Costimulation of Interleukin-2 Secretion and Association with Phosphatidylinositol 3'-Kinase," Mol. Cell. Biol. 14: 3392-3402 (1994).
Stong RC, et al., "Human acute leukemia cell line with the t(4;11) chromosomal rearrangement exhibits B lineage and monocytic characteristics," Blood, 1985,65:21-31.
Sun, J., et al., "Early transduction produces highly functional chimeric antigen receptor-modified virus-specific T-cells with central memory markers: a Production Assistant for Cell Therapy (PACT) translational application," J. Immunother. Cancer (2015).
Sundstrom and Nilsson, "Establishment and characterization of a human histiocytic lymphoma cell line (U-937)," Int J Cancer, May 1976, 17(5): 565-77.
Sussman et al., "Protein Data Bank (PDB): database of three-dimensional structural information of biological macromolecules," Acta Crystallogr D Biol Crystallogr., 54(Pt 6 Pt 1): 1078-1084, Nov. 1, 1998.
Swerdlow, S.H. et al., eds., "WHO Classification of Tumours of Haematopoietic and Lymphoid Tissues," International Agency for Research on Cancer (IARC) (4th ed. 2008) (Excerpts).
Tacke et al., "CD28-mediated induction of proliferation in resting T cells in vitro and in vivo without engagement of the T cell receptor: evidence for functionally distinct forms of CD28," Eur J Immunol., 27(1):239-247, Jan. 1997.
Tagaya, Y. et al., "IL-15: a pleiotropic cytokine with diverse receptor/signaling pathways whose expression is controlled at multiple levels," Immunity, 4(4): 329-336 (1996).
Takahashi C, et al., "Cutting edge: 4-1 BB is a bona fide CDS T cell survival signal", J Immunol. May 1, 1999; 162(9):5037-5040.
Thomas et al., "Monoclonal antibody therapy with rituximab for acute lymphoblastic leukemia," Hematol Oncol Clin North Am., 23(5):949-971, Oct. 2009.
Topp, M.S., et al., "Universal chimeric immunoreceptors for targeting B-cell malignancies with engineered CTL: combining CD19-specific TCR zeta signaling with engineered CD28-mediated co-stimulation," Mol. Ther. 3(5)(part 2 of 2): S21 (2001).
Tsukamoto, K. et al., "Juxtacrine function of interleukin-15/interleukin-15 receptor system in tumour derived human B-cell lines," *Clinical and Experimental Immunology*, 146(3): 559-566 (2006).
Trinchieri et al., "Response of resting human peripheral blood natural killer cells to interleukin 2," J Exp Med, Oct. 1984, 160(4): 1147-69.
Trompeter et al., "Rapid and highly efficient gene transfer into natural killer cells by nucelofection," J Immunol Methods, Mar. 2003, 274(1-2): 245-56.
Turtle, "Therapy of B Cell Malignancies with CD19-Specific Chimeric Antigen Receptor Modified T Cells of Defined Subset Composition," Blood 124(21): 384-384, 2014.
Turtle, C.J., et al., Abstract, " A Phase I/II Clinical Trial of Immunotherapy for CD19+ B Cell Malignancies With Defined Composition of CD4+ and CD8+ Central Memory T Cells Lentivirally Engineered to Express a CD19-Specific Chimeric Antigen Receptor" Mol. Ther., 2014, 22(Supp.1):296.
Upshaw et al., "NKG2D-mediated signaling requires a DAP10-bound Grb2-Vav! intermediate and hosphatidylinositol-3-kinase in human natural killer cells," Nature Immunology, vol. 7, No. 5, pp. 524-532, May 2006.
Verdonck et al., "Donor leukocyte infusions for recurrent hematologic malignancies after allogeneic bone marrow transplantation: impact of infused and residual donor T cells," Bone Marrow Transplant, Dec. 1998, 22(11): 1057-63.

(56) References Cited

OTHER PUBLICATIONS

Verma and Stock, "Management of adult acute lymphoblastic leukemia: moving toward a risk-adapted approach," Curr Opin Oncol, Jan. 2001, 13(1): 14-20.
Vinay, DS et al., "Role of 4-1 BB in immune responses", Seminars in Immunol. Dec. 1998; 10(6):481- 489.
Viola, "The amplification of TCR signaling by dynamic membrane microdomains," Trends Immunol., 22(6):322-327, Jun. 2001.
Vivier, E. et al., "Innate or adaptive immunity? The example of natural killer cells," Science, 331(6013): 44-49 (2011).
Voss et al., "Targeting p53, hdm2, and CD 19: vaccination and immunologic strategies," Bone Marrow Transplant., 25 Suppl 2:S43-S45, May 2000.
Vujanovic, L. et al., "Virally infected and matured human dendritic cells activate natural killer cells via cooperative activity of plasma membrane-bound TNF and IL-15," Blood, 116(4): 575-583 (2010).
Waldmann, T.A. et al., "Safety (toxicity), pharmacokinetics, immunogenicity, and impact on elements of the normal immune system of recombinant human IL-15 in rhesus macaques," *Blood, 117(18)*: 4787-4795 (2011).
Walter et al., "Reconstitution of cellular immunity against cytomegalovirus in recipients of allogeneic bone marrow by transfer of T-cell clones from the donor," N Engl J Med, Oct. 1995, 333(16): 1038-44.
Wang, et al., "Phase I Studies of central-memory-derived CD19 Car T cell therapy following autologous HSCT in patients with B-Cell NHL," Blood (forthcoming 2016).
Warrens AN, et al., "Splicing by overlap extension by PCR using asymmetric amplification: an improved technique for the generation of hybrid proteins of immunological interest," Gene 20;186: 29-35 (1997).
Watzl, C., et al., "Signal Transduction During Activation and Inhibition of Natural Killer Cells", Curr Protoc Immunol., Aug. 2010, pp. 1-19.
Weijtens, M.E.M., et al., "Functional balance between T cell chimeric receptor density and tumor associated antigen density: CTL mediated cytolysis and lymphokine production," Gene Ther. 7: 35-42 (2000).
Weissman et al., "Molecular cloning and chromosomal localization of the human T-cell receptor ~ chain: Distinction from the molecular CD3 complex," PNAS USA, 1988, 85:9709-9713.
Westwood, J.A., et al., "Adoptive transfer of T cells modified with a humanized chimeric receptor gene inhibits growth of Lewis-Y expressing tumors in mice," PNAS 102(52): 19051-19056 (2005).
WHO, "WHO Classification of Tumours of Haematopoietic and Lymphoid Tissues," International Agency for Research on Cancer (IARC), 4th Edition, 40 pages, 2008.
Willimsky, G. and Blankenstein, T., "Sporadic immunogenic tumours avoid destruction by inducing T-cell tolerance," Nature 437: 141-146 (2005).
Wittnebel, S. et al., "Membrane-bound interleukin (IL)-15 on renal tumor cells rescues natural killer cells from IL-2 starvation-induced apoptosis," Cancer Research, 67(12): 5594-5599 (2007).
Wu and Lanier, "Natural killer cells and cancer," Adv Cancer Res, 2003, 90: 127-56.
Wu, et al. "An Activating Immunoreceptor Complex Formed by NKG2D and DAP10," Science, vol. 285, pp. 730-732, Jul. 30, 1999.
Wyss-Coray, T., et al., "The B7 adhesion molecule is expressed on activated human T cells: functional involvement in T-T cell interactions," Eur. J. Immunol., 23: 2175-2180 (1993).
Xu, Y., et al., "Closely related T-memory stem cells correlate with in vivo expansion of CAR.CD19- T cells and are preserved by IL-7 and IL-15," Blood 123(24):3750-3759 (2014).
Yan et al., "Murine COB lymphocyte expansion in vitro by artificial antigen-presenting cells expressing CD137L (4-1 BBL) is superior to CD28, and CD137L expressed on neuroblastoma expands COB tumour-reactive effector cells in vivo," Immunology, 2004, 112(1):105-116.
Ye et al., "Gene therapy for cancer using single-chain Fv fragments specific for 4-1BB," Nat Med, Apr. 2002, 8(4): 343-8.

Yeoh et al., "Classification, subtype discovery, and prediction of outcome in pediatric acute lymphoblastic leukemia by gene expression profiling," Cancer Cell, Mar. 2002, 1(2): 133-43.
Yoshida et al., "A novel adenovirus expressing human 4-1BB ligand enhances antitumor immunity," Cancer Immunol Immunother, Feb. 2003, 52(2): 97-106.
Zanoni, I et al., "IL-15 cis presentation is required for optimal NK cell activation in lipopolysaccharide-mediated inflammatory conditions," *Cell Reports, 4*: 1235-1249 (2013).
Zeis, M. et al., "Allogeneic MHC-Mismatched Activated Natural Killer Cells Administered After Bone Marrow Transplantation Provide a Strong Graft-Versus-Leukemia Effect in Mice," BrJ Haematol, 1997, pp. 757-761, vol. 96.
Zhang et al., "Chimeric NKG2D-Modified T Cells Inhibit Systemic T-Cell Lymphoma Growth in a Manner Involving Multiple Cytokines and Cytotoxic Pathways," Cancer Research, vol. 67, No. 22, pp. 11029-11036, Nov. 15, 2007.
Zhang et al., "Chimeric NK-receptor-bearing T cells mediate antitumor immunotherapy," Gene Therapy, Blood, vol. 106, No. 5, pp. 1544-1551, Sep. 2005.
Zhang, J. et al., "Characterization of interleukin-15-gene-modified human natural killer cells: implications for adoptive cellular immunotherapy," Haematologica, 89(3): 338-347 (2004).
Zhang et al., "Generation of Antitumor Responses by Genetic Modification of Primary Human T Cells with a Chimeric NKG2D Receptor," Cancer Rescarch, vol. 66, No. 11, pp. 5927-5933, Jun. 1, 2006.
Zhang et al., "Mouse Tumor Vasculature Expresses NKG2D Ligands and Can Be Targeted by Chimeric NKG2D-Modified T Cells," The Journal of Immunology, pp. 2455-2463, (2013) Downloaded Feb. 20, 2018.
Brand, L.J. et al., "Abstract LB-185: A PSMA-directed natural killer cell approach for prostate cancer immunotherapy," Cancer Research, 77(13 Supplement): Abstract No. LB-185 (Jul. 2017).
Chang et al., "Five Different Anti-Prostate-specific Membrane Antigen (PSMA) Antibodies Confirm PSMA Expression in Tumor-associated Neovasculature," Cancer Res., 59: 3192-3198 (1999).
Grauer et al., "Identification, Purification, and Subcellular Localization of Prostate-specific Membrane Antigen PSM' Protein in the LNCaP Prostatic Carcinoma Cell Line," Cancer Res., 58: 4787-4789 (1998).
Kaiser, B.K et al., "Structural basis for NKG2A/CD94 Recognition of HLA-E," Proc Nat'l Acad Sci USA, 105(18): 6696-6701 (Apr. 2008).
LaBonte, M.L. et al., "Molecular Determinants Regulating the Pairing of NKG2 Molecules with CD94 for Cell Surface Heterodimer Expression," J Immunol, 172(11): 6902-6912 (May 2004).
Sullivan, L.C. et al., "The Heterodimeric Assembly of the CD94-NKG2 Receptor Family and Implications for Human Leukocyte Antigen-E Recognition," Immunity, 27(6): 900-911 (Demember 2007).
Zah, E. et al., "T Cells Expressing CD19/CD20 Bispecific Chimeric Antigen Receptors Prevent Antigen Escape by Malignant B Cells," Cancer Immunol Res, 4(6): 498-508 (Apr. 2016).
International Search Report and Written Opinion mailed Jul. 4, 2018 for International Application No. PCT/SG2018/050138, entitled "Stimulatory Cell Lines for Ex Vivo Expansion and Activation of Natural Killer Cells".
International Preliminary Report on Patentability for International Application No. PCT/SG2018/050138, entitled "Stimulatory Cell Lines for Ex Vivo Expansion and Activation of Natural Killer Cells," Date of Issuance: Oct. 1, 2019.
Ang, S.O. et al., "Avoiding the need for clinical-grade OKT3: ex vivo expansion of T cells using artificial antigen presenting cells genetically modified to crosslink CD3" Biology of Blood and Marrow Transplantation, Jan. 9, 2012, vol. 8, No. 2, pp. S258.
Bridgeman, J.S. et al., "The Optimal Antigen Response of Chimeric Antigen Receptors Harboring the CD3ζ Transmembrane Domain is Dependent upon Incorporation of the Receptor into the Endogenous TCR/CD3 Complex," J Immunol, 184(12): 6938-6949 (May 2010).
De La Chapelle, A. et al., "Truncated erythropoietin receptor causes dominantly inherited benign human erythrocytosis," Proc Natl Acad Sci USA., vol. 90, No. 10, pp. 4495-4499 (May 1993).

(56) References Cited

OTHER PUBLICATIONS

Galustian, C. et al., "MP84-07A Tale of Tails—A Novel Approach to Immunotherapy of Prostate Cancer," J Urol, 195(4S): e1092 (May 2016).
Hoffmann, S.C. et al. "2B4 Engagement Mediates Rapid LFA-1 and Actin-Dependent NK Cell Adhesion to Tumor Cells as Measured by Single Cell Force Spectroscopy," J. Immunol, 186(5): 2757-2764 (Jan. 2011).
Huang Q.S. et al., "Expansion of human natural killer cells ex vivo," Chine J Cell Mol Immunol, Dec. 31, 2008, vol. 24, No. 12, pp. 1167-1170.
International Preliminary Report on Patentability for International Application No. PCT/US2018/024650, titled "Truncated NKG2D Chimeric Receptors and Uses Thereof in Natural Killer Cell Immunotherapy," Date Issued: Oct. 1, 2019.
Li, Q. et al., "Bifacial effects of engineering tumour cell-derived exosomes on human natural killer cells" Experimental Cell Research, Dec. 19, 2017, vol. 363, No. 2, pp. 141-150.
Minamoto, S. et al., "Acquired Erythropoietin Responsiveness of Interleukin-2-dependent T lymphocytes Retrovirally Transduced with Genes Encoding Chimeric Erythropoietin/Interleukin-2 Receptors," Blood, vol. 86, No. 6, pp. 2281-2287 (1995).
Mohammed, S. et al., "Improving Chimeric Antigen Receptor-Modified T Cell Function by Reversing the Immunosuppressive Tumor Microenvironment of Pancreatic Cancer," Mol. Ther. 4, vol. 25, No. 1, pp. 249-258 (2017).
Qi L. et al., "Multiple effects of IL-21 on the ex vivo expansion of human primary NK cells," Immunology, Nov. 28, 2014, vol. 143, No. S2, p. 62-176, Poster Abstract 708.
Santegoets S.J. et al., "IL-21 promotes the expansion of CD27+CD28+ tumor infiltrating lymphocytes with high cytotoxic potential and low collateral expansion of regulatory T cells," Journal of Translational Medicine, Feb. 12, 2013, vol. 11, No. 37, pp. e1 -10.
Steel et al., "Interleukin-15 biology and its therapeutic implications in cancer," Trends Pharmacol. Sci. 33(1) :35-41, Jan. 2012.
Wilkie, S. et al., "Selective Expansion of Chimeric Antigen Receptor-targeted T-cells with Potent Effector Function Using Interleukin-4," J Biol Chem., vol. 295, No. 33, pp. 25538-25544 (2010).
Ye et al. "Effects of target cell overexpression of IL-15, 4-1 BBL and IL-18 1-102 combine with IL-2 on NK cell activation and cytotoxicity during ex vivo expansion" Chin J Cancer Biother, Oct. 31, 2014, vol. 21, No. 5, pp. 537-542 (Non-English, Copy Search Report for PCT/SG2018/050138 attached).
Gacerez, A, et al., "How Chimeric Antigen Receptor Design Affects Adoptive T Cell Therapy," Journal of Cellular Physiology, vol. 231, No. 12, pp. 2590-2598; Jun. 2, 2016.
Sadclain, M. et al., "The Basic Principles of Chimeric Antigen Receptor Design," Cancer Discovery, vol. 3, No. 4, pp. 388-398 (Apr. 1, 2013).
Caratelli et al., "FCγ Chimeric Receptor-Engineered T Cells: Methodology, Advantages, Limitations, and Clinical Relevance," Front Immunol., vol. 8, Article 457 , 8 pages (Apr. 27, 2017).
Kober, J., et al. "The capacity of the TNF family members 4-1BBL, OX40L, CD70, GITRL, CD30L and LIGHT to costimulate human T cells," Eur J Immuno, vol. 38, No. 10, pp. 2678-2688 (Oct. 28, 2008).
Abakushina, E.V., "Immunotherapy With Natural Killer Cells in the Treatment of Cancer," Russian Journal of Immunology, vol. 10, No. 2, pp. 131-142 (2016) (Abstract only).
Abken, H. et al., "Antigen-specific T-cell activation independently of the MHC: chimeric antigen receptor-redirected T cells," Frontiers in Immunology, V. 4, Article 371, c. 4 (2013).
Calabrese, et al., "IL-6 biology: implications for clinical targeting in rheumatic discase," S. Nat. Rev. Rheumatol, 10, 720-727 (2014); published online Aug. 19, 2014 (corrected online Sep. 19, 2014).
Cordoba, S. P. et al., "The large ectodomains of CD45 and CD148 regulate their segregation from and inhibition of ligated T-cell receptor," Blood, The Journal of the American Society of Hematology, V. 121, N. 21, p. 4295-4302, c. 4301 (2013).
Culpepper, D. J. et al., "Systematic mutation and thermodynamic analysis of central tyrosine pairs in polyspecific NKG2D receptor interactions," Molecular Immunology, V. 48, N. 4, p. 516-523, c. 521-522 (2011).
de Felipe, P., "Polycistronic Viral Vectors," Current Gene Therapy, V. 2, N. 3, p. 355-378, c. 360 (2002).
Denman et al., "Membrane-Bound IL-21 Promotes Sustained Ex Vivo Proliferation of Human Natural Killer Cells," PLoS ONE, vol. 7, Issue 1, Jan. 2012.
Lanicr, Lewis L., "NK Cell Recognition," Annual Review of Immunology, vol. 23, No. 1, pp. 225-274 (2005).
Lima, et al., "Interleukin-6 Neutralization by Antibodies Immobilized at the Surface of Polymeric Nanoparticles as a Therapeutic Strategy for Arthritic Diseases," ACS Appl. Mater. Interfaces 2018, 10, 13839-13850.
Pakula, A. A. et al., "Genetic analysis of protein stability and function," Annual Review of Genetics, V. 23, N. 1, p. 289-310, c. 305-306 (1989).
Zhao, Y. et al., "A Herceptin-Based Chimeric Antigen Receptor with Modified Signaling Domains Leads to Enhanced Survival of Transduced T Lymphocytes and Antitumor Activity," The Journal of Immunology, V. 183, N. 9, p. 5563-5574, c. 5568, 5571 (2009).
Gillet et al., "Selectable markers for gene therapy," Chapter 26 of Gene and Cell Therapy: Therapeutic Mechanisms and Strategies, $3^{rd}$ Ed. N.S. Templeton Ed, (CRC Press: Bpca Ratpm. FL), pp. 555 and 558, 2009.
Sureth et al., "Efficient generation of gene-modified human natural killer cells via alpharetroviral vectors," J. Mol. Med., 94: 83-93 (2016), published online Aug. 25, 2015.
Sokolic et al., "A selectable bicistronic retroviral vector corrects the molecular defect in a cell line derived from a patient with leukocyte adhesion deficiency," Biol. Blood Marrow Transpl., 12(2), Suppl. 1: 20-21, Feb. 2006.
Hombach et al., "Costimulation by chimeric antigen receptors revisited the T cell antitumor response benefits from combined CD28-OX40 signalling," Int. J. Cane. 129:2935-2944 (2011).
NCI Thesaurus, Bicistronic chimeric antigen receptor vector, Retrieved online from: <URL:https://ncit.nci.nih.gov/ncitbrowser/pages/home.jsf;jsessionid=12B0F7AF71E9A4035C38B5E4F6C055B0>, Retrieved on: Jan. 21, 2021, 2021.
Hurton et al., "Tethered IL-15 augments antitumor activity and promotes a stem-cell memory subsct in tumor-specific T cells," Proc. Natl. Acad. Sci, USA, 113(48):E7788-E7797 (Nov. 2016).
Eyquem et al., "Targeting a CAR to the TRAC locus with CRISPR/Cas9 enchances tumour rejction" Nature, 2017, 543(7643): 113-117.
Seif et al., "The role of JAK-STAT signaling pathway and its regulators in the fate of T helper cells" Cell Communication and Signaling (2017) 15:23, 13 pages.
Themeli et al., "Generation of tumor-targeted human T lymphocytes from Induced pluripotent stem cells for cancer therapy", Nat Biotechnol., 2013; 31(10): 028-933 928-933.
Watowich et al., "The Erythropoietin Receptor: Molecular Structure and Hematopoietic Signaling Pathways," J. Investig Med. 2011, 59(7): 1067-1072.
Dowell, A. C. , "Studies of Human T cell Costimulation:Potential for the Immunotherapy of Cancer," A thesis submitted to The University of Birmingham for the degree of Doctor of Philosophy, Cruk Institute for Cancer Studies, 2010.
GenBank Accession No. NM_172175.2, Homo sapiens interleukin 15 (IL 15), transcript variant 2, mRNA, dated Feb. 12, 2011, 4 pages.
Hasan, A.N., "Soluble and membrane-bound interleukin (IL)-15 Ra/IL-15 complexesmediate proliferation of high-avidity central memory CD81T cells foradoptive immunotherapy of cancer and infections," Clinical andExperimental Immunology, 186: 249-265, 2016.
Leitner et al., "T cell stimulator cells, an efficient and versatile cellular system to assess the role of costimulatory igands in the activation of human T cells," Journal of Immunological Methods, 362, 131-141, 2010.

(56) References Cited

OTHER PUBLICATIONS

Vinanica, N., et al., "Specific stimulation of T lymphocytes with erythropoietin for adoptive immunotherapy", Blood, 135(9): 668-679 (Feb. 27, 2020).
Oyer et al., "Natural killer cells stimulated with PM21 particles expand and biodistribute in vivo: Clinical implications for cancer treatment," Cytotherapy, 18: 653-663, 2016.
Wang et al., "Human NK cells maintain licensing status and are subject to killer immunoglobulin-like receptor (KIR) and KIR-ligand inhibition following ex vivo expansion," Cancer Immunol Immunother, 65:1047-1059, 2016.
Ye et al., "Gene therapy for cancer using single-chain Fv fragments specific for 4-1BB," Nat Med, Apr. 2002, 8(4): 343-348.
Zhang et al., "Improving Adoptive T Cell Therapy by Targeting and Controlling IL-12 Expression to the Tumor Environment," The American Society of Gene & Cell Therapy Molecular Therapy, vol. 19, No. 4, 751-759, 2011.
Ren, P.-P. et al., Anti-EGFRvIII Chimeric Antigen Receptor-Modified T Cells for Adoptive Cell Therapy of Glioblastoma, Current Pharmaceutical Design, 23(14), 2113-2116 (2017).
Morgan, R.A. et al., Recognition of Glioma Stem Cells by Genetically Modified T Cells Targeting EGFRvIII and Development of Adoptive Cell Therapy for Glioma, Human Gene Therapy, 23(10), 1043-1053 (2012).
Dalal, A.-R. et al., Third-Generation Human Epidermal Growth Factor Receptor 2 Chimeric Antigen Receptor Expression on Human T Cells Improves with Two-Signal Activation, Human Gene Therapy, 845-852 (2018) (Abstract).
Choi, B. D. et al., Chimeric antigen receptor T-cell immunotherapy for glioblastoma: practical insights for neurosurgeons, Neurosurg Focus, 44(6):E13, 1-6 (2018).
AASEQ1_05172022_135256_pep_vs_AASEQ2_05172022_135256_pep_align_4-1 BBL, May 17, 2022.
Call et al., "The structural basis for intramembrane assembly of an activating immunoreceptor complex" Nat Immunol Nov. 2010; 11(11): 1023-1029.
Figueiredo et al., "Permanent silencing of NKG2A expression for cell-based therapeutics" J. Mol. Med. (2009) 87:199-210.
Frankel et al., "Characterization of diphtheria fusion proteins targeted to the human interleukin-3 receptor" Protein Eng., 2000, v.13, n.8, p. 575-581.
Gillet et al., "Selectable markers for gene therapy," Chapter 27 of Gene and Cell Therapy: Therapeutic Mechanisms and Strategies, 3rd Ed. N.S. Templeton Ed, (CRC Press:Boca Raton, FL), pp. 701-738 (2009).
Hopp et al., "A Short Polypeptide Marker Sequence Useful for Recombinant Protein Identification and Purification" Bio/Technology, vol. 6, pp. 1204-1210 (Oct. 1988).
Hong, et al., "Interleukin-6 expands homeostatic space for peripheral T cells" Cytokine 64 (2013) pp. 532-540.
Iacobucci et al., Truncating Erythropoietin Receptor Rearrangements in Acute Lymphoblastic Leukemia, Cancer Cell, vol. 29, No. 2, pp. 186-200, published on Feb. 8, 2016.
Jiang, Z., et al., "IL-6 trans-signaling promotes the expansion and anti-tumor activity of CAR T cells" Leukemia (2021) 35; pp. 1380-1391.
Kontermann, et al., "Bispecific antibodies," Drug Discovery Today, 2015, v. 7, n. 20, p. 838-847.
Li, et al., "IL-6 Promotes T Cell Proliferation and Expansion under Inflammatory Conditions in Association with Low-Level ROR-γt Expression;" J. Immunol (2018) 201(10) pp. 2934-2946.
Nish, et al., "T cell-intrinsic role of IL-6 signaling in primary and memory responses" eLife 2014;3:e01949, 21 pages.
Qin et al., "Incorporation of a hinge domain improves the expansion of chimeric antigen receptor T cells" J. Hematol. Oneal. Mar. 13, 2017; 10(1):68. 11 pages.
Rochman, et al., "IL-6 Increases Primed Cell Expansion and Survival" The Journal of Immunology (2005) 174(8); pp. 4761-4767.

Teachey, et al., "Identification of Predictive Biomarkers for Cytokine Release Syndrome after Chimeric Antigen Receptor T-cell Therapy for Acute Lymphoblastic Leukemia" Cancer Discovery, Jun. 2016, pp. 664-679.
Aagaard et al., "RNAi therapeutics: Principles, prospects and challenges, Advanced Drug Delivery Reviews," 59 (2007) 75-86 (Year: 2007).
Arnau et al., "Current strategies for the use of affinity tags and tag removal for the purification of recombinant proteins" Protein expression and purification, 2006, v. 48, n. 1, p. 1-13.
Atreya, et al., "Blockade of interleukin 6 trans signaling suppresses T-cell resistance against apoptosis in chronic intestinal inflammation: Evidence in Crohn disease and experimental colitis in vivo" Nature Medicine, vol. 6, No. 5, May 2000; pp. 583-588.
Auerbach et al., "Angiogenesis assays: Problems and pitfalls," Cancer and Metastasis Reviews, 2000, 19: 167-172 (Year: 2000).
Barrett, et al., "Interleukin 6 Is Not Made By Chimeric Antigen Receptor T Cells and Does Not Impact Their Function" Blood (2016) 128(22):654.
Beans, "Targeting metastasis to halt cancer's spread," PNAS 2018; 115(50): 12539-12543 (Year: 2018).
Bedouelle, et al., "Diversity and junction residues as hotspots of binding energy in an antibody neutralizing the dengue virus" FEBS Journal 273 (2006) 34-46.
Berger, C. et al., "CD28 costimulation and immunoaffinity-based selection efficiently gernate primary gene-modified T cells for adoptive immunotherapy," Blood, 101: 476-484 (2003).
Blumberg et al., "Unraveling the autoimmune translational research process layer by layer," (Nat Med.; 18(1): 35-41) (Year: 2015).
Bork, "Powers and Pitfalls in Sequence Analysis: The 70% Hurdle, Genome Research," 2000, 10:398-400 (Year: 2000).
Brown, et al., "Tolerance to Single, but Not Multiple, Amino Acid Replacements in Antibody VH CDR2" J. Immunol. May 1, 1996;156(9):3285-91.
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue" J. Cell Biol. 111 :2129-2138, 1990 (Year: 1990).
Childs, et al., "Bringing natural killer cells to the clinic: ex vivo manipulation," Hematology Am Soc Hematol Educ Program. Dec. 6, 2013(1):234-246.
Colman, "Effects of amino acid sequence changes on antibody-antigen interactions" Research in Immunology 145:33-36 (1994).
de Sousa Abreu et al., "Global signatures of protein and mRNA expression levels" Mol. BioSys. 5:1512-1526, 2009.
Grabstein et al., "Cloning of a T cell growth factor that interacts with the β chain of the interleukin-2 receptor," Comparitive Study, Science, May 13, 1994;264(5161):965-8.
Gravanis et al., "The changing world of cancer drug development: the regulatory bodies' perspective," Chin Clin Oneal, 2014, 3, pp. 1-5 (Year: 2014).
Greenspan et al., "Defining epitopes: It's not as easy as it seems" Nature Biotechnology, 17:936-937 (Year: 1999).
Gura T, "Systems for Identifying New Drugs are Often Faulty," Science 1997, 278(5340): 1041-1042 (Year: 1997).
Hait., "Anticancer drug development: the grand challenges," Nature Reviews/Drug Discovery, 2010, 9, pp. 253-254 (Year: 2010).
Heberlein, C. et al., "The Gene for Erythropoietin Receptor Is Expressed in Multipotential Hematopoietic and Embryonal Stem Cells: Evidence for Differentiation Stage-Specific Regulation," Molecular and Cellular Biology 1992 1815-1826.
Heppner et al., "Tumor heterogeneity: biological implications and therapeutic consequences," 1983, Cancer Metastasis Reviews 2:5-23 (Year: 1983).
Hoshino S. et al., "Expression and Characterization of Erythropoietin Receptors on Normal Human Bone Marrow Cells," International Journal of Cell Cloning 1989, 7:156-167.
Hurton, L.V. et al., "Improved Costimulation of CD19-Specific T Cells Transpresenting a Membrane-Bound IL-15," Molecular Therapy vol. 19, Supplement 1, May 2011, S138.
Jain RK, "Barriers to Drug Delivery in Solid Tumors," 1994, Scientific American, pp. 58-645 (Year: 1994).

(56) References Cited

OTHER PUBLICATIONS

Kulmanov et al., "DeepGO: predicting protein functions from sequence and interactions using a deep ontology-aware classifier," Bioinformatics, 34(4), 2018, 660-668 (Year: 2018).
Lanier LL., "DAP10- and DAP12-associated receptors in innate immunity," Immunol Rev. Jan. 2009;227(1):150-60. doi: 10.1111/j.1600 -065X.2008.00720.x. PMID: 19120482; PMCID: PMC2794881. (Year: 2009).
Lazar et al., "Transforming Growth Factor • : Mutation of Aspartic Acid 47 and Leucine 48 Results in Different Biological Activities" Mol. Cell. Biol., vol. 8, No. 3, 1247-1252, 1988 (Year: 1988).
LeBien et al., "B lymphocytes: how they develop and function" Blood, vol. 112, No. 5, Sep. 1, 2008. pp. 1570-1580.
Lee et al., "Current concepts in the diagnosis and management of cytokine release syndrome" BLOOD, Jul. 10, 2014, vol. 124, No. 2, 188-195.
Lisowska, K.A. et al., "Erythropoietin receptor is expressed on human peripheral blood T and B lymphocytes and monocytes and is modulated by recombinant human erythropoietin treatment," Artif Organs. Aug. 2010;34(8):654-62.
Lu, et al., "Genetic engineering of dendritic cells to express immunosuppressive molecules (viral IL-10, TGF-•, and CTLA4lg)," J. Leukocyte Biol., Aug. 1999, 66:293-96.
McKeague, et al., "Challenges and Opportunities for Small Molecule Aptamer Development," Review Article, Journal of Nucleic Acids, vol. 2012, Article ID 748913.
Miosge, "Comparison of predicted and actual consequences of missense mutations," Proc Natl Acad Sci USA Sep. 15, 2015;112(37):E5189-98 (Year: 2015).
Morgan, et al., "Case Report of a Serious Adverse Event Following the Administration of T Cells Transduced With a Chimeric Antigen Receptor Recognizing ERBB2" Molecular Therapy, vol. 18, No. 4, 843-851, Apr. 2010.
Neely, et al., "Monocyte Surface-Bound IL-15 Can Function as an Activating Receptor and Participate in Reverse Signaling," The Journal of Immunology, 2004, 172(7): 4225-4234.
NIH National Cancer Institute, NCI Dictionary of Cancer Terms, Antigen-Presenting Cell, Retrieved online from: <URL: https://www.cancer.gov/publications/dictionaries/cancer-terms/def/antigen-presenting-cell > [retrieved on May 8, 2024], 2024.
Park et al., "Follicular Dendritic Cells Produce IL-15 That Enhances Germinal Center B Cell Proliferation in Membrane-Bound Form" J. Immunol. 173(11), 2004, pp. 6676-6683.
Pelechas et al., "Sirukumab: a promising therapy for rheumatoid arthritis" Expert Opinion On Biological Therapy, 2017, vol. 17, No. 6, 755-763.
Peng, et al., Erythropoietin and its derivatives: from tissue protection to immune regulation Cell Death & Disease 11, 79 (2020).
Rudikoff, et al., "Single amino acid substitution altering antigen-binding specificity " Proc. Natl Acad. Sci. USA, vol. 79, pp. 1979-1983, Mar. 1982.
Saikh, et al., "IL-15 induced conversion of monocytes to mature dendritic cells," Clin Exp Immunol 2001; 126(3):447-455.
Sarkis, et al., "Long term survival and limited migration of genetically modified monocytes/macrophages grafted into the mouse brain," J. Biomed. Sci. Engineer. (2013) 6(5): 561-71.
Shinjo K., et al., "Erythropoietin receptor expression on human bone marrow erythroid precursor cells by a newly-devised quantitative flow-cytometric assay," British Journal of Haematology, 1997, 551-558.
Skolnick et al., "From genes to protein structure and function: novel applications of computational approaches in the genomic era," Trends Biotechnol. Jan. 2000; 18(1 ):34-9 (Year: 2000).
Sporn et al., "Chemoprevention of Cancer," Carcinogenesis, vol. 21, No. 3 (2000), 525-530 (Year: 2000).
The Human Protein Atlas, KLRK1, Immune Cell, Retrieved online from: <URL:https://www.proteinatlas.org/ENSG00000213809-KLRK1/immune+cell> [retrieved on May 8, 2024], 2024.
The Human Protein Atlas, NCR3, Immune Cell, Retrieved online from: <URL:https://www.proteinatlas.org/ENSG00000204475-NCR3/immune+cell> [retrieved on May 8, 2024], 2024.
Torok et al., "Pharmacogenetics of Crohn's disease," Pharmacogenomics (2008) 9(7), 881-893 (Year: 2008).
UniProt P26717 NKG2C_HUMAN. Integrated into UniProtKB/Swiss-Prot Aug. 1, 1992. https://www.uniprot.org/uniprotkb/P26717/ entry. Accessed Jul. 17, 2024 (Year: 1992).
Vajdos, et al., "Comprehensive Functional Maps of the Antige••binding Site of an Anti-Erb82 Antibody Obtained with Shotgun Scanning Mutagenesis" J. Mol. Biol. (2002) 320, 415-428.
Warzocha et al., "Antisense Strategy: Biological Utility and Prospects in the Treatment of Hematological Malignancies," Leukemia and Lymphoma (1997) vol. 24. pp. 267-281 (Year: 1997).
Yan et al., "HER2 expression status in diverse cancers: review of results from 37,992 patients," Cancer Metastasis Rev (2015) 34:157-164 (Year: 2015).

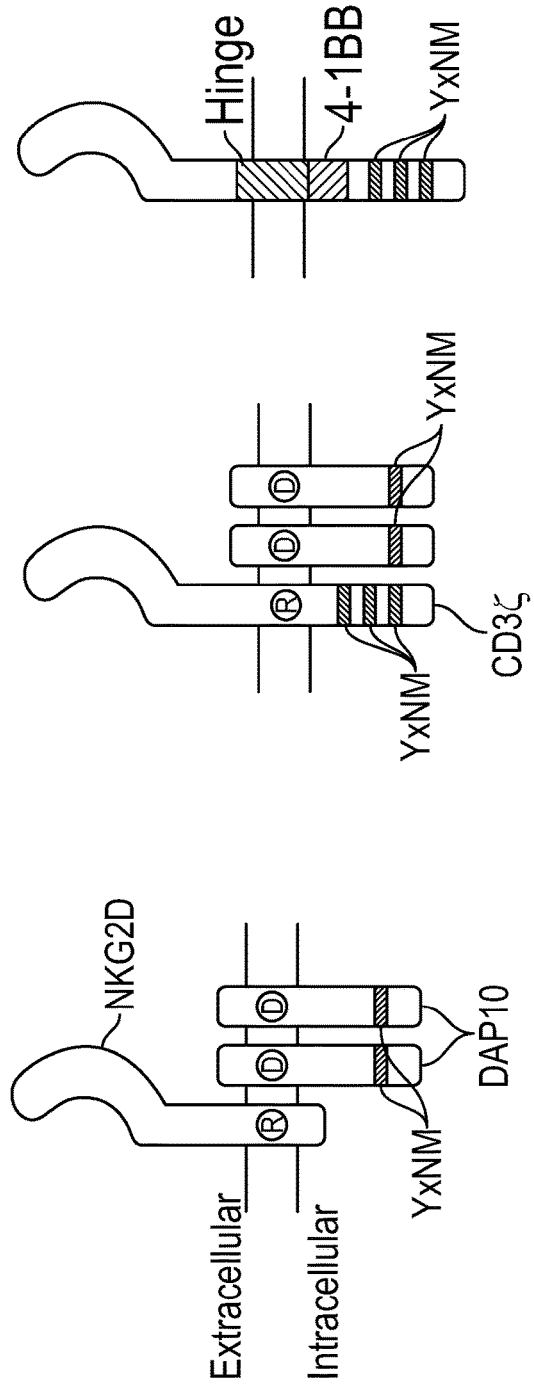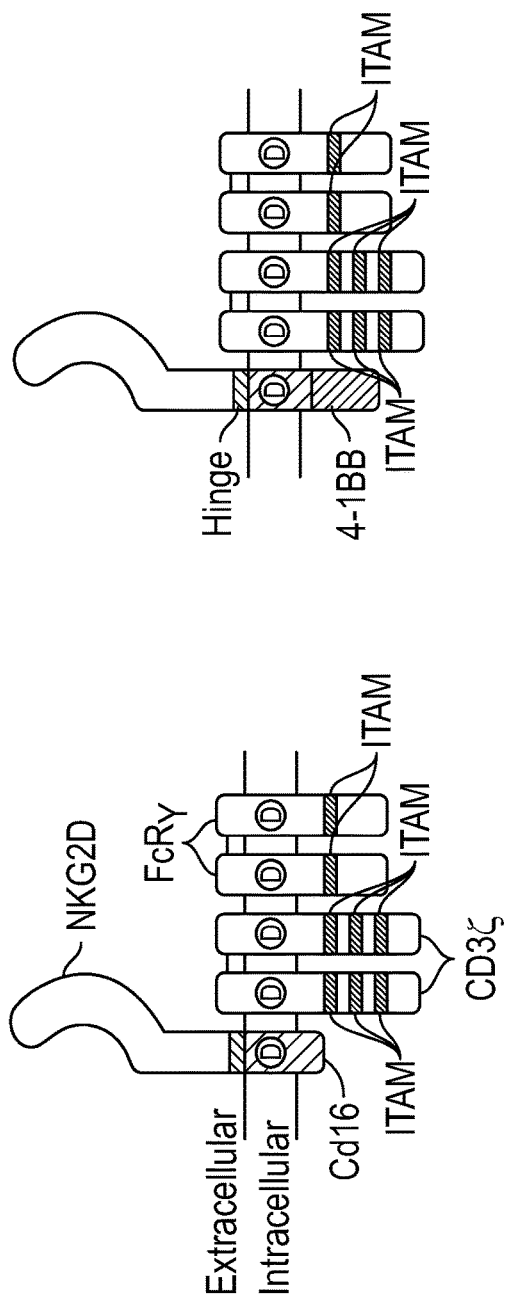

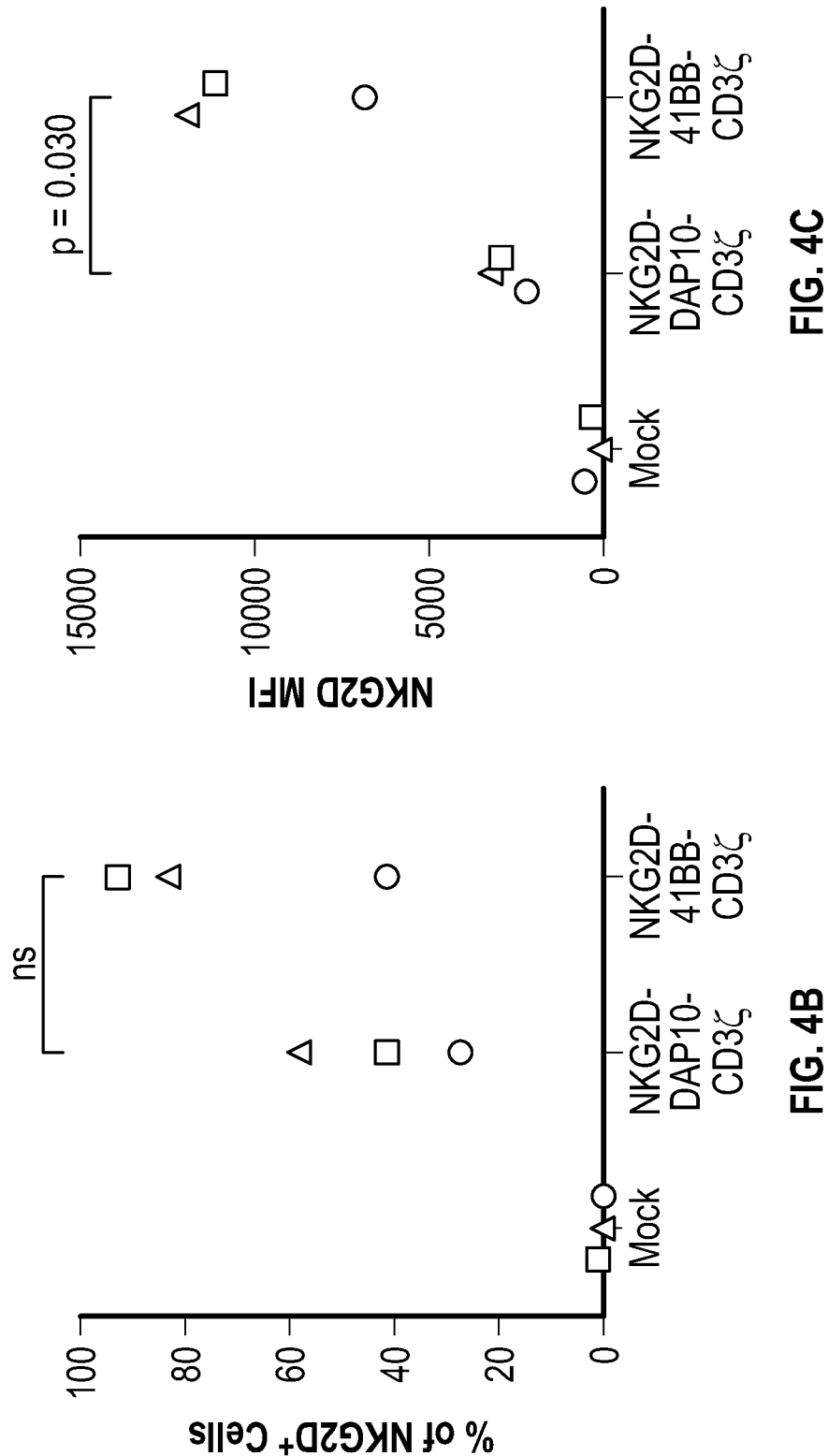

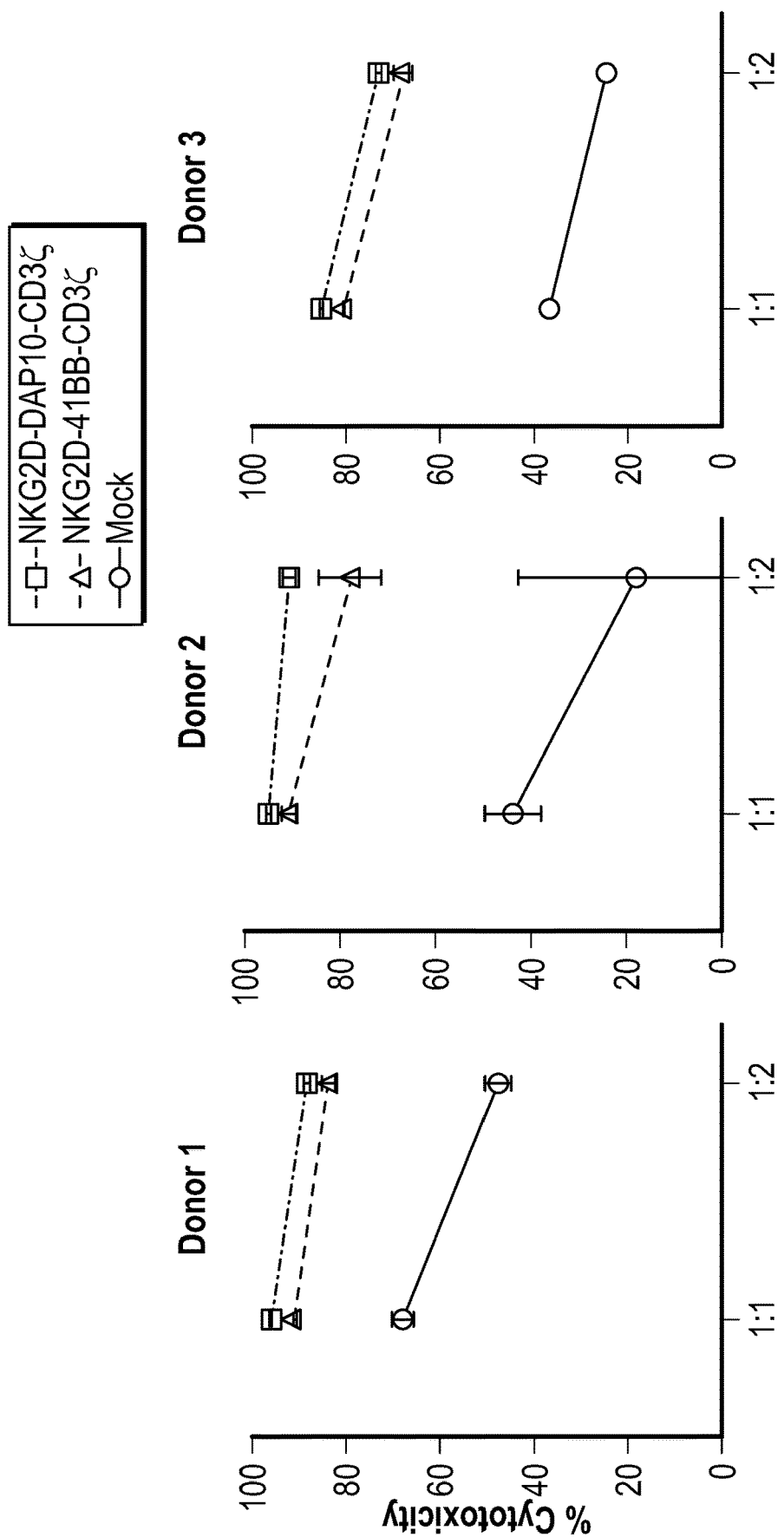

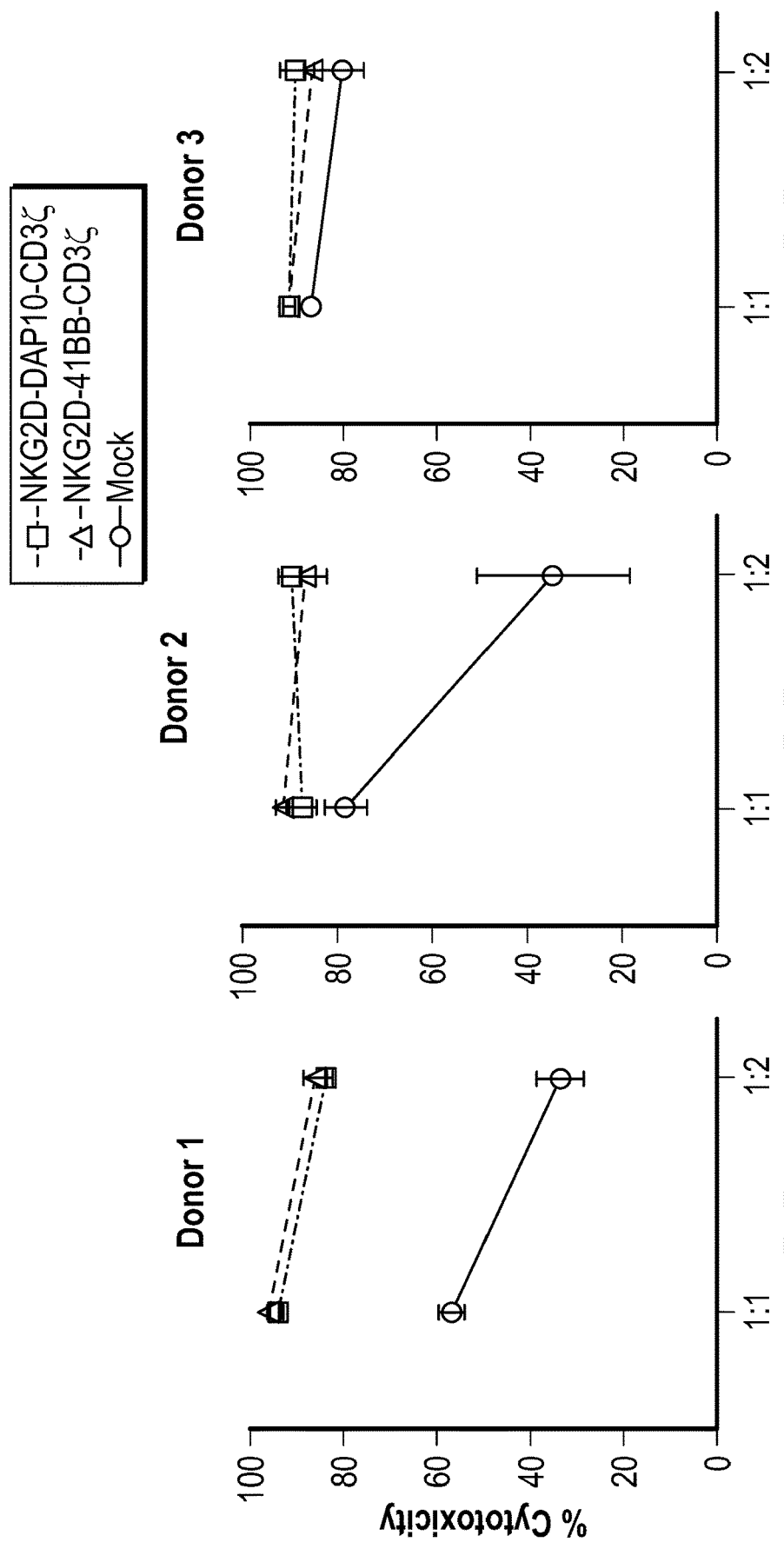

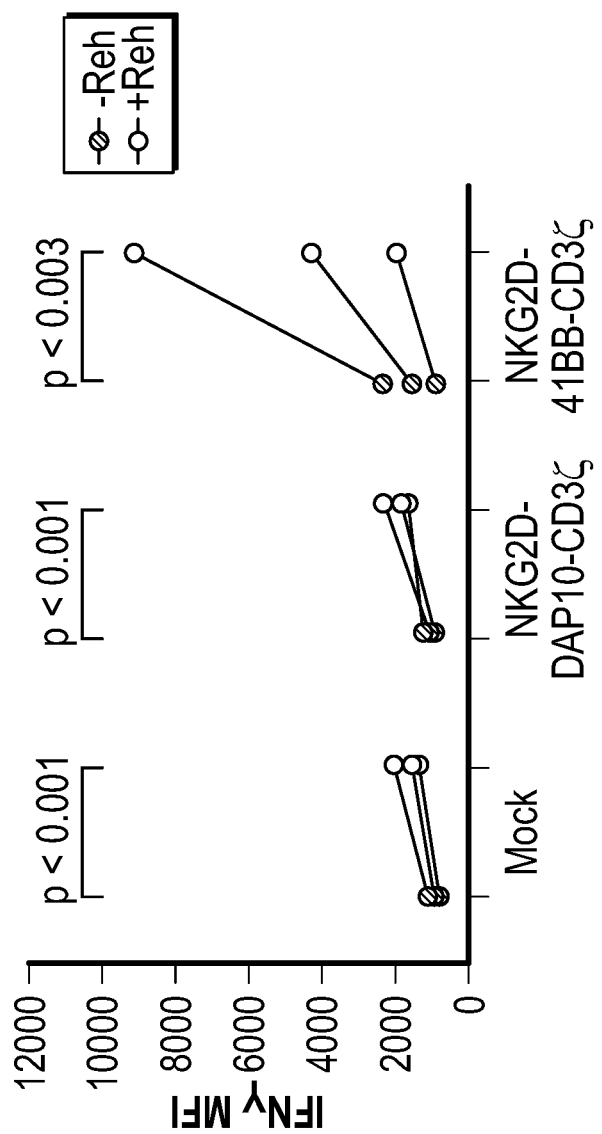

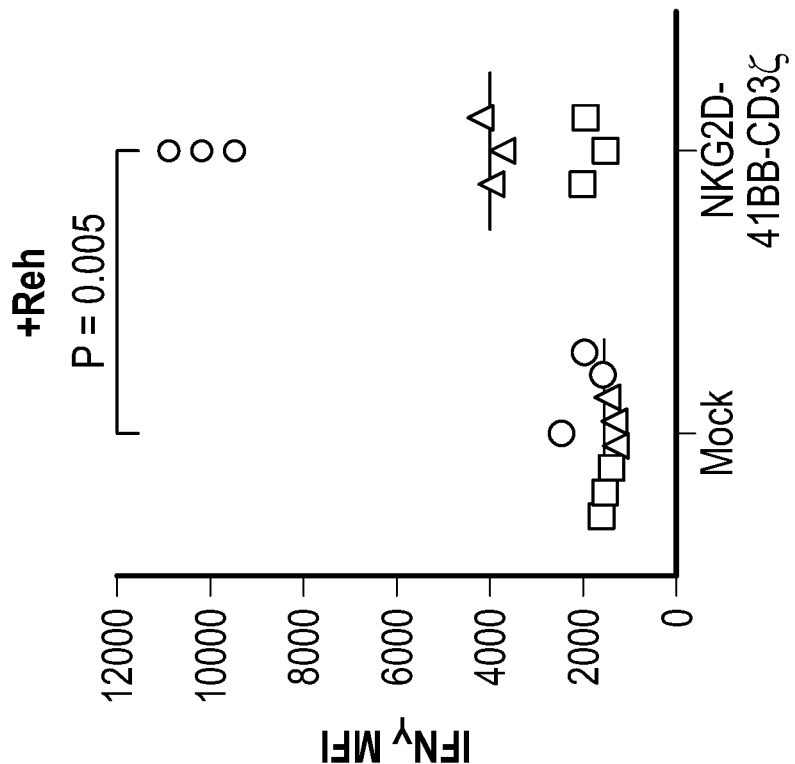
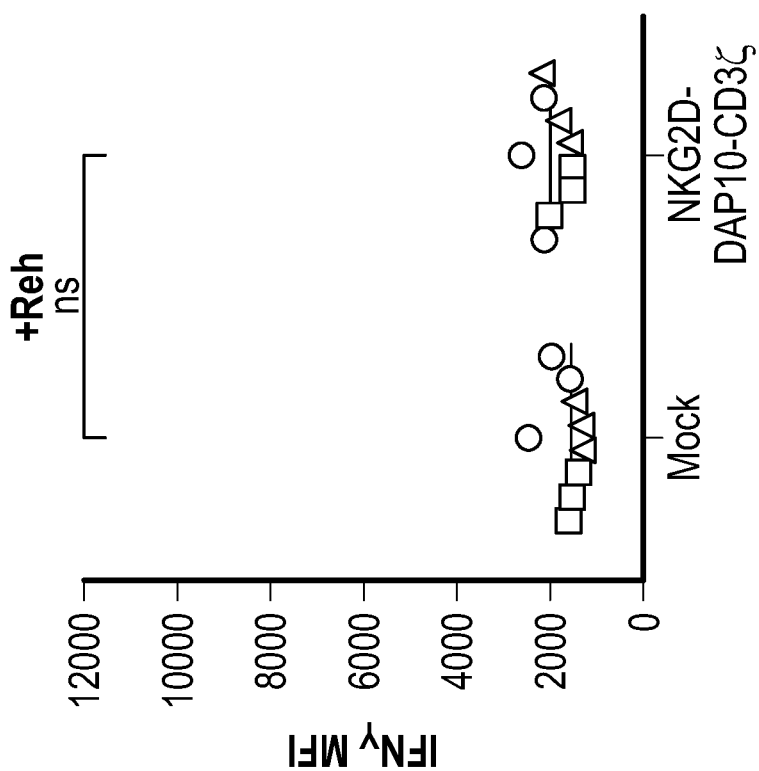
FIG. 7B

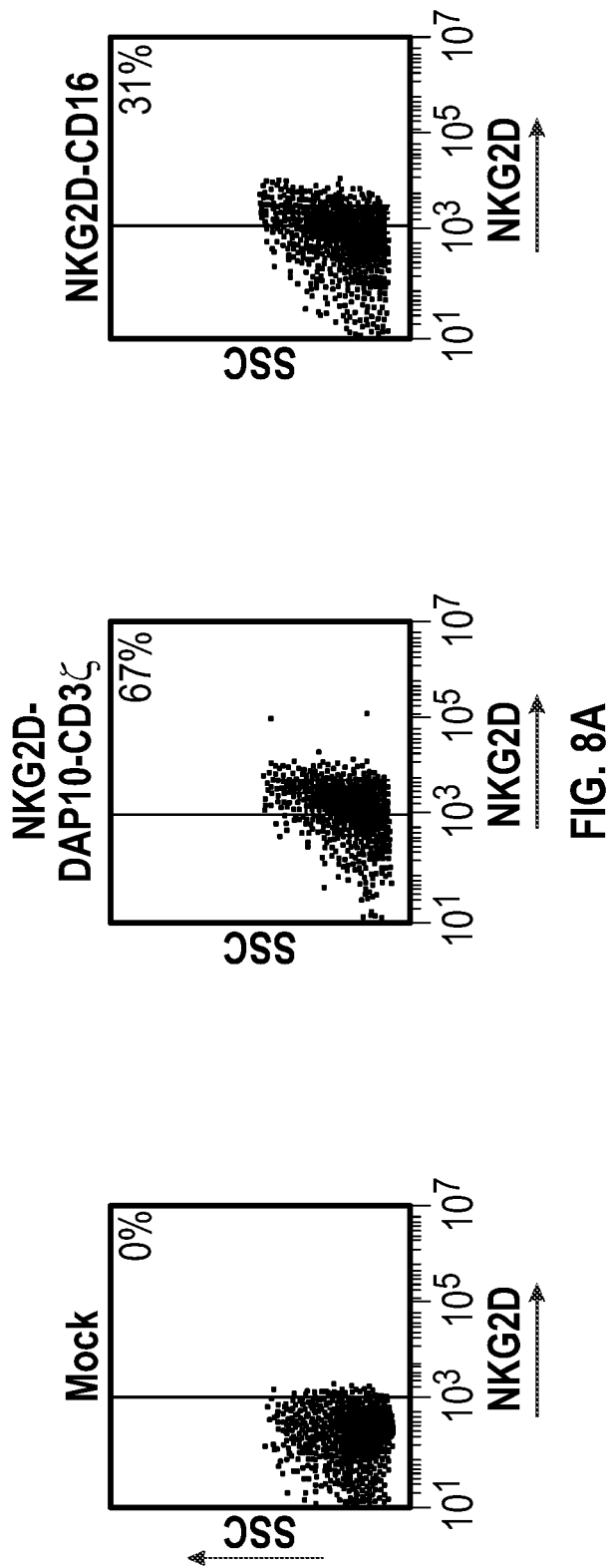

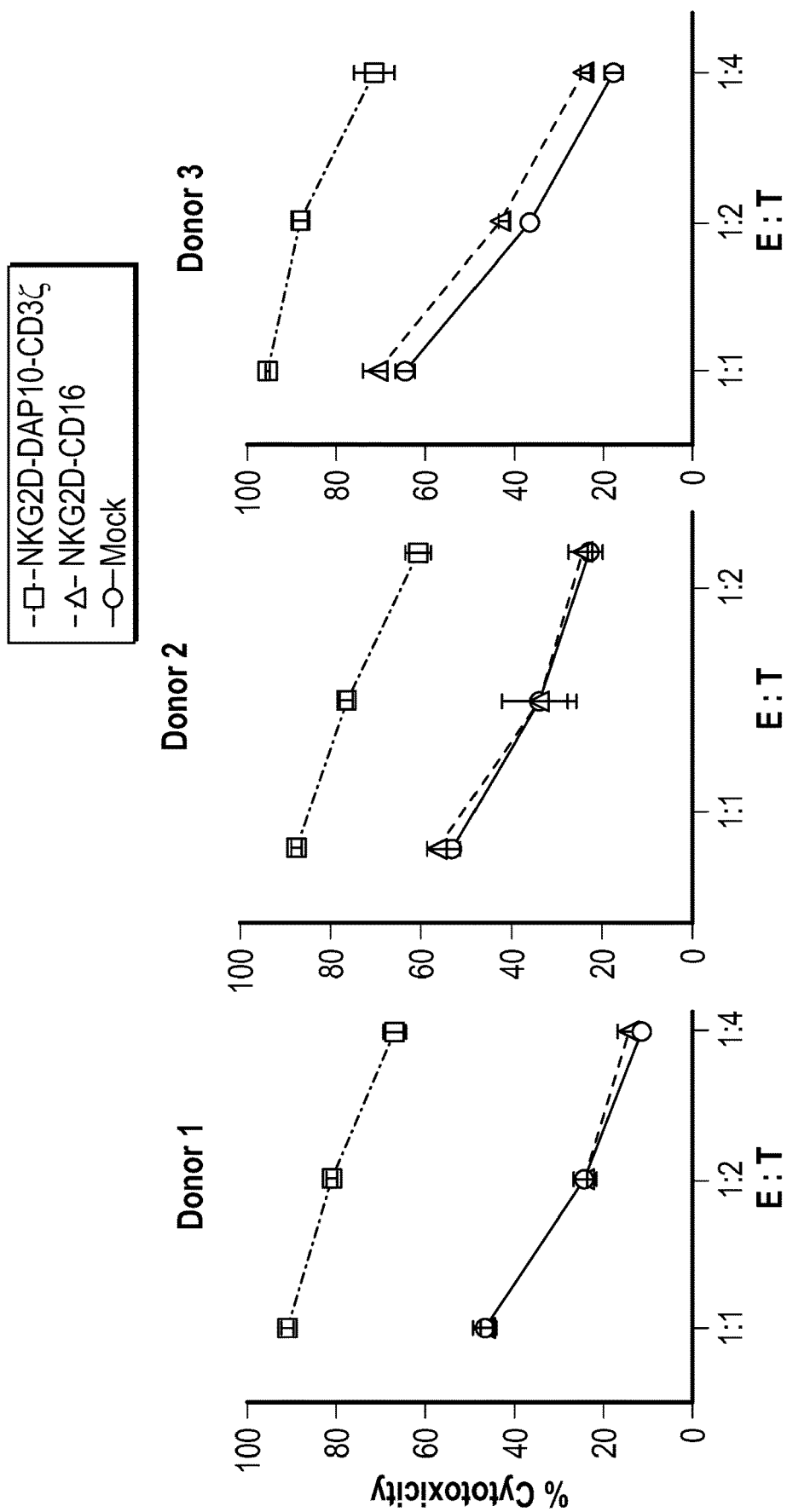

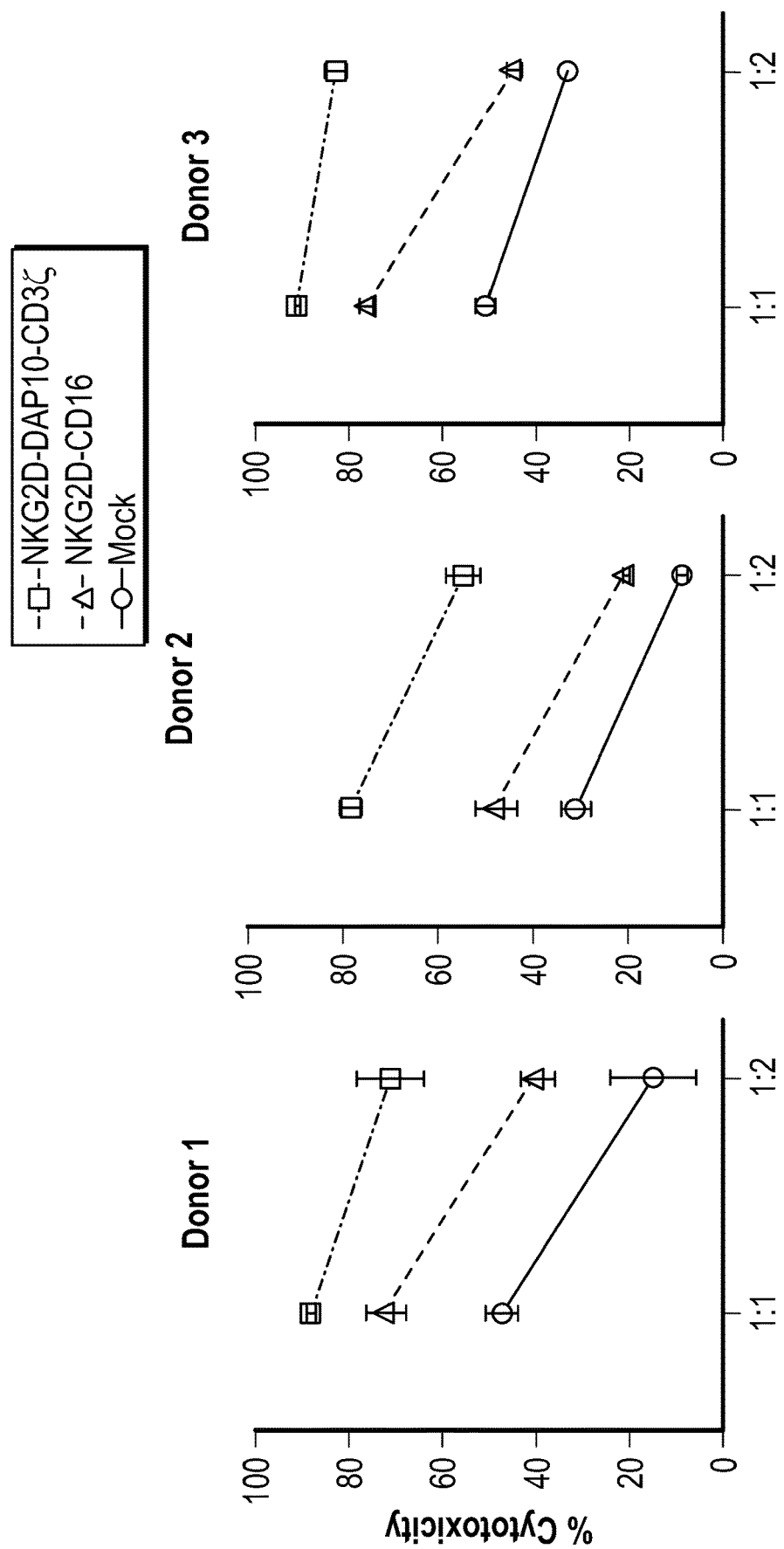

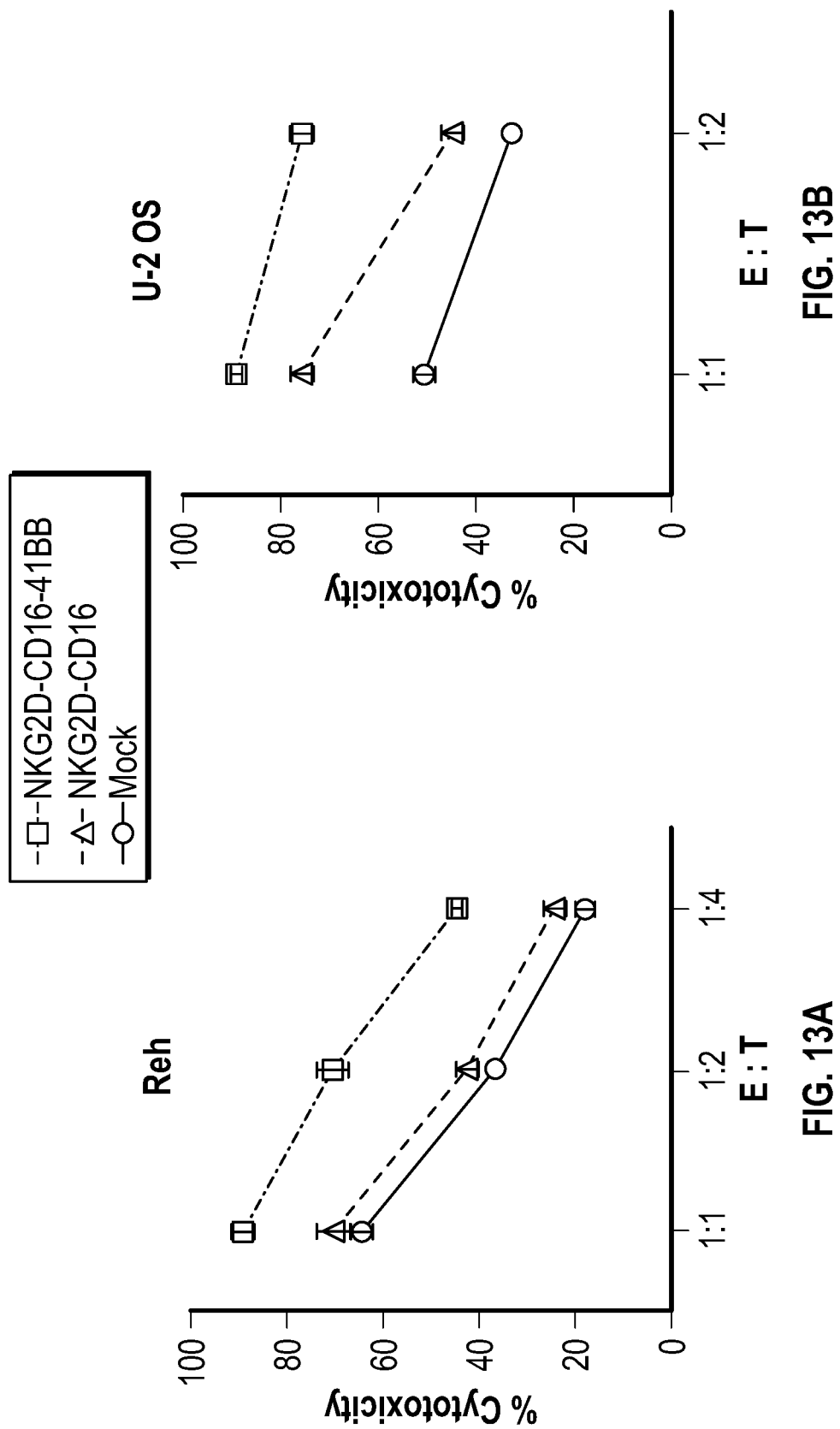

| | | | | | | |
|---|---|---|---|---|---|---|
| NK15 | NKG2D EC (Codon Optimized) | CD8α Hinge | CD16 TM/IC | 4-1BB | | |
| Variant 1 | NKG2D EC (Codon Optimized) | GS₃ | CD8α Hinge | CD16 TM/IC | 4-1BB | |
| Variant 2 | NKG2D EC (Codon Optimized) | GS₃ | CD16 TM/IC | 4-1BB | | |
| Variant 3 | NKG2D EC (Codon Optimized) | CD16 TM/IC | 4-1BB | | | |
| Variant 4 | NKG2D EC | CD8α Hinge | CD8α TM | 4-1BB | 2B4 | |
| Variant 5 | NKG2D EC | ADRB2 EC | ADRB2 TM | 4-1BB | 2B4 | |
| Variant 6 | NKG2D EC | CD8α Hinge | CD8α TM | 4-1BB | 2B4 | GS₃ | NKp80 |
| Variant 7 | NKG2D EC | CD8α Hinge | CD8α TM | 4-1BB | GS₃ | NKp80 |
| Variant 8 | NKG2D EC (Codon Optimized) | GS₃ | NKG2D EC | ADRB2 EC | ADRB2 TM | 4-1BB | GS₃ | NKp80 |
| Variant 9 | NKG2D EC (Codon Optimized) | GS₃ | NKG2D EC | CD8α Hinge | CD8α TM | 4-1BB | GS₃ | NKp80 |
| Variant 10 | NKG2D EC (Codon Optimized) | GS₃ | NKG2D EC | CD8α Hinge | CD16 TM/IC | 4-1BB | |
| Variant 11 | NKG2D EC (Codon Optimized) | CD8α Hinge | CD16 TM/IC | 4-1BB | 2B4 | |
| Variant 12 | NKG2D EC (Codon Optimized) | CD8α Hinge | CD16 TM/IC | 4-1BB | GS₃ | NKp80 |

FIG. 14

| Construct | Domains |
|---|---|
| NK16 | NKG2D EC \| CD8α Hinge \| CD8α TM \| 4-1BB \| CD3ζ ITAM |
| Variant 13 | NKG2D EC \| CD8α Hinge \| CD8α TM \| 4-1BB \| 2B4 \| CD3ζ ITAM |
| Variant 14 | NKG2D EC \| CD8α Hinge \| CD8α TM \| 4-1BB \| DAP10 IC |
| Variant 15 | NKG2D EC \| CD8α Hinge \| CD8α TM \| 4-1BB \| DAP10 IC \| 2B4 |
| Variant 16 | NKG2D EC \| CD8α Hinge \| CD8α TM \| 4-1BB \| 2B4 \| DAP10 IC |
| Variant 17 | NKG2D EC (Codon Optimized) \| GS₃ \| NKG2D EC \| CD8α Hinge \| CD8α TM \| 4-1BB \| CD3ζ ITAM |
| Variant 18 (NK39) | NKG2D EC (Codon Optimized) \| CD8α Hinge \| CD3ζ TM \| CD16 IC \| 4-1BB |
| NK39_1 | NKG2D EC (Codon Optimized) \| GS₃ \| NKG2D EC \| CD8α Hinge \| CD3ζ TM \| CD16 IC \| 4-1BB \| 2A \| mIL-15 |
| NK39_2 | NKG2D EC \| CD8α Hinge \| CD3ζ TM \| CD16 IC \| 4-1BB \| GS₃ \| NKp80 \| 2A \| mIL-15 |

FIG. 15

NK39_3 | NKG2D EC (Codon Optimized) | GS₃ | NKG2D EC | CD8α Hinge | CD3ζ TM | CD16 IC | 4-1BB | GS₃ | NKp80 | mIL-15

NK39_4 | NKG2D EC (Codon Optimized) | CD8α Hinge | CD3ζ TM | 4-1BB | 2A | mIL-15

NK39_5 | NKG2D EC (Codon Optimized) | CD8α Hinge | CD3ζ TM | 4-1BB | CD3Zeta | 2A | mIL-15

NK39_6 | NKG2D EC (Codon Optimized) | CD8α Hinge | CD3ζ TM | 4-1BB | GS₃ | NKp80 | 2A | mIL-15

NK39_7 | NKG2D EC (Codon Optimized) | CD8α Hinge | CD3ζ TM | 4-1BB | GS₃ | CD16 IC | 2A | mIL-15

NK39_8 | NKG2D EC | CD8α Hinge | CD3ζ TM | 4-1BB | FC Gamma | 2A | mIL-15

NK39_9 | IL-15 | GS₃ | NKG2D EC | CD8α Hinge | CD3ζ TM | 4-1BB | Cd3ζ ITAM

NK39_10 | NKG2D EC (Codon Optimized) | CD8α Hinge | CD3ζ TM | CD16 IC | 4-1BB | 2A | mIL-15

NK16_7 | NKG2D EC (Codon Optimized) | GS₃ | NKG2D EC | CD8α Hinge | CD8α TM | 4-1BB | Cd3ζ ITAM | 2A | mIL-15

FIG. 15
(Continued)

NKG2D(Short Hinge) - 41BB - Cd3z  IgG4 Hinge: ESKYGPPCPSCP)

| | | | | | | | |
|---|---|---|---|---|---|---|---|
| NK45-1 | NKG2D EC | Ig4 SH | CD8αTM | 4-1BB | Cd3ζ ITAM | 2A | mIL-15 |

NKG2D-CD28-CD3z

| | | | | | | | |
|---|---|---|---|---|---|---|---|
| NK45-2 | NKG2D EC | CD8α Hinge | CD28 TM | CD28 | Cd3ζ ITAM | 2A | mIL-15 |

NKG2D (SH)-CD28 - CD3z

| | | | | | | | |
|---|---|---|---|---|---|---|---|
| NK45-3 | NKG2D EC | Ig4SH | CD28 TM | CD28 | Cd3ζ ITAM | 2A | mIL-15 |

NKG2D-OX40-CD3z

| | | | | | | | |
|---|---|---|---|---|---|---|---|
| NK45-4 | NKG2D EC | CD8α Hinge | CD8αTM | OX40 | Cd3ζ ITAM | 2A | mIL-15 |

NKG2D (SH)-OX40-CD3z

| | | | | | | | |
|---|---|---|---|---|---|---|---|
| NK45-5 | NKG2D EC | Ig4SH | CD8αTM | OX40 | Cd3ζ ITAM | 2A | mIL-15 |

NKG2D-CD3TM-CD28-CD3z

| | | | | | | | |
|---|---|---|---|---|---|---|---|
| NK45-6 | NKG2D EC | CD8α Hinge | CD3α TM | CD28 | Cd3ζ ITAM | 2A | mIL-15 |

NKG2D-CD28-41BB-CD3z

| | | | | | | | | |
|---|---|---|---|---|---|---|---|---|---|
| NK45-7 | NKG2D EC | CD8α Hinge | CD28 TM | CD28 | 4-1BB | Cd3ζ ITAM | 2A | mIL-15 |

FIG. 22

SEQUENCE LISTING

```
<160> NUMBER OF SEQ ID NOS: 109

<210> SEQ ID NO 1
<211> LENGTH: 645
<212> TYPE: DNA
<213> ORGANISM: Homo sapiens
<220> FEATURE:
<221> NAME/KEY: misc_feature
<223> OTHER INFORMATION: Full length NKG2D

<400> SEQUENCE: 1
gggtggattc gtggtcggag gtctcgacac agctgggaga tgagtgaatt tcataattat      60
aacttggatc tgaagaagag tgattttca acacgatggc aaaagcaaag atgtccagta     120
gtcaaaagca aatgtagaga aaatgcatct ccatttttt tctgctgctt catcgctgta     180
gccatgggaa tccgtttcat tattatggta acaatatgga gtgctgtatt cctaaactca     240
ttattcaacc aagaagttca aattcccttg accgaaagtt actgtggccc atgtcctaaa     300
aactggatat gttacaaaaa taactgctac caattttttg atgagagtaa aaactggtat     360
gagagccagg cttcttgtat gtctcaaaat gccagccttc tgaaagtata cagcaaagag     420
gaccaggatt tacttaaact ggtgaagtca tatcattgga tgggactagt acacattcca     480
acaaatggat cttggcagtg ggaagatggc tccattctct cacccaacct actaacaata     540
attgaaatgc agaagggaga ctgtgcactc tatgcctcga gctttaaagg ctatatagaa     600
aactgttcaa ctccaaatac gtacatctgc atgcaaagga ctgtg                    645

<210> SEQ ID NO 2
<211> LENGTH: 405
<212> TYPE: DNA
<213> ORGANISM: Homo sapiens
<220> FEATURE:
<221> NAME/KEY: misc_feature
<223> OTHER INFORMATION: Truncated NKG2D

<400> SEQUENCE: 2
ttattcaacc aagaagttca aattcccttg accgaaagtt actgtggccc atgtcctaaa      60
aactggatat gttacaaaaa taactgctac caattttttg atgagagtaa aaactggtat     120
```

```
gagagccagg cttcttgtat gtctcaaaat gccagccttc tgaaagtata cagcaaagag    180
gaccaggatt tacttaaact ggtgaagtca tatcattgga tgggactagt acacattcca    240
acaaatggat cttggcagtg ggaagatggc tccattctct cacccaacct actaacaata    300
attgaaatgc agaagggaga ctgtgcactc tatgcctcga gctttaaagg ctatatagaa    360
aactgttcaa ctccaaatac gtacatctgc atgcaaagga ctgtg                   405

<210> SEQ ID NO 3
<211> LENGTH: 405
<212> TYPE: DNA
<213> ORGANISM: Homo sapiens
<220> FEATURE:
<221> NAME/KEY: misc_feature
<223> OTHER INFORMATION: Codon Optimized Truncated NKG2D

<400> SEQUENCE: 3
ctgttcaatc aggaagtcca gatccccctg acagagtctt actgcggccc atgtcccaag    60
aactggatct gctacaagaa caattgttat cagttctttg acgagagcaa gaactggtat    120
gagtcccagg cctcttgcat gagccagaat gcctctctgc tgaaggtgta cagcaaggag    180
gaccaggatt gctgaagct ggtgaagtcc tatcactgga tgggcctggt gcacatccct    240
acaaacggct cttggcagtg ggaggacggc tccatcctgt ctccaaatct gctgaccatc    300
atcgagatgc agaagggcga ttgcgccctg tacgccagct ccttcaaggg ctatatcgag    360
aactgctcca cacccaatac ctacatctgt atgcagagga ccgtg                   405

<210> SEQ ID NO 4
<211> LENGTH: 63
<212> TYPE: DNA
<213> ORGANISM: Homo sapiens
<220> FEATURE:
<221> NAME/KEY: misc_feature
<223> OTHER INFORMATION: CD8 Signaling Sequence

<400> SEQUENCE: 4
atggctctgc ccgtcaccgc actgctgctg cctctggctc tgctgctgca cgccgcacga    60
cca                                                                 63

<210> SEQ ID NO 5
<211> LENGTH: 135
<212> TYPE: DNA
<213> ORGANISM: Homo sapiens
<220> FEATURE:
<221> NAME/KEY: misc_feature
<223> OTHER INFORMATION: CD8 alpha hinge

<400> SEQUENCE: 5
accacaaccc ctgcaccacg ccccctaca ccagcaccta ccatcgcaag ccagcctctg     60
tccctgcggc cagaggcatg tagaccagca gcaggaggag cagtgcacac aagaggcctg    120
gacttcgcct gcgat                                                    135

<210> SEQ ID NO 6
<211> LENGTH: 1722
<212> TYPE: DNA
<213> ORGANISM: Homo sapiens
<220> FEATURE:
<221> NAME/KEY: misc_feature
<223> OTHER INFORMATION: CD8 beta
<220> FEATURE:
<221> NAME/KEY: misc_feature
<222> LOCATION: (674)..(773)
<223> OTHER INFORMATION: n is a, c, g, or t
```

<220> FEATURE:
<221> NAME/KEY: misc_feature
<222> LOCATION: (859)..(958)
<223> OTHER INFORMATION: n is a, c, g, or t

<400> SEQUENCE: 6

| | | | | | |
|---|---|---|---|---|---|
| atctaggtct | tgctgcaccc | gcacaaccta | caaacagcgt | cggggccttc | tctgcacctc | 60 |
| cagttcccag | ctcacctccc | tcagtgtcac | agccggttac | ctttccttcc | tccctggggg | 120 |
| agggcaagac | ttggggcttg | ctgactccag | gcccagccca | gccgggggca | cccaggagcc | 180 |
| cctcaattgc | tactcaaaca | gacaagaagc | ggcccgagtt | agtggccagc | tccaccatgc | 240 |
| actacacatc | ctgacctctc | tgagcctcta | ctgtcactcg | gggtcacaac | cctttcctga | 300 |
| gcacctcccg | gggcaggggg | cgatgacaca | catgcagctg | cctggggag | gccggcggtg | 360 |
| tccccctcctt | tctggaacgc | ggagggtcct | ggtgggctct | ggaaacgcag | cccagacctt | 420 |
| tgcaatgcta | ggaggatgag | ggcggagacc | tcgcggtccc | caacaccaga | ctcccgcagc | 480 |
| caccgcgccc | ggtcccgccc | tccccactgc | ccccccagct | cccgaccca | ggcgcccgc | 540 |
| ccggccagct | cctcacccac | cccagccgcg | actgtctccg | ccgagccccc | ggggccaggt | 600 |
| gtcccgggcg | cgccacgatg | cggccgcggc | tgtggtcct | cctggccgcg | cagctgacag | 660 |
| gtaaggcggc | ggcnnnnnnn | nnnnnnnnnn | nnnnnnnnnn | nnnnnnnnnn | nnnnnnnnnn | 720 |
| nnnnnnnnnn | nnnnnnnnnn | nnnnnnnnnn | nnnnnnnnnn | nnnnnnnnnn | nnnttgcttt | 780 |
| cctcttccag | gccggcggag | gagagcccgg | cttcgtttca | tgaaacagta | agtgtataac | 840 |
| ctgggtgtgg | ccttgggann | nnnnnnnnnn | nnnnnnnnnn | nnnnnnnnnn | nnnnnnnnnn | 900 |
| nnnnnnnnnn | nnnnnnnnnn | nnnnnnnnnn | nnnnnnnnnn | nnnnnnnnnn | nnnnnnnct | 960 |
| tgctgttgtt | ttcagatttt | acaaatgagc | agagaatacg | gttttggtgt | cctgctacaa | 1020 |
| aaagacatcg | gtcagtaacg | agcacgatgt | ggaaaaatga | gagaagggac | acattcaacc | 1080 |
| ctggagagtt | caatggctgc | tgaagctgcc | tgcttttcac | tgctgcaagg | cctttctgtg | 1140 |
| tgtgacgtgc | atgggagcaa | cttgttcgtg | ggtcatcggg | aatactaggg | agaaggtttc | 1200 |
| attgccccca | gggcacttca | cagagtgtgc | tggaggactg | agtaagaaat | gctgcccatg | 1260 |
| ccaccgcttc | cggctcctgt | gctttccctg | aactgggacc | tttagtggtg | gccatttagc | 1320 |
| caccatcttt | gcaggttgct | ttgccctggt | agggcagtaa | cattgggtcc | tgggtctttc | 1380 |
| atggggtgat | gctgggctgg | ctccctgttg | gtcttcccag | gctggggctg | accttcctcg | 1440 |
| cagagaggcc | aggtgcaggt | tgggaatgag | gcttgctgag | aggggctgtc | cagttcccag | 1500 |
| aaggcatatc | agtctctgag | ggcttccttt | ggggccggga | acttgcgggt | ttgaggatag | 1560 |
| gagttcactt | catcttctca | gctcccattt | ctactcttaa | gtttctcagc | tcccatttct | 1620 |
| actctcccat | ggcttaatgc | ttctttcatt | ttctgtttgt | tttatacaaa | tgtcttagtt | 1680 |
| gtaaaaataa | agtcccaggt | taaagataac | aaacgggtcc | tg | | 1722 |

<210> SEQ ID NO 7
<211> LENGTH: 2415
<212> TYPE: DNA
<213> ORGANISM: Homo sapiens
<220> FEATURE:
<221> NAME/KEY: misc_feature
<223> OTHER INFORMATION: CD16 alpha

<400> SEQUENCE: 7

| | | | | | |
|---|---|---|---|---|---|
| attcttggtg | ctgggtggat | ccaaatccag | gagatggggc | aagcatcctg | ggatggctga | 60 |
| gggcacactc | tggcagattc | tgtgtgtgtc | ctcagatgct | cagccacaga | cctttgaggg | 120 |

```
agtaaagggg gcagacccac ccaccttgcc tccaggctct ttccttcctg gtcctgttct    180
atggtggggc tcccttgcca gacttcagac tgagaagtca gatgaagttt caagaaaagg    240
aaattggtgg gtgacagaga tgggtggagg ggctggggaa aggctgttta cttcctcctg    300
tctagtcggt ttggtccctt tagggctccg gatatctttg gtgacttgtc cactccagtg    360
tggcatcatg tggcagctgc tcctcccaac tgctctgcta cttctagttt cagctggcat    420
gcggactgaa gatctcccaa aggctgtggt gttcctggag cctcaatggt acagggtgct    480
cgagaaggac agtgtgactc tgaagtgcca gggagcctac tcccctgagg acaattccac    540
acagtggttt cacaatgaga gcctcatctc aagccaggcc tcgagctact tcattgacgc    600
tgccacagtc gacgacagtg gagagtacag gtgccagaca acctctccca ccctcagtga    660
cccggtgcag ctagaagtcc atatcggctg gctgttgctc caggcccctc ggtgggtgtt    720
caaggaggaa gaccctattc acctgagctg tcacagctgg aagaacactg ctctgcataa    780
ggtcacatat ttacagaatg gcaaaggcag gaagtatttt catcataatt ctgacttcta    840
cattccaaaa gccacactca agacagcgg ctcctacttc tgcaggggc ttttgggag    900 taaaaatgtg tcttcagaga ctgtgaacat caccatcact caaggtttgg cagtgtcaac    960
catctcatca ttctttccac ctgggtacca agtctctttc tgcttggtga tggtactcct   1020 tttgcagtg gacacaggac tatatttctc tgtgaagaca aacattcgaa gctcaacaag   1080
agactggaag gaccataaat ttaaatggag aaaggaccct caagacaaat gaccccatc    1140 ccatgggggt aataagagca gtagcagcag catctctgaa catttctctg gatttgcaac   1200
cccatcatcc tcaggcctct ctacaagcag caggaaacat agaactcaga gccagatccc   1260
ttatccaact ctcgactttt ccttggtctc cagtggaagg gaaagcccca tgatcttcaa   1320
gcagggaagc cccagtgagt agctgcattc ctagaaattg aagtttcaga gctacacaaa   1380 cacttttctct gtcccaaccg ttccctcaca gcaaagcaac aatacaggct agggatggta   1440
atcctttaaa catacaaaaa ttgctcgtgt tataaattac ccagtttaga ggggaaaaaa   1500
aaacaattat tcctaaataa atggataagt agaattaatg gttgaggcag gaccatacag   1560
agtgtgggaa ctgctgggga tctagggaat tcagtgggac caatgaaagc atggctgaga   1620
aatagcaggt agtccaggat agtctaaggg aggtgttccc atctgagccc agagataagg   1680
gtgtcttcct agaacattag ccgtagtgga attaacagga aatcatgagg gtgacgtaga   1740
attgagtctt ccaggggact ctatcagaac tggaccatct ccaagtatat aacgatgagt   1800
cctcttaatg ctaggagtag aaaatggtcc taggaagggg actgaggatt gcggtggggg   1860
gtggggtgga aaagaaagta cagaacaaac cctgtgtcac tgtcccaagt tgctaagtga   1920
acagaactat ctcagcatca gaatgagaaa gcctgagaag aaagaaccaa ccacaagcac   1980
acaggaagga aagcgcagga ggtgaaaatg ctttcttggc cagggtagta agaattagag   2040
gttaatgcag ggactgtaaa accacctttt ctgcttcaat atctaattcc tgtgtagctt   2100
tgttcattgc atttattaaa caaatgttgt ataaccaata ctaaatgtac tactgagctt   2160
cgctgagtta agttatgaaa ctttcaaatc cttcatcatg tcagttccaa tgaggtgggg   2220
atggagaaga caattgttgc ttatgaaaga aagctttagc tgtctctgtt ttgtaagctt   2280
taagcgcaac atttcttggt tccaataaag cattttacaa gatcttgcat gctactctta   2340
gatagaagat gggaaaacca tggtaataaa atatgaatga taaaaaaaaa aaaaaaaaaa   2400
aaaaaaaaaa aaaaa                                                   2415
```

```
<210> SEQ ID NO 8
<211> LENGTH: 2473
<212> TYPE: DNA
<213> ORGANISM: Homo sapiens
<220> FEATURE:
<221> NAME/KEY: misc_feature
<223> OTHER INFORMATION: CD16 beta
<220> FEATURE:
<221> NAME/KEY: misc_feature
<222> LOCATION: (211)..(310)
<223> OTHER INFORMATION: n is a, c, g, or t
<220> FEATURE:
<221> NAME/KEY: misc_feature
<222> LOCATION: (537)..(636)
<223> OTHER INFORMATION: n is a, c, g, or t
<220> FEATURE:
<221> NAME/KEY: misc_feature
<222> LOCATION: (968)..(1067)
<223> OTHER INFORMATION: n is a, c, g, or t

<400> SEQUENCE: 8
```

| | | | | |
|---|---|---|---|---|
| aaagatgggt | ggagggactg | gggaaaggct | gtttactccc | tcctgtctag tcggcttggt | 60 |
| cccctttaggg | gtccggatat | ctttggtgac | ttgtccactc | cagtgtggca tcatgtggca | 120 |
| gctgctcctc | ccaactgctc | tgctacttct | aggtaagtag | gatctccctg gttgagggag | 180 |
| aagtttgaga | tgccttgggt | tcagcagaga | nnnnnnnnnn | nnnnnnnnnn nnnnnnnnnn | 240 |
| nnnnnnnnnn | nnnnnnnnnn | nnnnnnnnnn | nnnnnnnnnn | nnnnnnnnnn nnnnnnnnnn | 300 |
| nnnnnnnnnn | aagaggcatg | aacagtggaa | gaccagagag | caggtagcaa ggtttccacc | 360 |
| agaaacatcc | tgattcttgg | gaaaattggg | ctcctggggc | agaggagggc aggggagttt | 420 |
| taaactcact | ctatgttcta | atcactctga | tctctgcccc | tactcaatat ttgatttact | 480 |
| cttttttctt | gcagtttcag | ctggcatgcg | gactggtgag | tcagcttcat ggtcttnnnn | 540 |
| nnnnnnnnnn | nnnnnnnnnn | nnnnnnnnnn | nnnnnnnnnn | nnnnnnnnnn nnnnnnnnnn | 600 |
| nnnnnnnnnn | nnnnnnnnnn | nnnnnnnnnn | nnnnnncact | gagagctgag ctcccgggcc | 660 |
| tggggtgtct | ctgtgtcttt | caggctggct | gttgctccag | gcccctcggt gggtgttcaa | 720 |
| ggaggaagac | cctattcacc | tgaggtgtca | cagctggaag | aacactgctc tgcataaggt | 780 |
| cacatattta | cagaatggca | aagacaggaa | gtattttcat | cataattctg acttccacat | 840 |
| tccaaaagcc | acactcaaag | atagcggctc | ctacttctgc | aggggcttg ttgggagtaa | 900 |
| aaatgtgtct | tcagagactg | tgaacatcac | catcactcaa | ggtgagacat gtgccaccct | 960 |
| ggaatgcnnn | nnnnnnnnnn | nnnnnnnnnn | nnnnnnnnnn | nnnnnnnnnn nnnnnnnnnn | 1020 |
| nnnnnnnnnn | nnnnnnnnnn | nnnnnnnnnn | nnnnnnnnnn | nnnnnntttt tcatctctc | 1080 |
| cacttctcct | aataggtttg | gcagtgtcaa | ccatctcatc | attctctcca cctgggtacc | 1140 |
| aagtctcttt | ctgcttggtg | atggtactcc | tttttgcagt | ggacacagga ctatatttct | 1200 |
| ctgtgaagac | aaacatttga | agctcaacaa | gagactggaa | ggaccataaa cttaaatgga | 1260 |
| gaaaggaccc | tcaagacaaa | tgaccccat | cccatgggag | taataagagc agtggcagca | 1320 |
| gcatctctga | acatttctct | ggatttgcaa | ccccatcatc | ctcaggcctc tctacaagca | 1380 |
| gcaggaaaca | tagaactcag | agccagatcc | tttatccaac | tctcgatttt tccttggtct | 1440 |
| ccagtggaag | ggaaaagccc | atgatcttca | agcaggaag | ccccagtgag tagctgcatt | 1500 |
| cctagaaatt | gaagtttcag | agctacacaa | acactttttc | tgtcccaacc attccctcac | 1560 |
| agtaaaacaa | caatacaggc | tagggatggt | aatcctttaa | acatacaaaa attgctcgta | 1620 |
| ttataaatta | cccagtttag | accggaaaaa | agaaaataat | tattcctaaa caaatggata | 1680 |

```
agtagaatta atgattgagg caggacccta cagagtgtgg gaactgctgg ggatctagag    1740
aattcagtgg gaccaatgaa agcatggctg agaaatagca gggtagtcca ggagagtcta    1800
agggaggtgt tcccatctga gcccagagat aagggtgtct tcctagaaca ttagccgtag    1860
tggaattaac aggaaatcat gagggtgacg tagaattgag tcttccaggg gactctatca    1920
gaactggacc atttccaagt atataacgat gagccctcta atgctaggag tagcaaatgg    1980
tcctaggaag gggactgagg attggggtgg ggtggggtg gaaagaaag tacagaacaa     2040 accctgtgtc actgtcccaa gttaagctaa gtgaacagaa ctatctcagc atcagaatga    2100
gaaagcctga aagaaagaa ccaaccacaa gcacacagga aggaaagcgc aggaggtgaa     2160
aatgctttct tggccagggt agtaagaatt agaggttaat gcagggactg taaaaccacc    2220
ttttctgctt caatgtctag ttcctgtata gctttgttca ttgcatttat taaacaaatg    2280
ttgtataacc aatactaaat gtactactga gcttcactga gttacgctgt gaaactttca    2340
aatccttctt catgtcagtt ccaatgaggt ggggatggag aagacaattg ttgcttatga    2400
aaaaaagctt tagctgtctc tgttttgtaa gctttcagtg caacatttct tggttccaat    2460
aaagcatttt aca                                                      2473
```

<210> SEQ ID NO 9
<211> LENGTH: 370
<212> TYPE: PRT
<213> ORGANISM: Homo sapiens
<220> FEATURE:
<221> NAME/KEY: MISC_FEATURE
<223> OTHER INFORMATION: 2B4

<400> SEQUENCE: 9

```
Met Leu Gly Gln Val Val Thr Leu Ile Leu Leu Leu Leu Lys Val
1               5                   10                  15

Tyr Gln Gly Lys Gly Cys Gln Gly Ser Ala Asp His Val Val Ser Ile
                20                  25                  30

Ser Gly Val Pro Leu Gln Leu Gln Pro Asn Ser Ile Gln Thr Lys Val
            35                  40                  45

Asp Ser Ile Ala Trp Lys Lys Leu Leu Pro Ser Gln Asn Gly Phe His
50                  55                  60

His Ile Leu Lys Trp Glu Asn Gly Ser Leu Pro Ser Asn Thr Ser Asn
65                  70                  75                  80

Asp Arg Phe Ser Phe Ile Val Lys Asn Leu Ser Leu Leu Ile Lys Ala
                85                  90                  95

Ala Gln Gln Gln Asp Ser Gly Leu Tyr Cys Leu Glu Val Thr Ser Ile
                100                 105                 110

Ser Gly Lys Val Gln Thr Ala Thr Phe Gln Val Phe Val Phe Glu Ser
            115                 120                 125

Leu Leu Pro Asp Lys Val Glu Lys Pro Arg Leu Gln Gly Gln Gly Lys
130                 135                 140

Ile Leu Asp Arg Gly Arg Cys Gln Val Ala Leu Ser Cys Leu Val Ser
145                 150                 155                 160

Arg Asp Gly Asn Val Ser Tyr Ala Trp Tyr Arg Gly Ser Lys Leu Ile
                165                 170                 175

Gln Thr Ala Gly Asn Leu Thr Tyr Leu Asp Glu Glu Val Asp Ile Asn
                180                 185                 190

Gly Thr His Thr Tyr Thr Cys Asn Val Ser Asn Pro Val Ser Trp Glu
            195                 200                 205

Ser His Thr Leu Asn Leu Thr Gln Asp Cys Gln Asn Ala His Gln Glu
```

```
              210                 215                 220
Phe Arg Phe Trp Pro Phe Leu Val Ile Ile Val Ile Leu Ser Ala Leu
225                 230                 235                 240

Phe Leu Gly Thr Leu Ala Cys Phe Cys Val Trp Arg Arg Lys Arg Lys
                245                 250                 255

Glu Lys Gln Ser Glu Thr Ser Pro Lys Glu Phe Leu Thr Ile Tyr Glu
            260                 265                 270

Asp Val Lys Asp Leu Lys Thr Arg Arg Asn His Glu Gln Glu Gln Thr
        275                 280                 285

Phe Pro Gly Gly Gly Ser Thr Ile Tyr Ser Met Ile Gln Ser Gln Ser
    290                 295                 300

Ser Ala Pro Thr Ser Gln Glu Pro Ala Tyr Thr Leu Tyr Ser Leu Ile
305                 310                 315                 320

Gln Pro Ser Arg Lys Ser Gly Ser Arg Lys Arg Asn His Ser Pro Ser
                325                 330                 335

Phe Asn Ser Thr Ile Tyr Glu Val Ile Gly Lys Ser Gln Pro Lys Ala
            340                 345                 350

Gln Asn Pro Ala Arg Leu Ser Arg Lys Glu Leu Glu Asn Phe Asp Val
        355                 360                 365

Tyr Ser
    370

<210> SEQ ID NO 10
<211> LENGTH: 279
<212> TYPE: DNA
<213> ORGANISM: Homo sapiens
<220> FEATURE:
<221> NAME/KEY: misc_feature
<223> OTHER INFORMATION: DAP10

<400> SEQUENCE: 10
atgatccatc tgggtcacat cctcttcctg cttttgctcc cagtggctgc agctcagacg    60
actccaggag agagatcatc actccctgcc ttttaccctg gcacttcagg ctcttgttcc   120
ggatgtgggt ccctctctct gccgctcctg gcaggcctcg tggctgctga tgcggtggca   180
tcgctgctca tcgtggggc ggtgttcctg tgcgcacgcc acgccgcag ccccgcccaa    240 gatggcaaag tctacatcaa catgccaggc aggggctga                         279

<210> SEQ ID NO 11
<211> LENGTH: 575
<212> TYPE: DNA
<213> ORGANISM: Homo sapiens
<220> FEATURE:
<221> NAME/KEY: misc_feature
<223> OTHER INFORMATION: DAP12

<400> SEQUENCE: 11
agacttcctc cttcacttgc ctggacgctg cgccacatcc caccggccct tacactgtgg    60
tgtccagcag catccggctt catgggggga cttgaaccct gcagcaggct cctgctcctg   120
cctctcctgc tggctgtaag tgattgcagt tgctctacgg tgagcccggg cgtgctggca   180
gggatcgtga tgggagacct ggtgctgaca gtgctcattg ccctggccgt gtacttcctg   240
ggccggctgg tccctcgggg gcgagggggct gcggaggcag cgacccggaa acagcgtatc   300
actgagaccg agtcgcctta tcaggagctc cagggtcaga ggtcggatgt ctacagcgac   360
ctcaacacac agaggccgta ttacaaatga gcccgaatca tgcagtcag caacatgata   420 cctggatcca gccattcctg aagcccaccc tgcacctcat tccaactcct accgcgatac   480
```

```
agacccacag agtgccatcc ctgagagacc agaccgctcc ccaatactct cctaaaataa    540
acatgaagca caaaaacaaa aaaaaaaaaa aaaaa                                575

<210> SEQ ID NO 12
<211> LENGTH: 126
<212> TYPE: DNA
<213> ORGANISM: Homo sapiens
<220> FEATURE:
<221> NAME/KEY: misc_feature
<223> OTHER INFORMATION: 4-1BB

<400> SEQUENCE: 12
aaacggggca gaaagaaact cctgtatata ttcaaacaac catttatgag accagtacaa     60
actactcaag aggaagatgg ctgtagctgc cgatttccag aagaagaaga aggaggatgt    120
gaactg                                                               126

<210> SEQ ID NO 13
<211> LENGTH: 339
<212> TYPE: DNA
<213> ORGANISM: Homo sapiens
<220> FEATURE:
<221> NAME/KEY: misc_feature
<223> OTHER INFORMATION: CD3-zeta

<400> SEQUENCE: 13
agagtgaagt tcagcaggag cgcagacgcc cccgcgtacc agcagggcca gaaccagctc     60
tataacgagc tcaatctagg acgaagagag gagtacgatg ttttggacaa gagacgtggc    120
cgggaccctg agatgggggg aaagccgaga aggaagaacc ctcaggaagg cctgtacaat    180
gaactgcaga aagataagat ggcggaggcc tacagtgaga ttgggatgaa aggcgagcgc    240
cggaggggca aggggcacga tggcctttac cagggtctca gtacagccac caaggacacc    300
tacgacgccc ttcacatgca ggccctgccc cctcgctaa                           339

<210> SEQ ID NO 14
<211> LENGTH: 6
<212> TYPE: PRT
<213> ORGANISM: Homo sapiens
<220> FEATURE:
<221> NAME/KEY: MISC_FEATURE
<223> OTHER INFORMATION: Canonical hemi-tam
<220> FEATURE:
<221> NAME/KEY: MISC_FEATURE
<222> LOCATION: (4)..(5)
<223> OTHER INFORMATION: X = any amino acid

<400> SEQUENCE: 14

Asp Gly Tyr Xaa Xaa Leu
1               5

<210> SEQ ID NO 15
<211> LENGTH: 6
<212> TYPE: PRT
<213> ORGANISM: Homo sapiens
<220> FEATURE:
<221> NAME/KEY: MISC_FEATURE
<223> OTHER INFORMATION: ITSM Motif
<220> FEATURE:
<221> NAME/KEY: MISC_FEATURE
<222> LOCATION: (1)..(1)
<223> OTHER INFORMATION: N = S or T
<220> FEATURE:
<221> NAME/KEY: MISC_FEATURE
<222> LOCATION: (2)..(2)
<223> OTHER INFORMATION: x = any amino acid
```

```
<220> FEATURE:
<221> NAME/KEY: MISC_FEATURE
<222> LOCATION: (4)..(5)
<223> OTHER INFORMATION: x = any amino acid
<220> FEATURE:
<221> NAME/KEY: MISC_FEATURE
<222> LOCATION: (6)..(6)
<223> OTHER INFORMATION: N = L or I

<400> SEQUENCE: 15

Asn Xaa Tyr Xaa Xaa Asn
1               5

<210> SEQ ID NO 16
<211> LENGTH: 614
<212> TYPE: DNA
<213> ORGANISM: Homo sapiens
<220> FEATURE:
<221> NAME/KEY: misc_feature
<223> OTHER INFORMATION: Membrane-bound IL15

<400> SEQUENCE: 16
atggccttac cagtgaccgc cttgctcctg ccgctggcct tgctgctcca cgccgccagg     60
ccgaactggg tgaatgtaat aagtgatttg aaaaaaattg aagatcttat tcaatctatg    120
catattgatg ctactttata tacggaaagt gatgttcacc ccagttgcaa agtaacagca    180
atgaagtgct ttctcttgga gttacaagtt atttcacttg agtccggaga tgcaagtatt    240
catgatacag tagaaaatct gatcatccta gcaaacaaca gtttgtcttc aatgggaat     300 gtaacagaat ctggatgcaa agaatgtgag gaactgagg aaaaaaatat taaagaattt    360
ttgcagagtt ttgtacatat tgtccaaatg ttcatcaaca cttctaccac gacgccagcg    420
ccgcgaccac caacaccggc gcccaccatc gcgtcgcagc ccctgtccct gcgcccagag    480
gcgtgccggc cagcggcggg gggcgcagtg cacacgaggg ggctggactt cgcctgtgat    540
atctacatct gggcgccctt ggccgggact tgtggggtcc ttctcctgtc actggtatca    600 cccttactg ctaa                                                       614

<210> SEQ ID NO 17
<211> LENGTH: 204
<212> TYPE: PRT
<213> ORGANISM: Homo sapiens
<220> FEATURE:
<221> NAME/KEY: MISC_FEATURE
<223> OTHER INFORMATION: Membrane-bound IL15

<400> SEQUENCE: 17

Met Ala Leu Pro Val Thr Ala Leu Leu Leu Pro Leu Ala Leu Leu Leu
1               5                   10                  15

His Ala Ala Arg Pro Asn Trp Val Asn Val Ile Ser Asp Leu Lys Lys
            20                  25                  30

Ile Glu Asp Leu Ile Gln Ser Met His Ile Asp Ala Thr Leu Tyr Thr
        35                  40                  45

Glu Ser Asp Val His Pro Ser Cys Lys Val Thr Ala Met Lys Cys Phe
    50                  55                  60

Leu Leu Glu Leu Gln Val Ile Ser Leu Glu Ser Gly Asp Ala Ser Ile
65                  70                  75                  80

His Asp Thr Val Glu Asn Leu Ile Ile Leu Ala Asn Asn Ser Leu Ser
                85                  90                  95

Ser Asn Gly Asn Val Thr Glu Ser Gly Cys Lys Glu Cys Glu Glu Leu
            100                 105                 110
```

Glu Glu Lys Asn Ile Lys Glu Phe Leu Gln Ser Phe Val His Ile Val
            115                 120                 125
Gln Met Phe Ile Asn Thr Ser Thr Thr Thr Pro Ala Pro Arg Pro Pro
        130                 135                 140
Thr Pro Ala Pro Thr Ile Ala Ser Gln Pro Leu Ser Leu Arg Pro Glu
145                 150                 155                 160
Ala Cys Arg Pro Ala Ala Gly Gly Ala Val His Thr Arg Gly Leu Asp
                165                 170                 175
Phe Ala Cys Asp Ile Tyr Ile Trp Ala Pro Leu Ala Gly Thr Cys Gly
            180                 185                 190
Val Leu Leu Leu Ser Leu Val Ile Thr Leu Tyr Cys
            195                 200

<210> SEQ ID NO 18
<211> LENGTH: 1140
<212> TYPE: DNA
<213> ORGANISM: Homo sapiens
<220> FEATURE:
<221> NAME/KEY: misc_feature
<223> OTHER INFORMATION: NKG2D/CD8a/4-1BB/CD3z
<220> FEATURE:
<221> NAME/KEY: misc_feature
<223> OTHER INFORMATION: NKG2D/CD8a/4-1BB/CD3z (aka NK16)

<400> SEQUENCE: 18

```
atggccttac cagtgaccgc cttgctcctg ccgctggcct tgctgctcca cgccgccagg      60
ccgttattca accaagaagt tcaaattccc ttgaccgaaa gttactgtgg cccatgtcct     120
aaaaactgga tgttacaa aataactgc taccaatttt ttgatgagag taaaaactgg        180
tatgagagcc aggcttcttg tatgtctcaa atgccagcc ttctgaaagt atacagcaaa      240
gaggaccagg atttacttaa actggtgaag tcatatcatt ggatgggact agtacacatt     300
ccaacaaatg gatcttggca gtgggaagat ggctccattc tctcacccaa cctactaaca     360
ataattgaaa tgcagaaggg agactgtgca ctctatgcct cgagctttaa aggctatata     420
gaaaactgtt caactccaaa tacatacatc tgcatgcaaa ggactgtgac cacgacgcca     480
gcgccgcgac caccaacacc ggcgcccacc atcgcgtcgc agcccctgtc cctgcgccca     540
gaggcgtgcc ggccagcggc gggggggcgca gtgcacacga gggggctgga cttcgcctgt     600
gatatctaca tctgggcgcc cttggccggg acttgtgggg tccttctcct gtcactggtt     660
atcacccttt actgcaaacg gggcagaaag aaactcctgt atatattcaa caaccatttt     720
atgagaccag tacaaactac tcaagaggaa gatggctgta gctgccgatt tccagaagaa     780
gaagaaggag gatgtgaact gagagtgaag ttcagcagga gcgcagacgc ccccgcgtac     840
cagcagggcc agaaccagct ctataacgag ctcaatctag gacgaagaga ggagtacgat     900
gttttggaca gagacgtggg ccgggaccct gagatggggg gaaagccgag aaggaagaac     960
cctcaggaag gcctgtacaa tgaactgcag aaagataaga tggcggaggc ctacagtgag    1020
attgggatga aggcgagcg ccggaggggc aaggggcacg atggccttta ccagggtctc    1080
agtacagcca ccaaggacac ctacgacgcc ttcacatgc aggccctgcc cctcgctaa     1140
```

<210> SEQ ID NO 19
<211> LENGTH: 379
<212> TYPE: PRT
<213> ORGANISM: Homo sapiens
<220> FEATURE:
<221> NAME/KEY: MISC_FEATURE
<223> OTHER INFORMATION: Amino acid sequence of NKG2D/CD8a/4-1BB/CD3z
<220> FEATURE:

```
<221> NAME/KEY: MISC_FEATURE
<223> OTHER INFORMATION: Amino acid sequence of NKG2D/CD8a/4-1BB/CD3z
      (aka NK16)

<400> SEQUENCE: 19

Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Tyr His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Tyr Ile Glu Asn Cys Ser
    130                 135                 140

Thr Pro Asn Thr Tyr Ile Cys Met Gln Arg Thr Val Thr Thr Thr Pro
145                 150                 155                 160

Ala Pro Arg Pro Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
            180                 185                 190

Thr Arg Gly Leu Asp Phe Ala Cys Asp Ile Tyr Ile Trp Ala Pro Leu
        195                 200                 205

Ala Gly Thr Cys Gly Val Leu Leu Leu Ser Leu Val Ile Thr Leu Tyr
    210                 215                 220

Cys Lys Arg Gly Arg Lys Lys Leu Leu Tyr Ile Phe Lys Gln Pro Phe
225                 230                 235                 240

Met Arg Pro Val Gln Thr Thr Gln Glu Glu Asp Gly Cys Ser Cys Arg
                245                 250                 255

Phe Pro Glu Glu Glu Glu Gly Gly Cys Glu Leu Arg Val Lys Phe Ser
            260                 265                 270

Arg Ser Ala Asp Ala Pro Ala Tyr Gln Gln Gly Gln Asn Gln Leu Tyr
        275                 280                 285

Asn Glu Leu Asn Leu Gly Arg Arg Glu Glu Tyr Asp Val Leu Asp Lys
    290                 295                 300

Arg Arg Gly Arg Asp Pro Glu Met Gly Gly Lys Pro Arg Arg Lys Asn
305                 310                 315                 320

Pro Gln Glu Gly Leu Tyr Asn Glu Leu Gln Lys Asp Lys Met Ala Glu
                325                 330                 335

Ala Tyr Ser Glu Ile Gly Met Lys Gly Glu Arg Arg Arg Gly Lys Gly
            340                 345                 350

His Asp Gly Leu Tyr Gln Gly Leu Ser Thr Ala Thr Lys Asp Thr Tyr
        355                 360                 365

Asp Ala Leu His Met Gln Ala Leu Pro Pro Arg
    370                 375
```

```
<210> SEQ ID NO 20
<211> LENGTH: 46
<212> TYPE: PRT
<213> ORGANISM: Homo sapiens
<220> FEATURE:
<221> NAME/KEY: MISC_FEATURE
<223> OTHER INFORMATION: Amino acid for NCR1 TM/IC

<400> SEQUENCE: 20

Met Gly Leu Ala Phe Leu Val Leu Val Ala Leu Val Trp Phe Leu Val
1               5                   10                  15

Glu Asp Trp Leu Ser Arg Lys Arg Thr Arg Glu Arg Ala Ser Arg Ala
            20                  25                  30

Ser Thr Trp Glu Gly Arg Arg Leu Asn Thr Gln Thr Leu
        35                  40                  45

<210> SEQ ID NO 21
<211> LENGTH: 276
<212> TYPE: PRT
<213> ORGANISM: Homo sapiens
<220> FEATURE:
<221> NAME/KEY: MISC_FEATURE
<223> OTHER INFORMATION: Full length NCR2

<400> SEQUENCE: 21

Met Ala Trp Arg Ala Leu His Pro Leu Leu Leu Leu Leu Leu Leu Phe
1               5                   10                  15

Pro Gly Ser Gln Ala Gln Ser Lys Ala Gln Val Leu Gln Ser Val Ala
            20                  25                  30

Gly Gln Thr Leu Thr Val Arg Cys Gln Tyr Pro Pro Thr Gly Ser Leu
        35                  40                  45

Tyr Glu Lys Lys Gly Trp Cys Lys Glu Ala Ser Ala Leu Val Cys Ile
    50                  55                  60

Arg Leu Val Thr Ser Ser Lys Pro Arg Thr Met Ala Trp Thr Ser Arg
65                  70                  75                  80

Phe Thr Ile Trp Asp Asp Pro Asp Ala Gly Phe Phe Thr Val Thr Met
                85                  90                  95

Thr Asp Leu Arg Glu Glu Asp Ser Gly His Tyr Trp Cys Arg Ile Tyr
            100                 105                 110

Arg Pro Ser Asp Asn Ser Val Ser Lys Ser Val Arg Phe Tyr Leu Val
        115                 120                 125

Val Ser Pro Ala Ser Ala Ser Thr Gln Thr Ser Trp Thr Pro Arg Asp
    130                 135                 140

Leu Val Ser Ser Gln Thr Gln Thr Gln Ser Cys Val Pro Pro Thr Ala
145                 150                 155                 160

Gly Ala Arg Gln Ala Pro Glu Ser Pro Ser Thr Ile Pro Val Pro Ser
                165                 170                 175

Gln Pro Gln Asn Ser Thr Leu Arg Pro Gly Pro Ala Ala Pro Ile Ala
            180                 185                 190

Leu Val Pro Val Phe Cys Gly Leu Leu Val Ala Lys Ser Leu Val Leu
        195                 200                 205

Ser Ala Leu Leu Val Trp Trp Gly Asp Ile Trp Trp Lys Thr Met Met
    210                 215                 220

Glu Leu Arg Ser Leu Asp Thr Gln Lys Ala Thr Cys His Leu Gln Gln
225                 230                 235                 240

Val Thr Asp Leu Pro Trp Thr Ser Val Ser Ser Pro Val Glu Arg Glu
                245                 250                 255

Ile Leu Tyr His Thr Val Ala Arg Thr Lys Ile Ser Asp Asp Asp Asp
```

Glu His Thr Leu
    275

<210> SEQ ID NO 22
<211> LENGTH: 66
<212> TYPE: PRT
<213> ORGANISM: Homo sapiens
<220> FEATURE:
<221> NAME/KEY: MISC_FEATURE
<223> OTHER INFORMATION: NCR3 TM/IC domains

<400> SEQUENCE: 22

Ala Gly Thr Val Leu Leu Leu Arg Ala Gly Phe Tyr Ala Val Ser Phe
1               5                   10                  15

Leu Ser Val Ala Val Gly Ser Thr Val Tyr Tyr Gln Gly Lys Cys Leu
            20                  25                  30

Thr Trp Lys Gly Pro Arg Arg Gln Leu Pro Ala Val Val Pro Ala Pro
        35                  40                  45

Leu Pro Pro Pro Cys Gly Ser Ser Ala His Leu Leu Pro Pro Val Pro
    50                  55                  60

Gly Gly
65

<210> SEQ ID NO 23
<211> LENGTH: 741
<212> TYPE: DNA
<213> ORGANISM: Homo sapiens
<220> FEATURE:
<221> NAME/KEY: misc_feature
<223> OTHER INFORMATION: NKG2D/CD16

<400> SEQUENCE: 23 atggcctttac cagtgaccgc cttgctcctg ccgctggcct tgctgctcca cgccgcccgc      60
cccctgttca accaggaagt gcagatcccc ctgaccgagt cctattgtgg cccttgccct     120
aagaattgga tttgctataa aaacaactgc taccagttct ttgacgagtc taagaattgg     180
tatgagtccc aggcctcttg tatgagccag aacgcctctc tgctgaaggt gtacagcaag     240
gaggaccagg atctgctgaa gctggtgaag tcctatcact ggatgggcct ggtgcacatc     300
cccacaaacg gctcttggca gtgggaggac ggctccatcc tgtctcctaa tctgctgacc     360
atcatcgaga tgcagaaggg cgattgcgcc ctgtacgcca gctccttcaa gggctatatc     420
gagaactgca gcacacccaa tacctacatc tgtatgcagc ggacagtgac acaaccccca     480
gcacccaggc cccctacacc tgcaccaacc atcgcaagcc agccactgtc cctgaggcct     540
gaggcatgta ggccagcagc aggaggagca gtgcacacac ggggcctgga cttcgcctgc     600
gatgtgagct tttgtctggt catggtgctg ctgttcgccg tggataccgg cctgtatttt     660
tccgtgaaga caaatatccg gtctagcacc agagactgga aggatcacaa gttcaaatgg     720
aggaaggacc acaggacaa g                                                741

<210> SEQ ID NO 24
<211> LENGTH: 247
<212> TYPE: PRT
<213> ORGANISM: Homo sapiens
<220> FEATURE:
<221> NAME/KEY: MISC_FEATURE
<223> OTHER INFORMATION: NKG2D/CD16

<400> SEQUENCE: 24

| | | | | | | | | | | | | | | | |
|---|---|---|---|---|---|---|---|---|---|---|---|---|---|---|---|
|Met|Ala|Leu|Pro|Val|Thr|Ala|Leu|Leu|Leu|Pro|Leu|Ala|Leu|Leu|Leu|
|1| | | |5| | | | |10| | | | |15| |

His Ala Ala Arg Pro Leu Phe Asn Gln Glu Val Gln Ile Pro Leu Thr
         20                  25                30

Glu Ser Tyr Cys Gly Pro Cys Pro Lys Asn Trp Ile Cys Tyr Lys Asn
         35                  40              45

Asn Cys Tyr Gln Phe Phe Asp Glu Ser Lys Asn Trp Tyr Glu Ser Gln
50                 55                60

Ala Ser Cys Met Ser Gln Asn Ala Ser Leu Leu Lys Val Tyr Ser Lys
65               70              75              80

Glu Asp Gln Asp Leu Leu Lys Leu Val Lys Ser Tyr His Trp Met Gly
         85                  90              95

Leu Val His Ile Pro Thr Asn Gly Ser Trp Gln Trp Glu Asp Gly Ser
        100                105            110

Ile Leu Ser Pro Asn Leu Leu Thr Ile Ile Glu Met Gln Lys Gly Asp
        115                120            125

Cys Ala Leu Tyr Ala Ser Ser Phe Lys Gly Tyr Ile Glu Asn Cys Ser
        130                135            140

Thr Pro Asn Thr Tyr Ile Cys Met Gln Arg Thr Val Thr Thr Thr Pro
145                150              155            160

Ala Pro Arg Pro Pro Thr Pro Ala Pro Thr Ile Ala Ser Gln Pro Leu
        165                170            175

Ser Leu Arg Pro Glu Ala Cys Arg Pro Ala Ala Gly Gly Ala Val His
        180                185            190

Thr Arg Gly Leu Asp Phe Ala Cys Asp Val Ser Phe Cys Leu Val Met
        195                200            205

Val Leu Leu Phe Ala Val Asp Thr Gly Leu Tyr Phe Ser Val Lys Thr
        210                215            220

Asn Ile Arg Ser Ser Thr Arg Asp Trp Lys Asp His Lys Phe Lys Trp
225                230              235            240

Arg Lys Asp Pro Gln Asp Lys
        245

<210> SEQ ID NO 25
<211> LENGTH: 870
<212> TYPE: DNA
<213> ORGANISM: Homo sapiens
<220> FEATURE:
<221> NAME/KEY: misc_feature
<223> OTHER INFORMATION: CD8/NKG2DOpt/CD8a/CD16 TM/IC/4-1BB

<400> SEQUENCE: 25

```
atggctctgc ccgtcaccgc actgctgctg cctctggctc tgctgctgca cgccgcacga      60
ccactgttca tcaggaagt ccagatcccc ctgacagagt cttactgcgg cccatgtccc     120
aagaactgga tctgctacaa gaacaattgt tatcagttct ttgacgagag caagaactgg     180
tatgagtccc aggcctcttg catgagccag aatgcctctc tgctgaaggt gtacagcaag     240
gaggaccagg atctgctgaa gctggtgaag tcctatcact ggatgggcct ggtgcacatc     300
cctacaaaacg gctcttggca gtgggaggac ggctccatcc tgtctccaaa tctgctgacc     360
atcatcgaga tgcagaaggg cgattgcgcc ctgtacgcca gctccttcaa gggctatatc     420
gagaactgct ccacacccaa tacctacatc tgtatgcaga ggaccgtgac cacaaccct      480
gcaccacgcc ccctacacc agcacctacc atcgcaagcc agcctctgtc cctgcggcca     540
gaggcatgta gaccagcagc aggaggagca gtgcacacaa gaggcctgga cttcgcctgc     600
```

```
gatgtgagct tttgtctggt catggtgctg ctgttcgccg tggataccgg cctgtacttt    660
tccgtgaaga caaatatcag gtctagcacc cgcgactgga aggatcacaa gtttaagtgg    720
cggaaggacc ctcaggataa gaagcggggc agaaagaagc tgctgtatat cttcaagcag    780
cccttcatgc ggcccgtgca gacaacccag gaggaagacg gctgctcatg tagatttcct    840
gaagaagaag aaggggggctg tgaactgtaa                                     870
```

<210> SEQ ID NO 26
<211> LENGTH: 289
<212> TYPE: PRT
<213> ORGANISM: Homo sapiens
<220> FEATURE:
<221> NAME/KEY: MISC_FEATURE
<223> OTHER INFORMATION: CD8/NKG2DOpt/CD8a/CD16 TM/IC/4-1BB

<400> SEQUENCE: 26

```
Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Tyr His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Tyr Ile Glu Asn Cys Ser
    130                 135                 140

Thr Pro Asn Thr Tyr Ile Cys Met Gln Arg Thr Val Thr Thr Thr Pro
145                 150                 155                 160

Ala Pro Arg Pro Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
            180                 185                 190

Thr Arg Gly Leu Asp Phe Ala Cys Asp Val Ser Phe Cys Leu Val Met
        195                 200                 205

Val Leu Leu Phe Ala Val Asp Thr Gly Leu Tyr Phe Ser Val Lys Thr
    210                 215                 220

Asn Ile Arg Ser Ser Thr Arg Asp Trp Lys Asp His Lys Phe Lys Trp
225                 230                 235                 240

Arg Lys Asp Pro Gln Asp Lys Lys Arg Gly Lys Lys Leu Leu Tyr
                245                 250                 255

Ile Phe Lys Gln Pro Phe Met Arg Pro Val Gln Thr Thr Gln Glu Glu
            260                 265                 270

Asp Gly Cys Ser Cys Arg Phe Pro Glu Glu Glu Glu Gly Gly Cys Glu
        275                 280                 285

Leu
```

<210> SEQ ID NO 27

-continued

```
<211> LENGTH: 741
<212> TYPE: DNA
<213> ORGANISM: Homo sapiens
<220> FEATURE:
<221> NAME/KEY: misc_feature
<223> OTHER INFORMATION: NKG2D/NCR1

<400> SEQUENCE: 27
atggccttac cagtgaccgc cttgctcctg ccgctggcct tgctgctcca cgccgcccgc     60
cctctgttca accaggaagt gcagatccct ctgaccgaaa gctattgcgg accttgccct    120
aagaattgga tttgctataa aaacaactgc taccagttct ttgacgagtc taagaattgg    180
tatgagtctc aggccagctg tatgtcccag aacgcctctc tgctgaaggt gtacagcaag    240
gaggaccagg atctgctgaa gctggtgaag tcctatcact ggatgggcct ggtgcacatc    300
cccacaaacg ctcttggca gtgggaggac ggctctatcc tgagccctaa tctgctgacc    360
atcatcgaga tgcagaaggg cgattgcgcc ctgtacgcca gctccttcaa gggctatatc    420
gagaactgca gcacacccaa tacctacatc tgtatgcaga ggacagtgac cacaacccca    480
gcaccccgcc ccctacacc tgcaccaacc atcgcaagcc agccactgtc cctgcggcct    540
gaggcctgca gaccagcagc aggaggagca gtgcacaccc ggggcctgga cttcgcctgt    600
gatatgggcc tggcctttct ggtgctggtg gccctggtgt ggtttctggt ggaggattgg    660
ctgtcccgga gagaacaag ggagagggcc tcccgggcct ctacctggga aggaagaagg    720
agactgaaca cccagacact g                                              741

<210> SEQ ID NO 28
<211> LENGTH: 247
<212> TYPE: PRT
<213> ORGANISM: Homo sapiens
<220> FEATURE:
<221> NAME/KEY: MISC_FEATURE
<223> OTHER INFORMATION: NKG2D/NCR1

<400> SEQUENCE: 28

Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Tyr His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Tyr Ile Glu Asn Cys Ser
    130                 135                 140

Thr Pro Asn Thr Tyr Ile Cys Met Gln Arg Thr Val Thr Thr Thr Pro
145                 150                 155                 160

Ala Pro Arg Pro Pro Thr Pro Ala Pro Thr Ile Ala Ser Gln Pro Leu
                165                 170                 175
```

```
Ser Leu Arg Pro Glu Ala Cys Arg Pro Ala Ala Gly Gly Ala Val His
            180                 185                 190

Thr Arg Gly Leu Asp Phe Ala Cys Asp Met Gly Leu Ala Phe Leu Val
        195                 200                 205

Leu Val Ala Leu Val Trp Phe Leu Val Glu Asp Trp Leu Ser Arg Lys
    210                 215                 220

Arg Thr Arg Glu Arg Ala Ser Arg Ala Ser Thr Trp Glu Gly Arg Arg
225                 230                 235                 240

Arg Leu Asn Thr Gln Thr Leu
                245
```

<210> SEQ ID NO 29
<211> LENGTH: 801
<212> TYPE: DNA
<213> ORGANISM: Homo sapiens
<220> FEATURE:
<221> NAME/KEY: misc_feature
<223> OTHER INFORMATION: NKG2D/NCR3

<400> SEQUENCE: 29

```
atggccttac cagtgaccgc cttgctcctg ccgctggcct tgctgctcca cgccgccaga    60
cccctgttca accaggaggt gcagattccc ctgacagaaa gctattgtgg cccttgccct   120
aaaaattgga tttgctataa aaacaactgc taccagttct ttgacgagtc taagaattgg   180
tatgagtctc aggccagctg tatgtcccag aacgcctctc tgctgaaggt gtacagcaag   240
gaggaccagg atctgctgaa gctggtgaag tcctatcact ggatgggcct ggtgcacatc   300
cctacaaacg gctcttggca gtgggaggac ggctctatcc tgagcccaaa tctgctgacc   360
atcatcgaga tgcagaaggg cgattgcgcc ctgtacgcca gctccttcaa gggctatatc   420
gagaactgca gcacacccaa tacctacatc tgtatgcagc ggacagtgac cacaacccca   480
gcacccagac ccctacacc tgcaccaacc atcgccagcc agccactgtc cctgaggccc   540
gaggcatgca ggcctgcagc aggaggcgcc gtgcacacaa ggggcctgga ctttgcctgt   600
gatgcaggaa ccgtgctgct gctgagagca ggcttctatg ccgtgtcctt tctgtctgtg   660
gccgtgggct ccacagtgta ctatcagggc aagtgcctga cctggaaggg cccacggaga   720
cagctgcccg ccgtggtgcc cgcccctctg ccacccccct tgtggcagta gcgcccacctg   780
ctgccacccg tgcccggagg a                                               801
```

<210> SEQ ID NO 30
<211> LENGTH: 267
<212> TYPE: PRT
<213> ORGANISM: Homo sapiens
<220> FEATURE:
<221> NAME/KEY: MISC_FEATURE
<223> OTHER INFORMATION: NKG2D/NCR3

<400> SEQUENCE: 30

```
Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80
```

```
Glu Asp Gln Asp Leu Leu Lys Leu Val Lys Ser Tyr His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Tyr Ile Glu Asn Cys Ser
    130                 135                 140

Thr Pro Asn Thr Tyr Ile Cys Met Gln Arg Thr Val Thr Thr Thr Pro
145                 150                 155                 160

Ala Pro Arg Pro Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
            180                 185                 190

Thr Arg Gly Leu Asp Phe Ala Cys Asp Ala Gly Thr Val Leu Leu Leu
        195                 200                 205

Arg Ala Gly Phe Tyr Ala Val Ser Phe Leu Ser Val Ala Val Gly Ser
    210                 215                 220

Thr Val Tyr Tyr Gln Gly Lys Cys Leu Thr Trp Lys Gly Pro Arg Arg
225                 230                 235                 240

Gln Leu Pro Ala Val Val Pro Ala Pro Leu Pro Pro Cys Gly Ser
                245                 250                 255

Ser Ala His Leu Leu Pro Pro Val Pro Gly Gly
                260                 265

<210> SEQ ID NO 31
<211> LENGTH: 6
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: N is an integer indicating the number of GGGGS
      repeated

<400> SEQUENCE: 31

Gly Gly Gly Gly Ser Asn
1               5

<210> SEQ ID NO 32
<211> LENGTH: 60
<212> TYPE: PRT
<213> ORGANISM: Homo sapiens
<220> FEATURE:
<221> NAME/KEY: MISC_FEATURE
<223> OTHER INFORMATION: GS3/CD8a

<400> SEQUENCE: 32

Gly Gly Gly Gly Ser Gly Gly Gly Ser Gly Gly Gly Gly Ser Thr
1               5                   10                  15

Thr Thr Pro Ala Pro Arg Pro Pro Thr Pro Ala Pro Thr Ile Ala Ser
            20                  25                  30

Gln Pro Leu Ser Leu Arg Pro Glu Ala Cys Arg Pro Ala Ala Gly Gly
        35                  40                  45

Ala Val His Thr Arg Gly Leu Asp Phe Ala Cys Asp
    50                  55                  60

<210> SEQ ID NO 33
<211> LENGTH: 45
```

```
<212> TYPE: PRT
<213> ORGANISM: Homo sapiens
<220> FEATURE:
<221> NAME/KEY: MISC_FEATURE
<223> OTHER INFORMATION: GS9

<400> SEQUENCE: 33

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
                20                  25                  30

Gly Gly Ser Gly Gly Gly Gly Ser Gly Gly Gly Gly Ser
        35                  40                  45

<210> SEQ ID NO 34
<211> LENGTH: 15
<212> TYPE: PRT
<213> ORGANISM: Homo sapiens
<220> FEATURE:
<221> NAME/KEY: MISC_FEATURE
<223> OTHER INFORMATION: GS3

<400> SEQUENCE: 34

Gly Gly Gly Gly Ser Gly Gly Gly Gly Ser Gly Gly Gly Gly Ser
1               5                   10                  15

<210> SEQ ID NO 35
<211> LENGTH: 120
<212> TYPE: PRT
<213> ORGANISM: Homo sapiens
<220> FEATURE:
<221> NAME/KEY: MISC_FEATURE
<223> OTHER INFORMATION: 2B4 ICR

<400> SEQUENCE: 35

Trp Arg Arg Lys Arg Lys Glu Lys Gln Ser Glu Thr Ser Pro Lys Glu
1               5                   10                  15

Phe Leu Thr Ile Tyr Glu Asp Val Lys Asp Leu Lys Thr Arg Arg Asn
                20                  25                  30

His Glu Gln Glu Gln Thr Phe Pro Gly Gly Gly Ser Thr Ile Tyr Ser
            35                  40                  45

Met Ile Gln Ser Gln Ser Ser Ala Pro Thr Ser Gln Glu Pro Ala Tyr
        50                  55                  60

Thr Leu Tyr Ser Leu Ile Gln Pro Ser Arg Lys Ser Gly Ser Arg Lys
65              70                  75                  80

Arg Asn His Ser Pro Ser Phe Asn Ser Thr Ile Tyr Glu Val Ile Gly
                85                  90                  95

Lys Ser Gln Pro Lys Ala Gln Asn Pro Ala Arg Leu Ser Arg Lys Glu
            100                 105                 110

Leu Glu Asn Phe Asp Val Tyr Ser
        115                 120

<210> SEQ ID NO 36
<211> LENGTH: 360
<212> TYPE: DNA
<213> ORGANISM: Homo sapiens
<220> FEATURE:
<221> NAME/KEY: misc_feature
<223> OTHER INFORMATION: 2B4 ICR

<400> SEQUENCE: 36
tggaggagga aaaggaagga gaaacagagc gagacctccc ctaaggagtt cctgaccatc    60
```

```
tacgaggacg tgaaggacct gaagaccagg aggaaccacg agcaggaaca gacctttcct    120
ggcggaggca gcaccatcta cagcatgatc cagagccaga gcagcgcccc taccagccaa    180
gagcctgcct acaccctgta cagcctgatc cagcccagca ggaaaagcgg ctccaggaag    240
aggaaccaca gccccagctt caacagcacc atctatgagg tgatcggcaa gagccagccc    300
aaggcccaga ccctgccag gctgtccagg aaggagctgg agaacttcga cgtgtacagc    360
```

<210> SEQ ID NO 37
<211> LENGTH: 38
<212> TYPE: PRT
<213> ORGANISM: Homo sapiens
<220> FEATURE:
<221> NAME/KEY: MISC_FEATURE
<223> OTHER INFORMATION: NKp80 ICR

<400> SEQUENCE: 37

```
Met Gln Asp Glu Asp Gly Tyr Met Thr Leu Asn Val Gln Ser Lys Lys
1               5                   10                  15

Arg Ser Ser Ala Gln Thr Ser Gln Leu Thr Phe Lys Asp Tyr Ser Val
            20                  25                  30

Thr Leu His Trp Tyr Lys
        35
```

<210> SEQ ID NO 38
<211> LENGTH: 114
<212> TYPE: DNA
<213> ORGANISM: Homo sapiens
<220> FEATURE:
<221> NAME/KEY: misc_feature
<223> OTHER INFORMATION: NKp80 ICR

<400> SEQUENCE: 38

```
atgcaggatg aggacggcta tatgaccctg aacgtccagt ccaagaagag gtccagcgct     60
cagaccagcc agctgacctt caaggactac tccgtgaccc tgcactggta caag          114
```

<210> SEQ ID NO 39
<211> LENGTH: 30
<212> TYPE: PRT
<213> ORGANISM: Homo sapiens
<220> FEATURE:
<221> NAME/KEY: MISC_FEATURE
<223> OTHER INFORMATION: B2Ad N-term ECD

<400> SEQUENCE: 39

```
Met Gly Gln Pro Gly Asn Gly Ser Ala Phe Leu Leu Ala Pro Asn Arg
1               5                   10                  15

Ser His Ala Pro Asp His Asp Val Thr Gln Gln Arg Asp Glu
            20                  25                  30
```

<210> SEQ ID NO 40
<211> LENGTH: 90
<212> TYPE: DNA
<213> ORGANISM: Homo sapiens
<220> FEATURE:
<221> NAME/KEY: misc_feature
<223> OTHER INFORMATION: B2 AdR N-term ECD

<400> SEQUENCE: 40

```
atggggcaac ccgggaacgg cagcgccttc ttgctggcac ccaatagaag ccatgcgccg     60
gaccacgacg tcacgcagca aagggacgag                                     90
```

<210> SEQ ID NO 41

```
<211> LENGTH: 33
<212> TYPE: PRT
<213> ORGANISM: Homo sapiens
<220> FEATURE:
<221> NAME/KEY: MISC_FEATURE
<223> OTHER INFORMATION: B2 AdR TM helix

<400> SEQUENCE: 41
```

Val Trp Val Val Gly Met Gly Ile Val Met Ser Leu Ile Val Leu Ala
1               5                   10                  15

Ile Val Phe Gly Asn Val Leu Val Ile Thr Ala Ile Ala Lys Phe Glu
            20                  25                  30

Arg

```
<210> SEQ ID NO 42
<211> LENGTH: 99
<212> TYPE: DNA
<213> ORGANISM: Homo sapiens
<220> FEATURE:
<221> NAME/KEY: misc_feature
<223> OTHER INFORMATION: B2AdR TM helix

<400> SEQUENCE: 42
```

| | | | | | |
|---|---|---|---|---|---|
| gtgtgggtgg | tgggcatggg | catcgtcatg | tctctcatcg | tcctggccat | cgtgtttggc | 60 |
| aatgtgctgg | tcatcacagc | cattgccaag | ttcgagcgt | | | 99 |

```
<210> SEQ ID NO 43
<211> LENGTH: 924
<212> TYPE: DNA
<213> ORGANISM: Homo sapiens
<220> FEATURE:
<221> NAME/KEY: misc_feature
<223> OTHER INFORMATION: NK15_1

<400> SEQUENCE: 43
```

| | | | | | |
|---|---|---|---|---|---|
| gccgccacca | tggctctgcc | cgtcaccgca | ctgctgctgc | ctctggctct | gctgctgcac | 60 |
| gccgcacgac | cactgttcaa | tcaggaagtc | cagatccccc | tgacagagtc | ttactgcggc | 120 |
| ccatgtccca | gaactggat | ctgctacaag | aacaattgtt | atcagttctt | tgacgagagc | 180 |
| aagaactggt | atgagtccca | ggcctcttgc | atgagccaga | tgcctctct | gctgaaggtg | 240 |
| tacagcaagg | aggaccagga | tctgctgaag | ctggtgaagt | cctatcactg | gatgggcctg | 300 |
| gtgcacatcc | ctacaaacgg | ctcttggcag | tgggaggacg | gctccatcct | gtctccaaat | 360 |
| ctgctgacca | tcatcgagat | gcagaagggc | gattgcgccc | tgtacgccag | ctccttcaag | 420 |
| ggctatatcg | agaactgctc | cacacccaat | acctacatct | gtatgcagag | gaccgtgggt | 480 |
| ggcggtggct | cgggcggtgg | tgggtcgggt | ggcggcggat | ctaccacaac | ccctgcacca | 540 |
| cgcccccta | caccagcacc | taccatcgca | agccagcctc | tgtccctgcg | gccagaggca | 600 |
| tgtagaccag | cagcaggagg | agcagtgcac | acaagaggcc | tggacttcgc | ctgcgatgtg | 660 |
| agcttttgtc | tggtcatggt | gctgctgttc | gccgtggata | ccggcctgta | cttttccgtg | 720 |
| aagacaaata | tcaggtctag | cacccgcgac | tggaaggatc | acaagtttaa | gtggcggaag | 780 |
| gaccctcagg | ataagaagcg | gggcagaaag | aagctgctgt | atatcttcaa | gcagcccttc | 840 |
| atgcggcccg | tgcagacaac | ccaggaggaa | gacggctgct | catgtagatt | tcctgaagaa | 900 |
| gaagaagggg | gctgtgaact | gtaa | | | | 924 |

```
<210> SEQ ID NO 44
<211> LENGTH: 789
<212> TYPE: DNA
```

<213> ORGANISM: Homo sapiens
<220> FEATURE:
<221> NAME/KEY: misc_feature
<223> OTHER INFORMATION: NK15_2

<400> SEQUENCE: 44

| | | | | | |
|---|---|---|---|---|---|
| gccgccacca | tggctctgcc | cgtcaccgca | ctgctgctgc | ctctggctct | gctgctgcac | 60 |
| gccgcacgac | cactgttcaa | tcaggaagtc | cagatcccc | tgacagagtc | ttactgcggc | 120 |
| ccatgtccca | agaactggat | ctgctacaag | aacaattgtt | atcagttctt | tgacgagagc | 180 |
| aagaactggt | atgagtccca | ggcctcttgc | atgagccaga | atgcctctct | gctgaaggtg | 240 |
| tacagcaagg | aggaccagga | tctgctgaag | ctggtgaagt | cctatcactg | gatgggcctg | 300 |
| gtgcacatcc | ctacaaacgg | ctcttggcag | tgggaggacg | gctccatcct | gtctccaaat | 360 |
| ctgctgacca | tcatcgagat | gcagaagggc | gattgcgccc | tgtacgccag | ctccttcaag | 420 |
| ggctatatcg | agaactgctc | cacacccaat | acctacatct | gtatgcagag | gaccgtgggt | 480 |
| ggcggtggct | cgggcggtgg | tgggtcgggt | ggcggcggat | ctgtgagctt | ttgtctggtc | 540 |
| atggtgctgc | tgttcgccgt | ggataccggc | ctgtactttt | ccgtgaagac | aaatatcagg | 600 |
| tctagcaccc | gcgactggaa | ggatcacaag | tttaagtggc | ggaaggaccc | tcaggataag | 660 |
| aagcggggca | gaaagaagct | gctgtatatc | ttcaagcagc | ccttcatgcg | gcccgtgcag | 720 |
| acaacccagg | aggaagacgg | ctgctcatgt | agatttcctg | aagaagaaga | agggggctgt | 780 |
| gaactgtaa | | | | | | 789 |

<210> SEQ ID NO 45
<211> LENGTH: 744
<212> TYPE: DNA
<213> ORGANISM: Homo sapiens
<220> FEATURE:
<221> NAME/KEY: misc_feature
<223> OTHER INFORMATION: NK15_3

<400> SEQUENCE: 45

| | | | | | |
|---|---|---|---|---|---|
| gccgccacca | tggctctgcc | cgtcaccgca | ctgctgctgc | ctctggctct | gctgctgcac | 60 |
| gccgcacgac | cactgttcaa | tcaggaagtc | cagatcccc | tgacagagtc | ttactgcggc | 120 |
| ccatgtccca | agaactggat | ctgctacaag | aacaattgtt | atcagttctt | tgacgagagc | 180 |
| aagaactggt | atgagtccca | ggcctcttgc | atgagccaga | atgcctctct | gctgaaggtg | 240 |
| tacagcaagg | aggaccagga | tctgctgaag | ctggtgaagt | cctatcactg | gatgggcctg | 300 |
| gtgcacatcc | ctacaaacgg | ctcttggcag | tgggaggacg | gctccatcct | gtctccaaat | 360 |
| ctgctgacca | tcatcgagat | gcagaagggc | gattgcgccc | tgtacgccag | ctccttcaag | 420 |
| ggctatatcg | agaactgctc | cacacccaat | acctacatct | gtatgcagag | gaccgtggtg | 480 |
| agcttttgtc | tggtcatggt | gctgctgttc | gccgtggata | ccggcctgta | cttttccgtg | 540 |
| aagacaaata | tcaggtctag | cacccgcgac | tggaaggatc | acaagtttaa | gtggcggaag | 600 |
| gaccctcagg | ataagaagcg | gggcagaaag | aagctgctgt | atatcttcaa | gcagcccttc | 660 |
| atgcggcccg | tgcagacaac | ccaggaggaa | gacggctgct | catgtagatt | tcctgaagaa | 720 |
| gaagaagggg | gctgtgaact | gtaa | | | | 744 |

<210> SEQ ID NO 46
<211> LENGTH: 1164
<212> TYPE: DNA
<213> ORGANISM: Homo sapiens
<220> FEATURE:
<221> NAME/KEY: misc_feature

<223> OTHER INFORMATION: NK15_4

<400> SEQUENCE: 46

```
gccgccacca tggccctgcc tgtgacagcc ctgctgctgc ctctggctct gctgctgcac      60
gctgccagac ccttattcaa ccaagaagtt caaattccct tgaccgaaag ttactgtggc     120
ccatgtccta aaaactggat atgttacaaa ataactgct accaattttt tgatgagagt      180
aaaaactggt atgagagcca ggcttcttgt atgtctcaaa atgccagcct tctgaaagta     240
tacagcaaag aggaccagga tttacttaaa ctggtgaagt catatcattg gatgggacta     300
gtacacattc aacaaatgg atcttggcag tgggaagatg gctccattct ctcacccaac      360
ctactaacaa taattgaaat gcagaaggga gactgtgcac tctatgcctc gagctttaaa    420
ggctatatag aaaactgttc aactccaaat acgtacatct gcatgcaaag gactgtgacc    480
acaaccccg ctcccagacc tcctacccct gcccctacaa tcgccagcca gcccctgagc     540
ctgagacccg aagcctgtag acctgctgcc ggaggcgctg tgcacacaag aggcctggac    600
ttcgcctgcg atatctatat ctgggcccct ctggctggaa cctgtggcgt gctgctgctg    660
agcctggtga ttaccaagag gggcaggaag aagctgctgt acatcttcaa gcagcctttc    720
atgaggcccg tgcaaaccac ccaggaggag gacggctgca gctgcagatt ccctgaggag    780
gaggagggcg gatgcgagct gtggaggagg aaaaggaagg agaaacagag cgagacctcc    840
cctaaggagt tcctgaccat ctacgaggac gtgaaggacc tgaagaccag gaggaaccac    900
gagcaggaac agacctttcc tggcggaggc agcaccatct acagcatgat ccagagccag    960
agcagcgccc taccagcca agagcctgcc tacaccctgt acagcctgat ccagcccagc   1020
aggaaaagcg gctccaggaa gaggaaccac agccccagct tcaacagcac catctatgag   1080
gtgatcggca gagccagcc caaggcccag aaccctgcca ggctgtccag gaaggagctg   1140
gagaacttcg acgtgtacag ctga                                         1164
```

<210> SEQ ID NO 47
<211> LENGTH: 1155
<212> TYPE: DNA
<213> ORGANISM: Homo sapiens
<220> FEATURE:
<221> NAME/KEY: misc_feature
<223> OTHER INFORMATION: NK15_5

<400> SEQUENCE: 47

```
gccgccacca tggccctgcc tgtgacagcc ctgctgctgc ctctggctct gctgctgcac      60
gctgccagac ccttattcaa ccaagaagtt caaattccct tgaccgaaag ttactgtggc     120
ccatgtccta aaaactggat atgttacaaa ataactgct accaattttt tgatgagagt      180
aaaaactggt atgagagcca ggcttcttgt atgtctcaaa atgccagcct tctgaaagta     240
tacagcaaag aggaccagga tttacttaaa ctggtgaagt catatcattg gatgggacta     300
gtacacattc aacaaatgg atcttggcag tgggaagatg gctccattct ctcacccaac      360
ctactaacaa taattgaaat gcagaaggga gactgtgcac tctatgcctc gagctttaaa    420
ggctatatag aaaactgttc aactccaaat acgtacatct gcatgcaaag gactgtgatg    480
ggacagcctg gaaacggcag cgccttcctg ctggccccta acagaagcca cgcccccgat    540
cacgatgtga cccagcagag ggacgaggtg tgggtggtgg gcatgggcat cgtgatgagc    600
ctgatcgtgc tggctatcgt gttcggcaac gtgctggtga tcaccgccat cgccaagttc    660
gagaggaaga ggggcaggaa aaagctgctc tacatcttca gcagcccttt catgaggccc   720
```

| | |
|---|---|
| gtgcagacca cccaggaaga ggatggctgc tcctgtaggt ttcccgagga ggaggagggc | 780 |
| ggctgtgagc tgtggaggag aaaaaggaag gagaagcaga gcgagaccag ccccaaggag | 840 |
| ttcctgacca tctacgagga cgtgaaggac ctgaagacca ggaggaacca cgagcaggaa | 900 |
| cagaccttcc ccggcggagg cagcaccatc tacagcatga tccagagcca gtccagcgcc | 960 |
| cccacaagcc aggaacccgc ctacacactg tatagcctga tccagccctc caggaagagc | 1020 |
| ggcagcagga agaggaacca cagccccagc ttcaacagca ccatttacga ggtgatcgga | 1080 |
| aagagccagc ccaaggctca gaaccccgcc aggctgagca ggaaggagct cgaaaacttc | 1140 |
| gacgtgtaca gctga | 1155 |

<210> SEQ ID NO 48
<211> LENGTH: 1349
<212> TYPE: DNA
<213> ORGANISM: Homo sapiens
<220> FEATURE:
<221> NAME/KEY: misc_feature
<223> OTHER INFORMATION: NK15_6

<400> SEQUENCE: 48

| | |
|---|---|
| ggatccgaat tcgccgccac catggccctg cctgtgacag ccctgctgct gcctctggct | 60 |
| ctgctgctgc acgctgccag acccttattc aaccaagaag ttcaaattcc cttgaccgaa | 120 |
| agttactgtg gcccatgtcc taaaaactgg atatgttaca aaataactg ctaccaattt | 180 |
| tttgatgaga gtaaaaactg gtatgagagc caggcttctt gtatgtctca aaatgccagc | 240 |
| cttctgaaag tatacagcaa agaggaccag gatttactta aactggtgaa gtcatatcat | 300 |
| tggatgggac tagtacacat tccaacaaat ggatcttggc agtgggaaga tggctccatt | 360 |
| ctctcaccca acctactaac aataattgaa atgcagaagg gagactgtgc actctatgcc | 420 |
| tcgagcttta aaggctatat agaaaactgt tcaactccaa atacgtacat ctgcatgcaa | 480 |
| aggactgtga ccacaaccc tgctcccaga cctcccacac ccgccctac aatcgcctcc | 540 |
| cagcctctga gcctgagacc cgaagcctgt agacctgccg ccggcggagc tgtgcataca | 600 |
| agaggcctgg acttcgcctg cgacatctac atctgggccc ctctggctgg acatgcgga | 660 |
| gtcctgctgc tgagcctggt gatcaccaag aggggcagga gaagctgct gtacatcttc | 720 |
| aagcagccct tcatgaggcc tgtgcagacc acacaggagg aggacggctg ctcctgcagg | 780 |
| ttccctgagg aggaggaggg aggctgcgag ctgtggagga ggaagagaaa ggagaagcag | 840 |
| tccgagacct cccccaagga gttcctcacc atttacgagg acgtgaagga cctgaagacc | 900 |
| aggagaaacc acgagcagga acaaaccttc cccggcggcg gcagcaccat ctacagcatg | 960 |
| atccagagcc agtcctccgc ccctacaagc caggagcctg cctacaccct gtacagcctg | 1020 |
| atccagccta gcaggaagag cggctccagg aagaggaacc actcccccag cttcaacagc | 1080 |
| accatttatg aggtgatcgg caagtcccag cccaaggccc agaaccctgc cagactgtcc | 1140 |
| aggaaggagc tggagaactt cgacgtctac tccgcggcg cggcagcgg cggaggaggc | 1200 |
| tccggaggag gcggcagcat gcaggatgag gacggctata tgaccctgaa cgtccagtcc | 1260 |
| aagaagaggt ccagcgctca gaccagccag ctgaccttca aggactactc cgtgaccctg | 1320 |
| cactggtaca agtgagcggc cgcgtcgac | 1349 |

<210> SEQ ID NO 49
<211> LENGTH: 989
<212> TYPE: DNA
<213> ORGANISM: Homo sapiens
<220> FEATURE:

<221> NAME/KEY: misc_feature
<223> OTHER INFORMATION: NK15_7

<400> SEQUENCE: 49

```
ggatccgaat cgccgccac catggccctg cctgtgacag ccctgctgct gcctctggct        60
ctgctgctgc atgccgccag acccttattc aaccaagaag ttcaaattcc cttgaccgaa      120
agttactgtg cccatgtcc taaaaactgg atatgttaca aaataactg ctaccaattt        180
tttgatgaga gtaaaaactg gtatgagagc caggcttctt gtatgtctca aaatgccagc      240
cttctgaaag tatacagcaa agaggaccag gatttactta aactggtgaa gtcatatcat      300
tggatgggac tagtacacat tccaacaaat ggatcttggc agtgggaaga tggctccatt      360
ctctcaccca acctactaac aataattgaa atgcagaagg gagactgtgc actctatgcc      420
tcgagcttta aaggctatat agaaaactgt tcaactccaa atacgtacat ctgcatgcaa      480
aggactgtga ccaccacccc tgctcccaga cccctacac ctgcccctac aatcgccagc       540
cagcccctga gcctgagacc tgaggcctgc agacctgctg ctggaggcgc tgtgcacaca      600
aggggcctcg acttcgcctg cgacatctac atctgggccc ctctggccgg cacatgtgga      660
gtgctgctgc tgtccctggt gatcaccaag aggggcagga gaagctgct gtacatcttc       720
aagcagccct tcatgaggcc cgtgcagacc acccaggagg aggacggctg ctcctgcaga      780
ttccccgagg aggaggaggg cggatgtgaa ctgggcggag gaggcagcgg cggcggcggc      840
agcggcggcg gcggcagcat gcaggatgag gacggctaca tgaccctgaa cgtgcagagc      900
aagaagagga gcagcgccca gaccagccag ctgacccttca aggactacag cgtgaccctg      960
cactggtaca agtgagcggc cgcgtcgac                                       989
```

<210> SEQ ID NO 50
<211> LENGTH: 1430
<212> TYPE: DNA
<213> ORGANISM: Homo sapiens
<220> FEATURE:
<221> NAME/KEY: misc_feature
<223> OTHER INFORMATION: NK15_8

<400> SEQUENCE: 50

```
ggatccgaat cgccgccac catggccctg cccgtgacag ctctgctgct gcctctggcc        60
ctgctgctgc atgccgctag acccctgttc aaccaggagg tgcagatccc cctgaccgaa      120
agctactgcg cccctgccc caagaactgg atctgttaca gaacaactg ctatcagttc        180
ttcgacgaga gcaagaactg gtacgagagc caggccagct gtatgagcca gaacgccagc      240
ctgctgaaag tgtatagcaa ggaggaccag gacctgctga gctggtgaa gagctaccac      300
tggatgggcc tggtgcacat ccccaccaac ggaagctggc agtgggagga cggcagcatc      360
ctgagcccca acctgctgac catcatcgag atgcagaagg gcgactgcgc cctgtatgcc      420
agcagcttca aggctacat cgagaactgt agcaccccca cacctacat ctgcatgcag        480
aggaccgtgg gcgcggcgg cagcggcgga ggcggctccg gcgcggcgg cagcttattc       540
aaccaagaag ttcaaattcc cttgaccgaa agttactgtg cccatgtcc taaaaactgg       600
atatgttaca aaataactg ctaccaattt tttgatgaga gtaaaaactg gtatgagagc       660
caggcttctt gtatgtctca aaatgccagc cttctgaaag tatacagcaa agaggaccag      720
gatttactta aactggtgaa gtcatatcat tggatgggac tagtacacat tccaacaaat      780
ggatcttggc agtgggaaga tggctccatt ctctcaccca acctactaac aataattgaa      840
atgcagaagg gagactgtgc actctatgcc tcgagcttta aaggctatat agaaaactgt      900
```

```
tcaactccaa atacgtacat ctgcatgcaa aggactgtga tgggccagcc tggcaacggc      960
agcgcctttc tgctggcccc caacaggagc catgcccctg accacgacgt gacccagcag     1020
agggacgagg tgtgggtggt gggcatgggc atcgtgatga gcctgatcgt gctggccatc     1080
gtgttcggca acgtgctggt gatcaccgcc atcgccaagt cgagaggaa gaggggcagg      1140 aagaagctgc tgtacatctt caagcagccc ttcatgagac ccgtgcaaac cacccaggag     1200
gaggacggct gcagctgcag gtttcccgag gaggaggagg gcggatgcga actgggaggc     1260
ggaggaagcg gaggaggagg atccggagga ggcggaagca tgcaggacga ggacggctac     1320
atgaccctga acgtccagag caagaagagg agcagcgccc agacctccca gctgaccttc     1380
aaggactact ccgtgaccct gcactggtac aagtgagcgg ccgcgtcgac                1430
```

<210> SEQ ID NO 51
<211> LENGTH: 1439
<212> TYPE: DNA
<213> ORGANISM: Homo sapiens
<220> FEATURE:
<221> NAME/KEY: misc_feature
<223> OTHER INFORMATION: NK15_9

<400> SEQUENCE: 51

```
ggatccgaat tcgccgccac catggccctg cccgtgacag ctctgctgct gcctctggcc       60
ctgctgctgc atgccgctag acccctgttc aaccaggagc tgcagatccc cctgaccgaa      120
agctactgcg gcccctgccc caagaactgg atctgttaca agaacaactg ctatcagttc      180
ttcgacgaga gcaagaactg gtacgagagc caggccagct gtatgagcca gaacgccagc     240
ctgctgaaag tgtatagcaa ggaggaccag gacctgctga gctggtgaa gagctaccac      300 tggatgggcc tggtgcacat ccccaccaac ggaagctggc agtgggagga cggcagcatc     360
ctgagcccca acctgctgac catcatcgag atgcagaagg gcgactgcgc cctgtatgcc     420
agcagcttca agggctacat cgagaactgt agcaccccca cacctacat ctgcatgcag      480 aggaccgtgg gcggcggcgg cagcggcgga ggcggctccg gcggcggcgg cagcttattc      540
aaccaagaag ttcaaattcc cttgaccgaa agttactgtg gcccatgtcc taaaaactgg     600
atatgttaca aaataactg ctaccaattt tttgatgaga gtaaaaactg gtatgagagc       660
caggcttctt gtatgtctca aaatgccagc cttctgaaag tatacagcaa agaggaccag     720
gatttactta aactggtgaa gtcatatcat tggatgggac tagtacacat tccaacaaat     780
ggatcttggc agtgggaaga tggctccatt ctctcaccca acctactaac aataattgaa     840
atgcagaagg gagactgtgc actctatgcc tcgagcttta aaggctatat agaaaactgt     900
tcaactccaa atacgtacat ctgcatgcaa aggactgtga ccaccacccc tgctcccaga     960
ccccctacac ctgcccctac aatcgccagc cagcccctga gcctgagacc tgaggcctgc    1020
agacctgctg ctggaggcgc tgtgcacaca aggggcctcg acttcgcctg cgacatctac    1080
atctgggccc ctctggccgg cacatgtgga gtgctgctgc tgtccctggt gatcaccaag    1140
aggggcagga agaagctgct gtacatcttc aagcagccct tcatgaggcc cgtgcagacc    1200
acccaggagg aggacggctg ctcctgcaga ttccccgagg aggagggg cggatgtgaa      1260 ctgggcggag gaggcagcgg cggcggcggc agcgcggcg gcgcagcat gcaggatgag      1320 gacggctaca tgaccctgaa cgtgcagagc aagaagagga gcagcgccca gaccagccag    1380
ctgaccttca aggactacag cgtgaccctg cactggtaca agtgagcggc cgcgtcgac     1439
```

<210> SEQ ID NO 52
<211> LENGTH: 1329
<212> TYPE: DNA
<213> ORGANISM: Homo sapiens
<220> FEATURE:
<221> NAME/KEY: misc_feature
<223> OTHER INFORMATION: NK15_10

<400> SEQUENCE: 52

| | | | | | |
|---|---|---|---|---|---|
| gccgccacaa | tggccctgcc | tgtgacagcc | ctgctgctgc | ctctggccct | gctgctgcat | 60 |
| gctgccaggc | ctctgttcaa | ccaggaggtg | cagatccctc | tgaccgagag | ctactgcggc | 120 |
| ccctgcccca | agaactggat | ctgctacaag | aacaactgct | accagttctt | cgacgagagc | 180 |
| aagaactggt | acgagagcca | ggccagctgc | atgtcccaga | acgctagcct | gctgaaggtg | 240 |
| tatagcaagg | aggaccagga | cctgctgaag | ctggtgaaga | gctaccactg | gatgggcctg | 300 |
| gtgcacatcc | ccaccaacgg | ctcctggcag | tgggaggacg | gcagcatcct | gagccctaac | 360 |
| ctgctgacca | tcatcgagat | gcagaaggga | gactgcgccc | tgtacgccag | ctcctttaag | 420 |
| ggctacatcg | agaactgcag | cacccccaac | acctacatct | gtatgcagag | gaccgtggga | 480 |
| ggcggcggca | gcggcggcgg | cggcagcggc | ggcggcggca | gcttattcaa | ccaagaagtt | 540 |
| caaattccct | tgaccgaaag | ttactgtggc | ccatgtccta | aaaactggat | atgttacaaa | 600 |
| aataactgct | accaattttt | tgatgagagt | aaaaactggt | atgagagcca | ggcttcttgt | 660 |
| atgtctcaaa | atgccagcct | tctgaaagta | tacagcaaag | aggaccagga | tttacttaaa | 720 |
| ctggtgaagt | catatcattg | gatgggacta | gtacacattc | caacaaatgg | atcttggcag | 780 |
| tgggaagatg | gctccattct | ctcacccaac | ctactaacaa | taattgaaat | gcagaaggga | 840 |
| gactgtgcac | tctatgcctc | gagctttaaa | ggctatatag | aaaactgttc | aactccaaat | 900 |
| acgtacatct | gcatgcaaag | gactgtgacc | accaccctg | ccctagacc | ccctacacct | 960 |
| gcccctacca | tcgccagcca | gcctctgagc | ctgagacccg | aggcctgtag | acctgctgcc | 1020 |
| ggaggagccg | tgcacacaag | aggcctggac | ttcgcctgcg | acgtgagctt | ctgcctggtg | 1080 |
| atggtgctgc | tgttcgccgt | ggacaccggc | ctgtacttca | gcgtgaagac | caacatcagg | 1140 |
| agcagcacca | gggactggaa | ggaccacaaa | ttcaagtgga | ggaaggaccc | ccaggacaag | 1200 |
| aagaggggca | ggaagaagct | gctgtacatc | ttcaagcagc | ccttcatgag | gcctgtgcag | 1260 |
| accacccagg | aggaggacgg | ctgcagctgc | aggttccctg | aggaggaaga | gggcggctgc | 1320 |
| gagctgtga | | | | | 1329 |

<210> SEQ ID NO 53
<211> LENGTH: 1239
<212> TYPE: DNA
<213> ORGANISM: Homo sapiens
<220> FEATURE:
<221> NAME/KEY: misc_feature
<223> OTHER INFORMATION: NK15_11

<400> SEQUENCE: 53

| | | | | | |
|---|---|---|---|---|---|
| gccgccacca | tggctctgcc | cgtcaccgca | ctgctgctgc | ctctggctct | gctgctgcac | 60 |
| gccgcacgac | cactgttcaa | tcaggaagtc | cagatccccc | tgacagagtc | ttactgcggc | 120 |
| ccatgtccca | agaactggat | ctgctacaag | aacaattgtt | atcagttctt | tgacgagagc | 180 |
| aagaactggt | atgagtccca | ggcctcttgc | atgagccaga | atgcctctct | gctgaaggtg | 240 |
| tacagcaagg | aggaccagga | tctgctgaag | ctggtgaagt | cctatcactg | gatgggcctg | 300 |
| gtgcacatcc | ctacaaacgg | ctcttggcag | tgggaggacg | gctccatcct | gtctccaaat | 360 |

```
ctgctgacca tcatcgagat gcagaagggc gattgcgccc tgtacgccag ctccttcaag    420
ggctatatcg agaactgctc cacacccaat acctacatct gtatgcagag gaccgtgacc    480
acaacccctg caccacgccc ccctacacca gcacctacca tcgcaagcca gcctctgtcc    540
ctgcggccag aggcatgtag accagcagca ggaggagcag tgcacacaag aggcctggac    600
ttcgcctgcg atgtgagctt ttgtctggtc atggtgctgc tgttcgccgt ggataccggc    660
ctgtactttt ccgtgaagac aaatatcagg tctagcaccc gcgactggaa ggatcacaag    720
tttaagtggc ggaaggaccc tcaggataag aagcggggca gaaagaagct gctgtatatc    780
ttcaagcagc ccttcatgcg gcccgtgcag acaacccagg aggaagacgg ctgctcatgt    840
agatttcctg aagaagaaga aggggggctgt gaactgtgga ggaggaaaag gaaggagaaa    900
cagagcgaga cctcccctaa ggagttcctg accatctacg aggacgtgaa ggacctgaag    960
accaggagga accacgagca ggaacagacc tttcctggcg gaggcagcac catctacagc   1020
atgatccaga gccagagcag cgcccctacc agccaagagc ctgcctacac cctgtacagc   1080
ctgatccagc ccagcaggaa aagcggctcc aggaagagga ccacagccc cagcttcaac   1140 agcaccatct atgaggtgat cggcaagagc cagcccaagg cccagaaccc tgccaggctg   1200
tccaggaagg agctggagaa cttcgacgtg tacagctga                          1239

<210> SEQ ID NO 54
<211> LENGTH: 1064
<212> TYPE: DNA
<213> ORGANISM: Homo sapiens
<220> FEATURE:
<221> NAME/KEY: misc_feature
<223> OTHER INFORMATION: NK15_12

<400> SEQUENCE: 54
ggatccgaat cgccgccac catggctctg cccgtcaccg cactgctgct gcctctggct      60
ctgctgctgc acgccgcacg accactgttc aatcaggaag tccagatccc cctgacagag    120
tcttactgcg gcccatgtcc caagaactgg atctgctaca gaacaattg ttatcagttc    180 tttgacgaga gcaagaactg gtatgagtcc caggcctctt gcatgagcca gaatgcctct    240
ctgctgaagg tgtacagcaa ggaggaccag gatctgctga gctggtgaa gtcctatcac    300 tggatgggcc tggtgcacat ccctacaaac ggctcttggc agtgggagga cggctccatc    360
ctgtctccaa atctgctgac catcatcgag atgcagaagg gcgattgcgc cctgtacgcc    420
agctccttca gggctatat cgagaactgc tccacaccca ataccta cat ctgtatgcag    480 aggaccgtga ccacaacccc tgcaccacgc ccccctacac cagcacctac catcgcaagc    540
cagcctctgt ccctgcggcc agaggcatgt agaccagcag caggaggagc agtgcacaca    600
agaggcctga acttcgcctg cgatgtgagc ttttgtctgg tcatggtgct gctgttcgcc    660
gtggataccg gcctgtactt ttccgtgaag acaaatatca ggtctagcac ccgcgactgg    720
aaggatcaca agttttaagtg gcggaaggac cctcaggata agaagcgggg cagaaagaag    780
ctgctgtata tcttcaagca gcccttcatg cggcccgtgc agacaaccca ggaggaagac    840
ggctgctcat gtagatttcc tgaagaagaa gaagggggct gtgaactggg cggaggaggc    900
agcggcggcg gcgcagcgg cggcggcggc agcatgcagg atgaggacgg ctacatgacc    960
ctgaacgtgc agagcaagaa gaggagcagc gcccagacca gccagctgac cttcaaggac   1020
tacagcgtga ccctgcactg gtacaagtga gcggccgcgt cgac                    1064

<210> SEQ ID NO 55
```

```
<211> LENGTH: 8
<212> TYPE: PRT
<213> ORGANISM: Homo sapiens
<220> FEATURE:
<221> NAME/KEY: MISC_FEATURE
<223> OTHER INFORMATION: FLAG tag

<400> SEQUENCE: 55

Asp Tyr Lys Asp Asp Asp Asp Lys
1               5

<210> SEQ ID NO 56
<211> LENGTH: 6
<212> TYPE: PRT
<213> ORGANISM: Homo sapiens
<220> FEATURE:
<221> NAME/KEY: MISC_FEATURE
<223> OTHER INFORMATION: His tag

<400> SEQUENCE: 56

His His His His His His
1               5

<210> SEQ ID NO 57
<211> LENGTH: 10
<212> TYPE: PRT
<213> ORGANISM: Homo sapiens
<220> FEATURE:
<221> NAME/KEY: MISC_FEATURE
<223> OTHER INFORMATION: Myc tag

<400> SEQUENCE: 57

Glu Gln Lys Leu Ile Ser Glu Glu Asp Leu
1               5                   10

<210> SEQ ID NO 58
<211> LENGTH: 1499
<212> TYPE: DNA
<213> ORGANISM: Homo sapiens
<220> FEATURE:
<221> NAME/KEY: misc_feature
<223> OTHER INFORMATION: DNA Sequence for Variant 13

<400> SEQUENCE: 58
atggccttac cagtgaccgc cttgctcctg ccgctggcct tgctgctcca cgccgccagg      60
ccgttattca accaagaagt tcaaattccc ttgaccgaaa gttactgtgg ccatgtcct     120 aaaaactgga tatgttacaa aaataactgc taccaatttt ttgatgagag taaaaactgg     180
tatgagagcc aggcttcttg tatgtctcaa aatgccagcc ttctgaaagt atacagcaaa     240
gaggaccagg atttacttaa actggtgaag tcatatcatt ggatgggact agtacacatt     300
ccaacaaatg gatcttggca gtgggaagat ggctccattc tctcacccaa cctactaaca     360
ataattgaaa tgcagaaggg agactgtgca ctctatgcct cgagctttaa aggctatata     420
gaaaactgtt caactccaaa tacgtacatc tgcatgcaaa ggactgtgac cacgacgcca     480
gcgccgcgac caccaacacc ggcgcccacc atcgcgtcgc agcccctgtc cctgcgccca     540
gaggcgtgcc ggccagcggc gggggcgca gtgcacacga gggggctgga cttcgcctgt     600
gatatctaca tctgggcgcc cttggccggg acttgtgggg tccttctcct gtcactggtt     660 atcaccttt actgcaaacg gggcagaaag aaactcctgt atatattcaa acaaccattt     720
atgagaccag tacaaactac tcaagaggaa gatggctgta gctgccgatt tccagaagaa     780
gaagaaggag gatgtgaact gtggaggagg aaaaggaagg agaaacagag cgagacctcc     840
```

```
cctaaggagt tcctgaccat ctacgaggac gtgaaggacc tgaagaccag gaggaaccac    900
gagcaggaac agacctttcc tggcggaggc agcaccatct acagcatgat ccagagccag    960
agcagcgccc ctaccagcca agagcctgcc tacaccctgt acagcctgat ccagcccagc   1020
aggaaaagcg gctccaggaa gaggaaccac agccccagct tcaacagcac catctatgag   1080
gtgatcggca gagccagcc caaggcccag aaccctgcca ggctgtccag gaaggagctg   1140
gagaacttcg acgtgtacag cagagtgaag ttcagcagga gcgcagacgc ccccgcgtac   1200
cagcagggcc agaaccagct ctataacgag ctcaatctag gacgaagaga ggagtacgat   1260
gttttggaca agagacgtgg ccgggaccct gagatggggg gaaagccgag aaggaagaac   1320
cctcaggaag gcctgtacaa tgaactgcag aaagataaga tggcggaggc ctacagtgag   1380
attgggatga aggcgagcg ccggaggggc aaggggcacg atggccttta ccagggtctc   1440
agtacagcca ccaaggacac ctacgacgcc cttcacatgc aggccctgcc ccctcgcta   1499
```

<210> SEQ ID NO 59
<211> LENGTH: 499
<212> TYPE: PRT
<213> ORGANISM: Homo sapiens
<220> FEATURE:
<221> NAME/KEY: MISC_FEATURE
<223> OTHER INFORMATION: Amino Acid Sequence for Variant 13

<400> SEQUENCE: 59

```
Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Tyr His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Tyr Ile Glu Asn Cys Ser
    130                 135                 140

Thr Pro Asn Thr Tyr Ile Cys Met Gln Arg Thr Val Thr Thr Thr Pro
145                 150                 155                 160

Ala Pro Arg Pro Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
            180                 185                 190

Thr Arg Gly Leu Asp Phe Ala Cys Asp Ile Tyr Ile Trp Ala Pro Leu
        195                 200                 205

Ala Gly Thr Cys Gly Val Leu Leu Leu Ser Leu Val Ile Thr Leu Tyr
    210                 215                 220

Cys Lys Arg Gly Arg Lys Lys Leu Leu Tyr Ile Phe Lys Gln Pro Phe
225                 230                 235                 240

Met Arg Pro Val Gln Thr Thr Gln Glu Glu Asp Gly Cys Ser Cys Arg
```

```
                245                 250                 255
Phe Pro Glu Glu Glu Gly Gly Cys Glu Leu Trp Arg Arg Lys Arg
        260                 265                 270
Lys Glu Lys Gln Ser Glu Thr Ser Pro Lys Glu Phe Leu Thr Ile Tyr
            275                 280                 285
Glu Asp Val Lys Asp Leu Lys Thr Arg Arg Asn His Glu Gln Glu Gln
        290                 295                 300
Thr Phe Pro Gly Gly Ser Thr Ile Tyr Ser Met Ile Gln Ser Gln
305                 310                 315                 320
Ser Ser Ala Pro Thr Ser Gln Glu Pro Ala Tyr Thr Leu Tyr Ser Leu
            325                 330                 335
Ile Gln Pro Ser Arg Lys Ser Gly Ser Arg Lys Arg Asn His Ser Pro
            340                 345                 350
Ser Phe Asn Ser Thr Ile Tyr Glu Val Ile Gly Lys Ser Gln Pro Lys
            355                 360                 365
Ala Gln Asn Pro Ala Arg Leu Ser Arg Lys Glu Leu Glu Asn Phe Asp
        370                 375                 380
Val Tyr Ser Arg Val Lys Phe Ser Arg Ser Ala Asp Ala Pro Ala Tyr
385                 390                 395                 400
Gln Gln Gly Gln Asn Gln Leu Tyr Asn Glu Leu Asn Leu Gly Arg Arg
            405                 410                 415
Glu Glu Tyr Asp Val Leu Asp Lys Arg Gly Arg Asp Pro Glu Met
        420                 425                 430
Gly Gly Lys Pro Arg Arg Lys Asn Pro Gln Glu Gly Leu Tyr Asn Glu
            435                 440                 445
Leu Gln Lys Asp Lys Met Ala Glu Ala Tyr Ser Glu Ile Gly Met Lys
        450                 455                 460
Gly Glu Arg Arg Arg Gly Lys Gly His Asp Gly Leu Tyr Gln Gly Leu
465                 470                 475                 480
Ser Thr Ala Thr Lys Asp Thr Tyr Asp Ala Leu His Met Gln Ala Leu
            485                 490                 495
Pro Pro Arg
```

<210> SEQ ID NO 60
<211> LENGTH: 870
<212> TYPE: DNA
<213> ORGANISM: Homo sapiens
<220> FEATURE:
<221> NAME/KEY: misc_feature
<223> OTHER INFORMATION: DNA Sequence Variant 14

<400> SEQUENCE: 60

```
atggccttac cagtgaccgc cttgctcctg ccgctggcct tgctgctcca cgccgccagg      60
ccgttattca accaagaagt tcaaattccc ttgaccgaaa gttactgtgg cccatgtcct     120
aaaaactgga tatgttacaa aaataactgc taccaattt tgatgagag taaaaactgg      180
tatgagagcc aggcttcttg tatgtctcaa atgccagcc ttctgaaagt atacagcaaa      240
gaggaccagg atttacttaa actggtgaag tcatatcatt ggatgggact agtacacatt     300
ccaacaaatg gatcttggca gtgggaagat ggctccattc tctcacccaa cctactaaca     360
ataattgaaa tgcagaaggg agactgtgca ctctatgcct cgagctttaa aggctatata     420
gaaaactgtt caactccaaa tacgtacatc tgcatgcaaa ggactgtgac cacgacgcca     480
gcgccgcgac caccaacacc ggcgcccacc atcgcgtcgc agcccctgtc cctgcgccca     540
gaggcgtgcc ggccagcggc ggggggcgca gtgcacacga gggggctgga cttcgcctgt     600
```

```
gatatctaca tctgggcgcc cttggccggg acttgtgggg tccttctcct gtcactggtt    660
atcacccttt actgcaaacg gggcagaaag aaactcctgt atatattcaa acaaccattt    720
atgagaccag tacaaactac tcaagaggaa gatggctgta gctgccgatt ccagaagaa     780 gaagaaggag gatgtgaact gctgtgcgca cgcccacgcc gcagccccgc ccaagatggc    840
aaagtctaca tcaacatgcc aggcaggggc                                     870
```

<210> SEQ ID NO 61
<211> LENGTH: 290
<212> TYPE: PRT
<213> ORGANISM: Homo sapiens
<220> FEATURE:
<221> NAME/KEY: MISC_FEATURE
<223> OTHER INFORMATION: Amino Acid Sequence Variant 14

<400> SEQUENCE: 61

```
Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Tyr His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Tyr Ile Glu Asn Cys Ser
    130                 135                 140

Thr Pro Asn Thr Tyr Ile Cys Met Gln Arg Thr Val Thr Thr Thr Pro
145                 150                 155                 160

Ala Pro Arg Pro Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
            180                 185                 190

Thr Arg Gly Leu Asp Phe Ala Cys Asp Ile Tyr Ile Trp Ala Pro Leu
        195                 200                 205

Ala Gly Thr Cys Gly Val Leu Leu Leu Ser Leu Val Ile Thr Leu Tyr
    210                 215                 220

Cys Lys Arg Gly Arg Lys Lys Leu Leu Tyr Ile Phe Lys Gln Pro Phe
225                 230                 235                 240

Met Arg Pro Val Gln Thr Thr Gln Glu Glu Asp Gly Cys Ser Cys Arg
                245                 250                 255

Phe Pro Glu Glu Glu Glu Gly Gly Cys Glu Leu Leu Cys Ala Arg Pro
            260                 265                 270

Arg Arg Ser Pro Ala Gln Asp Gly Lys Val Tyr Ile Asn Met Pro Gly
        275                 280                 285

Arg Gly
    290
```

<210> SEQ ID NO 62
<211> LENGTH: 1230
<212> TYPE: DNA
<213> ORGANISM: Homo sapiens
<220> FEATURE:
<221> NAME/KEY: misc_feature
<223> OTHER INFORMATION: DNA Sequence Variant 15

<400> SEQUENCE: 62

```
atggccttac cagtgaccgc cttgctcctg ccgctggcct tgctgctcca cgccgccagg      60
ccgttattca accaagaagt tcaaattccc ttgaccgaaa gttactgtgg cccatgtcct     120
aaaaactgga tatgttacaa aaataactgc taccaatttt ttgatgagag taaaaactgg     180
tatgagagcc aggcttcttg tatgtctcaa aatgccagcc ttctgaaagt atacagcaaa     240
gaggaccagg atttacttaa actggtgaag tcatatcatt ggatgggact agtacacatt     300
ccaacaaatg gatcttggca gtgggaagat ggctccattc tctcacccaa cctactaaca     360
ataattgaaa tgcagaaggg agactgtgca ctctatgcct cgagctttaa aggctatata     420
gaaaactgtt caactccaaa tacgtacatc tgcatgcaaa ggactgtgac cacgacgcca     480
gcgccgcgac caccaacacc ggcgcccacc atcgcgtcgc agcccctgtc cctgcgccca     540
gaggcgtgcc ggccagcggc ggggggcgca gtgcacacga ggggctgga cttcgcctgt     600
gatatctaca tctgggcgcc cttggccggg acttgtgggg tccttctcct gtcactggtt     660
atcacccttt actgcaaacg gggcagaaag aaactcctgt atatattcaa acaaccattt     720
atgagaccag tacaaactac tcaagaggaa gatggctgta gctgccgatt ccagaagaa     780
gaagaaggag gatgtgaact gctgtgcgca cgcccacgcc gcagcccgc ccaagatggc     840
aaagtctaca tcaacatgcc aggcaggggc tggaggagga aaggaagga gaaacagagc     900
gagacctccc ctaaggagtt cctgaccatc tacgaggacg tgaaggacct gaagaccagg     960
aggaaccacg agcaggaaca gacctttcct ggcggaggca gcaccatcta gcatgatc    1020
cagagccaga gcagcgcccc taccagccaa gagcctgcct acaccctgta cagcctgatc   1080
cagcccagca ggaaaagcgg ctccaggaag aggaaccaca gcccagctt caacagcacc   1140
atctatgagg tgatcggcaa gagccagccc aaggcccaga ccctgccag gctgtccagg   1200
aaggagctgg agaacttcga cgtgtacagc                                    1230
```

<210> SEQ ID NO 63
<211> LENGTH: 410
<212> TYPE: PRT
<213> ORGANISM: Homo sapiens
<220> FEATURE:
<221> NAME/KEY: MISC_FEATURE
<223> OTHER INFORMATION: Amino Acid Sequence Variant 15

<400> SEQUENCE: 63

```
Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80
```

| | | | | | | | | | | | |
|---|---|---|---|---|---|---|---|---|---|---|---|
|Glu|Asp|Gln|Asp|Leu|Leu|Lys|Leu|Val|Lys|Ser|Tyr|His|Trp|Met|Gly|
| | | | |85| | | |90| | | |95| | | |

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
            115                 120                 125

Cys Ala Leu Tyr Ala Ser Ser Phe Lys Gly Tyr Ile Glu Asn Cys Ser
            130                 135                 140

Thr Pro Asn Thr Tyr Ile Cys Met Gln Arg Thr Val Thr Thr Thr Pro
145                 150                 155                 160

Ala Pro Arg Pro Pro Thr Pro Ala Pro Thr Ile Ala Ser Gln Pro Leu
            165                 170                 175

Ser Leu Arg Pro Glu Ala Cys Arg Pro Ala Ala Gly Gly Ala Val His
            180                 185                 190

Thr Arg Gly Leu Asp Phe Ala Cys Asp Ile Tyr Ile Trp Ala Pro Leu
            195                 200                 205

Ala Gly Thr Cys Gly Val Leu Leu Leu Ser Leu Val Ile Thr Leu Tyr
            210                 215                 220

Cys Lys Arg Gly Arg Lys Lys Leu Leu Tyr Ile Phe Lys Gln Pro Phe
225                 230                 235                 240

Met Arg Pro Val Gln Thr Thr Gln Glu Glu Asp Gly Cys Ser Cys Arg
            245                 250                 255

Phe Pro Glu Glu Glu Glu Gly Gly Cys Glu Leu Leu Cys Ala Arg Pro
            260                 265                 270

Arg Arg Ser Pro Ala Gln Asp Gly Lys Val Tyr Ile Asn Met Pro Gly
            275                 280                 285

Arg Gly Trp Arg Arg Lys Arg Lys Glu Lys Gln Ser Glu Thr Ser Pro
            290                 295                 300

Lys Glu Phe Leu Thr Ile Tyr Glu Asp Val Lys Asp Leu Lys Thr Arg
305                 310                 315                 320

Arg Asn His Glu Gln Glu Gln Thr Phe Pro Gly Gly Gly Ser Thr Ile
            325                 330                 335

Tyr Ser Met Ile Gln Ser Gln Ser Ser Ala Pro Thr Ser Gln Glu Pro
            340                 345                 350

Ala Tyr Thr Leu Tyr Ser Leu Ile Gln Pro Ser Arg Lys Ser Gly Ser
            355                 360                 365

Arg Lys Arg Asn His Ser Pro Ser Phe Asn Ser Thr Ile Tyr Glu Val
            370                 375                 380

Ile Gly Lys Ser Gln Pro Lys Ala Gln Asn Pro Ala Arg Leu Ser Arg
385                 390                 395                 400

Lys Glu Leu Glu Asn Phe Asp Val Tyr Ser
            405                 410

<210> SEQ ID NO 64
<211> LENGTH: 1232
<212> TYPE: DNA
<213> ORGANISM: Homo sapiens
<220> FEATURE:
<221> NAME/KEY: misc_feature
<223> OTHER INFORMATION: DNA Sequence Variant 16

<400> SEQUENCE: 64
atggccttac cagtgaccgc cttgctcctg ccgctggcct tgctgctcca cgccgccagg      60
ccgttattca accaagaagt tcaaattccc ttgaccgaaa gttactgtgg cccatgtcct     120
aaaaactgga tatgttacaa aaataactgc taccaatttt ttgatgagag taaaaactgg     180

```
tatgagagcc aggcttcttg tatgtctcaa aatgccagcc ttctgaaagt atacagcaaa      240
gaggaccagg atttacttaa actggtgaag tcatatcatt ggatgggact agtacacatt      300
ccaacaaatg gatcttggca gtgggaagat ggctccattc tctcacccaa cctactaaca      360
ataattgaaa tgcagaaggg agactgtgca ctctatgcct cgagctttaa aggctatata      420
gaaaactgtt caactccaaa tacgtacatc tgcatgcaaa ggactgtgac cacgacgcca      480
gcgccgcgac caccaacacc ggcgcccacc atcgcgtcgc agcccctgtc cctgcgccca      540
gaggcgtgcc ggccagcggc ggggggcgca gtgcacacga gggggctgga cttcgcctgt      600
gatatctaca tctgggcgcc cttggccggg acttgtgggg tccttctcct gtcactggtt      660
atcacccttt actgcaaacg gggcagaaag aaactcctgt atatattcaa caaccatttt     720
atgagaccag tacaaactac tcaagaggaa gatggctgta gctgccgatt tccagaagaa      780
gaagaaggag gatgtgaact gtggaggagg aaaaggaagg agaaacagag cgagacctcc      840
cctaaggagt tcctgaccat ctacgaggac gtgaaggacc tgaagaccag gaggaaccac      900
gagcaggaac agacctttcc tggcggaggc agcaccatct acagcatgat ccagagccag      960
agcagcgccc ctaccagcca agagcctgcc tacaccctgt acagcctgat ccagcccagc     1020
aggaaaagcg gctccaggaa gaggaaccac agcccagct tcaacagcac catctatgag      1080
gtgatcggca gagccagcc caaggccag aaccctgcca ggctgtccag gaaggagctg       1140
gagaacttcg acgtgtacag cctgtgcgca cgcccacgcc gcagccccgc ccaagatggc     1200
aaagtctaca tcaacatgcc aggcagggc tg                                    1232

<210> SEQ ID NO 65
<211> LENGTH: 410
<212> TYPE: PRT
<213> ORGANISM: Homo sapiens
<220> FEATURE:
<221> NAME/KEY: MISC_FEATURE
<223> OTHER INFORMATION: Amino Acid Sequence Variant 16

<400> SEQUENCE: 65

Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Tyr His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Tyr Ile Glu Asn Cys Ser
    130                 135                 140

Thr Pro Asn Thr Tyr Ile Cys Met Gln Arg Thr Val Thr Thr Pro
145                 150                 155                 160

Ala Pro Arg Pro Pro Thr Pro Ala Pro Thr Ile Ala Ser Gln Pro Leu
```

```
                165                 170                 175
Ser Leu Arg Pro Glu Ala Cys Arg Pro Ala Gly Gly Ala Val His
            180                 185                 190

Thr Arg Gly Leu Asp Phe Ala Cys Asp Ile Tyr Ile Trp Ala Pro Leu
            195                 200                 205

Ala Gly Thr Cys Gly Val Leu Leu Leu Ser Leu Val Ile Thr Leu Tyr
        210                 215                 220

Cys Lys Arg Gly Arg Lys Lys Leu Leu Tyr Ile Phe Lys Gln Pro Phe
225                 230                 235                 240

Met Arg Pro Val Gln Thr Thr Gln Glu Glu Asp Gly Cys Ser Cys Arg
                245                 250                 255

Phe Pro Glu Glu Glu Glu Gly Gly Cys Glu Leu Trp Arg Arg Lys Arg
            260                 265                 270

Lys Glu Lys Gln Ser Glu Thr Ser Pro Lys Glu Phe Leu Thr Ile Tyr
        275                 280                 285

Glu Asp Val Lys Asp Leu Lys Thr Arg Arg Asn His Glu Gln Glu Gln
    290                 295                 300

Thr Phe Pro Gly Gly Gly Ser Thr Ile Tyr Ser Met Ile Gln Ser Gln
305                 310                 315                 320

Ser Ser Ala Pro Thr Ser Gln Glu Pro Ala Tyr Thr Leu Tyr Ser Leu
                325                 330                 335

Ile Gln Pro Ser Arg Lys Ser Gly Ser Arg Lys Arg Asn His Ser Pro
            340                 345                 350

Ser Phe Asn Ser Thr Ile Tyr Glu Val Ile Gly Lys Ser Gln Pro Lys
        355                 360                 365

Ala Gln Asn Pro Ala Arg Leu Ser Arg Lys Glu Leu Glu Asn Phe Asp
    370                 375                 380

Val Tyr Ser Leu Cys Ala Arg Pro Arg Arg Ser Pro Ala Gln Asp Gly
385                 390                 395                 400

Lys Val Tyr Ile Asn Met Pro Gly Arg Gly
                405                 410

<210> SEQ ID NO 66
<211> LENGTH: 1587
<212> TYPE: DNA
<213> ORGANISM: Homo sapiens
<220> FEATURE:
<221> NAME/KEY: misc_feature
<223> OTHER INFORMATION: DNA Sequence Variant 17

<400> SEQUENCE: 66
atggccctgc cgtgacagc tctgctgctg cctctggccc tgctgctgca tgccgctaga        60
cccctgttca accaggaggt gcagatcccc ctgaccgaaa gctactgcgg cccctgcccc      120
aagaactgga tctgttacaa gaacaactgc tatcagttct tcgacgagag caagaactgg      180
tacgagagcc aggccagctg tatgagccag aacgccagcc tgctgaaagt gtatagcaag      240
gaggaccagg acctgctgaa gctggtgaag agctaccact ggatgggcct ggtgcacatc      300
cccaccaacg gaagctggca gtgggaggac ggcagcatcc tgagccccaa cctgctgacc      360
atcatcgaga tgcagaaggg cgactgcgcc ctgtatgcca gcagcttcaa gggctacatc      420
gagaactgta gcacccccaa cacctacatc tgcatgcaga ggaccgtggg cggcggcggc      480
agcggcggag gcggctccgg cggcggcggc agcttattca accaagaagt tcaaattccc      540
ttgaccgaaa gttactgtgg cccatgtcct aaaaactgga tatgttacaa aaataactgc      600
taccaatttt ttgatgagag taaaaactgg tatgagagcc aggcttcttg tatgtctcaa      660
```

```
aatgccagcc ttctgaaagt atacagcaaa gaggaccagg atttacttaa actggtgaag     720
tcatatcatt ggatgggact agtacacatt ccaacaaatg gatcttggca gtgggaagat     780
ggctccattc tctcacccaa cctactaaca ataattgaaa tgcagaaggg agactgtgca     840
ctctatgcct cgagctttaa aggctatata gaaaactgtt caactccaaa tacgtacatc     900
tgcatgcaaa ggactgtgac cacgacgcca gcgccgcgac caccaacacc ggcgcccacc     960
atcgcgtcgc agcccctgtc cctgcgccca gaggcgtgcc ggccagcggc gggggcgca    1020 gtgcacacga gggggctgga cttcgcctgt gatatctaca tctgggcgcc cttggccggg    1080
acttgtgggg tccttctcct gtcactggtt atcacccttt actgcaaacg ggcagaaag    1140 aaactcctgt atatattcaa acaaccattt atgagaccag tacaaactac tcaagaggaa    1200
gatggctgta gctgccgatt tccagaagaa gaagaaggag gatgtgaact gagagtgaag    1260
ttcagcagga gcgcagacgc ccccgcgtac cagcagggcc agaaccagct ctataacgag    1320
ctcaatctag gacgaagaga ggagtacgat gttttggaca agagacgtgg ccgggacct    1380 gagatggggg gaaagccgag aaggaagaac cctcaggaag gcctgtacaa tgaactgcag    1440
aaagataaga tggcggaggc ctacagtgag attgggatga aggcgagcg ccggaggggc    1500 aagggggcacg atggccttta ccagggtctc agtacagcca ccaaggacac ctacgacgcc    1560
cttcacatgc aggccctgcc ccctcgc                                        1587
```

<210> SEQ ID NO 67
<211> LENGTH: 529
<212> TYPE: PRT
<213> ORGANISM: Homo sapiens
<220> FEATURE:
<221> NAME/KEY: MISC_FEATURE
<223> OTHER INFORMATION: Amino Acid Sequence Variant 17

<400> SEQUENCE: 67

```
Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Tyr His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Tyr Ile Glu Asn Cys Ser
    130                 135                 140

Thr Pro Asn Thr Tyr Ile Cys Met Gln Arg Thr Val Gly Gly Gly Gly
145                 150                 155                 160

Ser Gly Gly Gly Gly Ser Gly Gly Gly Ser Leu Phe Asn Gln Glu
                165                 170                 175

Val Gln Ile Pro Leu Thr Glu Ser Tyr Cys Gly Pro Cys Pro Lys Asn
            180                 185                 190
```

```
Trp Ile Cys Tyr Lys Asn Asn Cys Tyr Gln Phe Phe Asp Glu Ser Lys
            195                 200                 205

Asn Trp Tyr Glu Ser Gln Ala Ser Cys Met Ser Gln Asn Ala Ser Leu
210                 215                 220

Leu Lys Val Tyr Ser Lys Glu Asp Gln Asp Leu Leu Lys Leu Val Lys
225                 230                 235                 240

Ser Tyr His Trp Met Gly Leu Val His Ile Pro Thr Asn Gly Ser Trp
            245                 250                 255

Gln Trp Glu Asp Gly Ser Ile Leu Ser Pro Asn Leu Leu Thr Ile Ile
            260                 265                 270

Glu Met Gln Lys Gly Asp Cys Ala Leu Tyr Ala Ser Ser Phe Lys Gly
            275                 280                 285

Tyr Ile Glu Asn Cys Ser Thr Pro Asn Thr Tyr Ile Cys Met Gln Arg
            290                 295                 300

Thr Val Thr Thr Thr Pro Ala Pro Arg Pro Thr Pro Ala Pro Thr
305                 310                 315                 320

Ile Ala Ser Gln Pro Leu Ser Leu Arg Pro Glu Ala Cys Arg Pro Ala
            325                 330                 335

Ala Gly Gly Ala Val His Thr Arg Gly Leu Asp Phe Ala Cys Asp Ile
            340                 345                 350

Tyr Ile Trp Ala Pro Leu Ala Gly Thr Cys Gly Val Leu Leu Leu Ser
            355                 360                 365

Leu Val Ile Thr Leu Tyr Cys Lys Arg Gly Arg Lys Lys Leu Leu Tyr
            370                 375                 380

Ile Phe Lys Gln Pro Phe Met Arg Pro Val Gln Thr Thr Gln Glu Glu
385                 390                 395                 400

Asp Gly Cys Ser Cys Arg Phe Pro Glu Glu Glu Glu Gly Gly Cys Glu
            405                 410                 415

Leu Arg Val Lys Phe Ser Arg Ser Ala Asp Ala Pro Ala Tyr Gln Gln
            420                 425                 430

Gly Gln Asn Gln Leu Tyr Asn Glu Leu Asn Leu Gly Arg Arg Glu Glu
            435                 440                 445

Tyr Asp Val Leu Asp Lys Arg Arg Gly Arg Asp Pro Glu Met Gly Gly
            450                 455                 460

Lys Pro Arg Arg Lys Asn Pro Gln Glu Gly Leu Tyr Asn Glu Leu Gln
465                 470                 475                 480

Lys Asp Lys Met Ala Glu Ala Tyr Ser Glu Ile Gly Met Lys Gly Glu
            485                 490                 495

Arg Arg Arg Gly Lys Gly His Asp Gly Leu Tyr Gln Gly Leu Ser Thr
            500                 505                 510

Ala Thr Lys Asp Thr Tyr Asp Ala Leu His Met Gln Ala Leu Pro Pro
            515                 520                 525

Arg

<210> SEQ ID NO 68
<211> LENGTH: 405
<212> TYPE: DNA
<213> ORGANISM: Homo sapiens
<220> FEATURE:
<221> NAME/KEY: misc_feature
<223> OTHER INFORMATION: DNA Sequence for alternative NKG2D codon-
      optimized extracellular domain

<400> SEQUENCE: 68
ctgttcaacc aggaggtgca gatccccctg accgaaagct actgcggccc ctgccccaag    60
```

```
aactggatct gttacaagaa caactgctat cagttcttcg acgagagcaa gaactggtac    120
gagagccagg ccagctgtat gagccagaac gccagcctgc tgaaagtgta tagcaaggag    180
gaccaggacc tgctgaagct ggtgaagagc taccactgga tgggcctggt gcacatcccc    240
accaacggaa gctggcagtg ggaggacggc agcatcctga gccccaacct gctgaccatc    300
atcgagatgc agaagggcga ctgcgccctg tatgccagca gcttcaaggg ctacatcgag    360
aactgtagca ccccaacac ctacatctgc atgcaggaa ccgtg                      405

<210> SEQ ID NO 69
<211> LENGTH: 21
<212> TYPE: PRT
<213> ORGANISM: Homo sapiens
<220> FEATURE:
<221> NAME/KEY: MISC_FEATURE
<223> OTHER INFORMATION: Amino Acid Sequence CD3zeta transmembrane

<400> SEQUENCE: 69

Leu Cys Tyr Leu Leu Asp Gly Ile Leu Phe Ile Tyr Gly Val Ile Leu
1               5                   10                  15

Thr Ala Leu Phe Leu
            20

<210> SEQ ID NO 70
<211> LENGTH: 876
<212> TYPE: DNA
<213> ORGANISM: Homo sapiens
<220> FEATURE:
<221> NAME/KEY: misc_feature
<223> OTHER INFORMATION: DNA Sequence Variant 18 (NK39)

<400> SEQUENCE: 70
atggctctgc ccgtcaccgc actgctgctg cctctggctc tgctgctgca cgccgcacga     60
ccactgttca atcaggaagt ccagatcccc ctgacagagt cttactgcgg cccatgtccc    120
aagaactgga tctgctacaa gaacaattgt tatcagttct ttgacgagag caagaactgg    180
tatgagtccc aggcctcttg catgagccag aatgcctctc tgctgaaggt gtacagcaag    240
gaggaccagg atctgctgaa gctggtgaag tcctatcact ggatgggcct ggtgcacatc    300
cctacaaacg ctcttggca gtgggaggac ggctccatcc tgtctccaaa tctgctgacc    360
atcatcgaga tgcagaaggg cgattgcgcc ctgtacgcca gctccttcaa gggctatatc    420
gagaactgct ccacacccaa tacctacatc tgtatgcaga ggaccgtgac cacaaccct    480 gcaccacgcc ccctacacc agcacctacc atcgcaagcc agcctctgtc cctgcggcca    540
gaggcatgta gaccagcagc aggaggagca gtgcacacaa gaggcctgga cttcgcctgc    600
gatcccaaac tctgctacct gctggatgga atcctcttca tctatggtgt cattctcact    660
gccttgttcc tgaagacaaa tatcaggtct agcacccgcg actggaagga tcacaagttt    720
aagtggcgga aggaccctca ggataagaag cggggcagaa agaagctgct gtatatcttc    780
aagcagccct tcatgcggcc cgtgcagaca acccaggagg aagacggctg ctcatgtaga    840
tttcctgaag aagaagaagg gggctgtgaa ctgtaa                              876

<210> SEQ ID NO 71
<211> LENGTH: 291
<212> TYPE: PRT
<213> ORGANISM: Homo sapiens
<220> FEATURE:
<221> NAME/KEY: MISC_FEATURE
<223> OTHER INFORMATION: Amino Acid Sequence Variant 18 (NK39)
```

<400> SEQUENCE: 71

Met Ala Leu Pro Val Thr Ala Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Tyr His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Tyr Ile Glu Asn Cys Ser
    130                 135                 140

Thr Pro Asn Thr Tyr Ile Cys Met Gln Arg Thr Val Thr Thr Thr Pro
145                 150                 155                 160

Ala Pro Arg Pro Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
            180                 185                 190

Thr Arg Gly Leu Asp Phe Ala Cys Asp Pro Lys Leu Cys Tyr Leu Leu
        195                 200                 205

Asp Gly Ile Leu Phe Ile Tyr Gly Val Ile Leu Thr Ala Leu Phe Leu
    210                 215                 220

Lys Thr Asn Ile Arg Ser Ser Thr Arg Asp Trp Lys Asp His Lys Phe
225                 230                 235                 240

Lys Trp Arg Lys Asp Pro Gln Asp Lys Lys Arg Gly Arg Lys Lys Leu
                245                 250                 255

Leu Tyr Ile Phe Lys Gln Pro Phe Met Arg Pro Val Gln Thr Thr Gln
            260                 265                 270

Glu Glu Asp Gly Cys Ser Cys Arg Phe Pro Glu Glu Glu Glu Gly Gly
        275                 280                 285

Cys Glu Leu
    290

<210> SEQ ID NO 72
<211> LENGTH: 1323
<212> TYPE: DNA
<213> ORGANISM: Homo sapiens
<220> FEATURE:
<221> NAME/KEY: misc_feature
<223> OTHER INFORMATION: DNA Sequence NK39_1

<400> SEQUENCE: 72
atggccctgc cgtgacagc tctgctgctg cctctggccc tgctgctgca tgccgctaga      60
cccctgttca accaggaggt gcagatcccc ctgaccgaaa gctactgcgg cccctgcccc    120
aagaactgga tctgttacaa gaacaactgc tatcagttct tcgacgagag caagaactgg    180
tacgagagcc aggccagctg tatgagccag aacgccagct gctgaaagt gtatagcaag    240

-continued

| | | | | |
|---|---|---|---|---|
| gaggaccagg | acctgctgaa | gctggtgaag | agctaccact | ggatgggcct ggtgcacatc | 300 |
| cccaccaacg | gaagctggca | gtgggaggac | ggcagcatcc | tgagcccaa cctgctgacc | 360 |
| atcatcgaga | tgcagaaggg | cgactgcgcc | ctgtatgcca | gcagcttcaa gggctacatc | 420 |
| gagaactgta | gcaccccaa | cacctacatc | tgcatgcaga | ggaccgtggg cggcggcggc | 480 |
| agcggcggag | gcggctccgg | cggcggcggc | agcttattca | accaagaagt tcaaattccc | 540 |
| ttgaccgaaa | gttactgtgg | cccatgtcct | aaaaactgga | tatgttacaa aaataactgc | 600 |
| taccaattt | ttgatgagag | taaaaactgg | tatgagagcc | aggcttcttg tatgtctcaa | 660 |
| aatgccagcc | ttctgaaagt | atacagcaaa | gaggaccagg | atttacttaa actggtgaag | 720 |
| tcatatcatt | ggatgggact | agtacacatt | ccaacaaatg | gatcttggca gtgggaagat | 780 |
| ggctccattc | tctcacccaa | cctactaaca | ataattgaaa | tgcagaaggg agactgtgca | 840 |
| ctctatgcct | cgagctttaa | aggctatata | gaaaactgtt | caactccaaa tacgtacatc | 900 |
| tgcatgcaaa | ggactgtgac | caccacccct | gctcccagac | cccctacacc tgccctaca | 960 |
| atcgccagcc | agcccctgag | cctgagacct | gaggcctgca | gacctgctgc tggaggcgct | 1020 |
| gtgcacacaa | ggggcctcga | cttcgcctgc | gaccccaaac | tctgctacct gctggatgga | 1080 |
| atcctcttca | tctatggtgt | cattctcact | gccttgttcc | tgaagacaaa tatcaggtct | 1140 |
| agcacccgcg | actggaagga | tcacaagttt | aagtggcgga | aggaccctca ggataagaag | 1200 |
| cggggcagaa | agaagctgct | gtatatcttc | aagcagccct | tcatgcggcc cgtgcagaca | 1260 |
| acccaggagg | aagacggctg | ctcatgtaga | tttcctgaag | aagaagaagg gggctgtgaa | 1320 |
| ctg | | | | | 1323 |

<210> SEQ ID NO 73
<211> LENGTH: 441
<212> TYPE: PRT
<213> ORGANISM: Homo sapiens
<220> FEATURE:
<221> NAME/KEY: MISC_FEATURE
<223> OTHER INFORMATION: Amino Acid Sequence NK39_1

<400> SEQUENCE: 73

Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Tyr His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Tyr Ile Glu Asn Cys Ser
    130                 135                 140

Thr Pro Asn Thr Tyr Ile Cys Met Gln Arg Thr Val Gly Gly Gly Gly
145                 150                 155                 160

Ser Gly Gly Gly Gly Ser Gly Gly Gly Ser Leu Phe Asn Gln Glu
            165                 170                 175

Val Gln Ile Pro Leu Thr Glu Ser Tyr Cys Gly Pro Cys Pro Lys Asn
        180                 185                 190

Trp Ile Cys Tyr Lys Asn Asn Cys Tyr Gln Phe Phe Asp Glu Ser Lys
        195                 200                 205

Asn Trp Tyr Glu Ser Gln Ala Ser Cys Met Ser Gln Asn Ala Ser Leu
        210                 215                 220

Leu Lys Val Tyr Ser Lys Glu Asp Gln Asp Leu Leu Lys Leu Val Lys
225                 230                 235                 240

Ser Tyr His Trp Met Gly Leu Val His Ile Pro Thr Asn Gly Ser Trp
                245                 250                 255

Gln Trp Glu Asp Gly Ser Ile Leu Ser Pro Asn Leu Leu Thr Ile Ile
            260                 265                 270

Glu Met Gln Lys Gly Asp Cys Ala Leu Tyr Ala Ser Ser Phe Lys Gly
        275                 280                 285

Tyr Ile Glu Asn Cys Ser Thr Pro Asn Thr Tyr Ile Cys Met Gln Arg
        290                 295                 300

Thr Val Thr Thr Thr Pro Ala Pro Arg Pro Thr Pro Ala Pro Thr
305                 310                 315                 320

Ile Ala Ser Gln Pro Leu Ser Leu Arg Pro Glu Ala Cys Arg Pro Ala
            325                 330                 335

Ala Gly Gly Ala Val His Thr Arg Gly Leu Asp Phe Ala Cys Asp Pro
            340                 345                 350

Lys Leu Cys Tyr Leu Leu Asp Gly Ile Leu Phe Ile Tyr Gly Val Ile
        355                 360                 365

Leu Thr Ala Leu Phe Leu Lys Thr Asn Ile Arg Ser Ser Thr Arg Asp
370                 375                 380

Trp Lys Asp His Lys Phe Lys Trp Arg Lys Asp Pro Gln Asp Lys Lys
385                 390                 395                 400

Arg Gly Arg Lys Lys Leu Leu Tyr Ile Phe Lys Gln Pro Phe Met Arg
            405                 410                 415

Pro Val Gln Thr Thr Gln Glu Glu Asp Gly Cys Ser Cys Arg Phe Pro
            420                 425                 430

Glu Glu Glu Glu Gly Gly Cys Glu Leu
            435                 440

<210> SEQ ID NO 74
<211> LENGTH: 1032
<212> TYPE: DNA
<213> ORGANISM: Homo sapiens
<220> FEATURE:
<221> NAME/KEY: misc_feature
<223> OTHER INFORMATION: DNA Sequence NK39_2

<400> SEQUENCE: 74
atggccctgc ccgtgacagc tctgctgctg cctctggccc tgctgctgca tgccgctaga      60
cccttattca accaagaagt tcaaattccc ttgaccgaaa gttactgtgg cccatgtcct     120
aaaaactgga tatgttacaa aaataactgc taccaatttt ttgatgagag taaaaactgg     180
tatgagagcc aggcttcttg tatgtctcaa atgccagcc ttctgaaagt atacagcaaa     240
gaggaccagg atttacttaa actggtgaag tcatatcatt ggatgggact agtacacatt     300
ccaacaaatg gatcttggca gtgggaagat ggctccattc tctcacccaa cctactaaca     360
ataattgaaa tgcagaaggg agactgtgca ctctatgcct cgagctttaa aggctatata     420

-continued

```
gaaaactgtt caactccaaa tacgtacatc tgcatgcaaa ggactgtgac caccaccct    480 gctcccagac ccctacacc tgcccctaca atcgccagcc agcccctgag cctgagacct    540
gaggcctgca gacctgctgc tggaggcgct gtgcacacaa ggggcctcga cttcgcctgc    600
gaccccaaac tctgctacct gctggatgga atcctcttca tctatggtgt cattctcact    660
gccttgttcc tgaagacaaa tatcaggtct agcacccgcg actggaagga tcacaagttt    720
aagtggcgga aggaccctca ggataagaag cggggcagaa agaagctgct gtatatcttc    780
aagcagccct tcatgcggcc cgtgcagaca acccaggagg aagacggctg ctcatgtaga    840
tttcctgaag aagaagaagg gggctgtgaa ctgggcggag gaggcagcgg cggcggcggc    900
agcggcggcg gcggcagcat gcaggatgag gacggctaca tgaccctgaa cgtgcagagc    960
aagaagagga gcagcgccca gaccagccag ctgaccttca aggactacag cgtgaccctg    1020
cactggtaca ag                                                        1032
```

<210> SEQ ID NO 75
<211> LENGTH: 344
<212> TYPE: PRT
<213> ORGANISM: Homo sapiens
<220> FEATURE:
<221> NAME/KEY: MISC_FEATURE
<223> OTHER INFORMATION: Amino Acid Sequence NK39_2

<400> SEQUENCE: 75

```
Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Tyr His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Tyr Ile Glu Asn Cys Ser
    130                 135                 140

Thr Pro Asn Thr Tyr Ile Cys Met Gln Arg Thr Val Thr Thr Thr Pro
145                 150                 155                 160

Ala Pro Arg Pro Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
            180                 185                 190

Thr Arg Gly Leu Asp Phe Ala Cys Asp Pro Lys Leu Cys Tyr Leu Leu
        195                 200                 205

Asp Gly Ile Leu Phe Ile Tyr Gly Val Ile Leu Thr Ala Leu Phe Leu
    210                 215                 220

Lys Thr Asn Ile Arg Ser Ser Thr Arg Asp Trp Lys Asp His Lys Phe
225                 230                 235                 240

Lys Trp Arg Lys Asp Pro Gln Asp Lys Lys Arg Gly Arg Lys Lys Leu
```

```
                  245                 250                 255
Leu Tyr Ile Phe Lys Gln Pro Phe Met Arg Pro Val Gln Thr Thr Gln
            260                 265                 270

Glu Glu Asp Gly Cys Ser Cys Arg Phe Pro Glu Glu Glu Gly Gly
        275                 280                 285

Cys Glu Leu Gly Gly Gly Ser Gly Gly Gly Ser Gly Gly Gly
    290                 295                 300

Gly Ser Met Gln Asp Glu Asp Gly Tyr Met Thr Leu Asn Val Gln Ser
305                 310                 315                 320

Lys Lys Arg Ser Ser Ala Gln Thr Ser Gln Leu Thr Phe Lys Asp Tyr
                325                 330                 335

Ser Val Thr Leu His Trp Tyr Lys
            340

<210> SEQ ID NO 76
<211> LENGTH: 1416
<212> TYPE: DNA
<213> ORGANISM: Homo sapiens
<220> FEATURE:
<221> NAME/KEY: misc_feature
<223> OTHER INFORMATION: DNA Sequence NK39_3

<400> SEQUENCE: 76
atggccctgc cgtgacagc tctgctgctg cctctggccc tgctgctgca tgccgctaga      60
cccctgttca accaggaggt gcagatcccc ctgaccgaaa gctactgcgg ccctgccc     120
aagaactgga tctgttacaa gaacaactgc tatcagttct cgacgagag caagaactgg    180
tacgagagcc aggccagctg tatgagccag aacgccagct gctgaaaagt gtatagcaag   240
gaggaccagg acctgctgaa gctggtgaag agctaccact ggatgggcct ggtgcacatc   300
cccaccaacg gaagctggca gtgggaggac ggcagcatcc tgagccccaa cctgctgacc   360
atcatcgaga tgcagaaggg cgactgcgcc ctgtatgcca gcagcttcaa gggctacatc   420
gagaactgta gcacccccaa cacctacatc tgcatgcaga ggaccgtggg cggcggcggc   480
agcggcggag cggctccgg cggcggcggc agcttattca accaagaagt tcaaattccc   540
ttgaccgaaa gttactgtgg cccatgtcct aaaaactgga tatgttacaa aaataactgc   600
taccaatttt tgatgagag taaaaactgg tatgagagcc aggcttcttg tatgtctcaa   660
aatgccagcc ttctgaaagt atacagcaaa gaggaccagg atttacttaa actggtgaag   720
tcatatcatt ggatgggact agtacacatt ccaacaaatg gatcttggca gtgggaagat   780
ggctccattc tctcacccaa cctactaaca ataattgaaa tgcagaaggg agactgtgca   840
ctctatgcct cgagctttaa aggctatata gaaaactgtt caactccaaa tacgtacatc   900
tgcatgcaaa ggactgtgac caccaccct gctcccagac ccctacacc tgccctaca    960
atcgccagcc agcccctgag cctgagacct gaggcctgca gacctgctgc tggaggcgct  1020
gtgcacacaa gggcctcga cttcgcctgc gaccccaaac tctgctacct gctggatgga  1080
atcctcttca tctatggtgt cattctcact gccttgttcc tgctttactg caagcggggc  1140
agaaagaagc tgctgtatat cttcaagcag cccttcatgc ggcccgtgca gacaacccag  1200
gaggaagacg gctgctcatg tagatttcct gaagaagaag aaggggggctg tgaactgggc  1260
ggaggaggca gcggcggcgg cggcagcggc ggcggcggca gcatgcagga tgaggacggc  1320
tacatgaccc tgaacgtgca gagcaagaag aggagcagcg cccagaccag ccagctgacc  1380
ttcaaggact acagcgtgac cctgcactgg tacaag                            1416
```

```
<210> SEQ ID NO 77
<211> LENGTH: 472
<212> TYPE: PRT
<213> ORGANISM: Homo sapiens
<220> FEATURE:
<221> NAME/KEY: MISC_FEATURE
<223> OTHER INFORMATION: Amino Acid Sequence NK39_3

<400> SEQUENCE: 77

Met Ala Leu Pro Val Thr Ala Leu Leu Pro Leu Ala Leu Leu Leu
1               5                   10                  15

His Ala Ala Arg Pro Leu Phe Asn Gln Glu Val Gln Ile Pro Leu Thr
                20                  25                  30

Glu Ser Tyr Cys Gly Pro Cys Pro Lys Asn Trp Ile Cys Tyr Lys Asn
            35                  40                  45

Asn Cys Tyr Gln Phe Phe Asp Glu Ser Lys Asn Trp Tyr Glu Ser Gln
50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Tyr His Trp Met Gly
                85                  90                  95

Leu Val His Ile Pro Thr Asn Gly Ser Trp Gln Trp Glu Asp Gly Ser
                100                 105                 110

Ile Leu Ser Pro Asn Leu Leu Thr Ile Ile Glu Met Gln Lys Gly Asp
            115                 120                 125

Cys Ala Leu Tyr Ala Ser Ser Phe Lys Gly Tyr Ile Glu Asn Cys Ser
130                 135                 140

Thr Pro Asn Thr Tyr Ile Cys Met Gln Arg Thr Val Gly Gly Gly Gly
145                 150                 155                 160

Ser Gly Gly Gly Gly Ser Gly Gly Gly Gly Ser Leu Phe Asn Gln Glu
                165                 170                 175

Val Gln Ile Pro Leu Thr Glu Ser Tyr Cys Gly Pro Cys Pro Lys Asn
            180                 185                 190

Trp Ile Cys Tyr Lys Asn Asn Cys Tyr Gln Phe Phe Asp Glu Ser Lys
        195                 200                 205

Asn Trp Tyr Glu Ser Gln Ala Ser Cys Met Ser Gln Asn Ala Ser Leu
    210                 215                 220

Leu Lys Val Tyr Ser Lys Glu Asp Gln Asp Leu Leu Lys Leu Val Lys
225                 230                 235                 240

Ser Tyr His Trp Met Gly Leu Val His Ile Pro Thr Asn Gly Ser Trp
                245                 250                 255

Gln Trp Glu Asp Gly Ser Ile Leu Ser Pro Asn Leu Leu Thr Ile Ile
            260                 265                 270

Glu Met Gln Lys Gly Asp Cys Ala Leu Tyr Ala Ser Ser Phe Lys Gly
        275                 280                 285

Tyr Ile Glu Asn Cys Ser Thr Pro Asn Thr Tyr Ile Cys Met Gln Arg
    290                 295                 300

Thr Val Thr Thr Thr Pro Ala Pro Arg Pro Pro Thr Pro Ala Pro Thr
305                 310                 315                 320

Ile Ala Ser Gln Pro Leu Ser Leu Arg Pro Glu Ala Cys Arg Pro Ala
                325                 330                 335

Ala Gly Gly Ala Val His Thr Arg Gly Leu Asp Phe Ala Cys Asp Pro
            340                 345                 350

Lys Leu Cys Tyr Leu Leu Asp Gly Ile Leu Phe Ile Tyr Gly Val Ile
        355                 360                 365
```

```
Leu Thr Ala Leu Phe Leu Leu Tyr Cys Lys Arg Gly Arg Lys Lys Leu
        370                 375                 380

Leu Tyr Ile Phe Lys Gln Pro Phe Met Arg Pro Val Gln Thr Thr Gln
385                 390                 395                 400

Glu Glu Asp Gly Cys Ser Cys Arg Phe Pro Glu Glu Glu Gly Gly
                405                 410                 415

Cys Glu Leu Gly Gly Gly Ser Gly Gly Gly Ser Gly Gly Gly
                420                 425                 430

Gly Ser Met Gln Asp Glu Asp Gly Tyr Met Thr Leu Asn Val Gln Ser
            435                 440                 445

Lys Lys Arg Ser Ser Ala Gln Thr Ser Gln Leu Thr Phe Lys Asp Tyr
        450                 455                 460

Ser Val Thr Leu His Trp Tyr Lys
465                 470

<210> SEQ ID NO 78
<211> LENGTH: 807
<212> TYPE: DNA
<213> ORGANISM: Homo sapiens
<220> FEATURE:
<221> NAME/KEY: misc_feature
<223> OTHER INFORMATION: DNA Sequence NK39_4

<400> SEQUENCE: 78
atggctctgc ccgtcaccgc actgctgctg cctctggctc tgctgctgca cgccgcacga    60
ccactgttca tcaggaagt ccagatcccc ctgacagagt cttactgcgg cccatgtccc    120
aagaactgga tctgctacaa gaacaattgt tatcagttct ttgacgagag caagaactgg    180
tatgagtccc aggcctcttg catgagccag aatgcctctc tgctgaaggt gtacagcaag    240
gaggaccagg atctgctgaa gctggtgaag tcctatcact ggatgggcct ggtgcacatc    300
cctacaaacg ctcttggca gtgggaggac ggctccatcc tgtctccaaa tctgctgacc    360
atcatcgaga tgcagaaggg cgattgcgcc ctgtacgcca gctccttcaa gggctatatc    420
gagaactgct ccacacccaa tacctacatc tgtatgcaga ggaccgtgac cacaaccct    480 gcaccacgcc ccctacacc agcacctacc atcgcaagcc agcctctgtc cctgcggcca    540
gaggcatgta gaccagcagc aggaggagca gtgcacacaa gaggcctgga cttcgcctgc    600
gatcccaaac tctgctacct gctggatgga atcctcttca tctatggtgt cattctcact    660
gccttgttcc tgctttactg caagcggggc agaaagaagc tgctgtatat cttcaagcag    720
cccttcatgc ggcccgtgca gacaacccag gaggaagacg gctgctcatg tagatttcct    780
gaagaagaag aagggggctg tgaactg                                        807

<210> SEQ ID NO 79
<211> LENGTH: 269
<212> TYPE: PRT
<213> ORGANISM: Homo sapiens
<220> FEATURE:
<221> NAME/KEY: MISC_FEATURE
<223> OTHER INFORMATION: Amino Acid Sequence NK39_4

<400> SEQUENCE: 79

Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
```

|  | | 35 | | | 40 | | | | 45 | | | |
|---|---|---|---|---|---|---|---|---|---|---|---|---|

Asn Cys Tyr Gln Phe Phe Asp Glu Ser Lys Asn Trp Tyr Glu Ser Gln
 50                     55                      60

Ala Ser Cys Met Ser Gln Asn Ala Ser Leu Leu Lys Val Tyr Ser Lys
 65                      70                  75                      80

Glu Asp Gln Asp Leu Leu Lys Leu Val Lys Ser Tyr His Trp Met Gly
                     85                      90                      95

Leu Val His Ile Pro Thr Asn Gly Ser Trp Gln Trp Glu Asp Gly Ser
                 100                    105                 110

Ile Leu Ser Pro Asn Leu Leu Thr Ile Ile Glu Met Gln Lys Gly Asp
             115                     120                 125

Cys Ala Leu Tyr Ala Ser Ser Phe Lys Gly Tyr Ile Glu Asn Cys Ser
         130                     135                 140

Thr Pro Asn Thr Tyr Ile Cys Met Gln Arg Thr Val Thr Thr Thr Pro
145                     150                     155                     160

Ala Pro Arg Pro Pro Thr Pro Ala Pro Thr Ile Ala Ser Gln Pro Leu
                 165                     170                     175

Ser Leu Arg Pro Glu Ala Cys Arg Pro Ala Ala Gly Gly Ala Val His
             180                     185                     190

Thr Arg Gly Leu Asp Phe Ala Cys Asp Pro Lys Leu Cys Tyr Leu Leu
         195                     200                     205

Asp Gly Ile Leu Phe Ile Tyr Gly Val Ile Leu Thr Ala Leu Phe Leu
210                     215                     220

Leu Tyr Cys Lys Arg Gly Arg Lys Lys Leu Leu Tyr Ile Phe Lys Gln
225                     230                     235                     240

Pro Phe Met Arg Pro Val Gln Thr Thr Gln Glu Glu Asp Gly Cys Ser
                     245                     250                     255

Cys Arg Phe Pro Glu Glu Glu Glu Gly Gly Cys Glu Leu
                 260                     265

<210> SEQ ID NO 80
<211> LENGTH: 1143
<212> TYPE: DNA
<213> ORGANISM: Homo sapiens
<220> FEATURE:
<221> NAME/KEY: misc_feature
<223> OTHER INFORMATION: DNA Sequence NK39_5

<400> SEQUENCE: 80

| | | |
|---|---|---|
| atggctctgc ccgtcaccgc actgctgctg cctctggctc tgctgctgca cgccgcacga | 60 |
| ccactgttca atcaggaagt ccagatcccc ctgacagagt cttactgcgg cccatgtccc | 120 |
| aagaactgga tctgctacaa gaacaattgt tatcagttct ttgacgagag caagaactgg | 180 |
| tatgagtccc aggcctcttg catgagccag aatgcctctc tgctgaaggt gtacagcaag | 240 |
| gaggaccagg atctgctgaa gctggtgaag tcctatcact ggatgggcct ggtgcacatc | 300 |
| cctacaaacg gctcttggca gtgggaggac ggctccatcc tgtctccaaa tctgctgacc | 360 |
| atcatcgaga tgcagaaggg cgattgcgcc ctgtacgcca gctccttcaa gggctatatc | 420 |
| gagaactgct ccacacccaa tacctacatc tgtatgcaga ggaccgtgac cacaaccccT | 480 |
| gcaccacgcc ccctacacc agcacctacc atcgcaagcc agcctctgtc cctgcggcca | 540 |
| gaggcatgta gaccagcagc aggaggagca gtgcacacaa gaggcctgga cttcgcctgc | 600 |
| gatcccaaac tctgctacct gctggatgga atcctcttca tctatggtgt cattctcact | 660 |
| gccttgttcc tgctttactg caagcggggc agaaagaagc tgctgtatat cttcaagcag | 720 |

```
cccttcatgc ggcccgtgca gacaacccag gaggaagacg gctgctcatg tagatttcct    780
gaagaagaag aagggggctg tgaactgaga gtgaagttca gcaggagcgc agacgccccc    840
gcgtaccagc agggccagaa ccagctctat aacgagctca atctaggacg aagagaggag    900
tacgatgttt tggacaagag acgtggccgg gaccctgaga tggggggaaa gccgagaagg    960
aagaaccctc aggaaggcct gtacaatgaa ctgcagaaag ataagatggc ggaggcctac   1020
agtgagattg ggatgaaagg cgagcgccgg aggggcaagg ggcacgatgg cctttaccag   1080
ggtctcagta cagccaccaa ggacacctac gacgcccttc acatgcaggc cctgccccct   1140
cgc                                                                  1143
```

<210> SEQ ID NO 81
<211> LENGTH: 381
<212> TYPE: PRT
<213> ORGANISM: Homo sapiens
<220> FEATURE:
<221> NAME/KEY: MISC_FEATURE
<223> OTHER INFORMATION: Amino Acid Sequence NK39_5

<400> SEQUENCE: 81

```
Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Tyr His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Tyr Ile Glu Asn Cys Ser
    130                 135                 140

Thr Pro Asn Thr Tyr Ile Cys Met Gln Arg Thr Val Thr Thr Thr Pro
145                 150                 155                 160

Ala Pro Arg Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
            180                 185                 190

Thr Arg Gly Leu Asp Phe Ala Cys Asp Pro Lys Leu Cys Tyr Leu Leu
        195                 200                 205

Asp Gly Ile Leu Phe Ile Tyr Gly Val Ile Leu Thr Ala Leu Phe Leu
    210                 215                 220

Leu Tyr Cys Lys Arg Gly Arg Lys Leu Leu Tyr Ile Phe Lys Gln
225                 230                 235                 240

Pro Phe Met Arg Pro Val Gln Thr Thr Gln Glu Glu Asp Gly Cys Ser
                245                 250                 255

Cys Arg Phe Pro Glu Glu Glu Glu Gly Gly Cys Glu Leu Arg Val Lys
            260                 265                 270

Phe Ser Arg Ser Ala Asp Ala Pro Ala Tyr Gln Gln Gly Gln Asn Gln
```

```
                275                 280                 285
Leu Tyr Asn Glu Leu Asn Leu Gly Arg Arg Glu Tyr Asp Val Leu
    290                 295                 300

Asp Lys Arg Arg Gly Arg Asp Pro Glu Met Gly Gly Lys Pro Arg Arg
305                 310                 315                 320

Lys Asn Pro Gln Glu Gly Leu Tyr Asn Glu Leu Gln Lys Asp Lys Met
                325                 330                 335

Ala Glu Ala Tyr Ser Glu Ile Gly Met Lys Gly Glu Arg Arg Gly
            340                 345                 350

Lys Gly His Asp Gly Leu Tyr Gln Gly Leu Ser Thr Ala Thr Lys Asp
                355                 360                 365

Thr Tyr Asp Ala Leu His Met Gln Ala Leu Pro Pro Arg
    370                 375                 380

<210> SEQ ID NO 82
<211> LENGTH: 965
<212> TYPE: DNA
<213> ORGANISM: Homo sapiens
<220> FEATURE:
<221> NAME/KEY: misc_feature
<223> OTHER INFORMATION: DNA Sequence NK39_6

<400> SEQUENCE: 82
atggctctgc cgtcaccgc actgctgctg cctctggctc tgctgctgca cgccgcacga      60
ccactgttca atcaggaagt ccagatcccc ctgacagagt cttactgcgg cccatgtccc    120
aagaactgga tctgctacaa gaacaattgt tatcagttct ttgacgagag caagaactgg    180
tatgagtccc aggcctcttg catgagccag aatgcctctc tgctgaaggt gtacagcaag    240
gaggaccagg atctgctgaa gctggtgaag tcctatcact ggatgggcct ggtgcacatc    300
cctacaaacg gctcttggca gtgggaggac ggctccatcc tgtctccaaa tctgctgacc    360
atcatcgaga tgcagaaggg cgattgcgcc ctgtacgcca gctccttcaa gggctatatc    420
gagaactgct ccacacccaa tacctacatc tgtatgcaga ggaccgtgac cacaacccct    480
gcaccacgcc ccctacacc agcacctacc atcgcaagcc agcctctgtc cctgcggcca    540
gaggcatgta gaccagcagc aggaggagca gtgcacacaa gaggcctgga cttcgcctgc    600
gatcccaaac tctgctacct gctggatgga atcctcttca tctatggtgt cattctcact    660
gccttgttcc tgctttactg caagcggggc agaaagaagc tgctgtatat cttcaagcag    720
cccttcatgc ggcccgtgca gacaacccag gaggaagacg gctgctcatg tagatttcct    780
gaagaagaag aaggggggctg tgaactgggc ggaggaggca gcggcggcgg cggcagcggc    840
ggcggcggca gcatgcagga tgaggacggc tacatgaccc tgaacgtgca gagcaagaag    900
aggagcagcg cccagaccag ccagctgacc ttcaaggact acagcgtgac cctgcactgg    960
tacaa                                                                965

<210> SEQ ID NO 83
<211> LENGTH: 322
<212> TYPE: PRT
<213> ORGANISM: Homo sapiens
<220> FEATURE:
<221> NAME/KEY: MISC_FEATURE
<223> OTHER INFORMATION: Amino Acid Sequence NK39_6

<400> SEQUENCE: 83

Met Ala Leu Pro Val Thr Ala Leu Leu Leu Pro Leu Ala Leu Leu Leu
1               5                   10                  15
```

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Tyr His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Tyr Ile Glu Asn Cys Ser
    130                 135                 140

Thr Pro Asn Thr Tyr Ile Cys Met Gln Arg Thr Val Thr Thr Thr Pro
145                 150                 155                 160

Ala Pro Arg Pro Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
            180                 185                 190

Thr Arg Gly Leu Asp Phe Ala Cys Asp Pro Lys Leu Cys Tyr Leu Leu
        195                 200                 205

Asp Gly Ile Leu Phe Ile Tyr Gly Val Ile Leu Thr Ala Leu Phe Leu
    210                 215                 220

Leu Tyr Cys Lys Arg Gly Arg Lys Lys Leu Leu Tyr Ile Phe Lys Gln
225                 230                 235                 240

Pro Phe Met Arg Pro Val Gln Thr Thr Gln Glu Glu Asp Gly Cys Ser
                245                 250                 255

Cys Arg Phe Pro Glu Glu Glu Glu Gly Gly Cys Glu Leu Gly Gly Gly
            260                 265                 270

Gly Ser Gly Gly Gly Gly Ser Gly Gly Gly Ser Met Gln Asp Glu
        275                 280                 285

Asp Gly Tyr Met Thr Leu Asn Val Gln Ser Lys Lys Arg Ser Ser Ala
    290                 295                 300

Gln Thr Ser Gln Leu Thr Phe Lys Asp Tyr Ser Val Thr Leu His Trp
305                 310                 315                 320

Tyr Lys

<210> SEQ ID NO 84
<211> LENGTH: 927
<212> TYPE: DNA
<213> ORGANISM: Homo sapiens
<220> FEATURE:
<221> NAME/KEY: misc_feature
<223> OTHER INFORMATION: DNA Sequence NK39_7

<400> SEQUENCE: 84
atggctctgc cgtcaccgc actgctgctg cctctggctc tgctgctgca cgccgcacga      60
ccactgttca atcaggaagt ccagatcccc ctgacagagt cttactgcgg cccatgtccc     120
aagaactgga tctgctacaa gaacaattgt tatcagttct ttgacgagag caagaactgg     180
tatgagtccc aggcctcttg catgagccag aatgcctctc tgctgaaggt gtacagcaag     240
gaggaccagg atctgctgaa gctggtgaag tcctatcact ggatgggcct ggtgcacatc     300

```
cctacaaacg gctcttggca gtgggaggac ggctccatcc tgtctccaaa tctgctgacc    360
atcatcgaga tgcagaaggg cgattgcgcc ctgtacgcca gctccttcaa gggctatatc    420
gagaactgct ccacacccaa tacctacatc tgtatgcaga ggaccgtgac cacaacccct    480
gcaccacgcc cccctacacc agcacctacc atcgcaagcc agcctctgtc cctgcggcca    540
gaggcatgta gaccagcagc aggaggagca gtgcacacaa gaggcctgga cttcgcctgc    600
gatcccaaac tctgctacct gctggatgga atcctcttca tctatggtgt cattctcact    660
gccttgttcc tgctttactg caagcggggc agaaagaagc tgctgtatat cttcaagcag    720
cccttcatgc ggcccgtgca gacaacccag gaggaagacg gctgctcatg tagatttcct    780
gaagaagaag aagggggctg tgaactgggc ggaggaggca gcggcggcgg cggcagcggc    840
ggcggcggca gcaagacaaa tatcaggtct agcacccgcg actggaagga tcacaagttt    900
aagtggcgga aggaccctca ggataag                                       927
```

<210> SEQ ID NO 85
<211> LENGTH: 309
<212> TYPE: PRT
<213> ORGANISM: Homo sapiens
<220> FEATURE:
<221> NAME/KEY: MISC_FEATURE
<223> OTHER INFORMATION: Amino Acid Sequence NK39_7

<400> SEQUENCE: 85

```
Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Tyr His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Tyr Ile Glu Asn Cys Ser
    130                 135                 140

Thr Pro Asn Thr Tyr Ile Cys Met Gln Arg Thr Val Thr Thr Thr Pro
145                 150                 155                 160

Ala Pro Arg Pro Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
            180                 185                 190

Thr Arg Gly Leu Asp Phe Ala Cys Asp Pro Lys Leu Cys Tyr Leu Leu
        195                 200                 205

Asp Gly Ile Leu Phe Ile Tyr Gly Val Ile Leu Thr Ala Leu Phe Leu
    210                 215                 220

Leu Tyr Cys Lys Arg Gly Arg Lys Lys Leu Leu Tyr Ile Phe Lys Gln
225                 230                 235                 240
```

```
Pro Phe Met Arg Pro Val Gln Thr Thr Gln Glu Glu Asp Gly Cys Ser
                245                 250                 255

Cys Arg Phe Pro Glu Glu Glu Gly Gly Cys Glu Leu Gly Gly Gly
            260                 265                 270

Gly Ser Gly Gly Gly Ser Gly Gly Gly Ser Lys Thr Asn Ile
            275                 280                 285

Arg Ser Ser Thr Arg Asp Trp Lys Asp His Lys Phe Lys Trp Arg Lys
        290                 295                 300

Asp Pro Gln Asp Lys
305

<210> SEQ ID NO 86
<211> LENGTH: 933
<212> TYPE: DNA
<213> ORGANISM: Homo sapiens
<220> FEATURE:
<221> NAME/KEY: misc_feature
<223> OTHER INFORMATION: DNA Sequence NK39_8

<400> SEQUENCE: 86
atggccctgc ccgtgacagc tctgctgctg cctctggccc tgctgctgca tgccgctaga      60
cccttattca accaagaagt tcaaattccc ttgaccgaaa gttactgtgg cccatgtcct     120
aaaaactgga tatgttacaa aaataactgc taccaatttt ttgatgagag taaaaactgg     180
tatgagagcc aggcttcttg tatgtctcaa aatgccagcc ttctgaaagt atacagcaaa     240
gaggaccagg atttacttaa actggtgaag tcatatcatt ggatgggact agtacacatt     300
ccaacaaatg atcttggca gtgggaagat ggctccattc tctcacccaa cctactaaca     360
ataattgaaa tgcagaaggg agactgtgca ctctatgcct cgagctttaa aggctatata     420
gaaaactgtt caactccaaa tacgtacatc tgcatgcaaa ggactgtgac caccacccct     480
gctcccagac cccctacacc tgcccctaca atcgccagcc agcccctgag cctgagacct     540
gaggcctgca gacctgctgc tggaggcgct gtgcacacaa ggggcctcga cttcgcctgc     600
gaccccaaac tctgctacct gctggatgga atcctcttca tctatggtgt cattctcact     660
gccttgttcc tgctttactg caagcggggc agaaagaagc tgctgtatat cttcaagcag     720
cccttcatgc ggcccgtgca gacaacccag gaggaagacg gctgctcatg tagatttcct     780
gaagaagaag aagggggctg tgaactgcga ctgaagatcc aagtgcgaaa ggcagctata     840
accagctatg agaaatcaga tggtgtttac acgggcctga gcaccaggaa ccaggagact     900
tacgagactc tgaagcatga gaaccacca cag                                   933

<210> SEQ ID NO 87
<211> LENGTH: 311
<212> TYPE: PRT
<213> ORGANISM: Homo sapiens
<220> FEATURE:
<221> NAME/KEY: MISC_FEATURE
<223> OTHER INFORMATION: Amino Acid Sequence NK39_8

<400> SEQUENCE: 87

Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
```

```
                50                  55                  60
Ala Ser Cys Met Ser Gln Asn Ala Ser Leu Leu Lys Val Tyr Ser Lys
 65                  70                  75                  80

Glu Asp Gln Asp Leu Leu Lys Leu Val Lys Ser Tyr His Trp Met Gly
                 85                  90                  95

Leu Val His Ile Pro Thr Asn Gly Ser Trp Gln Trp Glu Asp Gly Ser
                100                 105                 110

Ile Leu Ser Pro Asn Leu Leu Thr Ile Ile Glu Met Gln Lys Gly Asp
                115                 120                 125

Cys Ala Leu Tyr Ala Ser Ser Phe Lys Gly Tyr Ile Glu Asn Cys Ser
130                 135                 140

Thr Pro Asn Thr Tyr Ile Cys Met Gln Arg Thr Val Thr Thr Thr Pro
145                 150                 155                 160

Ala Pro Arg Pro Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
                180                 185                 190

Thr Arg Gly Leu Asp Phe Ala Cys Asp Pro Lys Leu Cys Tyr Leu Leu
                195                 200                 205

Asp Gly Ile Leu Phe Ile Tyr Gly Val Ile Leu Thr Ala Leu Phe Leu
210                 215                 220

Leu Tyr Cys Lys Arg Gly Arg Lys Lys Leu Leu Tyr Ile Phe Lys Gln
225                 230                 235                 240

Pro Phe Met Arg Pro Val Gln Thr Thr Gln Glu Glu Asp Gly Cys Ser
                245                 250                 255

Cys Arg Phe Pro Glu Glu Glu Glu Gly Gly Cys Glu Leu Arg Leu Lys
                260                 265                 270

Ile Gln Val Arg Lys Ala Ala Ile Thr Ser Tyr Glu Lys Ser Asp Gly
                275                 280                 285

Val Tyr Thr Gly Leu Ser Thr Arg Asn Gln Glu Thr Tyr Glu Thr Leu
                290                 295                 300

Lys His Glu Lys Pro Pro Gln
305                 310

<210> SEQ ID NO 88
<211> LENGTH: 1605
<212> TYPE: DNA
<213> ORGANISM: Homo sapiens
<220> FEATURE:
<221> NAME/KEY: misc_feature
<223> OTHER INFORMATION: DNA Sequence NK39_9

<400> SEQUENCE: 88
atgagaattt cgaaaccaca tttgagaagt atttccatcc agtgctactt gtgtttactt      60
ctaaacagtc attttctaac tgaagctggc attcatgtct tcattttggg ctgtttcagt     120
gcagggcttc ctaaaacaga agccaactgg gtcaacgtga ttagcgattt gaagaaaatc     180 gaggaccttatacagtctat gcatattgac gctacactgt atactgagag tgatgtacac     240
ccgtcctgta aggtaacggc catgaaatgc tttcttctgg agctccaggt catcagcttg     300
gagtctgggg acgcaagcat ccacgatacg gttgaaaacc tcatcatcct tgcgaacaac     360
tctctctcat ctaatggaaa cgttacagag agtgggtgta aggagtgcga agagttggaa     420
gaaaaaaaca tcaagaaatt tcttcaatcc ttcgttcaca tagtgcaaat gttcattaac     480
acgtccggcg aggaggcag cggcggcggc ggcagcggcg gcggcggcag cttattcaac     540
```

```
caagaagttc aaattccctt gaccgaaagt tactgtggcc catgtcctaa aaactggata    600
tgttacaaaa ataactgcta ccaattttttt gatgagagta aaaactggta tgagagccag   660
gcttcttgta tgtctcaaaa tgccagccct ctgaaagtat acagcaaaga ggaccaggat    720
ttacttaaac tggtgaagtc atatcattgg atgggactag tacacattcc aacaaatgga    780
tcttggcagt gggaagatgg ctccattctc tcacccaacc tactaacaat aattgaaatg    840
cagaagggag actgtgcact ctatgcctcg agctttaaag ctatataga aaactgttca     900
actccaaata cgtacatctg catgcaaagg actgtgacca cgacgccagc gccgcgacca    960
ccaacaccgg cgcccaccat cgcgtcgcag cccctgtccc tgcgcccaga ggcgtgccgg    1020
ccagcggcgg ggggcgcagt gcacacgagg gggctggact tcgcctgtga tatctacatc   1080
tgggcgccct tggccgggac ttgtggggtc cttctcctgt cactggttat cacccttttac   1140
tgcaaacggg gcagaaagaa actcctgtat atattcaaac aaccatttat gagaccagta    1200
caaactactc aagaggaaga tggctgtagc tgccgatttc cagaagaaga agaaggagga    1260
tgtgaactga gagtgaagtt cagcaggagc gcagacgccc ccgcgtacca gcagggccag    1320
aaccagctct ataacgagct caatctagga cgaagagagg agtacgatgt tttggacaag    1380
agacgtggcc gggaccctga gatgggggga aagccgagaa ggaagaaccc tcaggaaggc    1440
ctgtacaatg aactgcagaa agataagatg gcggaggcct acagtgagat tgggatgaaa    1500
ggcgagcgcc ggaggggcaa gggggcacgat ggcctttacc agggtctcag tacagccacc   1560
aaggacacct acgacgccct tcacatgcag gccctgcccc ctcgc                    1605
```

<210> SEQ ID NO 89
<211> LENGTH: 535
<212> TYPE: PRT
<213> ORGANISM: Homo sapiens
<220> FEATURE:
<221> NAME/KEY: MISC_FEATURE
<223> OTHER INFORMATION: Amino Acid Sequence NK39_9

<400> SEQUENCE: 89

```
Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser Gly Gly Gly Gly Ser Gly Gly Gly Gly Ser Gly Gly Gly Gly
                165                 170                 175
```

Ser Leu Phe Asn Gln Glu Val Gln Ile Pro Leu Thr Glu Ser Tyr Cys
            180                 185                 190

Gly Pro Cys Pro Lys Asn Trp Ile Cys Tyr Lys Asn Asn Cys Tyr Gln
            195                 200                 205

Phe Phe Asp Glu Ser Lys Asn Trp Tyr Glu Ser Gln Ala Ser Cys Met
            210                 215                 220

Ser Gln Asn Ala Ser Leu Leu Lys Val Tyr Ser Lys Glu Asp Gln Asp
225                 230                 235                 240

Leu Leu Lys Leu Val Lys Ser Tyr His Trp Met Gly Leu Val His Ile
            245                 250                 255

Pro Thr Asn Gly Ser Trp Gln Trp Glu Asp Gly Ser Ile Leu Ser Pro
            260                 265                 270

Asn Leu Leu Thr Ile Ile Glu Met Gln Lys Gly Asp Cys Ala Leu Tyr
            275                 280                 285

Ala Ser Ser Phe Lys Gly Tyr Ile Glu Asn Cys Ser Thr Pro Asn Thr
            290                 295                 300

Tyr Ile Cys Met Gln Arg Thr Val Thr Thr Pro Ala Pro Arg Pro
305                 310                 315                 320

Pro Thr Pro Ala Pro Thr Ile Ala Ser Gln Pro Leu Ser Leu Arg Pro
            325                 330                 335

Glu Ala Cys Arg Pro Ala Ala Gly Gly Ala Val His Thr Arg Gly Leu
            340                 345                 350

Asp Phe Ala Cys Asp Ile Tyr Ile Trp Ala Pro Leu Ala Gly Thr Cys
            355                 360                 365

Gly Val Leu Leu Leu Ser Leu Val Ile Thr Leu Tyr Cys Lys Arg Gly
            370                 375                 380

Arg Lys Lys Leu Leu Tyr Ile Phe Lys Gln Pro Phe Met Arg Pro Val
385                 390                 395                 400

Gln Thr Thr Gln Glu Glu Asp Gly Cys Ser Cys Arg Phe Pro Glu Glu
            405                 410                 415

Glu Glu Gly Gly Cys Glu Leu Arg Val Lys Phe Ser Arg Ser Ala Asp
            420                 425                 430

Ala Pro Ala Tyr Gln Gln Gly Gln Asn Gln Leu Tyr Asn Glu Leu Asn
            435                 440                 445

Leu Gly Arg Arg Glu Glu Tyr Asp Val Leu Asp Lys Arg Arg Gly Arg
450                 455                 460

Asp Pro Glu Met Gly Gly Lys Pro Arg Arg Lys Asn Pro Gln Glu Gly
465                 470                 475                 480

Leu Tyr Asn Glu Leu Gln Lys Asp Lys Met Ala Glu Ala Tyr Ser Glu
            485                 490                 495

Ile Gly Met Lys Gly Glu Arg Arg Arg Gly Lys Gly His Asp Gly Leu
            500                 505                 510

Tyr Gln Gly Leu Ser Thr Ala Thr Lys Asp Thr Tyr Asp Ala Leu His
            515                 520                 525

Met Gln Ala Leu Pro Pro Arg
            530                 535

<210> SEQ ID NO 90
<211> LENGTH: 1122
<212> TYPE: DNA
<213> ORGANISM: Homo sapiens
<220> FEATURE:
<221> NAME/KEY: misc_feature
<223> OTHER INFORMATION: DNA Sequence  NKG2D-Ox40-CD3z

<400> SEQUENCE: 90

```
atggccttac cagtgaccgc cttgctcctg ccgctggcct tgctgctcca cgccgccagg      60
ccgttattca accaagaagt tcaaattccc ttgaccgaaa gttactgtgg cccatgtcct     120
aaaaactgga tatgttacaa aaataactgc taccaattt ttgatgagag taaaaactgg     180
tatgagagcc aggcttcttg tatgtctcaa aatgccagcc ttctgaaagt atacagcaaa     240
gaggaccagg atttacttaa actggtgaag tcatatcatt ggatgggact agtacacatt     300
ccaacaaatg gatcttggca gtgggaagat ggctccattc tctcacccaa cctactaaca     360
ataattgaaa tgcagaaggg agactgtgca ctctatgcct cgagctttaa aggctatata     420
gaaaactgtt caactccaaa tacgtacatc tgcatgcaaa ggactgtgac cacgacgcca     480
gcgccgcgac caccaacacc ggcgcccacc atcgcgtcgc agcccctgtc cctgcgccca     540
gaggcgtgcc ggccagcggc ggggggcgca gtgcacacga gggggctgga cttcgcctgt     600
gatatctaca tctgggcgcc cttggccggg acttgtgggg tccttctcct gtcactggtt     660
atcaccctt actgccggag ggaccagagg ctgcccccg atgcccacaa gccccctggg     720
ggaggcagtt ccggacccc catccaagag gagcaggccg acgcccactc caccctggcc     780
aagatcagag tgaagttcag caggagcgca gacgcccccg cgtaccagca gggccagaac     840
cagctctata cgagctcaa tctaggacga agagaggagt acgatgtttt ggacaagaga     900
cgtggccggg accctgagat gggggaaaag ccgagaagga agaaccctca ggaaggcctg     960
tacaatgaac tgcagaaaga taagatggcg gaggcctaca gtgagattgg gatgaaaggc    1020
gagcgccgga ggggcaaggg gcacgatggc ctttaccagg gtctcagtac agccaccaag    1080
gacacctacg acgcccttca catgcaggcc ctgccccctc gc                        1122
```

<210> SEQ ID NO 91
<211> LENGTH: 341
<212> TYPE: PRT
<213> ORGANISM: Homo sapiens
<220> FEATURE:
<221> NAME/KEY: MISC_FEATURE
<223> OTHER INFORMATION: Amino Acid Sequence NKG2D-OX40-CD3z

<400> SEQUENCE: 91

```
Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Tyr His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Tyr Ile Glu Asn Cys Ser
    130                 135                 140

Thr Pro Asn Thr Tyr Ile Cys Met Gln Arg Thr Val Glu Ser Lys Tyr
```

| | | | | | | | | | | | |
|---|---|---|---|---|---|---|---|---|---|---|---|
|  | 145 |  |  |  | 150 |  |  |  | 155 |  | 160 |

Gly Pro Pro Cys Pro Ser Cys Pro Ile Tyr Ile Trp Ala Pro Leu Ala
                    165                  170              175

Gly Thr Cys Gly Val Leu Leu Leu Ser Leu Val Ile Thr Leu Tyr Cys
            180                      185                  190

Arg Arg Asp Gln Arg Leu Pro Pro Asp Ala His Lys Pro Gly Gly
          195                  200                205

Gly Ser Phe Arg Thr Pro Ile Gln Glu Glu Ala Asp Ala His Ser
    210                  215                220

Thr Leu Ala Lys Ile Arg Val Lys Phe Ser Arg Ser Ala Asp Ala Pro
225                  230                  235            240

Ala Tyr Gln Gln Gly Gln Asn Gln Leu Tyr Asn Glu Leu Asn Leu Gly
                  245                250              255

Arg Arg Glu Glu Tyr Asp Val Leu Asp Lys Arg Arg Gly Arg Asp Pro
            260                  265              270

Glu Met Gly Gly Lys Pro Arg Arg Lys Asn Pro Gln Glu Gly Leu Tyr
              275                280            285

Asn Glu Leu Gln Lys Asp Lys Met Ala Glu Ala Tyr Ser Glu Ile Gly
    290                  295              300

Met Lys Gly Glu Arg Arg Arg Gly Lys Gly His Asp Gly Leu Tyr Gln
305                  310                315            320

Gly Leu Ser Thr Ala Thr Lys Asp Thr Tyr Asp Ala Leu His Met Gln
                  325                330            335

Ala Leu Pro Pro Arg
          340

<210> SEQ ID NO 92
<211> LENGTH: 1143
<212> TYPE: DNA
<213> ORGANISM: Homo sapiens
<220> FEATURE:
<221> NAME/KEY: misc_feature
<223> OTHER INFORMATION: DNA Sequence NKG2D-CD28 - CD3z

<400> SEQUENCE: 92

| | |
|---|---|
| atggccttac cagtgaccgc cttgctcctg ccgctggcct tgctgctcca cgccgccagg | 60 |
| ccgttattca accaagaagt tcaaattccc ttgaccgaaa gttactgtgg cccatgtcct | 120 |
| aaaaactgga tatgttacaa aaataactgc taccaatttt ttgatgagag taaaaactgg | 180 |
| tatgagagcc aggcttcttg tatgtctcaa aatgccagcc ttctgaaagt atacagcaaa | 240 |
| gaggaccagg atttacttaa actggtgaag tcatatcatt ggatgggact agtacacatt | 300 |
| ccaacaaatg gatcttggca gtgggaagat ggctccattc tctcacccaa cctactaaca | 360 |
| ataattgaaa tgcagaaggg agactgtgca ctctatgcct cgagctttaa aggctatata | 420 |
| gaaaactgtt caactccaaa tacgtacatc tgcatgcaaa ggactgtgac cacgacgcca | 480 |
| gcgccgcgac caccaacacc ggcgcccacc atcgcgtcgc agccctgtc cctgcgccca | 540 |
| gaggcgtgcc ggccagcggc ggggggcgca gtgcacacga gggggctgga cttcgcctgt | 600 |
| gattttggg tgctggtggt ggttggtgga gtcctggctt gctatagctt gctagtaaca | 660 |
| gtggcccttta ttattttctg ggtgaggagt aagaggagca ggctcctgca cagtgactac | 720 |
| atgaacatga ctccccgccg ccccgggccc acccgcaagc attaccagcc ctatgcccca | 780 |
| ccacgcgact cgcagcccta tcgctccaga gtgaagttca gcaggagcgc agacgccccc | 840 |
| gcgtaccagc agggccagaa ccagctctat aacgagctca atctaggacg aagagaggag | 900 |

```
tacgatgttt tggacaagag acgtggccgg gaccctgaga tggggggaaa gccgagaagg   960
aagaaccctc aggaaggcct gtacaatgaa ctgcagaaag ataagatggc ggaggcctac  1020
agtgagattg ggatgaaagg cgagcgccgg aggggcaagg ggcacgatgg cctttaccag  1080
ggtctcagta cagccaccaa ggacacctac gacgcccttc acatgcaggc cctgcccccct 1140 cgc                                                                1143
```

<210> SEQ ID NO 93
<211> LENGTH: 381
<212> TYPE: PRT
<213> ORGANISM: Homo sapiens
<220> FEATURE:
<221> NAME/KEY: MISC_FEATURE
<223> OTHER INFORMATION: Amino Acid Sequence NKG2D-CD28 - CD3z

<400> SEQUENCE: 93

```
Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Tyr His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Tyr Ile Glu Asn Cys Ser
    130                 135                 140

Thr Pro Asn Thr Tyr Ile Cys Met Gln Arg Thr Val Thr Thr Thr Pro
145                 150                 155                 160

Ala Pro Arg Pro Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
            180                 185                 190

Thr Arg Gly Leu Asp Phe Ala Cys Asp Phe Trp Val Leu Val Val Val
        195                 200                 205

Gly Gly Val Leu Ala Cys Tyr Ser Leu Leu Val Thr Val Ala Phe Ile
    210                 215                 220

Ile Phe Trp Val Arg Ser Lys Arg Ser Arg Leu Leu His Ser Asp Tyr
225                 230                 235                 240

Met Asn Met Thr Pro Arg Arg Pro Gly Pro Thr Arg Lys His Tyr Gln
                245                 250                 255

Pro Tyr Ala Pro Pro Arg Asp Phe Ala Ala Tyr Arg Ser Arg Val Lys
            260                 265                 270

Phe Ser Arg Ser Ala Asp Ala Pro Ala Tyr Gln Gln Gly Gln Asn Gln
        275                 280                 285

Leu Tyr Asn Glu Leu Asn Leu Gly Arg Arg Glu Glu Tyr Asp Val Leu
    290                 295                 300

Asp Lys Arg Arg Gly Arg Asp Pro Glu Met Gly Gly Lys Pro Arg Arg
```

```
                305                  310                  315                  320
Lys Asn Pro Gln Glu Gly Leu Tyr Asn Glu Leu Gln Lys Asp Lys Met
                    325                  330                  335

Ala Glu Ala Tyr Ser Glu Ile Gly Met Lys Gly Glu Arg Arg Arg Gly
                340                  345                  350

Lys Gly His Asp Gly Leu Tyr Gln Gly Leu Ser Thr Ala Thr Lys Asp
            355                  360                  365

Thr Tyr Asp Ala Leu His Met Gln Ala Leu Pro Pro Arg
        370                  375                  380

<210> SEQ ID NO 94
<211> LENGTH: 1269
<212> TYPE: DNA
<213> ORGANISM: Homo sapiens
<220> FEATURE:
<221> NAME/KEY: misc_feature
<223> OTHER INFORMATION: DNA Sequence NKG2D - CD28 - 41BB - CD3z

<400> SEQUENCE: 94 atggcttac cagtgaccgc cttgctcctg ccgctggcct tgctgctcca cgccgccagg      60
ccgttattca accaagaagt tcaaattccc ttgaccgaaa gttactgtgg cccatgtcct    120
aaaaactgga tatgttacaa aataactgc taccaatttt ttgatgagag taaaaactgg    180
tatgagagcc aggcttcttg tatgtctcaa aatgccagcc ttctgaaagt atacagcaaa    240
gaggaccagg atttacttaa actggtgaag tcatatcatt ggatgggact agtacacatt    300
ccaacaaatg gatcttggca gtgggaagat ggctccattc tctcacccaa cctactaaca    360
ataattgaaa tgcagaaggg agactgtgca ctctatgcct cgagctttaa aggctatata    420
gaaaactgtt caactccaaa tacgtacatc tgcatgcaaa ggactgtgac cacgacgcca    480
gcgccgcgac caccaacacc ggcgcccacc atcgcgtcgc agcccctgtc cctgcgccca    540
gaggcgtgcc ggccagcggc gggggcgca gtgcacacga gggggctgga cttcgcctgt    600 gattttggg tgctggtggt ggttggtgga gtcctggctt gctatagctt gctagtaaca    660
gtggccttta ttattttctg ggtgaggagt aagaggagca ggctcctgca cagtgactac    720
atgaacatga ctccccgccg ccccgggccc acccgcaagc attaccagcc ctatgcccca    780
ccacgcgact cgcagcccta tcgctccaaa cggggcagaa agaaactcct gtatatattc    840
aaacaaccat ttatgagacc agtacaaact actcaagagg aagatggctg tagctgccga    900
tttccagaag aagaagaagg aggatgtgaa ctgagagtga agttcagcag gagcgcagac    960
gccccccgcg accagcaggg ccagaaccag ctctataacg agctcaatct aggacgaaga    1020
gaggagtacg atgttttgga caagagacgt ggccgggacc ctgagatggg gggaaagccg    1080
agaaggaaga accctcagga aggcctgtac aatgaactgc agaaagataa gatggcggag    1140
gcctacagtg agattgggat gaaaggcgag cgccggaggg gcaaggggca cgatggcctt    1200
taccagggtc tcagtacagc caccaaggac acctacgacg cccttcacat gcaggccctg    1260
ccccctcgc                                                          1269

<210> SEQ ID NO 95
<211> LENGTH: 423
<212> TYPE: PRT
<213> ORGANISM: Homo sapiens
<220> FEATURE:
<221> NAME/KEY: MISC_FEATURE
<223> OTHER INFORMATION: Amino Acid Sequence NKG2D - CD28 - 41BB - CD3z

<400> SEQUENCE: 95
```

```
Met Ala Leu Pro Val Thr Ala Leu Leu Leu Pro Ala Leu Leu Leu
1               5                   10                  15

His Ala Ala Arg Pro Leu Phe Asn Gln Glu Val Gln Ile Pro Leu Thr
                20                  25                  30

Glu Ser Tyr Cys Gly Pro Cys Pro Lys Asn Trp Ile Cys Tyr Lys Asn
            35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Tyr His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Tyr Ile Glu Asn Cys Ser
130                 135                 140

Thr Pro Asn Thr Tyr Ile Cys Met Gln Arg Thr Val Thr Thr Thr Pro
145                 150                 155                 160

Ala Pro Arg Pro Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
            180                 185                 190

Thr Arg Gly Leu Asp Phe Ala Cys Asp Phe Trp Val Leu Val Val Val
        195                 200                 205

Gly Gly Val Leu Ala Cys Tyr Ser Leu Leu Val Thr Val Ala Phe Ile
210                 215                 220

Ile Phe Trp Val Arg Ser Lys Arg Ser Arg Leu Leu His Ser Asp Tyr
225                 230                 235                 240

Met Asn Met Thr Pro Arg Arg Pro Gly Pro Thr Arg Lys His Tyr Gln
                245                 250                 255

Pro Tyr Ala Pro Pro Arg Asp Phe Ala Ala Tyr Arg Ser Lys Arg Gly
            260                 265                 270

Arg Lys Lys Leu Leu Tyr Ile Phe Lys Gln Pro Phe Met Arg Pro Val
        275                 280                 285

Gln Thr Thr Gln Glu Glu Asp Gly Cys Ser Cys Arg Phe Pro Glu Glu
290                 295                 300

Glu Glu Gly Gly Cys Glu Leu Arg Val Lys Phe Ser Arg Ser Ala Asp
305                 310                 315                 320

Ala Pro Ala Tyr Gln Gln Gly Gln Asn Gln Leu Tyr Asn Glu Leu Asn
                325                 330                 335

Leu Gly Arg Arg Glu Glu Tyr Asp Val Leu Asp Lys Arg Arg Gly Arg
            340                 345                 350

Asp Pro Glu Met Gly Gly Lys Pro Arg Arg Lys Asn Pro Gln Glu Gly
        355                 360                 365

Leu Tyr Asn Glu Leu Gln Lys Asp Lys Met Ala Glu Ala Tyr Ser Glu
370                 375                 380

Ile Gly Met Lys Gly Glu Arg Arg Arg Gly Lys Gly His Asp Gly Leu
385                 390                 395                 400

Tyr Gln Gly Leu Ser Thr Ala Thr Lys Asp Thr Tyr Asp Ala Leu His
                405                 410                 415
```

Met Gln Ala Leu Pro Pro Arg
              420

<210> SEQ ID NO 96
<211> LENGTH: 1038
<212> TYPE: DNA
<213> ORGANISM: Homo sapiens
<220> FEATURE:
<221> NAME/KEY: misc_feature
<223> OTHER INFORMATION: DNA Sequence NKG2D(short hinge) - 41BB - CD3z

<400> SEQUENCE: 96

```
atggccttac cagtgaccgc cttgctcctg ccgctggcct tgctgctcca cgccgccagg      60
ccgttattca accaagaagt tcaaattccc ttgaccgaaa gttactgtgg cccatgtcct     120
aaaaactgga tatgttacaa aaataactgc taccaatttt ttgatgagag taaaaactgg     180
tatgagagcc aggcttcttg tatgtctcaa aatgccagcc ttctgaaagt atacagcaaa     240
gaggaccagg atttacttaa actggtgaag tcatatcatt ggatgggact agtacacatt     300
ccaacaaatg gatcttggca gtgggaagat ggctccattc tctcacccaa cctactaaca     360
ataattgaaa tgcagaaggg agactgtgca ctctatgcct cgagctttaa aggctatata     420
gaaaactgtt caactccaaa tacgtacatc tgcatgcaaa ggactgtgga gtccaaatat     480
ggtccccat gcccatcatg cccaatctac atctgggcgc ccttggccgg acttgtggg      540
gtccttctcc tgtcactggt tatcaccctt tactgcaaac ggggcagaaa gaaactcctg     600
tatatattca acaaccatt tatgagacca gtacaaacta ctcaagagga agatggctgt     660
agctgccgat ttccagaaga agaagaagga ggatgtgaac tgagagtgaa gttcagcagg     720
agcgcagacg cccccgcgta ccagcagggc cagaaccagc tctataacga gctcaatcta     780
ggacgaagag aggagtacga tgttttggac aagagacgtg gccgggaccc tgagatgggg     840
ggaaagccga aggaagaa ccctcaggaa ggcctgtaca atgaactgca gaaagataag     900
atggcggagg cctacagtga gattgggatg aaaggcgagc gccggagggg caaggggcac    960
gatggccttt accagggtct cagtacagcc accaaggaca cctacgacgc ccttcacatg    1020
caggccctgc cccctcgc                                                1038
```

<210> SEQ ID NO 97
<211> LENGTH: 346
<212> TYPE: PRT
<213> ORGANISM: Homo sapiens
<220> FEATURE:
<221> NAME/KEY: MISC_FEATURE
<223> OTHER INFORMATION: Amino Acid Sequence NKG2D(short hinge) - 41BB - CD3z

<400> SEQUENCE: 97

Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
                20                  25                  30

Glu Ser Tyr Cys Gly Pro Cys Pro Lys Asn Trp Ile Cys Tyr Lys Asn
            35                  40                  45

Asn Cys Tyr Gln Phe Phe Asp Glu Ser Lys Asn Trp Tyr Glu Ser Gln
        50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Tyr His Trp Met Gly
                85                  90                  95

```
Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
            115                 120                 125

Cys Ala Leu Tyr Ala Ser Ser Phe Lys Gly Tyr Ile Glu Asn Cys Ser
            130                 135                 140

Thr Pro Asn Thr Tyr Ile Cys Met Gln Arg Thr Val Glu Ser Lys Tyr
145                 150                 155                 160

Gly Pro Pro Cys Pro Ser Cys Pro Ile Tyr Ile Trp Ala Pro Leu Ala
            165                 170                 175

Gly Thr Cys Gly Val Leu Leu Leu Ser Leu Val Ile Thr Leu Tyr Cys
            180                 185                 190

Lys Arg Gly Arg Lys Lys Leu Leu Tyr Ile Phe Lys Gln Pro Phe Met
            195                 200                 205

Arg Pro Val Gln Thr Thr Gln Glu Glu Asp Gly Cys Ser Cys Arg Phe
            210                 215                 220

Pro Glu Glu Glu Glu Gly Gly Cys Glu Leu Arg Val Lys Phe Ser Arg
225                 230                 235                 240

Ser Ala Asp Ala Pro Ala Tyr Gln Gln Gly Gln Asn Gln Leu Tyr Asn
            245                 250                 255

Glu Leu Asn Leu Gly Arg Arg Glu Glu Tyr Asp Val Leu Asp Lys Arg
            260                 265                 270

Arg Gly Arg Asp Pro Glu Met Gly Gly Lys Pro Arg Arg Lys Asn Pro
            275                 280                 285

Gln Glu Gly Leu Tyr Asn Glu Leu Gln Lys Asp Lys Met Ala Glu Ala
            290                 295                 300

Tyr Ser Glu Ile Gly Met Lys Gly Glu Arg Arg Arg Gly Lys Gly His
305                 310                 315                 320

Asp Gly Leu Tyr Gln Gly Leu Ser Thr Ala Thr Lys Asp Thr Tyr Asp
            325                 330                 335

Ala Leu His Met Gln Ala Leu Pro Pro Arg
            340                 345
```

<210> SEQ ID NO 98
<211> LENGTH: 1044
<212> TYPE: DNA
<213> ORGANISM: Homo sapiens
<220> FEATURE:
<221> NAME/KEY: misc_feature
<223> OTHER INFORMATION: DNA Sequence NKG2D (SH)-CD28 - CD3z

<400> SEQUENCE: 98

```
atggccttac cagtgaccgc cttgctcctg ccgctggcct tgctgctcca cgccgccagg      60
ccgttattca accaagaagt tcaaattccc ttgaccgaaa gttactgtgg cccatgtcct     120
aaaaactgga tatgttacaa aaataactgc taccaatttt ttgatgagag taaaaactgg     180
tatgagagcc aggcttcttg tatgtctcaa aatgccagcc ttctgaaagt atacagcaaa     240
gaggaccagg atttacttaa actggtgaag tcatatcatt ggatgggact agtacacatt     300
ccaacaaatg gatcttggca gtgggaagat ggctccattc tctcacccaa cctactaaca     360
ataattgaaa tgcagaaggg agactgtgca ctctatgcct cgagctttaa aggctatata     420
gaaaactgtt caactccaaa tacgtacatc tgcatgcaaa ggactgtgga gtccaaatat     480 ggtccccat gccatcatg cccatttttgg gtgctggtgg tggttggtgg agtcctggct     540
tgctatagct tgctagtaac agtggccttt attatttttct gggtgaggag taagaggagc     600
```

-continued

```
aggctcctgc acagtgacta catgaacatg actccccgcc gccccgggcc cacccgcaag    660
cattaccagc cctatgcccc accacgcgac ttcgcagcct atcgctccag agtgaagttc    720
agcaggagcg cagacgcccc cgcgtaccag cagggccaga accagctcta taacgagctc    780
aatctaggac gaagagagga gtacgatgtt ttggacaaga gacgtggccg ggaccctgag    840
atggggggaa agccgagaag gaagaaccct caggaaggcc tgtacaatga actgcagaaa    900
gataagatgg cggaggccta cagtgagatt gggatgaaag gcgagcgccg gaggggcaag    960
gggcacgatg gcctttacca gggtctcagt acagccacca aggacaccta cgacgccctt    1020
cacatgcagg ccctgccccc tcgc                                           1044
```

<210> SEQ ID NO 99
<211> LENGTH: 348
<212> TYPE: PRT
<213> ORGANISM: Homo sapiens
<220> FEATURE:
<221> NAME/KEY: MISC_FEATURE
<223> OTHER INFORMATION: Amino Acid Sequence NKG2D (SH)-CD28 - CD3z

<400> SEQUENCE: 99

```
Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Tyr His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Tyr Ile Glu Asn Cys Ser
    130                 135                 140

Thr Pro Asn Thr Tyr Ile Cys Met Gln Arg Thr Val Glu Ser Lys Tyr
145                 150                 155                 160

Gly Pro Pro Cys Pro Ser Cys Pro Phe Trp Val Leu Val Val Val Gly
                165                 170                 175

Gly Val Leu Ala Cys Tyr Ser Leu Leu Val Thr Val Ala Phe Ile Ile
            180                 185                 190

Phe Trp Val Arg Ser Lys Arg Ser Arg Leu Leu His Ser Asp Tyr Met
        195                 200                 205

Asn Met Thr Pro Arg Arg Pro Gly Pro Thr Arg Lys His Tyr Gln Pro
    210                 215                 220

Tyr Ala Pro Pro Arg Asp Phe Ala Ala Tyr Arg Ser Arg Val Lys Phe
225                 230                 235                 240

Ser Arg Ser Ala Asp Ala Pro Ala Tyr Gln Gln Gly Gln Asn Gln Leu
                245                 250                 255

Tyr Asn Glu Leu Asn Leu Gly Arg Arg Glu Glu Tyr Asp Val Leu Asp
            260                 265                 270
```

```
Lys Arg Arg Gly Arg Asp Pro Glu Met Gly Gly Lys Pro Arg Arg Lys
            275                 280                 285

Asn Pro Gln Glu Gly Leu Tyr Asn Glu Leu Gln Lys Asp Lys Met Ala
            290                 295                 300

Glu Ala Tyr Ser Glu Ile Gly Met Lys Gly Glu Arg Arg Arg Gly Lys
305                 310                 315                 320

Gly His Asp Gly Leu Tyr Gln Gly Leu Ser Thr Ala Thr Lys Asp Thr
            325                 330                 335

Tyr Asp Ala Leu His Met Gln Ala Leu Pro Pro Arg
            340                 345

<210> SEQ ID NO 100
<211> LENGTH: 1023
<212> TYPE: DNA
<213> ORGANISM: Homo sapiens
<220> FEATURE:
<221> NAME/KEY: misc_feature
<223> OTHER INFORMATION: DNA Sequence NKG2D (SH) - OX40 - CD3z

<400> SEQUENCE: 100
atggccttac cagtgaccgc cttgctcctg ccgctggcct tgctgctcca cgccgccagg       60
ccgttattca accaagaagt tcaaattccc ttgaccgaaa gttactgtgg cccatgtcct      120
aaaaactgga tatgttacaa aaataactgc taccaatttt ttgatgagag taaaaactgg      180
tatgagagcc aggcttcttg tatgtctcaa aatgccagcc ttctgaaagt atacagcaaa      240
gaggaccagg atttacttaa actggtgaag tcatatcatt ggatgggact agtacacatt      300
ccaacaaatg gatcttggca gtgggaagat ggctccattc tctcacccaa cctactaaca      360
ataattgaaa tgcagaaggg agactgtgca ctctatgcct cgagctttaa aggctatata      420
gaaaactgtt caactccaaa tacgtacatc tgcatgcaaa ggactgtgga gtccaaatat      480
ggtcccccat gcccatcatg cccaatctac atctgggcgc cttggccgg acttgtggg       540 gtccttctcc tgtcactggt tatcaccctt tactgccgga gggaccagag gctgccccc      600 gatgcccaca gccccctggg ggaggcagt ttccggaccc ccatccaaga ggagcaggcc      660
gacgcccact ccaccctggc caagatcaga gtgaagttca gcaggagcgc agacgccccc      720
gcgtaccagc agggccagaa ccagctctat aacgagctca atctaggacg aagagaggag      780
tacgatgttt tggacaagag acgtggccgg gaccctgaga tggggggaaa gccgagaagg      840
aagaaccctc aggaaggcct gtacaatgaa ctgcagaaag ataagatggc ggaggcctac      900
agtgagattg gcatgaaagg cgagcgccgg aggggcaagg ggcacgatgg cctttaccag      960
ggtctcagta cagccaccaa ggacacctac gacgcccttc acatgcaggc cctgcccct     1020 cgc                                                                   1023

<210> SEQ ID NO 101
<211> LENGTH: 346
<212> TYPE: PRT
<213> ORGANISM: Homo sapiens
<220> FEATURE:
<221> NAME/KEY: MISC_FEATURE
<223> OTHER INFORMATION: Amino Acid Seqeunce NKG2D (SH) - OX40 - CD3z

<400> SEQUENCE: 101

Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
            20                  25                  30
```

```
Glu Ser Tyr Cys Gly Pro Cys Pro Lys Asn Trp Ile Cys Tyr Lys Asn
             35                  40                  45

Asn Cys Tyr Gln Phe Phe Asp Glu Ser Lys Asn Trp Tyr Glu Ser Gln
 50                  55                  60

Ala Ser Cys Met Ser Gln Asn Ala Ser Leu Leu Lys Val Tyr Ser Lys
 65                  70                  75                  80

Glu Asp Gln Asp Leu Leu Lys Leu Val Lys Ser Tyr His Trp Met Gly
                 85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
            115                 120                 125

Cys Ala Leu Tyr Ala Ser Ser Phe Lys Gly Tyr Ile Glu Asn Cys Ser
130                 135                 140

Thr Pro Asn Thr Tyr Ile Cys Met Gln Arg Thr Val Glu Ser Lys Tyr
145                 150                 155                 160

Gly Pro Pro Cys Pro Ser Cys Pro Phe Trp Val Leu Val Val Val Gly
                165                 170                 175

Gly Val Leu Ala Cys Tyr Ser Leu Leu Val Thr Val Ala Phe Ile Ile
            180                 185                 190

Phe Trp Val Arg Ser Arg Arg Asp Gln Arg Leu Pro Pro Asp Ala His
            195                 200                 205

Lys Pro Pro Gly Gly Gly Ser Phe Arg Thr Pro Ile Gln Glu Glu Gln
210                 215                 220

Ala Asp Ala His Ser Thr Leu Ala Lys Ile Arg Val Lys Phe Ser Arg
225                 230                 235                 240

Ser Ala Asp Ala Pro Ala Tyr Gln Gln Gly Gln Asn Gln Leu Tyr Asn
                245                 250                 255

Glu Leu Asn Leu Gly Arg Arg Glu Glu Tyr Asp Val Leu Asp Lys Arg
            260                 265                 270

Arg Gly Arg Asp Pro Glu Met Gly Gly Lys Pro Arg Arg Lys Asn Pro
            275                 280                 285

Gln Glu Gly Leu Tyr Asn Glu Leu Gln Lys Asp Lys Met Ala Glu Ala
290                 295                 300

Tyr Ser Glu Ile Gly Met Lys Gly Glu Arg Arg Arg Gly Lys Gly His
305                 310                 315                 320

Asp Gly Leu Tyr Gln Gly Leu Ser Thr Ala Thr Lys Asp Thr Tyr Asp
                325                 330                 335

Ala Leu His Met Gln Ala Leu Pro Pro Arg
            340                 345
```

<210> SEQ ID NO 102
<211> LENGTH: 1125
<212> TYPE: DNA
<213> ORGANISM: Homo sapiens
<220> FEATURE:
<221> NAME/KEY: misc_feature
<223> OTHER INFORMATION: DNA Sequence NKG2D-CD3TM -CD28 - CD3z

<400> SEQUENCE: 102

```
atggccttac cagtgaccgc cttgctcctg ccgctggcct tgctgctcca cgccgccagg      60
ccgttattca accaagaagt tcaaattccc ttgaccgaaa gttactgtgg cccatgtcct     120
aaaaactgga tatgttacaa aaataactgc taccaatttt ttgatgagag taaaaactgg     180
tatgagagcc aggcttcttg tatgtctcaa aatgccagcc ttctgaaagt atacagcaaa     240
```

```
gaggaccagg atttacttaa actggtgaag tcatatcatt ggatgggact agtacacatt    300
ccaacaaatg gatcttggca gtgggaagat ggctccattc tctcacccaa cctactaaca    360
ataattgaaa tgcagaaggg agactgtgca ctctatgcct cgagctttaa aggctatata    420
gaaaactgtt caactccaaa tacgtacatc tgcatgcaaa ggactgtgac cacgacgcca    480
gcgccgcgac caccaacacc ggcgcccacc atcgcgtcgc agcccctgtc cctgcgccca    540
gaggcgtgcc ggccagcggc gggggcgca gtgcacacga gggggctgga cttcgcctgt    600
gatcccaaac tctgctacct gctggatgga atcctcttca tctatggtgt cattctcact    660
gccttgttcc tgaagaggag caggctcctg cacagtgact acatgaacat gactccccgc    720
cgccccgggc ccacccgcaa gcattaccag ccctatgccc caccacgcga cttcgcagcc    780
tatcgctcca gagtgaagtt cagcaggagc gcagacgccc ccgcgtacca gcagggccag    840
aaccagctct ataacgagct caatctagga cgaagagagg agtacgatgt tttggacaag    900
agacgtggcc gggaccctga gatgggggga aagccgagaa ggaagaaccc tcaggaaggc    960
ctgtacaatg aactgcagaa agataagatg gcggaggcct acagtgagat tgggatgaaa   1020
ggcgagcgcc ggaggggcaa ggggcacgat ggcctttacc agggtctcag tacagccacc   1080
aaggacacct acgacgccct tcacatgcag gccctgcccc ctcgc                   1125

<210> SEQ ID NO 103
<211> LENGTH: 375
<212> TYPE: PRT
<213> ORGANISM: Homo sapiens
<220> FEATURE:
<221> NAME/KEY: MISC_FEATURE
<223> OTHER INFORMATION: Amino Acid Sequence NKG2D-CD3TM -CD28 - CD3z

<400> SEQUENCE: 103

Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Tyr His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Tyr Ile Glu Asn Cys Ser
    130                 135                 140

Thr Pro Asn Thr Tyr Ile Cys Met Gln Arg Thr Val Thr Thr Thr Pro
145                 150                 155                 160

Ala Pro Arg Pro Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
            180                 185                 190

Thr Arg Gly Leu Asp Phe Ala Cys Asp Pro Lys Leu Cys Tyr Leu Leu
        195                 200                 205
```

```
Asp Gly Ile Leu Phe Ile Tyr Gly Val Ile Leu Thr Ala Leu Phe Leu
    210                 215                 220

Lys Arg Ser Arg Leu Leu His Ser Asp Tyr Met Asn Met Thr Pro Arg
225                 230                 235                 240

Arg Pro Gly Pro Thr Arg Lys His Tyr Gln Pro Tyr Ala Pro Pro Arg
                245                 250                 255

Asp Phe Ala Ala Tyr Arg Ser Arg Val Lys Phe Ser Arg Ser Ala Asp
                260                 265                 270

Ala Pro Ala Tyr Gln Gln Gly Gln Asn Gln Leu Tyr Asn Glu Leu Asn
            275                 280                 285

Leu Gly Arg Arg Glu Glu Tyr Asp Val Leu Asp Lys Arg Arg Gly Arg
        290                 295                 300

Asp Pro Glu Met Gly Gly Lys Pro Arg Arg Lys Asn Pro Gln Glu Gly
305                 310                 315                 320

Leu Tyr Asn Glu Leu Gln Lys Asp Lys Met Ala Glu Ala Tyr Ser Glu
                325                 330                 335

Ile Gly Met Lys Gly Glu Arg Arg Gly Lys Gly His Asp Gly Leu
                340                 345                 350

Tyr Gln Gly Leu Ser Thr Ala Thr Lys Asp Thr Tyr Asp Ala Leu His
            355                 360                 365

Met Gln Ala Leu Pro Pro Arg
    370                 375

<210> SEQ ID NO 104
<211> LENGTH: 36
<212> TYPE: DNA
<213> ORGANISM: Homo sapiens
<220> FEATURE:
<221> NAME/KEY: misc_feature
<223> OTHER INFORMATION: DNA Sequence IgG 4 hinge

<400> SEQUENCE: 104
gagtccaaat atggtccccc atgcccatca tgccca                               36

<210> SEQ ID NO 105
<211> LENGTH: 29
<212> TYPE: PRT
<213> ORGANISM: Homo sapiens
<220> FEATURE:
<221> NAME/KEY: MISC_FEATURE
<223> OTHER INFORMATION: Amino Acid Sequence CD28 Transmembrane domain

<400> SEQUENCE: 105

Phe Trp Val Leu Val Val Val Gly Gly Val Leu Ala Cys Tyr Ser Leu
1               5                   10                  15

Leu Val Thr Val Ala Phe Ile Ile Phe Trp Val Arg Ser
            20                  25

<210> SEQ ID NO 106
<211> LENGTH: 39
<212> TYPE: PRT
<213> ORGANISM: Homo sapiens
<220> FEATURE:
<221> NAME/KEY: MISC_FEATURE
<223> OTHER INFORMATION: Amino Acid Sequence CD28 IC domain

<400> SEQUENCE: 106

Lys Arg Ser Arg Leu Leu His Ser Asp Tyr Met Asn Met Thr Pro Arg
1               5                   10                  15

Arg Pro Gly Pro Thr Arg Lys His Tyr Gln Pro Tyr Ala Pro Pro Arg
```

```
                      20                  25                  30

Asp Phe Ala Ala Tyr Arg Ser
            35

<210> SEQ ID NO 107
<211> LENGTH: 37
<212> TYPE: PRT
<213> ORGANISM: Homo sapiens
<220> FEATURE:
<221> NAME/KEY: MISC_FEATURE
<223> OTHER INFORMATION: Amino Acid Sequence OX40 IC Domain

<400> SEQUENCE: 107

Arg Arg Asp Gln Arg Leu Pro Pro Asp Ala His Lys Pro Pro Gly Gly
1               5                   10                  15

Gly Ser Phe Arg Thr Pro Ile Gln Glu Glu Gln Ala Asp Ala His Ser
            20                  25                  30

Thr Leu Ala Lys Ile
        35

<210> SEQ ID NO 108
<211> LENGTH: 1140
<212> TYPE: DNA
<213> ORGANISM: Homo sapiens
<220> FEATURE:
<221> NAME/KEY: misc_feature
<223> OTHER INFORMATION: NKG2D-P-frag/CD8a/4-1BB/CD3z

<400> SEQUENCE: 108
atggccttac cagtgaccgc cttgctcctg ccgctggcct tgctgctcca cgccgccagg      60
ccgttattca accaagaagt tcaaattccc ttgaccgaaa gttactgtgg cccatgtcct     120
aaaaactgga tatgttacaa aaataactgc taccaatttt ttgatgagag taaaaactgg     180
tatgagagcc aggcttcttg tatgtctcaa aatgccagcc ttctgaaagt atacagcaaa     240
gaggaccagg atttacttaa actggtgaag tcatatcatt ggatgggact agtacacatt     300
ccaacaaatg gatcttggca gtgggaagat ggctccattc tctcacccaa cctactaaca     360
ataattgaaa tgcagaaggg agactgtgca ctctatgcct cgagctttaa aggctatata     420
gaaaactgtt caactccaaa tacgtacatc tgcatgcaaa ggactgtgac cacgacgcca     480
gcgccgcgac caccaacacc ggcgcccacc atcgcgtcgc agcccctgtc cctgcgccca     540
gaggcgtgcc ggccagcggc ggggggcgca gtgcacacga gggggctgga cttcgcctgt     600
gatatctaca tctgggcgcc cttggccggg acttgtgggg tccttctcct gtcactggtt     660
atcacccttt actgcaaacg gggcagaaag aaactcctgt atatattcaa acaaccattt     720
atgagaccag tacaaactac tcaagaggaa gatggctgta gctgccgatt tccagaagaa     780
gaagaaggag gatgtgaact gagagtgaag ttcagcagga gcgcagacgc ccccgcgtac     840
cagcagggcc agaaccagct ctataacgag ctcaatctag gacgaagaga ggagtacgat     900
gttttggaca gagacgtggc cgggaccct gagatggggg aaagccgag aaggaagaac     960 cctcaggaag gcctgtacaa tgaactgcag aaagataaga tggcggaggc ctacagtgag    1020
attgggatga aggcgagcg ccggagggc aaggggcacg atggccttta ccagggtctc    1080
agtacagcca ccaaggacac ctacgacgcc cttcacatgc aggccctgcc ccctcgctaa    1140

<210> SEQ ID NO 109
<211> LENGTH: 374
<212> TYPE: PRT
<213> ORGANISM: Homo sapiens
```

```
<220> FEATURE:
<221> NAME/KEY: MISC_FEATURE
<223> OTHER INFORMATION: NKG2D-V2-OX40-CD3z

<400> SEQUENCE: 109

Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Tyr His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Tyr Ile Glu Asn Cys Ser
130                 135                 140

Thr Pro Asn Thr Tyr Ile Cys Met Gln Arg Thr Val Thr Thr Thr Pro
145                 150                 155                 160

Ala Pro Arg Pro Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
            180                 185                 190

Thr Arg Gly Leu Asp Phe Ala Cys Asp Ile Tyr Ile Trp Ala Pro Leu
        195                 200                 205

Ala Gly Thr Cys Gly Val Leu Leu Leu Ser Leu Val Ile Thr Leu Tyr
210                 215                 220

Cys Arg Arg Asp Gln Arg Leu Pro Pro Asp Ala His Lys Pro Pro Gly
225                 230                 235                 240

Gly Gly Ser Phe Arg Thr Pro Ile Gln Glu Glu Gln Ala Asp Ala His
                245                 250                 255

Ser Thr Leu Ala Lys Ile Arg Val Lys Phe Ser Arg Ser Ala Asp Ala
            260                 265                 270

Pro Ala Tyr Gln Gln Gly Gln Asn Gln Leu Tyr Asn Glu Leu Asn Leu
        275                 280                 285

Gly Arg Arg Glu Glu Tyr Asp Val Leu Asp Lys Arg Arg Gly Arg Asp
290                 295                 300

Pro Glu Met Gly Gly Lys Pro Arg Arg Lys Asn Pro Gln Glu Gly Leu
305                 310                 315                 320

Tyr Asn Glu Leu Gln Lys Asp Lys Met Ala Glu Ala Tyr Ser Glu Ile
                325                 330                 335

Gly Met Lys Gly Glu Arg Arg Arg Gly Lys Gly His Asp Gly Leu Tyr
            340                 345                 350

Gln Gly Leu Ser Thr Ala Thr Lys Asp Thr Tyr Asp Ala Leu His Met
        355                 360                 365

Gln Ala Leu Pro Pro Arg
    370
```

IMMUNE CELLS COMPRISING TRUNCATED NKG2D CHIMERIC RECEPTORS

RELATED APPLICATIONS

This application is a continuation of U.S. application Ser. No. 16/497,678, filed on Mar. 27, 2018, which is the U.S. National Stage of International Application No. PCT/US2018/024650, filed on Mar. 27, 2018, which designates the U.S., published in English, and claims the benefit of U.S. Provisional Application No. 62/477,335, filed on Mar. 27, 2017 and U.S. Provisional Application No. 62/628,774, filed on Feb. 9, 2018. The entire teachings of the above applications are incorporated herein by reference.

INCORPORATION BY REFERENCE OF MATERIAL IN ASCII TEXT FILE

This application incorporates by reference the Sequence Listing contained in the following ASCII text file being submitted concurrently herewith:
  a) File name: 44591144019SequenceListing.txt; created May 9, 2022, 189,694 bytes in size.

BACKGROUND

The emergence and persistence of many diseases is characterized by an insufficient immune response to aberrant cells, including malignant and virally infected cells. Immunotherapy is the use and manipulation of the patient's immune system for treatment of various diseases.

SUMMARY

Immunotherapy presents a new technological advancement in the treatment of disease, wherein immune cells are engineered to express certain targeting and/or effector molecules that specifically identify and react to diseased or damaged cells. This represents a promising advance due, at least in part, to the potential for specifically targeting diseased or damaged cells, as opposed to more traditional approaches, such as chemotherapy, where all cells are impacted, and the desired outcome is that sufficient healthy cells survive to allow the patient to live. One immunotherapy approach is the recombinant expression of chimeric receptors in immune cells to achieve the targeted recognition and destruction of aberrant cells of interest.

To address this need for specifically targeting and destroying, disabling or otherwise rendering inert diseased or infected cells, there are provided for herein polynucleotides, amino acids, and vectors that encode chimeric receptors that impart enhanced targeting and cytotoxicity to cells, such as natural killer cells. Also provided for are methods for producing the cells, and methods of using the cells to target and destroy diseased or damaged cells. In several embodiments, there is provided a polynucleotide encoding a chimeric receptor comprising an extracellular receptor domain and an effector domain comprising a transmembrane region and an intracellular signaling domain, wherein the extracellular receptor domain comprises a peptide that binds native ligands of Natural Killer Group 2 member D (NKG2D), wherein the peptide that binds native ligands of NKG2D is a fragment of NKG2D.

In several embodiments, there is provided a polynucleotide encoding a chimeric receptor comprising one or both of: (a) an extracellular receptor domain and (b) an effector domain comprising a transmembrane region and an intracellular signaling domain. In several embodiments, the extracellular receptor domain comprises a peptide that binds native ligands of Natural Killer Group 2 member D (NKG2D). In several embodiments, the peptide that binds native ligands of NKG2D is a fragment of NKG2D, for example, a fragment of NKG2D is encoded by a polynucleotide comprising SEQ ID NO. 2. As disclosed, herein, additional NKG2D fragments are also used, depending on the embodiment. In several embodiments, the intracellular signaling domain comprises CD3zeta. In one embodiment, the CD3zeta is encoded by a polynucleotide comprising SEQ ID NO. 13, though, as disclosed herein, sequences that differ from CD3zeta, but share similar function may also be used, depending on the embodiment.

In several embodiments, the transmembrane region of the effector domain comprises a CD8α transmembrane domain. In one embodiment, the transmembrane region of the effector domain further comprises a CD8α hinge region. In several embodiments, the CD8α hinge region is encoded by a polynucleotide comprising SEQ ID NO: 5. In several embodiments, the intracellular signaling domain further comprises 4-1BB. In one embodiment, the 4-1BB is encoded by a polynucleotide comprising SEQ ID NO. 12, though, as disclosed herein, sequences that differ from 4-1BB, but share similar function may also be used, depending on the embodiment.

In several embodiments, the chimeric receptor comprises the fragment of NKG2D coupled to CD8α, 4-1BB and CD3zeta. In several embodiments, such a chimeric receptor is encoded by the nucleic acid sequence of SEQ ID NO. 18. In additional embodiments, the chimeric receptor is encoded by the nucleic acid sequence of SEQ ID NO. 108, though, as disclosed herein, sequences that differ from SEQ ID NO. 108, but share similar function may also be used, depending on the embodiment. In several embodiments, the chimeric receptor comprises the amino acid sequence of SEQ ID NO. 19.

In several embodiments, any of chimeric receptors disclosed herein can also be co-expressed with membrane-bound interleukin 15 (mbIL15). In some embodiments, the mbIL15 is encoded by a polynucleotide comprising SEQ ID NO. 16. In some embodiments, the mbIL15 comprises an amino acid sequence of SEQ ID NO: 17. Other sequences for mbIL15 may also be used, depending on the embodiment. In some embodiments, the mbIL15 is bicistronically expressed on the same polynucleotide as the chimeric receptor. In other embodiments, the mbIL15 is co-expressed on a separate construct. In several embodiments, the intracellular signaling domain is further enhanced by coupling its expression with that of membrane-bound interleukin 15 (mbIL15).

In several embodiments, the effector domain further comprises an OX-40 domain. In several embodiments, the OX-40 domain is either in place of, or in addition to mbIL15. In several embodiments, the chimeric receptor comprises the fragment of NKG2D coupled to a CD8α hinge, a CD8α transmembrane domain, the OX-40 domain, and the CD3zeta. In some embodiments, the polynucleotide construct is configured to bicistronically co-express mbIL15. In some such embodiments, the polynucleotide construct comprises one or more cleavage sites (e.g., T2A, P2A, E2A, and/or F2A cleavage site(s)) recognized and cleaved by, for example, a cytosolic protease. In some embodiments, the mbIL15 is coupled to the chimeric receptor by a cytosolic protease cleavage site. In several embodiments, the chimeric receptor is encoded by the nucleic acid sequence of SEQ ID NO: 90 coupled to the mbIL15 encoded by SEQ ID NO. 16 by a cytosolic protease cleavage site. In several embodiments, the chimeric receptor is encoded by the nucleic acid sequence of SEQ ID NO: 109 coupled to the mbIL15 encoded by SEQ ID NO. 16 by a cytosolic protease cleavage site. In several embodiments, the chimeric receptor comprises the amino acid sequence of SEQ ID NO: 91 and is co-expressed with mbIL15 comprising the amino acid sequence of SEQ ID NO. 17. As disclosed herein, sequences that differ from SEQ ID NOs: 90, 91, 109, 16, and/or 16, but share similar function may also be used, depending on the embodiment.

In several embodiments, the chimeric receptor comprises the fragment of NKG2D coupled to a IgG4 hinge, a CD8α transmembrane domain, the OX-40 domain, and the CD3zeta. In some embodiments, the polynucleotide construct is configured to bicistronically co-express mbIL15 with the chimeric receptor. In some such embodiments, the polynucleotide construct comprises one or more cleavage sites (e.g., T2A, P2A, E2A, and/or F2A cleavage site(s)) recognized and cleaved by a cytosolic protease. In some embodiments, the mbIL15 is coupled to the chimeric receptor by a cytosolic protease cleavage site. In several embodiments, the chimeric receptor is encoded by the nucleic acid sequence of SEQ ID NO: 100 coupled to the mbIL15 encoded by SEQ ID NO. 16 by a cytosolic protease cleavage site. In several embodiments, the chimeric receptor comprises the amino acid sequence of SEQ ID NO: 101 and is co-expressed with mbIL15 comprising the amino acid sequence of SEQ ID NO. 17. As disclosed herein, sequences that differ from SEQ ID NOs: 100, 101 and/or 16, but share similar function may also be used, depending on the embodiment.

In several embodiments, there are provided methods for treating cancer, comprising administering to a subject having a cancer a composition comprising a Natural Killer (NK) cell expressing the chimeric receptor encoded by the polynucleotides described above, or elsewhere herein.

In one embodiment, the NK cells are autologous cells isolated from a patient having a cancer or an infectious disease. In additional embodiments, the NK cells are allogeneic cells isolated from a donor.

Also provided for herein is use of a polynucleotide as described above, or elsewhere herein, in the manufacture of a medicament for enhancing NK cell cytotoxicity in a mammal in need thereof. In several embodiments, there is provided for the use of a polynucleotide as described above, or elsewhere herein, in the manufacture of a medicament for treating or preventing cancer or an infectious disease in a mammal in need thereof.

According to several embodiments, there is provided a polynucleotide encoding a chimeric receptor, the chimeric receptor comprising an extracellular receptor domain an effector domain comprising a transmembrane region and an intracellular signaling domain. As discussed in more detail herein, the extracellular receptor domain serves to recognize and bind ligands on a target cell. The effector domain serves to transmit signals (upon binding of a target cell by the extracellular domain) that set in motion a signal cascade that leads to cytotoxic activity against the target cell. In accordance with several embodiments, the polynucleotide encodes a chimeric receptor that provides unexpectedly increased cytotoxicity as compared to non-engineered NK cells.

In several embodiments, the extracellular receptor domain comprises a peptide that binds native ligands of Natural Killer Group 2 member D (NKG2D). According to several embodiments, the peptide that binds native ligands of NKG2D is a functional fragment of NKG2D (e.g., a truncation, fragment or portion of full length NKG2D. As used, herein the terms, "fragment", "truncation", and "portion" shall be given their ordinary meanings and shall also be interchangeable with one another. For example, in several embodiments, the fragment of NKG2D is encoded by a polynucleotide comprising a fragment of the sequence of SEQ ID NO: 1. In several embodiments, the fragment of NKG2D comprises the sequence of SEQ ID NO: 2, while in additional embodiments, the fragment encoding NKG2D is codon optimized, and comprises, for example, the sequence of SEQ ID NO: 3. In additional embodiments, the fragment encoding NKG2D is codon optimized, and comprises, for example, the sequence of SEQ ID NO: 68.

In several embodiments, the effector domain comprises one or more of CD16, NCR1, NCR2, NCR3, 4-1BB, NKp80, CD3zeta and 2B4. In several embodiments, these effector domains are coupled to CD8a.

In several embodiments, the chimeric receptor comprises a fragment of NKG2D coupled to CD16. As used herein, coupled shall be given its ordinary meaning and shall also refer to direct (e.g., a first nucleotide followed directly be a second nucleotide) or indirect (e.g., sequences are in frame with one another but separated by intervening nucleotides) linkage of nucleotide sequences in a manner that allows for expression of the nucleotide sequences in, for example, an in vitro transcription/translation system, a host cell (e.g., in vitro and/or in vivo). As used herein, "linked" and "coupled" are used interchangeably. In several embodiments, the NKG2D/CD16 chimeric receptor is encoded by the nucleic acid sequence of SEQ ID NO: 23. In several embodiments, the NKG2D/CD16 chimeric receptor comprises the amino acid sequence of SEQ ID NO: 24. In several embodiments, the chimeric receptor comprises a fragment of NKG2D coupled to NCR1. In several embodiments, such a chimeric receptor is encoded by the nucleic acid sequence of SEQ ID NO: 27. In several embodiments, the chimeric receptor comprises the amino acid sequence of SEQ ID NO: 28.

As discussed above, in several embodiments, the NKG2D fragment is coupled to NCR2, and the resultant chimeric receptor comprises at least a portion of the amino acid sequence of SEQ ID NO: 21. Several embodiments provide for a chimeric receptor comprising a fragment of NKG2D coupled to NCR3. In several embodiments, the chimeric receptor is encoded by the nucleic acid sequence of SEQ ID NO. 29, and the chimeric receptor comprises the amino acid sequence of SEQ ID NO. 30.

As discussed in more detail below, combinations of transmembrane and intracellular domains are used in several embodiments and provide for synergistic interactions between the components of the chimeric receptor and yield enhanced cytotoxic effects. In several embodiments, the chimeric receptor comprises the fragment of NKG2D coupled to a CD16 transmembrane/intracellular domain and 4-1BB. In several embodiments, the chimeric receptor comprises the fragment of NKG2D coupled to a CD8α hinge, a CD16 transmembrane/intracellular domain and 4-1BB. In several embodiments, such a chimeric receptor is encoded by the nucleic acid sequence of SEQ ID NO: 25. In several embodiments, the resultant chimeric receptor comprises the amino acid sequence of SEQ ID NO: 26.

In several embodiments, NCR1 is used in conjunction with the NKG2D fragment. In several embodiments, the NKG2D fragment is linked to NCR1 alone. In additional embodiments, the chimeric receptor comprises the fragment of NKG2D coupled to NCR1 and 4-1BB. In some such embodiments, the chimeric receptor comprises the NCR1 amino acid sequence of SEQ ID NO: 20.

In several embodiments, the chimeric receptor comprises the fragment of NKG2D coupled to CD8α, 4-1BB and CD3z CD3zeta. In several embodiments, such an NKG2D/CD8α/4-1BB/CD3zeta chimeric receptor is encoded by the nucleic acid sequence of SEQ ID NO. 18. In several embodiments, the chimeric receptor comprises the amino acid sequence of SEQ ID NO. 19.

In several embodiments, NCR3 is included in the chimeric receptor. For example, an NKG2D/NCR3 construct is provided for in several embodiments. The resultant chimeric receptor thereby comprises the NCR3 amino acid sequence of SEQ ID NO: 22. In several embodiments, the chimeric receptor comprises a NKG2D/NCR2/4-1BB construct or an NKG2D/NCR3/4-1BB construct.

In several embodiments, linkers, hinges, or other "spacing" elements are provided for in the chimeric receptor constructs. For example, in several embodiments, the effector domain comprises a linker. In several embodiments, the polynucleotides encode a GS linker between the portions of the construct, such as between any of 4-1BB, CD16, NCR1, NCR3, 2B4 or NKp80. In several embodiments, one or more GS linkers are provided for, for example, 1, 2, 3, 4, 5, 6, or more. In several embodiments, there is provided for a chimeric receptor comprising a hinge region. Depending on the location within a particular construct, a hinge region can be synonymous with a linker region, and vice versa. In several embodiments, the hinge region is encoded by the nucleic acid sequence of SEQ ID NO: 5. In some embodiments, the hinge region can be truncated to a desired length and is therefore encoded by a fragment of the nucleic acid sequence of SEQ ID NO: 5. In several embodiments, a glycine-serine motif is used as a hinge. In several embodiments, the hinge region is comprises a glycine-serine repeating motif having the amino acid sequence of (GGGGS)n (SEQ ID NO: 31) where n is the number of repeats. In several embodiments, 9 repeats are used, resulting in a hinge region comprising the amino acid sequence of SEQ ID NO: 33. In several embodiments, 3 repeats are used, resulting in a hinge region comprising the amino acid sequence of SEQ ID NO: 34.

In several embodiments, two separate molecules can be used as a hinge or linker, such as the amino acid sequence of SEQ ID NO: 32 (CD8α/GS3). In several embodiments, portions of a beta adrenergic receptor are used as a hinge or linker. In several embodiments, portions of the beta-2 adrenergic receptor are used. In one embodiment, an extracellular domain of the beta-2 adrenergic receptor is used, which is encoded by the nucleic acid sequence of SEQ ID NO: 40. In some embodiments, the first transmembrane helix of the beta-2 adrenergic receptor is used, which is encoded by the nucleic acid sequence of SEQ ID NO: 42. Depending on the embodiment, these two beta-2 adrenergic receptor portions are used together in the chimeric receptor. In several embodiments, the extracellular receptor domain further comprises a CD8α signal peptide, wherein the signal peptide comprises the nucleic acid sequence of SEQ ID NO. 4. Other signal peptides are optionally used, depending on the embodiment. Signal peptides may be employed in a multimeric format, according to some embodiments.

In several embodiments, the effector domain comprises one or more hemi-ITAM sequences. In some such embodiments, the hemi-ITAM comprises the amino acid motif DGYXXL (where X is any amino acid; SEQ ID NO: 14). Multiple hemi-ITAMs are used in some embodiments. In several embodiments, the hemi-ITAM comprises NKp80. In several embodiments, the effector domain comprises one or more ITSM sequences. ITSM sequences are used in conjunction with hemi-ITAM motifs in several embodiments. In several embodiments, the ITSM comprises the amino acid motif S/TXYXXL/I (where X is any amino acid; SEQ ID NO: 15). In several embodiments, the effector comprises a 2B4 domain.

In several embodiments, the chimeric receptor comprises a fragment of NKG2D coupled to a GS3 linker, a CD8α hinge, a CD16 transmembrane/intracellular domain and 4-1BB. In several embodiments, the chimeric receptor comprises a fragment of NKG2D coupled to a GS3 linker, a CD16 transmembrane/intracellular domain and 4-1BB. In several embodiments, the chimeric receptor comprises a fragment of NKG2D coupled to a CD16 transmembrane/intracellular domain and 4-1BB. In several embodiments, the chimeric receptor comprises a fragment of NKG2D coupled to a CD8α hinge, a CD8α transmembrane domain, 4-1BB, and 2B4. In several embodiments, the chimeric receptor comprises a fragment of NKG2D coupled to a beta-adrenergic extracellular domain, a beta-adrenergic transmembrane domain, 4-1BB, and 2B4. In several embodiments, the chimeric receptor comprises a fragment of NKG2D coupled to a CD8α hinge, a CD8α transmembrane domain, 4-1BB, 2B4, a GS3 linker, and NKp80. In several embodiments, the chimeric receptor comprises a fragment of NKG2D coupled to a CD8α hinge, a CD8α transmembrane domain, 4-1BB, a GS3 linker, and NKp80. In several embodiments, the chimeric receptor comprises a fragment of NKG2D, wherein the fragment is encoded by a sequence that is codon optimized coupled to a GS3 linker, an additional NKG2D fragment, a beta-adrenergic extracellular domain, a beta-adrenergic transmembrane domain, 4-1BB, an additional GS3 linker, and NKp80. In several embodiments, the chimeric receptor comprises a fragment of NKG2D that is codon optimized coupled to a GS3 linker, an additional NKG2D fragment, a CD8α hinge, a CD8α transmembrane domain, 4-1BB, an additional GS3 linker, and NKp80. In several embodiments, the chimeric receptor comprises a fragment of NKG2D that is codon optimized coupled to a GS3 linker, an additional NKG2D fragment, a CD8α hinge, a CD16 transmembrane/intracellular domain, and 4-1BB. In several embodiments, chimeric receptor comprises a fragment of NKG2D coupled to a CD8α hinge, a CD16 transmembrane/intracellular domain, 4-1BB, and 2B4. In several embodiments, the chimeric receptor comprises a fragment of NKG2D coupled to a CD8α hinge, a CD16 transmembrane/intracellular domain, 4-1BB, a GS3 linker, and NKp80. In several embodiments, the chimeric receptor comprises a fragment of NKG2D that is coupled to a CD8α hinge and a CD8α transmembrane domain. In several embodiments, the effector comprises 4-1BB. In some such embodiments the effector comprises 4-1BB optionally in conjunction with one or more of NKp80, 2B4, CD3zeta, Dap10, Dap12, CD28, or other signaling domains provided for herein). In several embodiments, the effector domain further comprises CD3zeta. In several embodiments, the effector domain comprises an intracellular domain of 2B4. In several embodiments, the effector domain further comprises an intracellular domain of DAP10.

In several embodiments, the chimeric receptor comprises a fragment of NKG2D coupled to a CD8α hinge, a CD8α transmembrane domain, 4-1BB, 2B4, and CD3zeta. In several embodiments, the chimeric receptor is encoded by the nucleic acid sequence of SEQ ID NO: 58. In several embodiments, the chimeric receptor comprises the amino acid sequence of SEQ ID NO: 59.

Additionally, any of chimeric receptors disclosed herein can also be co-expressed with membrane-bound interleukin 15 (mbIL15). For example, provided for in several embodiments is a polynucleotide encoding a chimeric receptor comprising an extracellular receptor domain, wherein the extracellular receptor domain comprises a peptide that binds native ligands of NKG2D, wherein the peptide that binds native ligands of NKG2D is a fragment of NKG2D, a transmembrane region, an effector domain, the polynucleotide being co-expressed with an additional construct encoding membrane-bound interleukin 15 (mbIL15). In several embodiments, chimeric receptors as discussed herein are co-expressed with mbIL-15. In several embodiments, the effector domain comprises 4-1BB and CD3 zeta, and the transmembrane region comprises CD8α.

In several embodiments, the chimeric receptors are engineered such that they do not include DNAX-activating protein 10 (DAP10). Additionally, in several embodiments, the chimeric receptors are engineered such that they do not include an ITAM motif.

In several embodiments, there is provided a polynucleotide encoding a chimeric receptor comprising, one, two, or all of: (a) an extracellular receptor domain comprising a fragment of NKG2D that binds native ligands of NKG2D, (b) a transmembrane region, wherein the transmembrane region comprises CD8α, and (c) an effector domain, wherein the effector domain comprises 4-1BB and the intracellular domain of 2B4 or DAP10. In several embodiments, the effector domain comprises 2B4 followed by 4-1BB. In additional embodiments, the effector domain comprises 4-1BB followed by 2B4. In several embodiments, the effector domain comprises DAP10 followed by 4-1BB. In additional embodiments, the effector domain comprises 4-1BB followed by DAP10. In several embodiments, the chimeric receptor comprises the fragment of NKG2D coupled to a CD8α hinge, a CD8α transmembrane domain, 4-1BB, and DAP10. In several embodiments, the chimeric receptor is encoded by the nucleic acid sequence of SEQ ID NO: 60. In several embodiments, the chimeric receptor comprises the amino acid sequence of SEQ ID NO: 61. In several embodiments, the chimeric receptor comprises the fragment of NKG2D coupled to a CD8α hinge, a CD8α transmembrane domain, 4-1BB, 2B4, and DAP10. In several embodiments, the effector domain comprises 4-1BB, followed by DAP10, followed by 2B4. In several embodiments, the chimeric receptor is encoded by the nucleic acid sequence of SEQ ID NO: 62. In several embodiments, the chimeric receptor comprises the amino acid sequence of SEQ ID NO: 63. In several embodiments, the effector domain comprises 4-1BB, followed by 2B4, followed by DAP10. In several embodiments, the chimeric receptor is encoded by the nucleic acid sequence of SEQ ID NO: 64. In several embodiments, the chimeric receptor comprises the amino acid sequence of SEQ ID NO: 65.

In several embodiments, the chimeric receptor comprises a codon-optimized fragment of NKG2D coupled to an intracellular effector domain. In several embodiments, multiple fragments of NKG2D are employed, for example, an additional NKG2D fragment (optionally codon optimized) is coupled to the first fragment by, for example, a GS3 linker. In several embodiments, such chimeric receptors further comprise a CD8α hinge, a CD8α transmembrane domain, 4-1BB, and CD3zeta. In several embodiments, the chimeric receptor is encoded by the nucleic acid sequence of SEQ ID NO: 66. In several embodiments, the chimeric receptor comprises the amino acid sequence of SEQ ID NO: 67. In several embodiments, the polynucleotide is co-expressed with an additional construct encoding membrane-bound interleukin 15 (mbIL15).

In several embodiments, there is provided a polynucleotide encoding a chimeric receptor comprising an extracellular receptor domain, comprising a fragment of NKG2D that binds a native ligand of NKG2D and is encoded by a fragment of SEQ ID NO: 1, a transmembrane region comprising a CD3zeta transmembrane region, and an effector domain. In several embodiments, there is provided a polynucleotide encoding a chimeric receptor comprising an extracellular receptor domain, comprising a fragment of NKG2D that binds a native ligand of NKG2D and is encoded by SEQ ID NO. 2, a transmembrane region comprising a CD3zeta transmembrane region, and an effector domain. In several embodiments, there is provided a polynucleotide encoding a chimeric receptor comprising an extracellular receptor domain, comprising a fragment of NKG2D that binds a native ligand of NKG2D and is encoded by SEQ ID NO. 3, a transmembrane region comprising a CD3zeta transmembrane region, and an effector domain. In several embodiments, there is provided a polynucleotide encoding a chimeric receptor comprising an extracellular receptor domain, comprising a fragment of NKG2D that binds a native ligand of NKG2D and is encoded by SEQ ID NO. 68, a transmembrane region comprising a CD3zeta transmembrane region, and an effector domain. In several embodiments, fragments of the NKG2D encoded by any of SEQ ID NO. 2, 3, or 68 may also be used. In several embodiments, the CD3zeta transmembrane region comprises the amino acid sequence of SEQ ID NO: 69. Fragments of the sequence of SEQ ID NO: 69 are also use, in several embodiments, the fragments retaining the ability to transduce at least about 65%, about 75%, about 85%, or about 95% of the signal transduction of a native CD3 zeta subunit (including dimers). In several embodiments, the extracellular receptor domain further comprises additional resides adjacent to the CD3zeta transmembrane region. In several embodiments, the additional amino acids are extracellular residues of a native CD3zeta sequence. In other embodiments, the additional amino acids are randomly selected. In several embodiments, there are 2, 3, 4, 5, 6, 8, 10, 15, or 20 additional amino acids. In several embodiments, the chimeric receptor domain comprises a hinge region, which in several embodiments, a CD8α hinge encoded by the nucleic acid sequence of SEQ ID NO: 5. In several embodiments, the hinge region is a CD8α hinge encoded by a fragment of the nucleic acid sequence of SEQ ID NO: 5. Depending on the embodiment, the fragment is about 75%, about 80%, about 85%, about 90%, about 95% of the length of the nucleic acid sequence of SEQ ID NO: 5. Depending on the embodiment, the fragment is about 75%, about 80%, about 85%, about 90%, about 95%, about 98%, or about 99% homologous to the nucleic acid sequence of SEQ ID NO: 5. In several embodiments, the extracellular receptor domain further comprises a CD8α signal peptide, which, depending on the embodiment, can comprise the nucleic acid sequence of SEQ ID NO. 4. In several embodiments, the effector domain comprises 4-1BB. In several embodiments, the effector domain comprises a CD16 intracellular domain. In several embodiments, the effector domain comprises 4-1BB and CD16 (with either moiety being "first" vs. "second" in the construct). In several embodiments, repeats of one or more of 4-1BB and/or CD16 are used.

In several embodiments, the chimeric receptor comprises a fragment of NKG2D that is codon optimized and is coupled to a CD8α hinge, a CD3zeta transmembrane region, and an effector domain comprising 4-1BB. In several embodiments, the chimeric receptor is encoded by the nucleic acid sequence of SEQ ID NO: 78. In several embodiments, the chimeric receptor comprises the amino acid sequence of SEQ ID NO: 79.

In several embodiments, the chimeric receptor comprises a fragment of NKG2D that is codon optimized coupled to a CD8α hinge, a CD3zeta transmembrane region, and an effector domain comprising CD16 followed by 4-1BB. In several embodiments, the chimeric receptor comprises the amino acid sequence of SEQ ID NO: 71. In several embodiments, the chimeric receptor is encoded by the nucleic acid sequence of SEQ ID NO: 70.

In several embodiments, the chimeric receptor comprises a fragment of NKG2D that is codon optimized and coupled to a CD8α hinge, a CD3zeta transmembrane region, and an effector domain comprising 4-1BB followed by CD16, optionally coupled by a GS3 linker. In several embodiments, the chimeric receptor comprises the amino acid sequence of SEQ ID NO: 85. In several embodiments, the chimeric receptor is encoded by the nucleic acid sequence of SEQ ID NO: 84.

In several embodiments, the chimeric receptor comprises a fragment of NKG2D that is codon optimized and is coupled to a GS3 linker, an additional NKG2D fragment, a CD8α hinge, a CD3zeta transmembrane region, and an effector domain comprising a CD16 and 4-1BB. In several embodiments, the chimeric receptor is encoded by the nucleic acid sequence of SEQ ID NO: 72. In several embodiments, the chimeric receptor comprises the amino acid sequence of SEQ ID NO: 73.

In several embodiments, the effector domain includes NKp80. In several embodiments, the effector domain is NKp80. In several embodiments, the chimeric receptor comprises a fragment of NKG2D that is coupled to a CD8α hinge, a CD3zeta transmembrane region, and an effector domain comprising a CD16, 4-1BB, and NKp80, and optionally including a GS3 linker. In several embodiments, the chimeric receptor is encoded by the nucleic acid sequence of SEQ ID NO: 74. In several embodiments, the chimeric receptor comprises the amino acid sequence of SEQ ID NO: 75. In several embodiments, the chimeric receptor comprises the fragment of NKG2D that is codon optimized and is coupled to a GS3 linker, an additional NKG2D fragment (optionally codon optimized), a CD8α hinge, a CD3zeta transmembrane region, and an effector domain comprising a CD16, 4-1BB, and NKp80, and optionally including a GS3 linker. In several embodiments, the chimeric receptor is encoded by the nucleic acid sequence of SEQ ID NO: 76. In several embodiments, the chimeric receptor comprises the amino acid sequence of SEQ ID NO: 77. In several embodiments, the chimeric receptor comprises a fragment of NKG2D that is codon optimized and is coupled to a CD8α hinge, a CD3zeta transmembrane region, and an effector domain comprising 4-1BB and NKp80, and optionally including a GS3 linker. In several embodiments, the chimeric receptor is encoded by the nucleic acid sequence of SEQ ID NO: 82. In several embodiments, the chimeric receptor comprises the amino acid sequence of SEQ ID NO: 83.

In several embodiments, the effector domain comprises CD3zeta. In several embodiments, the chimeric receptor comprises a fragment of NKG2D that is codon optimized and is coupled to a CD8α hinge, a CD3zeta transmembrane region, and an effector domain comprising 4-1BB and CD3zeta. In several embodiments, the chimeric receptor is encoded by the nucleic acid sequence of SEQ ID NO: 80. In several embodiments, the chimeric receptor comprises the amino acid sequence of SEQ ID NO: 81.

In several embodiments, the effector domain comprises FcRγ. In several embodiments, the chimeric receptor comprises a fragment of NKG2D coupled to a CD8α hinge, a CD3zeta transmembrane region, and an effector domain comprising 4-1BB and FcRγ. In several embodiments, the chimeric receptor is encoded by the nucleic acid sequence of SEQ ID NO: 86. In several embodiments, the chimeric receptor comprises the amino acid sequence of SEQ ID NO: 87.

In several embodiments, the effector domain comprises CD28. In several embodiments, the chimeric receptor comprises a fragment of NKG2D coupled to a CD8α hinge, a CD3zeta transmembrane region, and an effector domain comprising CD28 and CD3zeta. In several embodiments, the chimeric receptor is encoded by the nucleic acid sequence of SEQ ID NO: 102. In several embodiments, the chimeric receptor comprises the amino acid sequence of SEQ ID NO: 103.

In several embodiments, the effector domain comprises a GS linker.

In several embodiments, the polynucleotides disclosed herein are co-expressed with membrane-bound interleukin 15 (mbIL15).

In several embodiments, a polynucleotide encoding a chimeric receptor comprising an extracellular receptor domain comprising a fragment of NKG2D that is capable of binding a native ligand of NKG2D and is encoded by a fragment of any one of the sequence of SEQ ID NO: 1, of SEQ ID NO. 2, of SEQ ID NO. 3, or SEQ ID NO. 68, and an effector domain comprising a transmembrane region and an intracellular signaling domain. In several embodiments, there is provided a polynucleotide encoding a chimeric receptor comprising an extracellular receptor domain comprising a fragment of NKG2D that is capable of binding a native ligand of NKG2D and is encoded by (i) a fragment of the sequence of SEQ ID NO: 1, (ii) the sequence of SEQ ID NO. 2, (iii) the sequence of SEQ ID NO. 3, or (iv) the sequence of SEQ ID NO. 68, and an effector domain comprising a transmembrane region and an intracellular signaling domain. In several embodiments, a polynucleotide encoding a chimeric receptor comprising an extracellular receptor domain comprising a fragment of NKG2D that is capable of binding a native ligand of NKG2D and is encoded by the sequence of SEQ ID NO. 2, and an effector domain comprising a transmembrane region and an intracellular signaling domain. In several embodiments, a polynucleotide encoding a chimeric receptor comprising an extracellular receptor domain comprising a fragment of NKG2D that is capable of binding a native ligand of NKG2D and is encoded by the sequence of SEQ ID NO. 3, and an effector domain comprising a transmembrane region and an intracellular signaling domain. In several embodiments, a polynucleotide encoding a chimeric receptor comprising an extracellular receptor domain comprising a fragment of NKG2D that is capable of binding a native ligand of NKG2D and is encoded by a fragment of the sequence of SEQ ID NO. 68, and an effector domain comprising a transmembrane region and an intracellular signaling domain. In several embodiments, the extracellular receptor domain comprises a hinge region. In several embodiments, the hinge region is a CD8α hinge encoded by the nucleic acid sequence of SEQ ID NO: 5, or optionally a fragment of the nucleic acid sequence of SEQ ID NO: 5 (e.g., a fragment having about 75%, about 85%, about 95% homology to SEQ ID NO: 5). In several embodiments, the hinge region is an Immunoglobulin G4 (IgG4) hinge encoded by the nucleic acid sequence of SEQ ID NO: 104. In several embodiments, the hinge region is an Immunoglobulin G4 (IgG4) hinge encoded by a fragment of the nucleic acid sequence of SEQ ID NO: 104 (e.g., a fragment having about 75%, about 85%, about 95% homology to SEQ ID NO: 104). In several embodiments, the extracellular receptor domain further comprises a CD8α signal peptide, wherein the signal peptide comprises the nucleic acid sequence of SEQ ID NO. 4. In several embodiments, the effector domain comprises at least one signaling domains selected from the group consisting of OX40 (CD134), CD3zeta, 4-1BB, CD28 and DAP12. In several embodiments, the chimeric receptor transmembrane domain comprises a CD8 transmembrane domain. In several embodiments, the chimeric receptor comprises IL-15 linked (optionally by a GS3 linker) to the fragment of NKG2D coupled to a CD8α hinge, a CD8α transmembrane domain, 4-1BB, and CD3zeta. In several embodiments, the chimeric receptor is encoded by the nucleic acid sequence of SEQ ID NO: 88. In several embodiments, the chimeric receptor comprises the amino acid sequence of SEQ ID NO: 89.

In several embodiments, the chimeric receptor comprises a fragment of NKG2D coupled to an IgG4 hinge, a CD8α transmembrane domain, 4-1BB, and CD3zeta. In several embodiments, the chimeric receptor is encoded by the nucleic acid sequence of SEQ ID NO: 96. In several embodiments, the chimeric receptor comprises the amino acid sequence of SEQ ID NO: 97.

In several embodiments, the effector domain comprises OX40. In several embodiments, the chimeric receptor comprises the fragment of NKG2D coupled to a CD8α hinge, a CD8α transmembrane domain, OX40, and CD3zeta. In several embodiments, the chimeric receptor is encoded by the nucleic acid sequence of SEQ ID NO: 90. In several embodiments, the chimeric receptor is encoded by the nucleic acid sequence of SEQ ID NO: 109. In several embodiments, the chimeric receptor comprises the amino acid sequence of SEQ ID NO: 91. In several embodiments, the chimeric receptor comprises a fragment of NKG2D coupled to an IgG4 hinge, a CD8α transmembrane domain, OX40 and CD3zeta. In several embodiments, the chimeric receptor is encoded by the nucleic acid sequence of SEQ ID NO: 100. In several embodiments, the chimeric receptor comprises the amino acid sequence of SEQ ID NO: 101.

In several embodiments, the chimeric receptor comprises a CD28 transmembrane/intracellular domain. In several embodiments, the chimeric receptor comprises the fragment of NKG2D coupled to a CD8α hinge, a CD28 transmembrane/intracellular domain, and CD3zeta. In several embodiments, the chimeric receptor is encoded by the nucleic acid sequence of SEQ ID NO: 92. In several embodiments, the chimeric receptor comprises the amino acid sequence of SEQ ID NO: 93.

In several embodiments, the chimeric receptor comprises a fragment of NKG2D coupled to a CD8α hinge, a CD28 transmembrane/intracellular domain, 4-1BB, and CD3zeta. In several embodiments, the chimeric receptor is encoded by the nucleic acid sequence of SEQ ID NO: 94. In several embodiments, the chimeric receptor comprises the amino acid sequence of SEQ ID NO: 95.

In several embodiments, the chimeric receptor comprises a fragment of NKG2D coupled to an IgG4 hinge, a CD28 transmembrane/intracellular domain and CD3zeta. In several embodiments, the chimeric receptor is encoded by the nucleic acid sequence of SEQ ID NO: 98. In several embodiments, the chimeric receptor comprises the amino acid sequence of SEQ ID NO: 99.

In several embodiments, the effector domain comprises a GS linker. In several embodiments, the polynucleotides disclosed herein are configured to be co-expressed (either on the same polynucleotide, or another polynucleotide) with membrane-bound interleukin 15 (mbIL15).

Any of the chimeric receptors can optionally include an extracellular receptor domain that includes a second peptide that binds native ligands of NKG2D. In several embodiments, the second peptide is homologous with NKG2D, while in other embodiments, the second peptide is heterologous with respect to the NKG2D. Whether the chimeric receptor includes a dimerized extracellular receptor domain, the extracellular receptor domains can recognize at least the following native ligands of NKG2D: MICA, MICB, ULBP1, ULBP2, ULBP3, ULBP4, ULBP5 or ULBP6.

As discussed in more detail below, functional variants of the NKG2D ligand binding domains are employed in several embodiments. For example the peptide that binds native ligands of NKG2D has, in several embodiments, at least 80% homology to SEQ ID NO: 1, SEQ ID NO: 2, SEQ ID NO: 3, or SEQ ID NO: 68. In several embodiments, the peptide that binds native ligands of NKG2D has at least 70%, at least 75%, at least 80%, at least 85%, at least 90%, or at least 95% homology to SEQ ID NO: 1, SEQ ID NO: 2, SEQ ID NO: 3, or SEQ ID NO: 68.

Additionally provided for herein in several embodiments are vectors for expressing the chimeric receptors. In several embodiments, the polynucleotides provided for herein are mRNA and can include an operable linkage to least one regulatory element for the expression of the chimeric receptor. In several embodiments, the polynucleotides further include one or more internal ribosome entry site (IRES). In several embodiments, the vector is a retrovirus.

Engineered natural killer cells are also provided for, in several embodiments, that express any of the chimeric receptor constructs disclosed herein, the engineered NK cells exhibiting enhanced cytotoxic effects against target cells. Enhanced cytotoxic effects include, but are not limited to, higher affinity for target (e.g., cancerous) cells as compared to normal (e.g., non-cancerous) cells, a greater killing effect directed against target cells, reduced off-target effects, increased duration of cytotoxic effects, more efficient cytotoxicity, and the like. Such enhanced effects can be identified through the use of various in vitro cytotoxicity assays (e.g., measurement of cytokine production, etc.), measurement of target cell death, or through various clinical outcomes (e.g., reduction in tumor burden). In several embodiments, the engineered NK cells are an autologous cell isolated from a patient. In additional embodiments, the engineered NK cells are generated from allogeneic cells isolated from a donor. Such engineered NK cells as disclosed herein are used, in several embodiments, to enhance NK cell cytotoxicity in a mammal in need thereof, by administering the NK cells. These engineered NK cells are used, in several embodiments for treating or preventing cancer or an infectious disease in a mammal. The polynucleotides encoding, the vectors carrying, and the NK cells expressing the various chimeric receptors disclosed herein can also be used, in several embodiments in the manufacture of a medicament for enhancing NK cell cytotoxicity (e.g., to treat or prevent cancer or an infectious disease). In several embodiments, the chimeric receptor constructs disclosed herein do not significantly increase the cytotoxicity of the engineered NK cells against normal cells and, as described herein, are advantageously improved as compared to non-engineered NK cells.

In several embodiments, there is provided a polynucleotide encoding a chimeric receptor comprising an extracellular receptor domain, a transmembrane region, and an effector domain. In several embodiments, the extracellular receptor domain comprises a peptide that binds native ligands of Natural Killer Group 2 member D (NKG2D), wherein the peptide that binds native ligands of NKG2D is a fragment of NKG2D. Several embodiments, relate to a polynucleotide encoding a chimeric receptor comprising: (a) an extracellular receptor domain, wherein said extracellular receptor domain comprises a peptide that binds native ligands of Natural Killer Group 2 member D (NKG2D), wherein the peptide that binds native ligands of NKG2D is a fragment of NKG2D, wherein the fragment of NKG2D is encoded by a polynucleotide comprising: (i) a fragment of the sequence of SEQ ID NO: 1, (ii) the sequence of SEQ ID NO. 2, (iii) the sequence of SEQ ID NO. 3, or (iv) the sequence of SEQ ID NO. 68, (b) a transmembrane region, and (c) an effector domain.

In several embodiments, there is provided a polynucleotide encoding a chimeric receptor comprising: (a) an extracellular receptor domain, wherein said extracellular receptor domain comprises a peptide that binds native ligands of Natural Killer Group 2 member D (NKG2D), wherein the peptide that binds native ligands of NKG2D is a fragment of NKG2D, wherein the fragment of NKG2D is encoded by a polynucleotide comprising: (i) a fragment of the sequence of SEQ ID NO: 1, (ii) the sequence of SEQ ID NO. 2, (iii) the sequence of SEQ ID NO. 3, (iv) or the sequence of SEQ ID NO. 68; and (b) an effector domain comprising a transmembrane region and an intracellular signaling domain.

In several embodiments, the transmembrane region comprises a CD3zeta transmembrane region. In several embodiments, the CD3zeta transmembrane region comprises the amino acid sequence of SEQ ID NO: 69. In several embodiments, the transmembrane region comprises CD8α. In several embodiments, the effector domain comprises 4-1BB, an intracellular domain of 2B4, NKp80, a CD16 intracellular domain, Natural Cytotoxicity Triggering Receptor 1 (NCR1), Natural Cytotoxicity Triggering Receptor 2 (NCR2), Natural Cytotoxicity Triggering Receptor 3 (NCR3), and/or an intracellular domain of DAP10. In one embodiment, the effector domain comprises 4-1BB and CD16. In several embodiments, the effector domain comprises 4-1BB and CD3 zeta. In several embodiments, the effector domain comprises 4-1BB and an intracellular domain of 2B4 or DAP10. In several embodiments, the effector domain comprises 2B4 followed by 4-1BB while in other embodiments the effector domain comprises 4-1BB followed by 2B4. In several embodiments, the effector domain comprises DAP10 followed by 4-1BB. In several embodiments, the effector domain comprises 4-1BB followed by DAP10. In several embodiments, the effector domain further comprises CD3zeta. In several embodiments, the effector domain comprises at least one signaling domain selected from the group consisting of OX40 (CD134), CD3zeta, 4-1BB, CD28 and DAP12. In several embodiments the effector domain comprises one or more hemi-ITAM sequences. In several embodiments, the hemi-ITAM comprises the amino acid sequence of SEQ ID NO. 14. In several embodiments, the hemi-ITAM comprises the amino acid sequence of SEQ ID NO. 37. In several embodiments, the effector domain comprises one or more ITSM sequences. In several embodiments, the ITSM comprises the amino acid sequence of SEQ ID NO. 15 or the amino acid sequence of SEQ ID NO. 35

In several embodiments, the chimeric receptor comprises a fragment of NKG2D coupled to a CD8α hinge, a CD8α transmembrane domain, 4-1BB, 2B4, and CD3zeta. In one embodiment, the chimeric receptor is encoded by the nucleic acid sequence of SEQ ID NO: 58. In one embodiment, the chimeric receptor comprises the amino acid sequence of SEQ ID NO: 59. In several embodiments, the chimeric receptor comprises a fragment of NKG2D coupled to a CD8α hinge, a CD8α transmembrane domain, 4-1BB, and DAP10. In several embodiments, the chimeric receptor is encoded by the nucleic acid sequence of SEQ ID NO: 60 and comprises the amino acid sequence of SEQ ID NO: 61.

In several embodiments, the chimeric receptor comprises a fragment of NKG2D coupled to a CD8α hinge, a CD8α transmembrane domain, 4-1BB, 2B4, and DAP10. In several embodiments, the effector domain comprises 4-1BB, followed by DAP10, followed by 2B4. In some embodiments, the chimeric receptor is encoded by the nucleic acid sequence of SEQ ID NO: 62 and the chimeric receptor comprises the amino acid sequence of SEQ ID NO: 63. In several embodiments, the effector domain comprises 4-1BB, followed by 2B4, followed by DAP10. In several embodiments, the chimeric receptor is encoded by the nucleic acid sequence of SEQ ID NO: 64 and the chimeric receptor comprises the amino acid sequence of SEQ ID NO: 65.

In several embodiments, the chimeric receptor comprises a fragment of NKG2D that is codon optimized coupled to a GS3 linker, an additional NKG2D fragment, a CD8α hinge, a CD8α transmembrane domain, 4-1BB, and CD3zeta. In one embodiment, the chimeric receptor is encoded by the nucleic acid sequence of SEQ ID NO: 66. In several embodiments, the chimeric receptor comprises the amino acid sequence of SEQ ID NO: 67.

In several embodiments, the chimeric receptor comprises a fragment of NKG2D that is codon optimized coupled to a CD8α hinge, a CD3zeta transmembrane region, and an effector domain comprising 4-1BB, is encoded by the nucleic acid sequence of SEQ ID NO: 78 and/or comprises the amino acid sequence of SEQ ID NO: 79.

In several embodiments, the chimeric receptor comprises a fragment of NKG2D that is codon optimized coupled to a CD8α hinge, a CD3zeta transmembrane region, and an effector domain comprising CD16 followed by 4-1BB. In several embodiments, the chimeric receptor is encoded by the nucleic acid sequence of SEQ ID NO: 70 and/or comprises the amino acid sequence of SEQ ID NO: 71.

In several embodiments, the chimeric receptor comprises a fragment of NKG2D that is codon optimized coupled to a CD8α hinge, a CD3zeta transmembrane region, and an effector domain comprising 4-1BB followed by a GS3 linker and CD16. In one embodiment, the chimeric receptor comprises the amino acid sequence of SEQ ID NO: 85 and/or is encoded by the nucleic acid sequence of SEQ ID NO: 84.

In several embodiments, the chimeric receptor comprises a fragment of NKG2D that is codon optimized coupled to a GS3 linker, an additional NKG2D fragment, a CD8α hinge, a CD3zeta transmembrane region, and an effector domain comprising a CD16 and 4-1BB. In one embodiment, the chimeric receptor is encoded by the nucleic acid sequence of SEQ ID NO: 72 and/or comprises the amino acid sequence of SEQ ID NO: 73.

In several embodiments, the chimeric receptor comprises IL-15 linked by a GS3 linker to the fragment of NKG2D coupled to a CD8α hinge, a CD8α transmembrane domain, 4-1BB, and CD3zeta, is encoded by the nucleic acid sequence of SEQ ID NO: 88 and/or comprises the amino acid sequence of SEQ ID NO: 89.

In several embodiments, the chimeric receptor comprises the fragment of NKG2D coupled to a IgG4 hinge, a CD8α transmembrane domain, 4-1BB, and CD3zeta is encoded by the nucleic acid sequence of SEQ ID NO: 96, and/or comprises the amino acid sequence of SEQ ID NO: 97.

In several embodiments, the chimeric receptor comprises the fragment of NKG2D coupled to a CD8α hinge, a CD8α transmembrane domain, OX40, and CD3zeta, is encoded by the nucleic acid sequence of SEQ ID NO: 90, and/or comprises the amino acid sequence of SEQ ID NO: 91.

In several embodiments, the chimeric receptor comprises the fragment of NKG2D coupled to an IgG4 hinge, a CD8α transmembrane domain, OX40 and CD3zeta, is encoded by the nucleic acid sequence of SEQ ID NO: 100, and/or comprises the amino acid sequence of SEQ ID NO: 101.

In several embodiments, the chimeric receptor comprises the fragment of NKG2D coupled to a CD8α hinge, a CD28 transmembrane/intracellular domain, and CD3zeta, is encoded by the nucleic acid sequence of SEQ ID NO: 92, and/or comprises the amino acid sequence of SEQ ID NO: 93.

In several embodiments, the chimeric receptor comprises the fragment of NKG2D coupled to a CD8α hinge, a CD28 transmembrane/intracellular domain, 4-1BB, and CD3zeta, is encoded by the nucleic acid sequence of SEQ ID NO: 94, and/or comprises the amino acid sequence of SEQ ID NO: 95.

In several embodiments, the chimeric receptor comprises the fragment of NKG2D coupled to an IgG4 hinge, a CD28 transmembrane/intracellular domain and CD3zeta, is encoded by the nucleic acid sequence of SEQ ID NO: 98, and/or comprises the amino acid sequence of SEQ ID NO: 99.

In several embodiments, the chimeric receptor comprises a fragment of NKG2D coupled to a CD8α hinge, a CD3zeta transmembrane region, and an effector domain comprising a CD16, 4-1BB, a GS3 linker, and NKp80. In one embodiment, the chimeric receptor is encoded by the nucleic acid sequence of SEQ ID NO: 74 and/or comprises the amino acid sequence of SEQ ID NO: 75.

In several embodiments, the chimeric receptor comprises the fragment of NKG2D that is codon optimized coupled to a GS3 linker, an additional NKG2D fragment, a CD8α hinge, a CD3zeta transmembrane region, and an effector domain comprising a CD16, 4-1BB, a GS3 linker, and NKp80. In one embodiment, the chimeric receptor is encoded by the nucleic acid sequence of SEQ ID NO: 76 and/or comprises the amino acid sequence of SEQ ID NO: 77. In several embodiments, the chimeric receptor comprises a fragment of NKG2D that is codon optimized coupled to a CD8α hinge, a CD3zeta transmembrane region, and an effector domain comprising 4-1BB, a GS3 linker, and NKp80. In one embodiment, the chimeric receptor is encoded by the nucleic acid sequence of SEQ ID NO: 82 and/or comprises the amino acid sequence of SEQ ID NO: 83.

In several embodiments, the chimeric receptor comprises a fragment of NKG2D that is codon optimized coupled to a CD8α hinge, a CD3zeta transmembrane region, and an effector domain comprising 4-1BB and CD3zeta. In one embodiment, the chimeric receptor is encoded by the nucleic acid sequence of SEQ ID NO: 80 and/or comprises the amino acid sequence of SEQ ID NO: 81.

Depending on the embodiment, the effector domain may also comprise FcRγ. For example, in several embodiments, the chimeric receptor comprises a fragment of NKG2D coupled to a CD8α hinge, a CD3zeta transmembrane region, and an effector domain comprising 4-1BB and FcRγ. In one embodiment, the chimeric receptor is encoded by the nucleic acid sequence of SEQ ID NO: 86 and/or comprises the amino acid sequence of SEQ ID NO: 87.

Depending on the embodiment, the effector domain may also comprise CD28. For example, in several embodiments, the chimeric receptor comprises a fragment of NKG2D coupled to a CD8α hinge, a CD3zeta transmembrane region, and an effector domain comprising CD28 and CD3zeta. In several embodiments, the chimeric receptor is encoded by the nucleic acid sequence of SEQ ID NO: 102 and/or comprises the amino acid sequence of SEQ ID NO: 103.

In several embodiments, the effector domain comprises a GS linker.

In several embodiments, the extracellular receptor domain further comprises a CD8α signal peptide, wherein the signal peptide comprises the nucleic acid sequence of SEQ ID NO. 4. In several embodiments, the extracellular receptor domain further comprises 2 extracellular residues of CD3zeta directly adjacent to the CD3zeta transmembrane region. In several embodiments, the extracellular receptor domain comprises a CD8α signal peptide, wherein the signal peptide comprises the nucleic acid sequence of SEQ ID NO. 4.

In several embodiments, the chimeric receptor comprises one or more GS3 linkers. In several embodiments, the chimeric receptor domain comprises a hinge region. In several embodiments, the hinge region is encoded by the nucleic acid sequence of SEQ ID NO: 5, while in some embodiments, the hinge region is encoded by a fragment of the nucleic acid sequence of SEQ ID NO: 5. In several embodiments, the hinge region is a CD8α hinge. In several embodiments, the hinge region comprises a glycine-serine repeating motif having the amino acid sequence of SEQ ID NO: 31. In several embodiments, the hinge region comprises the amino acid sequence of SEQ ID NO: 32 and in some embodiments, the hinge region comprises the amino acid sequence of SEQ ID NO: 33. In additional embodiments, the hinge region is encoded by the nucleic acid sequence of SEQ ID NO: 34. In several embodiments, the hinge region comprises a portion of the beta-adrenergic receptor. In some such embodiments, the hinge region is encoded by the nucleic acid sequence of SEQ ID NO: 40. In additional embodiments, the hinge region is encoded by the nucleic acid sequence of SEQ ID NO: 42. In several embodiments, the hinge region is Immunoglobulin G4 (IgG4) hinge encoded by the nucleic acid sequence of SEQ ID NO: 104. In several embodiments, the hinge region is an Immunoglobulin G4 (IgG4) hinge encoded by a fragment of the nucleic acid sequence of SEQ ID NO: 104. In several embodiments, the chimeric receptor comprises the fragment of NKG2D coupled to a CD8α hinge and a CD8α transmembrane domain.

In one embodiment, the chimeric receptor comprises the fragment of NKG2D coupled to CD16, is encoded by the nucleic acid sequence of SEQ ID NO: 23, and/or comprises the amino acid sequence of SEQ ID NO: 24. In one embodiment, the chimeric receptor comprises the fragment of NKG2D coupled to NCR1. In some such embodiments, the chimeric receptor is encoded by the nucleic acid sequence of SEQ ID NO: 27 and/or comprises the amino acid sequence of SEQ ID NO: 28. In several embodiments, the chimeric receptor comprises at least a portion of the amino acid sequence of SEQ ID NO: 21. In several embodiments, the chimeric receptor comprises the fragment of NKG2D coupled to NCR3, in several embodiments is encoded by the nucleic acid sequence of SEQ ID NO. 29 and/or comprises the amino acid sequence of SEQ ID NO. 30.

In several embodiments, the chimeric receptor comprises the fragment of NKG2D coupled to a CD16 transmembrane/intracellular domain and 4-1BB. In several embodiments, the chimeric receptor comprises the fragment of NKG2D coupled to a CD8α hinge, a CD16 transmembrane/intracellular domain and 4-1BB, is encoded by the nucleic acid sequence of SEQ ID NO: 25, and/or comprises the amino acid sequence of SEQ ID NO: 26.

In several embodiments, the chimeric receptor comprises the fragment of NKG2D coupled to NCR1 and 4-1BB, wherein the chimeric receptor comprises the NCR1 amino acid sequence of SEQ ID NO: 20.

In several embodiments, the chimeric receptor comprises the fragment of NKG2D coupled to CD8α, 4-1BB and CD3zeta, is encoded by the nucleic acid sequence of SEQ ID NO. 18 and/or comprises the amino acid sequence of SEQ ID NO. 19.

In several embodiments, the chimeric receptor comprises the fragment of NKG2D coupled to NCR3 and 4-1BB, and wherein the NCR3 comprises the amino acid sequence of SEQ ID NO: 22. In one embodiment, the chimeric receptor comprises one or more of the NCR1 transmembrane/intracellular domain of SEQ ID NO: 20 or the NCR3 transmembrane/intracellular domain of SEQ ID NO: 22.

In several embodiments, the chimeric receptor comprises the fragment of NKG2D coupled to a GS3 linker, a CD8α hinge, a CD16 transmembrane/intracellular domain and 4-1BB. In several embodiments, the chimeric receptor is encoded by the nucleic acid sequence of SEQ ID NO: 43. In several embodiments, the chimeric receptors comprises the fragment of NKG2D coupled to a GS3 linker, a CD16 transmembrane/intracellular domain and 4-1BB. In one embodiment, the chimeric receptor is encoded by the nucleic acid sequence of SEQ ID NO: 44.

In several embodiments, the chimeric receptor comprises the fragment of NKG2D coupled to a CD16 transmembrane/intracellular domain and 4-1BB and is encoded by the nucleic acid sequence of SEQ ID NO: 45.

In several embodiments, the chimeric receptor comprises the fragment of NKG2D coupled to a CD8α hinge, a CD8α transmembrane domain, 4-1BB, and 2B4 and is encoded by the nucleic acid sequence of SEQ ID NO: 46.

In several embodiments, the chimeric receptor comprises the fragment of NKG2D coupled to a beta-adrenergic extracellular domain, a beta-adrenergic transmembrane domain, 4-1BB, and 2B4 and is encoded by the nucleic acid sequence of SEQ ID NO: 47.

In several embodiments the chimeric receptor comprises the fragment of NKG2D coupled to a CD8α hinge, a CD8α transmembrane domain, 4-1BB, 2B4, a GS3 linker, and NKp80 and is encoded by the nucleic acid sequence of SEQ ID NO: 48.

In several embodiments, the chimeric receptor comprises the fragment of NKG2D coupled to a CD8α hinge, a CD8α transmembrane domain, 4-1BB, a GS3 linker, and NKp80 and is encoded by the nucleic acid sequence of SEQ ID NO: 49.

In several embodiments, the chimeric receptor comprises the fragment of NKG2D that is codon optimized coupled to a GS3 linker, an additional NKG2D fragment, a beta-adrenergic extracellular domain, a beta-adrenergic transmembrane domain, 4-1BB, an additional GS3 linker, and NKp80 and is encoded by the nucleic acid sequence of SEQ ID NO: 50.

In several embodiments, the chimeric receptor comprises the fragment of NKG2D that is codon optimized coupled to a GS3 linker, an additional NKG2D fragment, a CD8α hinge, a CD8α transmembrane domain, 4-1BB, an additional GS3 linker, and NKp80 and is encoded by the nucleic acid sequence of SEQ ID NO: 51.

In several embodiments, the chimeric receptor comprises the fragment of NKG2D that is codon optimized coupled to a GS3 linker, an additional NKG2D fragment, a CD8α hinge, a CD16 transmembrane/intracellular domain, and 4-1BB and is encoded by the nucleic acid sequence of SEQ ID NO: 52.

In several embodiments, the chimeric receptor comprises the fragment of NKG2D coupled to a CD8α hinge, a CD16 transmembrane/intracellular domain, 4-1BB, and 2B4 and is encoded by the nucleic acid sequence of SEQ ID NO: 53.

In several embodiments, the chimeric receptor comprises the fragment of NKG2D coupled to a CD8α hinge, a CD16 transmembrane/intracellular domain, 4-1BB, a GS3 linker, and NKp80 and is encoded by the nucleic acid sequence of SEQ ID NO: 54.

In several embodiments, the chimeric receptor constructs are encoded by a polynucleotide that encodes a chimeric receptor wherein the extracellular receptor domain comprises a second peptide that binds native ligands of NKG2D, (e.g., one or more of MICA, MICB, ULBP1, ULBP2, ULBP3, ULBP4, ULBP5 or ULBP6. Depending on the embodiment, the peptide that binds native ligands of NKG2D has at least 80% homology to SEQ ID NO: 1, SEQ ID NO: 2, or SEQ ID NO. 3.

In several embodiments, the polynucleotide is co-expressed with an additional construct encoding membrane-bound interleukin 15 (mbIL15). In several embodiments, the chimeric receptor is encoded by the nucleic acid sequence of SEQ ID NO: 18. In several embodiments, the chimeric receptor is encoded by the amino acid sequence of SEQ ID NO: 19.

According to several embodiments, the chimeric receptor does not comprise DNAX-activating protein 10 (DAP10) and/or the chimeric receptor does not encode an immunoreceptor tyrosine-based activation (ITAM) motif.

In several embodiments, the polynucleotides disclosed herein are mRNA. Additionally, in several embodiments, the polynucleotide disclosed herein are operably linked to at least one regulatory element for the expression of the chimeric receptor.

Also provided for herein are vectors that comprise the polynucleotides disclosed herein. In several embodiments, the polynucleotide is operatively linked to at least one regulatory element for expression of the chimeric receptor. In several embodiments, the vector is a retrovirus.

Also provided for herein are genetically engineered natural killer cells comprising the any one or more of the polynucleotides disclosed herein. In several embodiments, the natural killer cells are for autologous use, while in some embodiments they are for allogeneic use.

Also provided for herein are methods of enhancing NK cell cytotoxicity in a mammal in need thereof, comprising administering to the mammal NK cells, wherein said NK cells express a chimeric receptor encoded by a polynucleotide disclosed herein.

Additionally, there are provided methods for treating or preventing cancer or an infectious disease in a mammal in need thereof, said method comprising administering to said mammal a therapeutically effective amount of NK cells, wherein said NK cells express a chimeric receptor encoded by a polynucleotide disclosed herein. As disclosed above, the NK cells can be allogeneic or autologous.

There is provided a use of a polynucleotide as disclosed herein in the manufacture of a medicament for enhancing NK cell cytotoxicity in a mammal in need thereof. Further there is provided a use of a polynucleotide in the manufacture of a medicament for treating or preventing cancer or an infectious disease in a mammal in need thereof.

Also provided is the use of a vector comprising a polynucleotide disclosed herein in the manufacture of a medicament for enhancing NK cell cytotoxicity in a mammal in need thereof. Also provided is the use of a vector comprising a polynucleotide disclosed herein in the manufacture of a medicament for treating or preventing cancer or an infectious disease in a mammal in need thereof.

Also provided is the use of an isolated genetically engineered natural killer cell expressing a chimeric receptor as disclosed herein for enhancing NK cell cytotoxicity in a mammal in need thereof. Also provided is the use of an isolated genetically engineered natural killer cell expressing a chimeric receptor as disclosed herein for treating or preventing cancer or an infectious disease in a mammal in need thereof.

The compositions and related methods summarized above and set forth in further detail below describe certain actions taken by a practitioner; however, it should be understood that they can also include the instruction of those actions by another party. Thus, actions such as "administering a population of NK cells expressing a chimeric receptor" include "instructing the administration of a population of NK cells expressing a chimeric receptor."

BRIEF DESCRIPTION OF THE DRAWINGS

The descriptions of the figures below are related to experiments and results that represent non-limiting embodiments of the inventions disclosed herein.

FIGS. 1A-1C depict schematic representations of the chimeric receptors according to several embodiments disclosed herein. FIG. 1A depicts endogenous NKG2D, FIG. 1B depicts NKG2D-DAP10-CD3zeta, and FIG. 1C depicts NKG2D-41BB-CD3zeta.

FIGS. 2A-2B depict schematic representations of the chimeric receptors, according to several embodiments disclosed herein. FIG. 2A depicts NKG2DCD16 and FIG. 2B depicts NKG2D-CD16-41BB.

FIG. 3A shows gene constructs for NKG2D-DAP10-CD3zeta and NKG2D-41BB-CD3zeta that were inserted into the EcoRI and NotI restriction sites, with removal the IRES-GFP sequence in the vector. FIG. 3B depicts the plasmids for NKG2D-CD16 and NKG2D-CD16-41BB that were inserted into EcoRI and XhoI restriction sites located in the multiple cloning site (MCS). IRES-GFP sequence in the vector allows for the tracing of transduction efficiency.

FIGS. 4A-4C depict data related to the expression of NKG2D-DAP10-CD3zeta and NKG2D-41BB-CD3zeta in NK cells. FIG. 4A shows flow cytometry data illustrating the percentage of NKG2D-positive NK cells after transduction. FIG. 4B shows a dot plots summarizing the percentage of NKG2D-positive NK cells. FIG. 4C shows data related to the mean fluorescence intensity (MFI) in different group of NK cells after transduction.

FIGS. 5A-5C depict data related to the cytotoxicity of the various constructs generated from NK cells from Donor 1, Donor 2, and Donor 3 (FIGS. 5A, 5B, and 5C, respectively) against cultured REH cells.

FIGS. 6A-6C depict data related to the cytotoxicity of the various constructs generated from NK cells from Donor 1, Donor 2, and Donor 3 (FIGS. 6A, 6B, and 6C, respectively) against cultured U-2 OS cells.

FIGS. 7A-7B depict data related to the production of interferon-gamma by NK cells expressing various NKG2D constructs in the presence and absence of stimulation with REH cells. FIG. 7A depicts the relative amount of IFNγ in the different groups of NK cells with or without stimulation by REH cells. FIG. 7B depicts levels of IFNγ between different groups of NK cells after stimulation (median values represented).

FIGS. 8A-8C depict data related to the expression of NKG2D-DAP10-CD3zeta and NKG2D-CD16 in NK cells. FIG. 8A shows flow cytometry data illustrating the percentage of NKG2D-positive NK cells after transduction. FIG. 8B shows a dot plots summarizing the percentage of NKG2D-positive NK cells. FIG. 8C shows data related to the mean fluorescence intensity (MFI) in different group of NK cells after transduction.

FIGS. 9A-9C depict data related to the cytotoxicity of the various constructs generated from NK cells from 3 donors (FIGS. 9A, 9B, and 9C, respectively) against cultured REH cells.

FIGS. 10A-10C depict data related to the cytotoxicity of the various constructs generated from NK cells from 3 donors (FIGS. 10A, 10B, and 10C, respectively) against cultured U-2 OS cells.

FIG. 12A shows flow cytometry data illustrating the percentage of NKG2D-positive NK cells after transduction. FIG. 12B shows a histogram related to relative amount of surface expression of the various constructs on NK cells.

FIGS. 13A-13B depict data related to the degree of cytotoxicity of various NKG2d constructs. FIG. 13A depicts the degree of cytotoxicity against cultured REH cells.

FIG. 13B depicts the degree of cytotoxicity against cultured U2OS cells.

FIG. 14 schematically depicts construct maps of several NKG2D constructs according to some embodiments disclosed herein.

FIG. 15 schematically depicts construct maps of additional NKG2D constructs according to some embodiments disclosed herein.

FIG. 16A shows data related to the mean fluorescence intensity (MFI) of the various NKG2D constructs in NK cells. FIG. 16B shows flow cytometry data illustrating the percentage of NKG2D-positive and CD56-positive NK cells after transduction of various NKG2D constructs into the NK cells of two donors (505 and 870). FIG. 16C shows data related to the mean fluorescence intensity (MFI) in NK cells from 2 donors seven days after transduction.

FIG. 18A shows data related to the mean fluorescence intensity (MFI) in NK cells seven days after transduction. FIG. 18B shows data related to the fold-change in MFI of the various NKG2D constructs relative to the mock-transduced NK cells.

FIG. 19A shows data related to the cytotoxicity of the various NKG2D constructs transduced into NK cells at a 1:1 E:T ratio. FIG. 19B shows data related to the percent change in cytotoxicity of the various NKG2D constructs relative to the mock-transduced NK cells.

FIG. 22 schematically depicts construct maps of additional NKG2D constructs according to embodiments disclosed herein.

FIG. 26A depicts the accumulated levels of IFNγ, FIG. 26B depicts the levels of TNFα, and FIG. 26C depicts the levels of GM-CSF in the different groups of NK cells following stimulation. Prior to analysis NK cells were cultured in media supplemented with 40 IU of IL-2/mL.

DETAILED DESCRIPTION

General

Figures 3A, 3B:
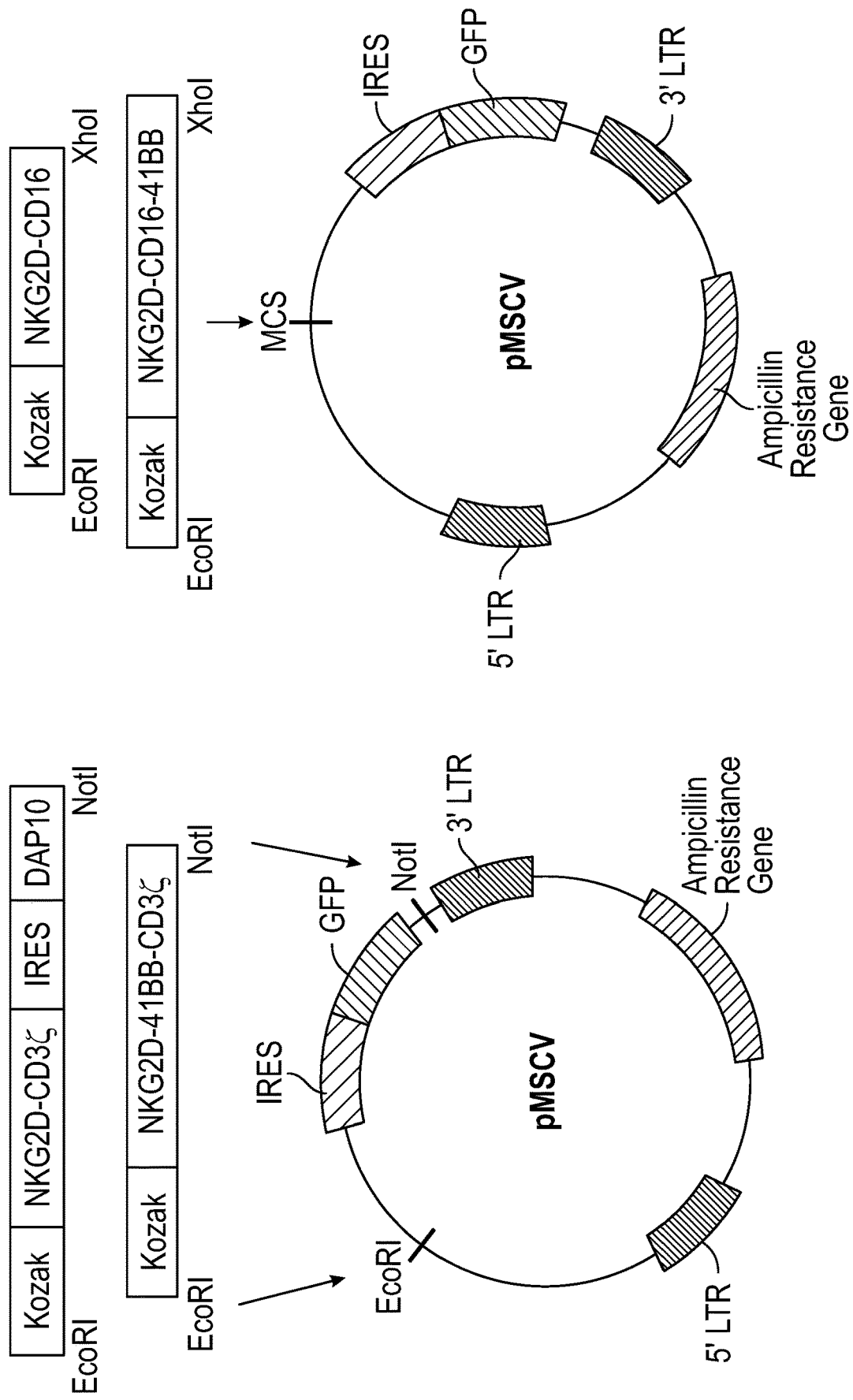
FIGS. 3A-3B depict plasmid maps illustrating the point of insertion of certain constructs according to several embodiments into the plasmids, illustrated is a Murine Stem Cell Virus (MSCV) plasmid.

The emergence and persistence of aberrant cells (including virally infected and malignant cells) underlying many diseases is enabled by an insufficient immune response to said aberrant cells. A goal of immunotherapy is to initiate or augment the response of the patient's immune system, for example, to boost the ability of immune cells, such as Natural Killer (NK) cells to damage, kill, or otherwise inhibit damaged or diseased cells. One immunotherapy approach is the recombinant expression of chimeric receptors in immune cells for targeted recognition and destruction of the aberrant cells. In general, chimeric receptors comprise an extracellular receptor domain that recognizes ligands on target cells, an anchoring transmembrane domain, and an effector domain that transduces activating signals upon ligand binding. Some embodiments disclosed herein utilize chimeric receptors having that general structure, or having variations in that general structure. Additionally, in several embodiments, the transmembrane domain and the effector domain are separate peptides fused together. In several other embodiments, the transmembrane and the effector domain are derived from the same peptide. In some such embodiments, the transmembrane and effector domains comprise a single peptide (e.g., one peptide that passes through the membrane and is also poised to initiate a signaling cascade). As discussed in more detail below, truncations, mutations, additional linkers/spacer elements, dimers, and the like are used to generate chimeric receptor constructs that exhibit a desired degree of expression in an immune cell (e.g., an NK cell), induce cytotoxic activity from the NK cell, balanced with a degree of target avidity that avoids adverse effects on non-target cells. The recombinant expression of chimeric receptors as disclosed herein on the surface of immune cells can redirect the targeting of immune cells to aberrant cells of interest as well as augment the immune activation upon engagement.

NK Cells for Immunotherapy

One immunotherapy approach involves administering to patients T cells engineered to express chimeric receptors to elicit a positive immune response. However, a drawback of this approach is that it necessitates the use of autologous cells to prevent the induction of graft-versus-host-disease in the patient. As is provided in several embodiments disclosed herein, compositions comprising engineered NK cells enjoy several advantages. For example, either autologous or donor-derived allogeneic cells can be employed with an NK cell approach. Additionally, according to several embodiments, the engineered NK cells as provided for herein do not significantly increase cytotoxicity against normal cells. Further, NK cells have a significant cytotoxic effect, once activated. In view of this, it is unexpected that the engineered NK cells as provided for herein, are able to further elevate that cytotoxic effect, thus providing an even more effective means of selectively killing diseased target cells. Accordingly, in several embodiments, there is provided a method of treating or preventing cancer or an infectious disease, comprising administering a therapeutically effective amount of NK cells expressing the chimeric receptors described herein. In one embodiment, the NK cells administered are autologous cells. In a further embodiment, the NK cells administered are donor-derived (allogeneic) cells.

In several embodiments, engagement and activation of a recombinant NK cell (e.g., by binding to a ligand on a target cell) expressing a chimeric receptor leads to the direct killing of the stressed and/or aberrant cell (e.g., tumor cells, virally-infected cells, etc.) by cytolysis. Accordingly, in several embodiments, there is provided a method of enhancing NK cell cytotoxicity, comprising administering NK cells engineered to express the chimeric receptors described herein. In one embodiment, the NK cells administered are autologous cells. In a further embodiment, the NK cells are donor-derived (allogenic) cells. In several embodiments, engineered NK cells lead to indirect destruction or inhibition of stressed and/or aberrant cell (e.g., tumor cells, virally-infected cells, etc.).

Ligand Binding Domains

As mentioned above, in several embodiments NK cells recognize and destroy aberrant cells, including tumor cells and virally-infected cells. The cytotoxic activity of these innate immune cells is regulated by the balance of signaling from inhibitory and activating receptors, respectively, that reside on the cell surface. The former bind self-molecules expressed on the surface of healthy cells while the latter bind ligands expressed on aberrant cells. The increased engagement of activating receptors relative to inhibitory receptors leads to NK cell activation and target cell lysis. Natural killer Group 2 member D (NKG2D) is an important NK cell activating receptor that recognizes a number of ligands expressed on stressed and aberrant cells. The surface expression of various NKG2D ligands is generally low in healthy cells but is upregulated upon malignant transformation or viral infection. Non-limiting examples of ligands recognized by NKG2D include, but are not limited to, MICA, MICB, ULBP1, ULBP2, ULBP3, ULBP4, ULBP5, and ULBP6, as well as other molecules expressed on target cells that control the cytolytic or cytotoxic function of NK cells.

NKG2D's ability to recognize a plurality of surface markers of cell stress and infection make it a potentially useful component of a chimeric receptor-based immunotherapy approach. However, complicating the use of NKG2D as a chimeric receptor is its relationship with partner DAP10. NKG2D is a type II transmembrane glycoprotein that forms homodimers and assembles with two homodimers of DNAX-activating protein 10 (DAP10) to yield hexameric complexes on the membrane surface. This NKG2D-DAP10 association is necessary for both surface membrane expression of endogenous NKG2D as well as for transduction of the activation signal upon ligand binding. In several embodiments, a full length NKG2D is used. In one embodiment, full length NKG2D has the nucleic acid sequence of SEQ ID NO. 1. According to several embodiments disclosed herein, polynucleotides encoding chimeric receptors are provided wherein the extracellular receptor domain is a fragment of NKG2D that lacks its native transmembrane or intracellular domains yet advantageously retains its ability to bind native ligands of NKG2D, as well as transduce activation signals upon ligand binding. Thus, in several embodiments, the chimeric receptor encoded by the polypeptides disclosed herein does not comprise DAP10. In several embodiments, the NKG2D fragment is encoded by SEQ ID NO. 2. In several embodiments, the fragment of NKG2D is at least 70%, at least 75%, at least 80%, at least 85%, at least 90%, or at least 95% homologous with full-length wild-type NKG2D. In several embodiments, the fragment may have one or more additional mutations from SEQ ID NO. 2, but retains, or in some embodiments, has enhanced, ligand-binding function. In several embodiments, the NKG2D fragment is provided as a dimer, trimer, or other concatameric format, such embodiments providing enhanced ligand-binding activity. In several embodiments, the sequence encoding the NKG2D fragment is optionally fully or partially codon optimized. In one embodiment, a sequence encoding a codon optimized NKG2D fragment comprises the sequence of SEQ ID NO. 3. Additionally, in several embodiments signal peptides are used. The species or sequence of the signal peptide can vary with the construct. However, in several embodiments, a signal peptide derived from CD8 is used. In one embodiment, the signal peptide is from CD8α and has the sequence of SEQ ID NO. 4. In one embodiment, a sequence encoding a codon optimized NKG2D fragment comprises the sequence of SEQ ID NO. 68. In several embodiments, the fragment may have one or more additional mutations from SEQ ID NO. 68, but retains ligand-binding function. In several embodiments, the fragment may have one or more additional mutations from SEQ ID NO. 68, but has improved ligand-binding function.

Transmembrane, Signaling and Combination Domains

As mentioned above, the general chimeric antigen receptor structure comprises at least one transmembrane domain, linking the ligand binding domain to a signaling domain(s). In several embodiments, however, a transmembrane domain can also serve to provide signaling function.

In several embodiments, the NKG2D fragment retains at least a portion of its normal transmembrane domain. In several embodiments, the transmembrane domain comprises at least a portion of CD8, which is a transmembrane glycoprotein normally expressed on both T cells and NK cells. In several embodiments, the transmembrane domain comprises CD8α, while in some embodiments CD80 is used. In several embodiments, the "hinge" of CD8α has the sequence of SEQ ID NO. 5. In several embodiments, the CD8α can be truncated or modified, such that it is at least 70%, at least 75%, at least 80%, at least 85%, at least 90%, at least 95% homologous with the CD8α having the sequence of SEQ ID NO. 5. In several embodiments, CD80 has the sequence of SEQ ID NO. 6. In several embodiments, the CD80 can be truncated or modified, such that it is at least 70%, at least 75%, at least 80%, at least 85%, at least 90%, at least 95% homologous with the CD80 having the sequence of SEQ ID NO. 6. In several embodiments, dimers of CD8α and CD80 are used.

In several embodiments, the transmembrane domain comprises CD16, which serves as a signaling domain as well. CD16 exists in two isoforms, a and b (also known as Fc gamma receptor IIIa and IIIb, respectively). These receptors normally bind to the Fc portion of IgG antibodies that in turn activates NK cells. Accordingly, in several embodiments, the transmembrane domain comprises CD16a, while in some embodiments CD16b is used. In several embodiments, CD16a has the sequence of SEQ ID NO. 7. In several embodiments, the CD16a can be truncated or modified, such that it is at least 70%, at least 75%, at least 80%, at least 85%, at least 90%, at least 95% homologous with the CD16a having the sequence of SEQ ID NO. 7. In several embodiments, CD16b has the sequence of SEQ ID NO. 8. In several embodiments, the CD16b can be truncated or modified, such that it is at least 70%, at least 75%, at least 80%, at least 85%, at least 90%, at least 95% homologous with the CD16b having the sequence of SEQ ID NO. 8. In several embodiments, dimers of CD16a and CD16b are used. In several embodiments the modifications to the CD16 transmembrane domain comprise additional nucleic acid residues to increase the length of the domain. Alternatively, CD16 may be shortened. The modifications to the length of CD16 advantageously can facilitate enhanced ligand-receptor interactions.

In several embodiments, the chimeric receptor comprises the Natural Killer Receptor 2B4 domain (referred to herein as "2B4", and also known as CD244), which serves as a signaling domain as well. 2B4 is expressed on NK cells and regulates non-major histocompatibility complex (MHC) restricted killing through interactions between this receptor and its ligands on target cells. In several embodiments, the transmembrane domain comprises 2B4, while in several embodiments the 2B4 domain is an intracellular signaling domain. In several embodiments, 2B4 has the sequence of SEQ ID NO. 9. In several embodiments, the 2B4 can be truncated or modified, such that it is at least 70%, at least 75%, at least 80%, at least 85%, at least 90%, at least 95% homologous with the 2B4 having the sequence of SEQ ID NO. 9. In several embodiments, 2B4 is used as the sole transmembrane/signaling domain in the construct, however, in several embodiments, 2B4 can be used with one or more other domains. For example, combinations of CD16, 4-1BB, and/or 2B4 are used in some embodiments.

In some embodiments, signaling is achieved through DAP10, as mentioned above. In several embodiments, the fragment of NKG2D associates with DAP10 to provide pro-cytotoxic signals to the NK cell. In several embodiments, dimers of DAP10 are used. In several embodiments, the transmembrane domain comprises DAP10. In several embodiments, DAP10 has the sequence of SEQ ID NO. 10. In several embodiments, DAP10 can be truncated or modified, such that it is at least 70%, at least 75%, at least 80%, at least 85%, at least 90%, at least 95% homologous with the DAP10 having the sequence of SEQ ID NO. 10. Similarly, in some embodiments, DAP12 can be used, as it can also transduce such signals. In several embodiments, DAP12 has the sequence of SEQ ID NO. 11. In several embodiments, DAP12 can be truncated or modified, such that it is at least 70%, at least 75%, at least 80%, at least 85%, at least 90%, at least 95% homologous with the DAP12 having the sequence of SEQ ID NO. 11. In several embodiments, heterodimers of DAP10 and DAP12 are used.

In several embodiments, signaling is provided through 4-1BB (also known as CD137 and tumor necrosis factor receptor superfamily member 9 (TNFRSF 9)). 4-1BB is a co-stimulatory immune checkpoint molecule, typically functioning as a stimulatory molecule for activated T cells (e.g., crosslinking of 4-1BB enhances T cell proliferation and cytolytic activity). However, in several embodiments, the function of 4-1BB is advantageously used in conjunction with NK cells. In several embodiments, 4-1BB has the sequence of SEQ ID NO. 12. In several embodiments, 4-1BB can be truncated or modified, such that it is at least 70%, at least 75%, at least 80%, at least 85%, at least 90%, at least 95% homologous with the 4-1BB having the sequence of SEQ ID NO. 12. In several embodiments, 4-1BB is the sole signaling domain, but as discussed above, in several embodiments, 4-1BB functions unexpectedly well in combination with one or more of the other transmembrane/signaling domains disclosed herein. For example, in several embodiments, CD16 in conjunction with 4-1BB provides synergistic stimulation effects, resulting in particularly effective (e.g., cytotoxic) NK cells. In several embodiments, DAP10 in conjunction with 4-1BB provides synergistic stimulation effects, resulting in particularly effective (e.g., cytotoxic) NK cells. In several embodiments, DAP10 in conjunction with 4-1BB and/or 2B4 provides synergistic stimulation effects, resulting in particularly effective (e.g., cytotoxic) NK cells. Other improved characteristics result, in several embodiments, such as improved expression, improved persistence, and the like.

In several embodiments, the signaling domain comprises at least a portion of the CD3 T cell receptor complex. The T cell receptor complex comprises multiple subunits, including the zeta, alpha, beta, gamma, delta, and epsilon subunits. In several embodiments, the NK cells engineered according to several embodiments disclosed herein comprise at least one of these subunits (or a fragment thereof). In several embodiments, the signaling domain comprises the CD3 zeta subunit. In several embodiments, CD3 zeta has the sequence of SEQ ID NO. 13. In several embodiments, CD3 zeta can be truncated or modified, such that it is at least 70%, at least 75%, at least 80%, at least 85%, at least 90%, at least 95% homologous with the CD3 zeta having the sequence of SEQ ID NO. 13. In several embodiments, the CD3 zeta is mutated (e.g., amino acid mutations, insertions, or deletions) such that the domain no longer is consistent with the canonical immunoreceptor tyrosine-based activation motif or ITAM motif. Thus, in several embodiments, the NK cells comprise an engineered receptor that does not contain an ITAM motif. In some embodiments, the resultant engineered NK cells exhibit particularly enhanced cytotoxicity against target cells, with limited or reduced adverse side effects. This, in several embodiments, results from the synergistic interactions of the various portions of the chimeric receptor that are used in that given embodiment. In several embodiments, CD3zeta in conjunction with 4-1BB provides synergistic stimulation effects, resulting in particularly effective (e.g., cytotoxic) NK cells. In several embodiments, CD3zeta in conjunction with 2B4 provides synergistic stimulation effects, resulting in particularly effective (e.g., cytotoxic) NK cells. In several embodiments, CD3zeta in combination with 2B4 and 4-1BB provides synergistic stimulation effects, resulting in particularly effective (e.g., cytotoxic) NK cells. In several embodiments, the chimeric receptors leverage the dimerization of CD3zeta via its transmembrane domain. Thus, in several embodiments, the transmembrane domain comprises the CD3zeta transmembrane domain (or a fragment thereof). In some embodiments, 1, 2, 3, 4, 5, 6 or more extracellular CD3zeta residues (the "juxta-membrane portion") are directly adjacent to the CD3zeta transmembrane domain. In some embodiments, CD3zeta transmembrane domain has the sequence of SEQ ID NO. 69. In several embodiments, the CD3zeta transmembrane domain can be truncated or modified, such that it is at least 70%, at least 75%, at least 80%, at least 85%, at least 90%, at least 95% homologous with the CD3zeta transmembrane domain having the sequence of SEQ ID NO. 69. In several embodiments the modifications to the CD3zeta transmembrane domain comprise additional nucleic acid residues to increase the length of the domain. In several embodiments, the CD3zeta transmembrane domain and CD3zeta juxta-membrane portion recruits full-length CD3zeta molecule to the synapse. In several embodiments, the recruitment of native CD3zeta to the engineered receptor (as compared to a receptor without a CD3zeta transmembrane domain) is increased by about 20%, by about 30%, by about 40% by about 50%, or more, depending on the embodiment. In several embodiments, the CD3zeta transmembrane domain is coupled to an effector domain comprising one or more of CD16, NCR1, NCR2, NCR3, 4-1BB, NKp80, FcRγ, CD3zeta and 2B4.

In several embodiments, the chimeric receptor comprises a CD28 domain. In several embodiments, the transmembrane domain comprises CD28, while in several embodiments the CD28 domain is an intracellular signaling domain, while in several embodiments the CD28 domain is a transmembrane/intracellular signaling domain. In several embodiments, the CD28 transmembrane domain has the sequence of SEQ ID NO. 105. In several embodiments, the CD28 transmembrane domain can be truncated or modified, such that it is at least 70%, at least 75%, at least 80%, at least 85%, at least 90%, at least 95% homologous with the CD28 having the sequence of SEQ ID NO. 105. In several embodiments, the CD28 intracellular signaling domain has the sequence of SEQ ID NO. 106. In several embodiments, the CD28 intracellular signaling domain can be truncated or modified, such that it is at least 70%, at least 75%, at least 80%, at least 85%, at least 90%, at least 95% homologous with the CD28 having the sequence of SEQ ID NO. 106. In several embodiments, CD28 is used as the sole transmembrane/signaling domain in the construct, however, in several embodiments, CD28 can be used with one or more other domains. For example, combinations of CD28, OX40, 4-1BB, and/or CD3zeta are used in some embodiments.

In several embodiments, the chimeric receptor comprises an OX40 domain. In several embodiments the OX40 domain is an intracellular signaling domain. In several embodiments, the OX40 intracellular signaling domain has the sequence of SEQ ID NO. 107. In several embodiments, the OX40 intracellular signaling domain can be truncated or modified, such that it is at least 70%, at least 75%, at least 80%, at least 85%, at least 90%, at least 95% homologous with the OX40 having the sequence of SEQ ID NO. 107. In several embodiments, OX40 is used as the sole transmembrane/signaling domain in the construct, however, in several embodiments, OX40 can be used with one or more other domains. For example, combinations of CD28, OX40, 4-1BB, and/or CD3zeta are used in some embodiments.

In still further embodiments, the signaling portion of the chimeric receptor comprises a portion of an ITAM, for example a hemi-tam. In several embodiments, these portions do not make up the canonical ITAM sequence, but rather comprise a portion that still can convey the signal required for NK cell cytotoxicity. In several embodiments, the hemi-tam has the sequence of SEQ ID NO. 14 (wherein X can be any residue). In several embodiments, the hemi-tam can be truncated or modified, such that it is at least 70%, at least 75%, at least 80%, at least 85%, at least 90%, at least 95% homologous with the hemi-tam having the sequence of SEQ ID NO. 14. In several embodiments, the chimeric receptor construct comprises the hemi-tam of SEQ ID NO. 14. In several embodiments, multiple hemi-tams can be used, for example in a head to tail, tail to head, head to head, or tail to tail configuration. In several embodiments, the presence of at least on hemi-tam confers enhanced signaling and cytotoxicity to the NK cells comprising a chimeric receptor employing the at least one hemi-tam. As discussed in more detail below, in several chimeric receptor comprises NKp80, which is one nonlimiting example of a hemi-tam.

In several embodiments, additional signaling regions are used, including, for example, signaling regions derived from receptors of the signaling lymphocytic activation molecule (SLAM) family. These receptors include, but are not limited to 2B4 (discussed above). Receptors of the SLAM family share a consensus motif that is tyrosine-based, in their cytoplasmic tails. That motif is S/TxYxxL/I, which are referred to as immunoreceptor tyrosine-based switch motifs (ITSM) (SEQ ID NO. 15). These receptors transmit activation signals through the SLAM-associated protein (SAP, encoded by the gene SH2D1A), which recruits the tyrosine kinase Fyn. Thus, according to several embodiments, the signaling region comprise a polypeptide sequence (or the nucleic acid encoding the same) comprising an ITSM motif. In several embodiments, the ITSM motif need not be fully encoded, but the signaling region is able to transmit an activation signal through SAP (or another similar pathway). In several embodiments, the ITSM motif has the sequence of SEQ ID NO. 15 (wherein X can be any amino acid residue). In several embodiments, the ITSM motif can be truncated or modified, such that it is at least 70%, at least 75%, at least 80%, at least 85%, at least 90%, at least 95% homologous with the ITSM motif having the sequence of SEQ ID NO. 15. In several embodiments, the ITSM motif comprises the sequence of SEQ ID NO. 15.

In addition to these variations in the NKG2D receptor, the transmembrane domain and signaling domain (and the combination transmembrane/signaling domains), additional co-activating molecules can be provided, in several embodiments. For example, in several embodiments, the NK cells are engineered to express membrane-bound interleukin 15 (mbIL15). In such embodiments, the presence of the mbIL15 on the NK cell function to further enhance the cytotoxic effects of the NK cell by synergistically enhancing the proliferation and longevity of the NK cells. In several embodiments, mbIL15 has the nucleic acid sequence of SEQ ID NO. 16. In several embodiments, mbIL15 can be truncated or modified, such that it is at least 70%, at least 75%, at least 80%, at least 85%, at least 90%, at least 95% homologous with the sequence of SEQ ID NO. 16. In several embodiments, the mbIL15 has the amino acid sequence of SEQ ID NO. 17. In conjunction with the chimeric receptors disclosed herein, such embodiments provide particularly effective NK cell compositions for targeting and destroying particular target cells.

Chimeric Receptor Constructs

In view of the disclosure provided herein, there are a variety of chimeric receptors that can be generated and expressed in NK cells in order to target and destroy particular target cells, such as diseased or cancerous cells. Non-limiting examples of such chimeric receptors are discussed in more detail below.

As discussed above, portions of the T cell receptor complex, in particular CD3zeta, serve as potent activators of immune signaling cascades. Likewise, the receptor 4-1BB, a tumor necrosis factor superfamily member, activates NK cells upon ligand binding. In several embodiments, these two signaling components act in a synergistic manner to activate NK cells upon binding of a ligand to the chimeric receptor. Thus, in several embodiments, there are provided polynucleotides encoding a NKG2D/CD8α/4-1BB/CD3zeta chimeric receptor, which comprises an NKG2D fragment extracellular receptor domain that binds native ligands of NKG2D, a CD8 transmembrane region, and an effector domain comprising the signaling domains of 4-1BB and CD3zeta. In one embodiment, this chimeric receptor is encoded by the nucleic acid sequence of SEQ ID NO: 18. In one embodiment, this chimeric receptor is encoded by the nucleic acid sequence of SEQ ID NO: 108. In yet another embodiment, the NKG2D/CD8α/4-1BB/CD3zeta chimeric receptor comprises the amino acid sequence of SEQ ID NO:

19. In several embodiments, this construct is particularly efficacious when the NK cells concurrently express mbIL15, the mbIL15 provides a further synergistic effect with respect to the activation and cytotoxic nature of the NK cells. In some embodiments, the sequence of the chimeric receptor may vary from SEQ ID NO. 18 (such as, for example, SEQ ID NO: 108), but remains, depending on the embodiment, at least 70%, at least 75%, at least 80%, at least 85%, at least 90%, or at least 95% homologous with SEQ ID NO. 18. In several embodiments, while the chimeric receptor may vary from SEQ ID NO. 18 (such as, for example, SEQ ID NO: 108), the chimeric receptor retains, or in some embodiments, has enhanced, NK cell activating and/or cytotoxic function.

The receptor 2B4 possesses several immunoreceptor tyrosine-based switch motifs (ITSMs) and has the potential to transduce activating signals. Likewise, signaling through the receptor 4-1BB, a tumor necrosis factor superfamily member, also activates NK cells upon ligand binding. Thus, capitalizing on the ability of these signaling molecules to cooperate to generate unexpectedly effectively cytotoxic NK cells, in several embodiments, there are provided polynucleotides encoding a NKG2D/CD8α/2B4/4-1BB chimeric receptor, which comprises an NKG2D fragment extracellular receptor domain that binds native ligands of NKG2D, a CD8α transmembrane region, and an effector domain comprising the signaling domains of 4-1BB and 2B4. Additionally, in several embodiments, this construct can optionally be co-expressed with mbIL15.

In several embodiments, combinations of 2B4 with CD3zeta are used with NK cells to generate enhanced cytotoxicity against target cells. Thus, in several embodiments, there are provided polynucleotides encoding a NKG2D/CD8α/2B4/CD3zeta chimeric receptor, which comprises an NKG2D fragment extracellular receptor domain that binds native ligands of NKG2D, a CD8α transmembrane region, and an effector domain comprising the signaling domains of CD3zeta and 2B4. Additionally, in several embodiments, this construct can optionally be co-expressed with mbIL15. As discussed above, 4-1BB, like CD3zeta and 2B4, can function as a potent activator of immune signaling cascades. In several embodiments, these three signaling components act in a synergistic manner to activate NK cells upon binding of a ligand to the chimeric receptor. Thus, in several embodiments, there are provided polynucleotides encoding a NKG2D/CD8α/4-1BB/2B4/CD3zeta chimeric receptor, which comprises an NKG2D fragment extracellular receptor domain that binds native ligands of NKG2D, a CD8 transmembrane region, and an effector domain comprising the signaling domains of 4-1BB, 2B4 and CD3zeta. In one embodiment, this chimeric receptor is encoded by the nucleic acid sequence of SEQ ID NO: 58. In yet another embodiment, the NKG2D/CD8α/4-1BB/CD3zeta chimeric receptor comprises the amino acid sequence of SEQ ID NO: 59. In several embodiments, this construct is particularly efficacious when the NK cells concurrently express mbIL15, the mbIL15 provides a further synergistic effect with respect to the activation and/or cytotoxic nature of the NK cells. In some embodiments, the sequence of the chimeric receptor may vary from SEQ ID NO. 58, but remains, depending on the embodiment, at least 70%, at least 75%, at least 80%, at least 85%, at least 90%, or at least 95% homologous with SEQ ID NO. 58. In several embodiments, while the chimeric receptor may vary from SEQ ID NO. 58, the chimeric receptor retains, or in some embodiments, has enhanced, NK cell activating and/or cytotoxic function.

In several alternative embodiments, there are provided polynucleotides encoding a NKG2D/CD8α/DAP10/4-1BB chimeric receptor, which comprises an NKG2D fragment extracellular receptor domain that binds native ligands of NKG2D, a CD8α transmembrane region, and an effector domain comprising the signaling domains of 4-1BB and DAP10. In one embodiment, this chimeric receptor is encoded by the nucleic acid sequence of SEQ ID NO: 60. In yet another embodiment, the NKG2D/CD8α/4-1BB/DAP10 chimeric receptor comprises the amino acid sequence of SEQ ID NO: 61. Additionally, in several embodiments, this construct can optionally be co-expressed with mbIL15. In several embodiments, this construct is particularly efficacious when the NK cells concurrently express mbIL15, the mbIL15 provides a further synergistic effect with respect to the activation and cytotoxic nature of the NK cells. In some embodiments, the sequence of the chimeric receptor may vary from SEQ ID NO. 60, but remains, depending on the embodiment, at least 70%, at least 75%, at least 80%, at least 85%, at least 90%, or at least 95% homologous with SEQ ID NO. 60. In several embodiments, while the chimeric receptor may vary from SEQ ID NO. 60, the chimeric receptor retains, or in some embodiments, has enhanced, NK cell activating and/or cytotoxic function. Further, as discussed above, 2B4, like DAP10 and 4-1BB, is a potent activator of immune signaling cascades. In several embodiments, these three signaling components act in a synergistic manner to activate NK cells upon binding of a ligand to the chimeric receptor. Thus, in several embodiments, there are provided polynucleotides encoding a NKG2D/CD8α/4-1BB/DAP10/2B4 chimeric receptor, which comprises an NKG2D fragment extracellular receptor domain that binds native ligands of NKG2D, a CD8 transmembrane region, and an effector domain comprising the signaling domains of 4-1BB, 2B4 and DAP10, wherein 4-1BB is followed by DAP10, and DAP10 is followed by 2B4. In one embodiment, this chimeric receptor is encoded by the nucleic acid sequence of SEQ ID NO: 62. In yet another embodiment, the NKG2D/CD8α/4-1BB/CD3zeta chimeric receptor comprises the amino acid sequence of SEQ ID NO: 63. In several embodiments, this construct is particularly efficacious when the NK cells concurrently express mbIL15, the mbIL15 provides a further synergistic effect with respect to the activation and cytotoxic nature of the NK cells. In some embodiments, the sequence of the chimeric receptor may vary from SEQ ID NO. 62, but remains, depending on the embodiment, at least 70%, at least 75%, at least 80%, at least 85%, at least 90%, or at least 95% homologous with SEQ ID NO. 62. In several embodiments, while the chimeric receptor may vary from SEQ ID NO. 62, the chimeric receptor retains, or in some embodiments, has enhanced, NK cell activating and/or cytotoxic function. In several other embodiments, there are provided polynucleotides encoding a NKG2D/CD8α/4-1BB/2B4/DAP10 chimeric receptor, which comprises an NKG2D fragment extracellular receptor domain that binds native ligands of NKG2D, a CD8 transmembrane region, and an effector domain comprising the signaling domains of 4-1BB, 2B4 and DAP10, wherein 4-1BB is followed by 2B4, and 2B4 is followed by DAP10. In one embodiment, this chimeric receptor is encoded by the nucleic acid sequence of SEQ ID NO: 64. In yet another embodiment, the NKG2D/CD8α/4-1BB/CD3zeta chimeric receptor comprises the amino acid sequence of SEQ ID NO: 65. In several embodiments, this construct is particularly efficacious when the NK cells concurrently express mbIL15, the mbIL15 provides a further synergistic effect with respect to the activation and cytotoxic nature of the NK cells. In some embodiments, the sequence of the chimeric receptor may vary from SEQ ID NO. 64, but remains, depending on the embodiment, at least 70%, at least 75%, at least 80%, at least 85%, at least 90%, or at least 95% homologous with SEQ ID NO. 64. In several embodiments, while the chimeric receptor may vary from SEQ ID NO. 64, the chimeric receptor retains, or in some embodiments, has enhanced, NK cell activating and/or cytotoxic function.

In several additional embodiments, transmembrane and effector domains (and associated function) of the chimeric receptor are derived from the same peptide. CD16 is a potent activating receptor expressed on the surface of NK cells. Thus, in several embodiments, polynucleotides are provided encoding a NKG2D/CD16 chimeric receptor, which comprises an NKG2D fragment extracellular receptor domain that binds native ligands of NKG2D and a CD16 peptide comprising both the transmembrane region and intracellular effector domain. In one embodiment, this chimeric receptor comprises the nucleic acid sequence of SEQ ID NO: 23. In yet another embodiment, this chimeric receptor is encoded by the amino acid sequence of SEQ ID NO: 24. In some embodiments, the sequence of the chimeric receptor may vary from SEQ ID NO. 23, but remains, depending on the embodiment, at least 70%, at least 75%, at least 80%, at least 85%, at least 90%, or at least 95% homologous with SEQ ID NO. 23. In several embodiments, while the chimeric receptor may vary from SEQ ID NO. 23, the chimeric receptor retains, or in some embodiments, has enhanced, NK cell activating and/or cytotoxic function. Additionally, in several embodiments, this construct can optionally be co-expressed with mbIL15.

In several additional embodiments, polynucleotides are provided encoding a NKG2D/CD16/4-1BB chimeric receptor, wherein the signaling domain of 4-1BB acts as a second transducer of activating signals in the effector domain. Additionally, in several embodiments, this construct can optionally be co-expressed with mbIL15.

CD3zeta dimerizes via its transmembrane domain. Thus, in several embodiments, chimeric receptors are provided wherein a CD3zeta transmembrane domain recruits full-length CD3zeta molecule to the synapse. In several embodiments, there are provided polynucleotides encoding a chimeric receptor which comprises a NKG2D fragment that binds native ligands of NKG2D, a CD8α hinge, 0, 1, 2, 3, 4, 5, 6 or more extracellular CD3zeta residues (the "juxtamembrane portion") directly adjacent to a CD3zeta transmembrane domain, and an effector domain comprising one or more of CD16, NCR1, NCR2, NCR3, 4-1BB, NKp80, FcRγ, CD3zeta and 2B4.

In several embodiments, chimeric receptors are provided wherein a CD3zeta transmembrane domain is coupled to an effector domain comprising one or both of 4-1BB and CD16. Thus, in several embodiments, polynucleotides are provided encoding a NKG2D/CD3zetaTM/4-1BB chimeric receptor, which comprises a fragment of NKG2D that is codon optimized coupled to a CD8α hinge, a CD3zeta transmembrane region, and an effector domain comprising 4-1BB. In one embodiment, this chimeric receptor comprises the nucleic acid sequence of SEQ ID NO: 78. In yet another embodiment, this chimeric receptor is encoded by the amino acid sequence of SEQ ID NO: 79. In some embodiments, the sequence of the chimeric receptor may vary from SEQ ID NO. 78, but remains, depending on the embodiment, at least 70%, at least 75%, at least 80%, at least 85%, at least 90%, or at least 95% homologous with SEQ ID NO. 78. In several embodiments, while the chimeric receptor may vary from SEQ ID NO. 78, the chimeric receptor retains, or in some embodiments, has enhanced, NK cell activating and/or cytotoxic function. Additionally, in several embodiments, this construct can optionally be co-expressed with mbIL15.

In several embodiments, polynucleotides are provided encoding a NKG2D/CD3zetaTM/CD16/4-1BB chimeric receptor, which comprises a fragment of NKG2D that is codon optimized coupled to a CD8α hinge, a CD3zeta transmembrane region, and an effector domain comprising CD16 followed by 4-1BB. In one embodiment, this chimeric receptor comprises the nucleic acid sequence of SEQ ID NO: 70. In yet another embodiment, this chimeric receptor is encoded by the amino acid sequence of SEQ ID NO: 71. In some embodiments, the sequence of the chimeric receptor may vary from SEQ ID NO. 70, but remains, depending on the embodiment, at least 70%, at least 75%, at least 80%, at least 85%, at least 90%, or at least 95% homologous with SEQ ID NO. 70. In several embodiments, while the chimeric receptor may vary from SEQ ID NO. 70, the chimeric receptor retains, or in some embodiments, has enhanced, NK cell activating and/or cytotoxic function. Additionally, in several embodiments, this construct can optionally be co-expressed with mbIL15. Further, in several embodiments, polynucleotides are provided encoding a NKG2D/CD3zetaTM/4-1BB/CD16 chimeric receptor, which comprises a fragment of NKG2D that is codon optimized coupled to a CD8α hinge, a CD3zeta transmembrane region, and an effector domain comprising 4-1BB followed by CD16. In some embodiments, the effector domain further comprises a GS3 linker. In some embodiments, the GS3 linker is positioned between 4-1BB and CD16. In one embodiment, this chimeric receptor comprises the nucleic acid sequence of SEQ ID NO: 84. In yet another embodiment, this chimeric receptor is encoded by the amino acid sequence of SEQ ID NO: 85. In some embodiments, the sequence of the chimeric receptor may vary from SEQ ID NO. 84, but remains, depending on the embodiment, at least 70%, at least 75%, at least 80%, at least 85%, at least 90%, or at least 95% homologous with SEQ ID NO. 84. In several embodiments, while the chimeric receptor may vary from SEQ ID NO. 84, the chimeric receptor retains, or in some embodiments, has enhanced, NK cell activating and/or cytotoxic function. Additionally, in several embodiments, this construct can optionally be co-expressed with mbIL15. Further, in several embodiments, polynucleotides are provided encoding a NKG2Dx2/CD3zetaTM/CD16/4-1BB chimeric receptor, which comprises the fragment of NKG2D that is codon optimized coupled to a GS3 linker, an additional NKG2D fragment, a CD8α hinge, a CD3zeta transmembrane region, and an effector domain comprising a CD16 and 4-1BB. In one embodiment, this chimeric receptor comprises the nucleic acid sequence of SEQ ID NO: 72. In yet another embodiment, this chimeric receptor is encoded by the amino acid sequence of SEQ ID NO: 73. In some embodiments, the sequence of the chimeric receptor may vary from SEQ ID NO. 72, but remains, depending on the embodiment, at least 70%, at least 75%, at least 80%, at least 85%, at least 90%, or at least 95% homologous with SEQ ID NO. 72. In several embodiments, while the chimeric receptor may vary from SEQ ID NO. 72, the chimeric receptor retains, or in some embodiments, has enhanced, NK cell activating and/or cytotoxic function. Additionally, in several embodiments, this construct can optionally be co-expressed with mbIL15.

In several embodiments, chimeric receptors are provided wherein a CD3zeta transmembrane domain is coupled to an effector domain comprising NKp80. Thus, in several embodiments, polynucleotides are provided encoding a NKG2D/CD3zetaTM/CD16/4-1BB/NKp80 chimeric receptor, which chimeric receptor comprises a fragment of NKG2D coupled to a CD8α hinge, a CD3zeta transmembrane region, and an effector domain comprising a CD16, 4-1BB, and NKp80. In some embodiments, the effector domain further comprises a GS3 linker. In some embodiments, the GS3 linker is positioned between 4-1BB and NKp80. In one embodiment, this chimeric receptor comprises the nucleic acid sequence of SEQ ID NO: 74. In yet another embodiment, this chimeric receptor is encoded by the amino acid sequence of SEQ ID NO: 75. In some embodiments, the sequence of the chimeric receptor may vary from SEQ ID NO. 74, but remains, depending on the embodiment, at least 70%, at least 75%, at least 80%, at least 85%, at least 90%, or at least 95% homologous with SEQ ID NO. 74. In several embodiments, while the chimeric receptor may vary from SEQ ID NO. 74, the chimeric receptor retains, or in some embodiments, has enhanced, NK cell activating and/or cytotoxic function. Additionally, in several embodiments, this construct can optionally be co-expressed with mbIL15. Further, in several embodiments, polynucleotides are provided encoding a 2×NKG2D/CD3zetaTM/CD16/4-1BB/NKp80 chimeric receptor, which comprises the fragment of NKG2D that is codon optimized coupled to a GS3 linker, an additional NKG2D fragment, a CD8α hinge, a CD3zeta transmembrane region, and an effector domain comprising a CD16, 4-1BB, and NKp80. In some embodiments, the effector domain further comprises a GS3 linker. In some embodiments, the GS3 linker is positioned between 4-1BB and NKp80. In one embodiment, this chimeric receptor comprises the nucleic acid sequence of SEQ ID NO: 76. In yet another embodiment, this chimeric receptor is encoded by the amino acid sequence of SEQ ID NO: 77. In some embodiments, the sequence of the chimeric receptor may vary from SEQ ID NO. 76, but remains, depending on the embodiment, at least 70%, at least 75%, at least 80%, at least 85%, at least 90%, or at least 95% homologous with SEQ ID NO. 76. In several embodiments, while the chimeric receptor may vary from SEQ ID NO. 76, the chimeric receptor retains, or in some embodiments, has enhanced, NK cell activating and/or cytotoxic function. Additionally, in several embodiments, this construct can optionally be co-expressed with mbIL15. Further, in several embodiments, polynucleotides are provided encoding a NKG2D/CD3zetaTM/4-1BB/NKp80 chimeric receptor, which comprises a fragment of NKG2D that is codon optimized coupled to a CD8α hinge, a CD3zeta transmembrane region, and an effector domain comprising 4-1BB and NKp80. In some embodiments, the effector domain further comprises a GS3 linker. In some embodiments, the GS3 linker is positioned between 4-1BB and NKp80. In one embodiment, this chimeric receptor comprises the nucleic acid sequence of SEQ ID NO: 82. In yet another embodiment, this chimeric receptor is encoded by the amino acid sequence of SEQ ID NO: 83. In some embodiments, the sequence of the chimeric receptor may vary from SEQ ID NO. 82, but remains, depending on the embodiment, at least 70%, at least 75%, at least 80%, at least 85%, at least 90%, or at least 95% homologous with SEQ ID NO. 82. In several embodiments, while the chimeric receptor may vary from SEQ ID NO. 82, the chimeric receptor retains, or in some embodiments, has enhanced, NK cell activating and/or cytotoxic function. Additionally, in several embodiments, this construct can optionally be co-expressed with mbIL15.

In several embodiments, chimeric receptors are provided wherein a CD3zeta transmembrane domain is coupled to an effector domain comprising CD3zeta. Thus, in several embodiments, polynucleotides are provided encoding a NKG2D/CD3zetaTM/4-1BB/CD3zeta chimeric receptor, which comprises a fragment of NKG2D that is codon optimized coupled to a CD8α hinge, a CD3zeta transmembrane region, and an effector domain comprising 4-1BB and CD3zeta. In one embodiment, this chimeric receptor comprises the nucleic acid sequence of SEQ ID NO: 80. In yet another embodiment, this chimeric receptor is encoded by the amino acid sequence of SEQ ID NO: 81. In some embodiments, the sequence of the chimeric receptor may vary from SEQ ID NO. 80, but remains, depending on the embodiment, at least 70%, at least 75%, at least 80%, at least 85%, at least 90%, or at least 95% homologous with SEQ ID NO. 80. In several embodiments, while the chimeric receptor may vary from SEQ ID NO. 80, the chimeric receptor retains, or in some embodiments, has enhanced, NK cell activating and/or cytotoxic function. Additionally, in several embodiments, this construct can optionally be co-expressed with mbIL15.

In several embodiments, chimeric receptors are provided wherein a CD3zeta transmembrane domain is coupled to an effector domain comprising FcRγ. Thus, in several embodiments, polynucleotides are provided encoding a NKG2D/CD3zetaTM/4-1BB/FcRγ chimeric receptor, which comprises a fragment of NKG2D coupled to a CD8α hinge, a CD3zeta transmembrane region, and an effector domain comprising 4-1BB and FcRγ. In one embodiment, this chimeric receptor comprises the nucleic acid sequence of SEQ ID NO: 86. In yet another embodiment, this chimeric receptor is encoded by the amino acid sequence of SEQ ID NO: 87. In some embodiments, the sequence of the chimeric receptor may vary from SEQ ID NO. 86, but remains, depending on the embodiment, at least 70%, at least 75%, at least 80%, at least 85%, at least 90%, or at least 95% homologous with SEQ ID NO. 86. In several embodiments, while the chimeric receptor may vary from SEQ ID NO. 86, the chimeric receptor retains, or in some embodiments, has enhanced, NK cell activating and/or cytotoxic function. Additionally, in several embodiments, this construct can optionally be co-expressed with mbIL15.

In several embodiments, chimeric receptors are provided wherein a CD3zeta transmembrane domain is coupled to an effector domain comprising CD28. Thus, in several embodiments, polynucleotides are provided encoding a NKG2D/CD3zetaTM/CD28/CD3zeta chimeric receptor, which comprises an NKG2D fragment extracellular receptor domain that binds native ligands of NKG2D, a CD8α hinge, a CD3zeta transmembrane region, and intracellular effector domain comprising CD28 and CD3zeta. In one embodiment, this chimeric receptor comprises the nucleic acid sequence of SEQ ID NO: 102. In yet another embodiment, this chimeric receptor is encoded by the amino acid sequence of SEQ ID NO: 103. In some embodiments, the sequence of the chimeric receptor may vary from SEQ ID NO. 102, but remains, depending on the embodiment, at least 70%, at least 75%, at least 80%, at least 85%, at least 90%, or at least 95% homologous with SEQ ID NO. 102. In several embodiments, while the chimeric receptor may vary from SEQ ID NO. 102, the chimeric receptor retains, or in some embodiments, has enhanced, NK cell activating and/or cytotoxic function. Additionally, in several embodiments, this construct can optionally be co-expressed with mbIL15.

In several embodiments, chimeric receptors are provided wherein the extracellular domain comprises a fragment of NKG2D coupled IL15. Thus, in several embodiments, polynucleotides are provided encoding an IL15/NKG2D/CD8α/4-1BB/CD3zeta chimeric receptor, which comprises an NKG2D fragment extracellular receptor domain that binds native ligands of NKG2D linked to IL-15, a CD8α hinge, a CD8α transmembrane domain, and intracellular effector domain comprising 4-1BB and CD3zeta. In some embodiments, the extracellular domain further comprises a GS3 linker. In some embodiments, the GS3 linker is positioned between IL15 and the NKG2D fragment extracellular receptor domain. In one embodiment, this chimeric receptor comprises the nucleic acid sequence of SEQ ID NO: 88. In yet another embodiment, this chimeric receptor is encoded by the amino acid sequence of SEQ ID NO: 89. In some embodiments, the sequence of the chimeric receptor may vary from SEQ ID NO. 88, but remains, depending on the embodiment, at least 70%, at least 75%, at least 80%, at least 85%, at least 90%, or at least 95% homologous with SEQ ID NO. 88. In several embodiments, while the chimeric receptor may vary from SEQ ID NO. 88, the chimeric receptor retains, or in some embodiments, has enhanced, NK cell activating and/or cytotoxic function.

In several embodiments, chimeric receptors are provided wherein the extracellular domain comprises a fragment of NKG2D coupled to a IgG4 short hinge. Thus, in several embodiments, polynucleotides are provided encoding a NKG2D/IgG4/CD8α/4-1BB/CD3zeta chimeric receptor, which comprises an NKG2D fragment extracellular receptor domain that binds native ligands of NKG2D, an IgG4 short hinge, a CD8α transmembrane domain, and intracellular effector domain comprising 4-1BB, and CD3zeta. In one embodiment, this chimeric receptor comprises the nucleic acid sequence of SEQ ID NO: 96. In yet another embodiment, this chimeric receptor is encoded by the amino acid sequence of SEQ ID NO: 97. In some embodiments, the sequence of the chimeric receptor may vary from SEQ ID NO. 96, but remains, depending on the embodiment, at least 70%, at least 75%, at least 80%, at least 85%, at least 90%, or at least 95% homologous with SEQ ID NO. 96. In several embodiments, while the chimeric receptor may vary from SEQ ID NO. 96, the chimeric receptor retains, or in some embodiments, has enhanced, NK cell activating and/or cytotoxic function. Additionally, in several embodiments, this construct can optionally be co-expressed with mbIL15.

In several embodiments, chimeric receptors are provided wherein the effector domain comprises OX40. Thus, in several embodiments, polynucleotides are provided encoding a NKG2D/CD8α/OX40/CD3zeta chimeric receptor, which comprises an NKG2D fragment extracellular receptor domain that binds native ligands of NKG2D, a CD8α hinge, a CD8α transmembrane domain, and an intracellular effector domain comprising OX40, and CD3zeta. In one embodiment, this chimeric receptor comprises the nucleic acid sequence of SEQ ID NO: 90. In yet another embodiment, this chimeric receptor is encoded by the amino acid sequence of SEQ ID NO: 91. In some embodiments, the sequence of the chimeric receptor may vary from SEQ ID NO. 90, but remains, depending on the embodiment, at least 70%, at least 75%, at least 80%, at least 85%, at least 90%, or at least 95% homologous with SEQ ID NO. 90. In several embodiments, while the chimeric receptor may vary from SEQ ID NO. 90, the chimeric receptor retains, or in some embodiments, has enhanced, NK cell activating and/or cytotoxic function. Additionally, in several embodiments, this construct can optionally be co-expressed with mbIL15. In several embodiments, polynucleotides are provided encoding a NKG2D/IgG4/CD8α/OX40/CD3zeta chimeric receptor, which comprises an NKG2D fragment extracellular receptor domain that binds native ligands of NKG2D, an IgG4 hinge, a CD8α transmembrane domain, and intracellular effector domain comprising OX40 and CD3zeta. In one embodiment, this chimeric receptor comprises the nucleic acid sequence of SEQ ID NO: 100. In yet another embodiment, this chimeric receptor is encoded by the amino acid sequence of SEQ ID NO: 101. In some embodiments, the sequence of the chimeric receptor may vary from SEQ ID NO. 100, but remains, depending on the embodiment, at least 70%, at least 75%, at least 80%, at least 85%, at least 90%, or at least 95% homologous with SEQ ID NO. 100. In several embodiments, while the chimeric receptor may vary from SEQ ID NO. 100, the chimeric receptor retains, or in some embodiments, has enhanced, NK cell activating and/or cytotoxic function. Additionally, in several embodiments, this construct can optionally be co-expressed with mbIL15.

In several embodiments, chimeric receptors are provided comprising a CD28 peptide comprising both the transmembrane region and intracellular effector domain. Thus, in several embodiments, polynucleotides are provided encoding a NKG2D/CD28/CD3zeta chimeric receptor, which comprises an NKG2D fragment extracellular receptor domain that binds native ligands of NKG2D, a CD8α hinge, a CD28 transmembrane/intracellular domain, and CD3zeta. In one embodiment, this chimeric receptor comprises the nucleic acid sequence of SEQ ID NO: 92. In yet another embodiment, this chimeric receptor is encoded by the amino acid sequence of SEQ ID NO: 93. In some embodiments, the sequence of the chimeric receptor may vary from SEQ ID NO. 92, but remains, depending on the embodiment, at least 70%, at least 75%, at least 80%, at least 85%, at least 90%, or at least 95% homologous with SEQ ID NO. 92. In several embodiments, while the chimeric receptor may vary from SEQ ID NO. 92, the chimeric receptor retains, or in some embodiments, has enhanced, NK cell activating and/or cytotoxic function. Additionally, in several embodiments, this construct can optionally be co-expressed with mbIL15. In further embodiments, polynucleotides are provided encoding a NKG2D/CD28/CD3zeta/4-1BB chimeric receptor, which comprises an NKG2D fragment extracellular receptor domain that binds native ligands of NKG2D, a CD8α hinge, a CD28 transmembrane/intracellular domain, and 4-1BB and CD3zeta. In one embodiment, this chimeric receptor comprises the nucleic acid sequence of SEQ ID NO: 94. In yet another embodiment, this chimeric receptor is encoded by the amino acid sequence of SEQ ID NO: 95. In some embodiments, the sequence of the chimeric receptor may vary from SEQ ID NO. 94, but remains, depending on the embodiment, at least 70%, at least 75%, at least 80%, at least 85%, at least 90%, or at least 95% homologous with SEQ ID NO. 94. In several embodiments, while the chimeric receptor may vary from SEQ ID NO. 94, the chimeric receptor retains, or in some embodiments, has enhanced, NK cell activating and/or cytotoxic function. Additionally, in several embodiments, this construct can optionally be co-expressed with mbIL15. In further embodiments, polynucleotides are provided encoding a NKG2D/IgG4/CD28/CD3zeta chimeric receptor, which comprises an NKG2D fragment extracellular receptor domain that binds native ligands of NKG2D, an IgG4 hinge, a CD28 transmembrane/intracellular domain, and CD3zeta. In one embodiment, this chimeric receptor comprises the nucleic acid sequence of SEQ ID NO: 98. In yet another embodiment, this chimeric receptor is encoded by the amino acid sequence of SEQ ID NO: 99. In some embodiments, the sequence of the chimeric receptor may vary from SEQ ID NO. 98, but remains, depending on the embodiment, at least 70%, at least 75%, at least 80%, at least 85%, at least 90%, or at least 95% homologous with SEQ ID NO. 98. In several embodiments, while the chimeric receptor may vary from SEQ ID NO. 98, the chimeric receptor retains, or in some embodiments, has enhanced, NK cell activating and/or cytotoxic function. Additionally, in several embodiments, this construct can optionally be co-expressed with mbIL15.

NCR1 (NKp46), NCR2 (NKp44) and NCR3 (NKp30) are receptors on NK cells that transduce activation signals upon ligand binding. Thus, in several embodiments, polynucleotides are provided encoding a NKG2D/NCR1 chimeric receptor, which comprises an NKG2D fragment extracellular receptor domain that binds native ligands of NKG2D and a NCR1 peptide comprising both the transmembrane region and intracellular effector domain. In one embodiment, this chimeric receptor comprises the nucleic acid sequence of SEQ ID NO: 27. In yet another embodiment, this chimeric receptor is encoded by the amino acid sequence of SEQ ID NO: 28. In some embodiments, the sequence of the chimeric receptor may vary from SEQ ID NO. 30, but remains, depending on the embodiment, at least 70%, at least 75%, at least 80%, at least 85%, at least 90%, or at least 95% homologous with SEQ ID NO: 27. In several embodiments, while the chimeric receptor may vary from SEQ ID NO. 27, the chimeric receptor retains, or in some embodiments, has enhanced, NK cell activating and/or cytotoxic function. Additionally, in several embodiments, this construct can optionally be co-expressed with mbIL15.

In several additional embodiments, polynucleotides are provided encoding a NKG2D/NCR1/4-1BB chimeric receptor, wherein the signaling domain of 4-1BB acts as a second transducer of activating signals in the effector domain, leading to synergistically enhanced NK cell activation and cytotoxicity. In several additional embodiments, polynucleotides are provided encoding a NKG2D/NCR2 chimeric receptor, which comprises an NKG2D fragment extracellular receptor domain that binds native ligands of NKG2D and a NCR2 peptide comprising both the transmembrane region and intracellular effector domain. As with NCR1, in several embodiments these constructs are particularly amenable for use in creating NK cells expressing the chimeric receptor, due to their relatively small size and simplicity on sequence. However, they retain the ability, in several embodiments, to yield highly effective NK cells, despite the apparent simplicity of the construct. Additionally, in several embodiments, these constructs can optionally be co-expressed with mbIL15.

In several additional embodiments, polynucleotides are provided encoding a NKG2D/NCR3 chimeric receptor, which comprises an NKG2D fragment extracellular receptor domain that binds native ligands of NKG2D and a NCR3 peptide comprising both the transmembrane region and intracellular effector domain. As with NCR1 and or NCR2, in several embodiments these constructs are particularly amenable for use in creating NK cells expressing the chimeric receptor, due to their relatively small size and simplicity on sequence. However, they retain the ability, in several embodiments, to yield highly effective NK cells, despite the apparent simplicity of the construct. In one embodiment, this chimeric receptor comprises the nucleic acid sequence of SEQ ID NO: 29. In yet another embodiment, this chimeric receptor is encoded by the amino acid sequence of SEQ ID NO: 30. In some embodiments, the sequence of the chimeric receptor may vary from SEQ ID NO. 29, but remains, depending on the embodiment, at least 70%, at least 75%, at least 80%, at least 85%, at least 90%, or at least 95% homologous with SEQ ID NO. 29. In several embodiments, while the chimeric receptor may vary from SEQ ID NO. 29, the chimeric receptor retains, or in some embodiments, has enhanced, NK cell activating and/or cytotoxic function. Additionally, in several embodiments, this construct can optionally be co-expressed with mbIL15.

In several additional embodiments, polynucleotides are provided encoding a NKG2D/NCR2/4-1BB chimeric receptor, wherein the signaling domain of 4-1BB acts as a second transducer of activating signals in the effector domain, thereby leading to a synergistic effect between the signaling domains, and unexpectedly effectively cytotoxic NK cells. Additionally, in several embodiments, this construct can optionally be co-expressed with mbIL15.

In several additional embodiments, polynucleotides are provided encoding a NKG2D/NCR3/4-1BB chimeric receptor, wherein the signaling domain of 4-1BB acts as a second transducer of activating signals in the effector domain, thereby leading to a synergistic effect between the signaling domains, and unexpectedly effectively cytotoxic NK cells. Additionally, in several embodiments, this construct can optionally be co-expressed with mbIL15.

In some embodiments the surface expression and efficacy of the chimeric receptors disclosed herein are enhanced by variations in a spacer region (hinge), which, in several embodiments, are located in the extracellular domain between the NKG2D fragment and the transmembrane domain. In some embodiments, the hinge regions can be included between other portions of the chimeric receptor (e.g., between intracellular and transmembrane domains, or between multiple intracellular domains). In some embodiments, domains that serve certain purposes as disclosed elsewhere herein, can serve additional functions. For example, in several embodiments, CD8α is repurposed to serve as a hinge region (encoded, in several embodiments, by the nucleic acid sequence of SEQ ID NO: 5). In yet another embodiment, the hinge region comprises an N-terminal truncated form of CD8α and/or a C-terminal truncated form of CD8α. Depending on the embodiment, these truncations can be at least about 50%, at least about 60%, at least about 70%, at least about 80%, or at least about 90% homologous to the hinge encoded by SEQ ID NO. 5. In several additional embodiments, the hinge comprises spans of Glycine and Serine residues (herein termed "GS linkers") where GSn represents the sequence (Gly-Gly-Gly-Gly-Ser)n (SEQ ID NO. 42). In one embodiment, the hinge comprises both CD8α and GS3, and is encoded by the amino acid sequence of SEQ ID NO: 32, for example, where n=3. In additional embodiments, the value of n may be equal to 1, 2, 4, 5, 6, 7, 8, 9, 10, 11, 12, 13, 14, 15 or greater depending on the embodiment. In several embodiments, the hinge could also be structured as GSn/CD8α. Alternatively, the GS linker can comprise the entire hinge region. In one such embodiment, the hinge region is encoded by the nucleic acid sequence of SEQ ID NO: 33. In another such embodiment, the hinge region is encoded by the nucleic acid sequence of SEQ ID NO: 34. In several embodiments, IgG4 is repurposed as a hinge region (encoded, in several embodiments, by the nucleic acid sequence of SEQ ID NO: 104). In yet another embodiment, the hinge region comprises an N-terminal truncated form of IgG4 and/or a C-terminal truncated form of IgG4. Depending on the embodiment, these truncations can be at least about 50%, at least about 60%, at least about 70%, at least about 80%, or at least about 90% homologous to the hinge encoded by SEQ ID NO. 104.

In several embodiments, the chimeric receptor constructs employ a 2B4 intracellular signaling domain. In several embodiments, this domain is encoded by the amino acid sequence of SEQ ID NO. 35. In some embodiments, the 2B4 domain is encoded by the nucleic acid sequence of SEQ ID NO. 36. In some embodiments, the sequence of the 2B4 intracellular domain used in a chimeric receptor may vary from SEQ ID NO. 36, but remains, depending on the embodiment, at least 70%, at least 75%, at least 80%, at least 85%, at least 90%, or at least 95% homologous with SEQ ID NO. 36. In several embodiments, while the signaling domain of the chimeric receptor may vary from SEQ ID NO. 36, the chimeric receptor retains, or in some embodiments, has enhanced, NK cell activating and/or cytotoxic function. Likewise, in several embodiments an NKp80 intracellular domain is used, in several embodiments. In some embodiments, the NKp80 domain is the sole intracellular signaling domain, while in some embodiments, that domain is used in conjunction with one or more additional domains. In several embodiments, the NKp80 is encoded by the amino acid sequence of SEQ ID NO. 37. In some embodiments, the NKp80 domain is encoded by the nucleic acid sequence of SEQ ID NO. 38. In some embodiments, the sequence of the NKp80 intracellular domain used in a chimeric receptor may vary from SEQ ID NO. 38, but remains, depending on the embodiment, at least 70%, at least 75%, at least 80%, at least 85%, at least 90%, or at least 95% homologous with SEQ ID NO. 38. In several embodiments, while the signaling domain of the chimeric receptor may vary from SEQ ID NO. 38, the chimeric receptor retains, or in some embodiments, has enhanced, NK cell activating and/or cytotoxic function.

In several embodiments, the chimeric receptor uses a portion of a beta-adrenergic receptor as a transmembrane domain. In several embodiments, the portion comprises a portion of the beta-adrenergic extracellular domain. In several embodiments, the portion is a portion of the beta-adrenergic receptor transmembrane domain. In several embodiments, a combination of an extracellular domain and a transmembrane domain of the beta adrenergic receptor is used. Depending on the embodiment the portions are from the beta-1 and/or beta-2 adrenergic receptor. In several embodiments, a portion of the N-terminal extracellular region of the beta-2 adrenergic receptor is used. In several embodiments that portion has the amino acid sequence of SEQ ID NO. 39. In some embodiments, the extracellular beta-2 adrenergic domain is encoded by the nucleic acid sequence of SEQ ID NO. 40. In some embodiments, the sequence of the extracellular beta-2 adrenergic domain used in a chimeric receptor may vary from SEQ ID NO. 39, but remains, depending on the embodiment, at least 70%, at least 75%, at least 80%, at least 85%, at least 90%, or at least 95% homologous with SEQ ID NO. 39. In several embodiments, the first transmembrane helix of the beta-2 adrenergic receptor is used, optionally in conjunction with the extracellular beta-2 adrenergic domain. In several embodiments, the first transmembrane helix of the beta-2 adrenergic receptor has the amino acid sequence of SEQ ID NO. 41. In some embodiments, the first transmembrane helix of the beta-2 adrenergic receptor is encoded by the nucleic acid sequence of SEQ ID NO. 42. In some embodiments, the sequence of the first transmembrane helix of the beta-2 adrenergic receptor used in a chimeric receptor may vary from SEQ ID NO. 41, but remains, depending on the embodiment, at least 70%, at least 75%, at least 80%, at least 85%, at least 90%, or at least 95% homologous with SEQ ID NO. 41.

In one embodiment, the chimeric receptor comprises CD8, truncated NKG2D, CD8α, transmembrane domain, a CD16 intracellular domain, and 4-1BB as a costimulatory molecule. In several embodiments, such a construct is encoded by SEQ ID NO. 25. In some embodiments, the chimeric receptor may vary from SEQ ID NO. 25, but remains, depending on the embodiment, at least 70%, at least 75%, at least 80%, at least 85%, at least 90%, or at least 95% homologous with SEQ ID NO. 25. In several embodiments, hinge regions surrounding CD8 are increased by way of addition of GS linkers (disclosed herein), such as GS3, by way of non-limiting example. In such embodiments, the construct is encoded by the nucleic acid of SEQ ID NO. 43. In some embodiments, the chimeric receptor may vary from SEQ ID NO. 43, but remains, depending on the embodiment, at least 70%, at least 75%, at least 80%, at least 85%, at least 90%, or at least 95% homologous with SEQ ID NO. 43. In several embodiments, hinge regions surrounding CD8 are increased by way of addition of longer GS linkers, such as GS12, or other linker. In several embodiments, hinge regions are decreased by way of truncating CD8. For example, in several embodiments, the N-terminal region of CD8α is truncated by at least 20%, at least 30%, at least 40%, or at least 50%. In several embodiments, the CD8 hinge is replaced with a GS linker. For example, in several embodiments, the hinge region comprises a GS3 linker, thereby the construct comprises NKG2D-GS3-CD16-4-1BB. In one embodiment, such a construct is encoded by the nucleic acid of SEQ ID NO. 44. In some embodiments, the chimeric receptor may vary from SEQ ID NO. 44, but remains, depending on the embodiment, at least 70%, at least 75%, at least 80%, at least 85%, at least 90%, or at least 95% homologous with SEQ ID NO. 44. In several embodiments, neither CD8 nor GSn are used. In one embodiment, such a construct is encoded by the nucleic acid of SEQ ID NO. 45. In some embodiments, the chimeric receptor may vary from SEQ ID NO. 45, but remains, depending on the embodiment, at least 70%, at least 75%, at least 80%, at least 85%, at least 90%, or at least 95% homologous with SEQ ID NO. 45.

As discussed above, in several embodiments, codon optimized sequences are employed. For example in several embodiments, codon optimization (full or partial) is performed on the NKG2D domain of a chimeric receptor. In several embodiments, however, codon optimization is not performed. In several embodiments, a chimeric receptor construct is provided with an NKG2D extracellular domain that is not optimized, a CD8α hinge, and a 4-1BB signaling domain. In several embodiments, a chimeric receptor construct is provided with an NKG2D extracellular domain that is not optimized, a CD8α hinge and transmembrane domain, and a 4-1BB signaling domain. In several embodiments, a chimeric receptor construct is provided with an NKG2D extracellular domain that is not optimized, a CD8α hinge and transmembrane domain, a 4-1BB signaling domain and a 2B4 signaling domain. In several embodiments, such a construct has the nucleic acid sequence of SEQ ID NO. 46. In some embodiments, the chimeric receptor may vary from SEQ ID NO. 46, but remains, depending on the embodiment, at least 70%, at least 75%, at least 80%, at least 85%, at least 90%, or at least 95% homologous with SEQ ID NO. 46.

In several embodiments, a chimeric receptor construct is provided with an NKG2D extracellular domain that is not optimized, a beta-adrenergic derived transmembrane domain, and a 4-1BB signaling domain. In several embodiments, a chimeric receptor construct is provided with an NKG2D extracellular domain that is not optimized, a beta-adrenergic derived transmembrane domain made up of the extracellular region of the beta-2 adrenergic receptor and the first transmembrane helix of the beta-2 adrenergic receptor, and a 4-1BB signaling domain. In several embodiments, a chimeric receptor construct is provided with an NKG2D extracellular domain that is not optimized, a beta-adrenergic derived transmembrane domain made up of the extracellular region of the beta-2 adrenergic receptor and the first transmembrane helix of the beta-2 adrenergic receptor, a 4-1BB signaling domain and a 2B4 signaling domain. In several embodiments, such a construct has the nucleic acid sequence of SEQ ID NO. 47. In some embodiments, the chimeric receptor may vary from SEQ ID NO. 47, but remains, depending on the embodiment, at least 70%, at least 75%, at least 80%, at least 85%, at least 90%, or at least 95% homologous with SEQ ID NO. 47.

In several embodiments, a chimeric receptor construct is provided with an NKG2D extracellular domain that is not optimized, a CD8α hinge, and a 2B4 signaling domain. In several embodiments, a chimeric receptor construct is provided with an NKG2D extracellular domain that is not optimized, a CD8α hinge and transmembrane domain, and both a 2B4 and a 4-1BB signaling domain. In several embodiments, a chimeric receptor construct is provided with an NKG2D extracellular domain that is not optimized, a CD8α hinge and transmembrane domain, a 4-1BB signaling domain and a 2B4 signaling domain, as well as a NKp80 domain. In several embodiments, a GS linker, such as a GS3 linker joins the 2B4 and NKp80 domains. In several embodiments, such a construct has the nucleic acid sequence of SEQ ID NO. 48. In some embodiments, the chimeric receptor may vary from SEQ ID NO. 48, but remains, depending on the embodiment, at least 70%, at least 75%, at least 80%, at least 85%, at least 90%, or at least 95% homologous with SEQ ID NO. 48.

In several embodiments, a chimeric receptor construct is provided with an NKG2D extracellular domain that is not optimized, a CD8α hinge, and a NKp80 signaling domain. In several embodiments, a chimeric receptor construct is provided with an NKG2D extracellular domain that is not optimized, a CD8α hinge and transmembrane domain, and a NKp80 signaling domain. In several embodiments, a chimeric receptor construct is provided with an NKG2D extracellular domain that is not optimized, a CD8α hinge and transmembrane domain, a 4-1BB signaling domain and a NKp80 domain. In several embodiments, a GS linker, such as a GS3 linker joins the 4-1BB and NKp80 domains. In several embodiments, such a construct has the nucleic acid sequence of SEQ ID NO. 49. In some embodiments, the chimeric receptor may vary from SEQ ID NO. 49, but remains, depending on the embodiment, at least 70%, at least 75%, at least 80%, at least 85%, at least 90%, or at least 95% homologous with SEQ ID NO. 49.

In several embodiments, a CD8 transmembrane domain is coupled with a 2B4 intracellular domain. In several embodiments, a CD8 transmembrane domain is replaced with a 2B4 domain that is transmembrane and intracellular. In several embodiments, the CD8 transmembrane domain is replaced with 2B4 and 4-1BB is expressed in a proximal configuration.

In several embodiments, a CD16 intracellular signaling domain is coupled with a CD3zeta or gamma subunit which are exogenously expressed in trans to the chimeric receptors described herein. As discussed above, such constructs can result in unexpectedly enhanced signal transduction, and thus an unexpected increase in cytotoxic effects of the NK cells.

In several embodiments, the chimeric receptors are configured to dimerize, as discussed in additional detail herein. In several embodiments a truncated NKG2D receptor according to several embodiments disclosed herein is optionally dimerized. Dimerization may comprise homodimers or heterodimers, depending on the embodiment. In several embodiments, dimerization results in a shift of avidity of the chimeric receptor (and hence the NK cells expressing the receptor) to better ligand recognition with a coordinate balance in reduced (or lack) of adverse toxic effects. In still further embodiments, the extracellular receptor domain further comprises a CD8α signal peptide. In several embodiments, the chimeric receptors employ internal dimers, or repeats of one or more component subunits. For example, in several embodiments, the chimeric receptor comprises a NKG2D extracellular domain coupled to a second NKG2D extracellular domain, and a transmembrane/signaling region (or a separate transmembrane region along with a separate signaling region). In several embodiments, one or more of the NKG2D extracellular domains are codon optimized. In several embodiments, the two NKG2D extracellular domains are separated by a linker, for example a GSn linker. In one embodiment, a GS3 linker is used. In several embodiments, the transmembrane domain comprises an extracellular region of the beta-adrenergic receptor. In several embodiments, the transmembrane domain transmembrane domain comprises an extracellular region of the beta-2 adrenergic receptor and further comprises the first transmembrane domain of the beta-2 adrenergic receptor. In several embodiments, the signaling region comprises 4-1BB. In several embodiments, the signaling region comprises NKp80. In several embodiments, the signaling region comprises a CD16 transmembrane-intracellular domain. In several embodiments, the signaling region comprises 4-1BB in conjunction with NKp80 or a CD16 transmembrane-intracellular domain. In several embodiments, the chimeric receptor has the nucleic acid sequence of SEQ ID NO. 50. In some embodiments, the chimeric receptor may vary from SEQ ID NO. 50, but remains, depending on the embodiment, at least 70%, at least 75%, at least 80%, at least 85%, at least 90%, or at least 95% homologous with SEQ ID NO. 50. In several embodiments, the chimeric receptor has the nucleic acid sequence of SEQ ID NO. 51. In some embodiments, the chimeric receptor may vary from SEQ ID NO. 51, but remains, depending on the embodiment, at least 70%, at least 75%, at least 80%, at least 85%, at least 90%, or at least 95% homologous with SEQ ID NO. 51. In several embodiments, the chimeric receptor has the nucleic acid sequence of SEQ ID NO. 52. In some embodiments, the chimeric receptor may vary from SEQ ID NO. 52, but remains, depending on the embodiment, at least 70%, at least 75%, at least 80%, at least 85%, at least 90%, or at least 95% homologous with SEQ ID NO. 52. In several embodiments, the chimeric receptor comprises a hinge region. In several embodiments, CD8α is repurposed to serve as a hinge region (encoded, in several embodiments, by the nucleic acid sequence of SEQ ID NO: 5). In several embodiments, the chimeric receptor comprises a CD8α transmembrane domain. In several embodiments, the signaling region comprises 4-1BB in conjunction with 2B4 and CD3zeta. In some embodiments, the chimeric receptor comprises the fragment of NKG2D that is codon optimized coupled to a GS3 linker, an additional NKG2D fragment, a CD8α hinge, a CD8α transmembrane domain, and an effector domain comprising 4-1BB and CD3zeta. In several embodiments, the chimeric receptor has the nucleic acid sequence of SEQ ID NO. 66. In some embodiments, the chimeric receptor may vary from SEQ ID NO. 66, but remains, depending on the embodiment, at least 70%, at least 75%, at least 80%, at least 85%, at least 90%, or at least 95% homologous with SEQ ID NO. 50. In several embodiments, the chimeric receptor chimeric receptor comprises the amino acid sequence of SEQ ID NO: 67. In some embodiments, the chimeric receptor may vary from SEQ ID NO. 66, but remains, depending on the embodiment, at least 70%, at least 75%, at least 80%, at least 85%, at least 90%, or at least 95% homologous with SEQ ID NO. 50.

In several embodiments, the chimeric receptors are configured to be bispecific, as discussed in additional detail herein. In several embodiments, a truncated NKG2D receptor according to several embodiments disclosed herein is bispecific due to a second peptide that binds, for example, non-NKG2D ligands. In several embodiments, bi-specificity results in a shift of the targeting of the chimeric receptor (and hence the NK cells expressing the receptor) to better target cell recognition with a coordinate balance in reduced (or lack) of adverse toxic effects. In still further embodiments, the extracellular receptor domain further comprises a CD8α signal peptide. For example, in several embodiments, the chimeric receptor comprises a NKG2D extracellular domain coupled to a second extracellular domain that binds other (non-NKG2D) ligands, and a transmembrane/signaling region (or a separate transmembrane region along with a separate signaling region). In several embodiments, the two extracellular domains are separated by a linker, for example a GSn linker. In one embodiment, a GS3 linker is used.

According to several embodiments disclosed herein, additional chimeric receptors employing codon optimized NKG2D domains are provided for (optionally, these constructs can also be replicated with non-optimized or partially optimized domains). For example, in several embodiments, a codon optimized extracellular domain is coupled with a hinge and at least two transmembrane/signaling domains. In several embodiments, the multiple signaling domains provide enhanced cytotoxic efficacy of the NK cells because multiple, non-redundant signal cascades are set in motion. While in some embodiments these multiple pathways may converge on a single signaling molecule (e.g., IFNγ), the overall cytotoxic effect is unexpectedly increased because of the overall magnitude of signaling molecules driving a cytotoxic endpoint. As a non-limiting example, in several embodiments an NKG2D is coupled to a CD8α hinge followed by a CD16 transmembrane-intracellular signaling domain and a 4-1BB signaling domain. In several embodiments, this construct further comprises a 2B4 signaling domains. In several embodiments, such a chimeric receptor has the nucleic acid sequence of SEQ ID NO. 53. In some embodiments, the chimeric receptor may vary from SEQ ID NO. 53, but remains, depending on the embodiment, at least 70%, at least 75%, at least 80%, at least 85%, at least 90%, or at least 95% homologous with SEQ ID NO. 53. In additional embodiments, the NKG2D-CD8α-CD16IC/TM construct further comprises a NKp80 signaling domain. In several embodiments, such a construct further comprises a GS3 linker between the 4-1BB and NKp80 domains. In several embodiments, such a chimeric receptor has the nucleic acid sequence of SEQ ID NO. 54. In some embodiments, the chimeric receptor may vary from SEQ ID NO. 54, but remains, depending on the embodiment, at least 70%, at least 75%, at least 80%, at least 85%, at least 90%, or at least 95% homologous with SEQ ID NO. 54.

In still additional embodiments, certain components of a chimeric receptor can be replaced with one or more additional subunits that lead to enhanced efficacy (e.g., activation or cytotoxicity of NK cells). For example, in one embodiment, a CD16 intracellular signaling domain can be replaced with a quad-repeat of DAP10 (e.g., 4×DAP10). In an additional embodiment, a CD16 intracellular signaling domain can be replaced with a Zap70 subunit. Certain such embodiments lead to unexpectedly enhanced NK cell cytotoxicity.

In several additional embodiments, the effector domain comprises one or more consensus hemi-ITAM sequences to enhance the transduction of activation signaling upon ligand binding. In additional embodiments, the inclusion of a GS linker between the signaling domains of 4-1BB, CD16, NCR1, NCR2 and/or NCR3 enhances signal transduction. Moreover, in several embodiments one or both of CD3zeta and FcRγ are additionally expressed along with the chimeric receptors described herein (either on the same or a separate construct), which results in unexpectedly enhanced signal transduction, and thus an unexpected increase in cytotoxic effects of the NK cells. Depending on the embodiment, the engineered expression of one or more of CD3zeta and FcRγ supplements endogenous expression of these molecules by NK cells, thereby further enhancing the signaling and ultimate cytotoxic potency of the NK cells.

Optionally, depending on the embodiment, any of the polynucleotides disclosed herein may also encode truncations and/or variants of one or more of the constituent subunits of a chimeric receptor, yet retain their ability to direct NK cells to target cells and in several embodiments unexpectedly enhance cytotoxicity upon binding. In addition, any of the polynucleotides disclosed herein may also optionally include codon-optimized nucleotide sequences encoding the various constituent subunits of a chimeric receptor. As used herein, the terms "fragment" and "truncated" shall be given their ordinary meaning and shall also include N- and C-terminal deletion variants of proteins.

The polynucleotides encoding the chimeric receptors described herein may be inserted into vectors to achieve recombinant protein expression in NK cells. In one embodiment, the polynucleotide is operably linked to at least one regulatory element for the expression of the chimeric receptor. In specific embodiments, transcriptional regulatory elements heterologous, such as, for example an internal ribosome entry site (IRES) or enhancer element, to the peptides disclosed herein are employed to direct the transcription of the chimeric receptor. In some embodiments, the polynucleotide comprises one or more cytosolic protease cleavage sites. In some embodiments, the cleavage site is recognized and cleaved by a cytosolic protease. In some embodiments, this cleavage site is selected from the group comprising a T2A cleavage site, a P2A cleavage site, an E2A cleavage site, and an F2A cleavage site. Depending on the embodiment, the various constituent parts of a chimeric receptor can be delivered to an NK cell in a single vector, or alternatively in multiple vectors. In some embodiments, a chimeric receptor construct is delivered in a single vector, while another factor that enhances efficacy of the chimeric receptor, such as mbIL15, is delivered in a separate vector. In several embodiments, a chimeric receptor and a factor that enhances efficacy of the chimeric receptor (e.g., mbIL15), is delivered in a single vector. Regardless of the number of vectors used, any polynucleotide may optionally include a tag sequence, allowing identification of the presence of NK cells expressing the construct. For example, in several embodiments a FLAG tag (DYKDDDDK, SEQ ID NO. 55) is used. Also available are other tag sequences, such as a polyhistidine tag (His-tag) (HHHHHH, SEQ ID NO. 56), HA-tag or myc-tag (EQKLISEEDL; SEQ ID NO: 57). Alternatively, green fluorescent protein, or other fluorescent moiety, is used. Combinations of tag types can also be used, to individually recognize sub-components of a chimeric receptor.

In several embodiments, the polynucleotide encoding the chimeric receptor is an mRNA that may be introduced into NK cells by electroporation. In another embodiment, the vector is a virus, preferably a retrovirus, which may be introduced into NK cells by transduction. In several embodiments, the vector is a Murine Stem Cell Virus (MSCV). In additional embodiments, other vectors may be used, for example lentivirus, adenovirus, adeno-associated virus, and the like may be used. In several embodiments, non-HIV-derived retroviruses are used. The vector chosen will depend upon a variety of factors, including, without limitation, the strength of the transcriptional regulatory elements and the cell to be used to express a protein. The vector can be a plasmid, phagemid, cosmid, viral vector, phage, artificial chromosome, and the like. In additional embodiments, the vectors can be episomal, non-homologously, or homologously integrating vectors, which can be introduced into the appropriate cells by any suitable means (transformation, transfection, conjugation, protoplast fusion, electroporation, calcium phosphate-precipitation, direct microinjection, etc.) to transform them. Other approaches to induce expression of chimeric receptors in NK cells are used in several embodiments, including for example, the SV40 early promoter region, the promoter contained in the 3' long terminal repeat of Rous sarcoma virus, the herpes thymidine kinase promoter, the regulatory sequences of the metallothionein gene, an adenovirus (ADV) promoter, a cytomegalovirus (CMV) promoter, the bovine papilloma virus (BPV) promoter, the parovirus B19p6 promoter, the beta-lactamase promoter, the tac promoter, the nopaline synthetase promoter region or the cauliflower mosaic virus 35S RNA promoter, the promoter of ribulose biphosphate carboxylase, the Gal 4 promoter, the ADC (alcohol dehydrogenase) promoter, the PGK (phosphoglycerol kinase) promoter, the synthetic MND promoter containing the U3 region of a modified MoMuLV LTR with the myeloproliferative sarcoma virus enhancer, and the alkaline phosphatase promoter.

Natural killer cells may be engineered to express the chimeric receptors disclosed herein. Chimeric receptor expression constructs may be introduced into NK cells using any of the techniques known to one of skill in the art. In one embodiment, the chimeric receptors are transiently expressed in the NK cells. In another embodiment, the chimeric receptors are stably expressed in NK cells. In an additional embodiment, the NK cells are autologous cells. In yet another embodiment, the NK cells are donor-derived (allogeneic) cells.

Further provided herein are methods of treating a subject having cancer or an infectious disease comprising administering to the subject a composition comprising NK cells engineered to express a chimeric receptor as disclosed herein, the chimeric receptor designed to target a marker or ligand expressed differentially on the damaged or diseased cells or tissue (e.g., expressed to a different degree as compared to a normal cell or tissue). As used herein, the terms "express", "expressed" and "expression" be given their ordinary meaning and shall refer to allowing or causing the information in a gene or polynucleotide sequence to become manifest, for example producing a protein by activating the cellular functions involved in transcription and translation of a corresponding gene or DNA sequence. The expression product itself, e.g., the resulting protein, may also be said to be "expressed" by the cell. An expression product may be characterized as intracellular, extracellular or transmembrane. The term "intracellular" shall be given its ordinary meaning and shall refer to inside a cell. The term "extracellular" shall be given its ordinary meaning and shall refer to outside a cell. The term "transmembrane" shall be given its ordinary meaning and shall refer to at least a portion of a polypeptide is embedded in a cell membrane. The term "cytoplasmic" shall be given its ordinary meaning and shall refer to residing within the cell membrane, outside the nucleus. As used herein, the terms "treat," "treating," and "treatment" in the context of the administration of a therapy to a subject shall be given their ordinary meaning and shall refer to the beneficial effects that a subject derives from a therapy. In certain embodiments, treatment of a subject with a genetically engineered cell(s) described herein achieves one, two, three, four, or more of the following effects, including, for example: (i) reduction or amelioration the severity of disease or symptom associated therewith; (ii) reduction in the duration of a symptom associated with a disease; (iii) protection against the progression of a disease or symptom associated therewith; (iv) regression of a disease or symptom associated therewith; (v) protection against the development or onset of a symptom associated with a disease; (vi) protection against the recurrence of a symptom associated with a disease; (vii) reduction in the hospitalization of a subject; (viii) reduction in the hospitalization length; (ix) an increase in the survival of a subject with a disease; (x) a reduction in the number of symptoms associated with a disease; (xi) an enhancement, improvement, supplementation, complementation, or augmentation of the prophylactic or therapeutic effect(s) of another therapy. Administration can be by a variety of routes, including, without limitation, intravenous, intra-arterial, subcutaneous, intramuscular, intrahepatic, intraperitoneal and/or local delivery to an affected tissue. Doses of NK cells can be readily determined for a given subject based on their body mass, disease type and state, and desired aggressiveness of treatment, but range, depending on the embodiments, from about $10^5$ cells per kg to about $10^{12}$ cells per kg (e.g., $10^{5-}$, $10^7$, $10^{7-}$, $10^{10}$, $10^{10-}$, $10^{12}$ and overlapping ranges therein). In one embodiment, a dose escalation regimen is used. In several embodiments, a range of NK cells is administered, for example between about $1\times10^6$ cells/kg to about $1\times10^8$ cells/kg. Depending on the embodiment, various types of cancer or infection disease can be treated. Various embodiments provided for herein include treatment or prevention of the following non-limiting examples of cancers including, but not limited to, acute lymphoblastic leukemia (ALL), acute myeloid leukemia (AML), adrenocortical carcinoma, Kaposi sarcoma, lymphoma, gastrointestinal cancer, appendix cancer, central nervous system cancer, basal cell carcinoma, bile duct cancer, bladder cancer, bone cancer, brain tumors (including but not limited to astrocytomas, spinal cord tumors, brain stem glioma, craniopharyngioma, ependymoblastoma, ependymoma, medulloblastoma, medulloepithelioma), breast cancer, bronchial tumors, Burkitt lymphoma, cervical cancer, colon cancer, chronic lymphocytic leukemia (CLL), chronic myelogenous leukemia (CML), chronic myeloproliferative disorders, ductal carcinoma, endometrial cancer, esophageal cancer, gastric cancer, Hodgkin lymphoma, non-Hodgkin lymphoma, hairy cell leukemia, renal cell cancer, leukemia, oral cancer, nasopharyngeal cancer, liver cancer, lung cancer (including but not limited to, non-small cell lung cancer, (NSCLC) and small cell lung cancer), pancreatic cancer, bowel cancer, lymphoma, melanoma, ocular cancer, ovarian cancer, pancreatic cancer, prostate cancer, pituitary cancer, uterine cancer, and vaginal cancer.

Further, various embodiments provided for herein include treatment or prevention of the following non-limiting examples of infectious diseases including, but not limited to, infections of bacterial origin may include, for example, infections with bacteria from one or more of the following genera: *Bordetella, Borrelia, Brucella, Campylobacter, Chlamydia* and *Chlamydophila, Clostridium, Corynebacte-* rium, *Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio,* and *Yersinia,* and mutants or combinations thereof. In several embodiments, methods are provided to treat a variety to treat viral infections, such as those caused by one or more viruses, such as adenovirus, Coxsackievirus, Epstein-Barr virus, hepatitis a virus, hepatitis b virus, hepatitis c virus, herpes simplex virus, type 1, herpes simplex virus, type 2, cytomegalovirus, ebola virus, human herpesvirus, type 8, HIV, influenza virus, measles virus, mumps virus, human papillomavirus, parainfluenza virus, poliovirus, rabies virus, respiratory syncytial virus, rubella virus, and varicella-zoster virus.

In some embodiments, also provided herein are nucleic acid and amino acid sequences that have homology of at least 80%, 85%, 90%, 95%, 96%, 97%, 98%, 99% (and ranges therein) as compared with the respective nucleic acid or amino acid sequences of SEQ ID NOS. 1-68 and that also exhibit one or more of the functions as compared with the respective SEQ ID NOS. 1-68: including but not limited to, (i) enhanced proliferation, (ii) enhanced activation, (iii) enhanced cytotoxic activity against cells presenting ligands to which NK cells harboring receptors encoded by the nucleic acid and amino acid sequences bind, (iv) enhanced homing to tumor or infected sites, (v) reduced off target cytotoxic effects, (vi) enhanced secretion of immunostimulatory cytokines and chemokines (including, but not limited to IFNg, TNFa, IL-22, CCL3, CCL4, and CCL5), (vii) enhanced ability to stimulate further innate and adaptive immune responses, and (viii) combinations thereof.

Additionally, in several embodiments, there are provided amino acid sequences that correspond to any of the nucleic acids disclosed herein, while accounting for degeneracy of the nucleic acid code. Furthermore, those sequences (whether nucleic acid or amino acid) that vary from those expressly disclosed herein, but have functional similarity or equivalency are also contemplated within the scope of the present disclosure. The foregoing includes mutants, truncations, substitutions, or other types of modifications.

There are provided for herein, according to several embodiments, polynucleotides encoding chimeric receptors, comprising an extracellular receptor domain, wherein the extracellular receptor domain comprises a peptide that binds native ligands of Natural Killer Group 2 member D (NKG2D), wherein the peptide that binds native ligands of NKG2D is a fragment of NKG2D, an effector domain comprising a transmembrane region and an intracellular signaling domain. In several embodiments, the fragment of NKG2D is encoded by a polynucleotide comprising the sequence of SEQ ID NO. 2 or 3 or 68, or functional equivalent thereof. In several embodiments, the polynucleotide encodes an effector domain comprising CD16. In several embodiments, the polynucleotide encodes an effector domain comprising NCR1. In several embodiments, the polynucleotide encodes an effector domain comprising NCR2. In several embodiments, the polynucleotide encodes an effector domain comprising NCR3. In some embodiments, the polynucleotide encodes an additional effector domain portion comprising 4-1BB. In several embodiments, the polynucleotide encodes a chimeric receptor made up of NKG2D and CD16. In several embodiments, the polynucleotide encodes a chimeric receptor made up of NKG2D and NCR1. In several embodiments, the polynucleotide encodes a chimeric receptor made up of NKG2D and NCR2. In additional embodiments, the polynucleotide encodes a chimeric receptor made up of NKG2D coupled to CD16 and optionally 4-1BB. In several embodiments, CD16 is replaced by NCR1, and in some embodiments, by NCR2, or even NCR3, depending on the embodiment. In several embodiments, the effector domain further comprises a GS linker between, for example, 4-1BB and one of CD16, NCR1, NCR2, or NCR3.

In several embodiments, the extracellular receptor domain further comprises a hinge region. In several embodiments, the hinge region comprises CD8α. However, in additional embodiments, the hinge region further comprises one or more linkers, which in some embodiments, comprise GS9, CD8α/GS3, truncated CD8α, GS3, and the like.

In several embodiments, the extracellular receptor domain further comprises a CD8α signal peptide. In several embodiments, the effector domain comprises one or more hemi-ITAM sequences. In several embodiments, the chimeric receptor does not comprise DNAX-activating protein 10 (DAP10). In several embodiments, the chimeric receptor does not comprise an ITAM motif, but rather employs an alternative signaling region, such as an ITSM, hemi-tam or other co-stimulatory region.

In one embodiment, there is provided a polynucleotide encoding a chimeric receptor comprising an extracellular receptor domain, wherein the extracellular receptor domain comprises a peptide that binds native ligands of Natural Killer Group 2 member D (NKG2D), wherein the peptide that binds native ligands of NKG2D is a fragment of NKG2D, a transmembrane region, wherein the transmembrane region comprises CD8α, and an effector domain, wherein the effector domain comprises 4-1BB and CD3 zeta, wherein the polynucleotide is co-expressed with an additional construct encoding membrane-bound interleukin 15 (mbIL15).

There is also provided in several embodiments, a polynucleotide encoding a chimeric receptor comprising an extracellular receptor domain, wherein the extracellular receptor domain comprises a peptide that binds native ligands of Natural Killer Group 2 member D (NKG2D), wherein the peptide that binds native ligands of NKG2D is a fragment of NKG2D, a transmembrane region, wherein the transmembrane region comprises CD8α, and an effector domain, wherein the effector domain comprises 4-1BB and the intracellular domain of 2B4 or DAP10. The polynucleotide encoding a chimeric receptor as described herein comprises a second peptide that binds native ligands of NKG2D. In several embodiments, the native ligands of NKG2D include, but are not limited to, MICA, MICB, ULBP1, ULBP2, ULBP3, ULBP4, ULBP5 or ULBP6. In several embodiments, the portion of the chimeric receptor that binds native ligands of NKG2D has at least 80% homology to SEQ ID NO: 1, 2, 3, or 68.

In several embodiments, the provided polynucleotide is an mRNA. In some embodiments, the polynucleotide is operably linked to at least one regulatory element for the expression of the chimeric receptor. As used herein, the terms "nucleic acid," "nucleotide," and "polynucleotide" shall be given their ordinary meanings and shall include deoxyribonucleotides, deoxyribonucleic acids, ribonucleotides, and ribonucleic acids, and polymeric forms thereof, and includes either single- or double-stranded forms. Nucleic acids include naturally occurring nucleic acids, such as deoxyribonucleic acid ("DNA") and ribonucleic acid ("RNA") as well as nucleic acid analogs. Nucleic acid analogs include those which include non-naturally occurring bases, nucleotides that engage in linkages with other nucleotides other than the naturally occurring phosphodiester bond or which include bases attached through linkages other than phosphodiester bonds. Thus, nucleic acid analogs include, for example and without limitation, phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), locked-nucleic acids (LNAs), and the like. As used herein, the term "operably linked," for example in the context of a regulatory nucleic acid sequence being "operably linked" to a heterologous nucleic acid sequence, shall be given its ordinary meaning and shall mean that the regulatory nucleic acid sequence is placed into a functional relationship with the heterologous nucleic acid sequence. In the context of an IRES, "operably linked to" refers to a functional linkage between a nucleic acid sequence containing an internal ribosome entry site and a heterologous coding sequence initiation in the middle of an mRNA sequence resulting in translation of the heterologous coding sequence. As used herein, the term "vector" shall be given its ordinary meaning and shall refer to a vehicle by which a DNA or RNA sequence (e.g., a foreign gene) can be introduced into a genetically engineered cell, so as to transform the genetically engineered cell and promote expression (e.g., transcription and/or translation) of the introduced sequence. Vectors include viruses, plasmids, phages, etc. The term "chimeric receptor" as used herein shall be given its ordinary meaning and shall refer to a cell-surface receptor comprising at least two polypeptide domains not naturally found together on a single protein. The term "chimeric receptor complex" as used herein refers to a first polypeptide, which may comprise at least two polypeptide domains in a combination that are not naturally found together on a single protein, which first polypeptide is associated with a second polypeptide, for example, an adaptor polypeptide, a signaling molecule, or a stimulatory molecule. Additional terms relating to generation and use of chimeric receptors as disclosed here are readily understood by one of ordinary skill in the art and can also be found in International Publication WO 2014/117121 and U.S. Pat. No. 7,994,298, each of which are incorporated by reference in their entirety herein.

Additionally provided, according to several embodiments, is a vector comprising the polynucleotide encoding any of the polynucleotides provided for herein, wherein the polynucleotides are optionally operatively linked to at least one regulatory element for expression of a chimeric receptor. In several embodiments, the vector is a retrovirus.

Further provided herein are engineered natural killer cells comprising the polynucleotide, vector, or chimeric receptors as disclosed herein. In several embodiments, these NK cells are suitable for use in the treatment of prevention of disease, such as, for example, cancer and/or infectious disease.

EXAMPLES

Methods

The following experimental methods and materials were used in the non-limiting experimental examples disclosed below.

Cell Lines and Culture Conditions

The human acute lymphoblastic leukemia cell line REH, human osteosarcoma cell line U-2 OS and human embryonic kidney fibroblast 293T (HEK 293T) cells were obtained from the American Type Culture Collection (ATCC; Manassas, Virginia). REH cells were maintained and grown in Roswell Park Memorial Institute series 1640 (RPMI-1640; Gibco, Carlsbad, California) supplemented with 10% fetal bovine serum (FBS; Hyclone, Logan, Utah) and 1% penicillin-streptomycin. Both HEK 293T and U-2 OS cells were maintained and grown in Dulbecco's modified Eagles Medium (DMEM; Hyclone) supplemented with 10% FBS and 1% penicillinstreptomycin. All mammalian cells were incubated at 37° C. with 5% CO2.

DNA Plasmids

A DNA plasmid containing the chimeric receptor NKG2D-DAP10-CD3zeta was made as previously described (see Chang et al. Cancer Research, Vol. 73 (6): 2013). Splicing by overlapping extension polymerase chain reaction (SOE-PCR) was used to fuse the individual domains forming the NKG2D-41BB-CD3zeta construct. That construct was then inserted into the Murine Stem Cell Virus (MSCV) retroviral vector (FIG. 3A). The constructs for NKG2D-CD16 and NKG2D-CD16-41BB were codon optimized and inserted into the MSCV vector (FIG. 3B) by GenScript (Nanjing, China). The sequences of the constructs were verified by DNA sequencing.

Expansion of Human NK Cells

Human peripheral blood mononuclear cells (PBMCs) were obtained by Ficoll density centrifugation of blood samples from healthy adult donors. To expand the NK cells, PBMCs were cultured with K562 genetically modified with membrane bound IL-15 and 4-1BB ligand (K562-mb15-41BBL). Cells were cultured in Stem Cell Growth Medium (SCGM; Cell Genix, Freiburg, Germany) supplemented with 40 IU of IL-2/ml every two days.

After 7 days of culture, NK cells were T-cell depleted using anti-CD3 Dynabeads (Invitrogen, Carlsbad, California). NK cells were then cultured in SCGM supplemented with 40-200 IU of IL-2/ml every two days.

Production of Retrovirus and Transduction of NK Cells

Production of retrovirus was carried out by transiently transfecting HEK 293T cells with retroviral packaging plasmids. HEK 293T cells were first seeded to a concentration of $2.5 \times 10^6$ cells in 12 ml of DMEM 18 hours before the transfection. The cells were then transfected with 3.5 µg of MSCV vector containing the respective NKG2D chimeric receptors (non-limiting constructs are illustrated schematically in FIGS. 1B-1C and 2A-2B), 3.5 µg of pEQ-PAM3, and 3.0 µg of pRDF. For control, empty MSCV vector containing GFP was used. X-tremeGENE 9 DNA Transfection Reagent (Roche, Basel, Switzerland) was used for the transfection. DMEM was replaced with conditioned RPMI-1640 24 hours after the transfection.

Transduction of NKG2D chimeric receptor transgene into NK cells was done 18 hours after the changing of media. NK cells were first suspended at a concentration of $0.25 \times 10^6$ cells in 2 ml of conditioned RPMI-1640. Cells were subsequently seeded into RetroNectin (TaKaRa, Otsu, Japan) coated tubes. RPMI-1640 containing the retrovirus (virus supernatant) was harvested from the HEK 293T cell cultures and fresh conditioned medium was added back to the cultures. The viral supernatant was supplemented with 200 IU of IL-2/ml and 3 ml of the viral supernatant was dispensed into each RetroNectin coated tubes (containing the seeded NK cells). In accordance with certain embodiments of producing NK cells, seeded NK cells were transduced six times, once every 12 hours with fresh viral media. Transduced NK cells were then harvested 48 hours after the last transduction, and cultured in SCGM with the addition of 200 IU of IL-2/ml every two days. The transduced NK cells were used for experiments 14 to 28 days after expansion.

Detection of Chimeric Receptor Expression by Flow Cytometry

Transduced NK cells were washed once with phosphate-buffered saline containing albumin, and 2 μl of rabbit serum was added. The cells were then stained with peridinin chlorophyll (PerCP)-conjugated anti-human NKG2D antibody (clone 149810; R&D Systems, Minneapolis, USA) for 10 minutes in the dark. For controls, the transduced NK cells were stained with the respective PerCP-conjugated IgG isotype antibody. All NK cells were washed again and fixed with 300 μl 0.5% formaldehyde before analysis using Accuri C6 flow cytometer (BD, Franklin Lakes, New Jersey). Data was analyzed using a paired t-test.

Cytotoxicity Assays

REH cells were stained with calcein AM red-orange (Thermo Fisher Scientific, Waltham, Massachusetts). REH cells were seeded into a 96-well round bottom plate (CoStar, Corning, New York). Transduced NK cells were then added at various effector:target (E:T) ratio. The cell cultures were incubated for four hours at 37° C. and 5% $CO_2$. Stained viable target cells were counted using the Accuri C6 flow cytometer. U-2 OS cells were seeded into 96-well flat bottom white plate (Costar) and incubated for four hours. Transduced NK cells was then added according to different E:T ratios. Cell cultures were then incubated for another four hours. Prior to analysis, Bright-Glo substrate (Promega, Madison, Wisconsin) was added to the cells. Intensity of luminescence from viable target cells was measured using FLx800 Fluorescence Reader (Bio Tek, Winooski, Vermont). Differences between intensity of luminescence and control were converted to percentage cytotoxicity.

Interferon Gamma (IFNγ) Production Assay

To determine the amount of IFNγ produced by the NK cells, effector and target cells were first cultured with (E:T of 1:1) or without REH in a 96-well round bottom plate. Cells were incubated for one hour before the addition of GolgiPlug (brefeldin A; BD Biosciences). After another 5 hours of culture, cells were labeled with phycoerythrin (PE)-conjugated anti-human CD56 antibody (clone MY31, BD Biosciences). Cells were permeabilized using a proprietary permeabilization reagent and incubated for 40 minutes in the dark. The cells were then washed with a proprietary wash buffer. Intracellular IFNγ was detected with allophycocyanin (APC)-conjugated IFNγ antibody (clone 25723.11; BD Biosciences) for 45 minutes. The cells were then fixed and analyzed using Accuri C6 flow cytometer.

Example 1—CD3-Zeta Containing NKG2D Constructs

As disclosed herein, various constructs comprising NKG2D and/or NKG2D variants coupled with various transmembrane and/or signaling domains are provided. The present experiment was conducted to evaluate the expression and cytotoxic activity of constructs comprising CD3zeta signaling domains. Two CD3zeta constructs were prepared and tested according to the methods and materials described above. Depending on the construct, the methods used can be readily adjusted to account for variations required for generating, expressing and testing a construct. The two constructs were NKG2D-DAP10-CD3zeta and NKG2D-41BB-CD3zeta. For reference FIG. 1A schematically depicts an endogenous NKG2D. In NK cells, ionic interactions between the transmembrane region of NKG2D allow association with its adaptor protein DAP10 (Wu et al., 1999). Upon ligand binding, NKG2D signals are transduced through the signaling motif, YxNM, found on DAP10. CD3zeta transduce signals through its immunoreceptor tyrosine-based activation motif (ITAM; Lanier, 2008). The two experimental constructs are illustrated schematically in FIGS. 1B and 1C, respectively. FIG. 1B shows NKG2D-DAP10-CD3zeta, with signaling occurring through both the YxNM and ITAM motifs. FIG. 1C shows the NKG2D-41BB-CD3zeta construct, which employs a CD8α hinge region as a transmembrane domain and 4-1BB and CD3zeta as signaling domains.

Figure 4A:
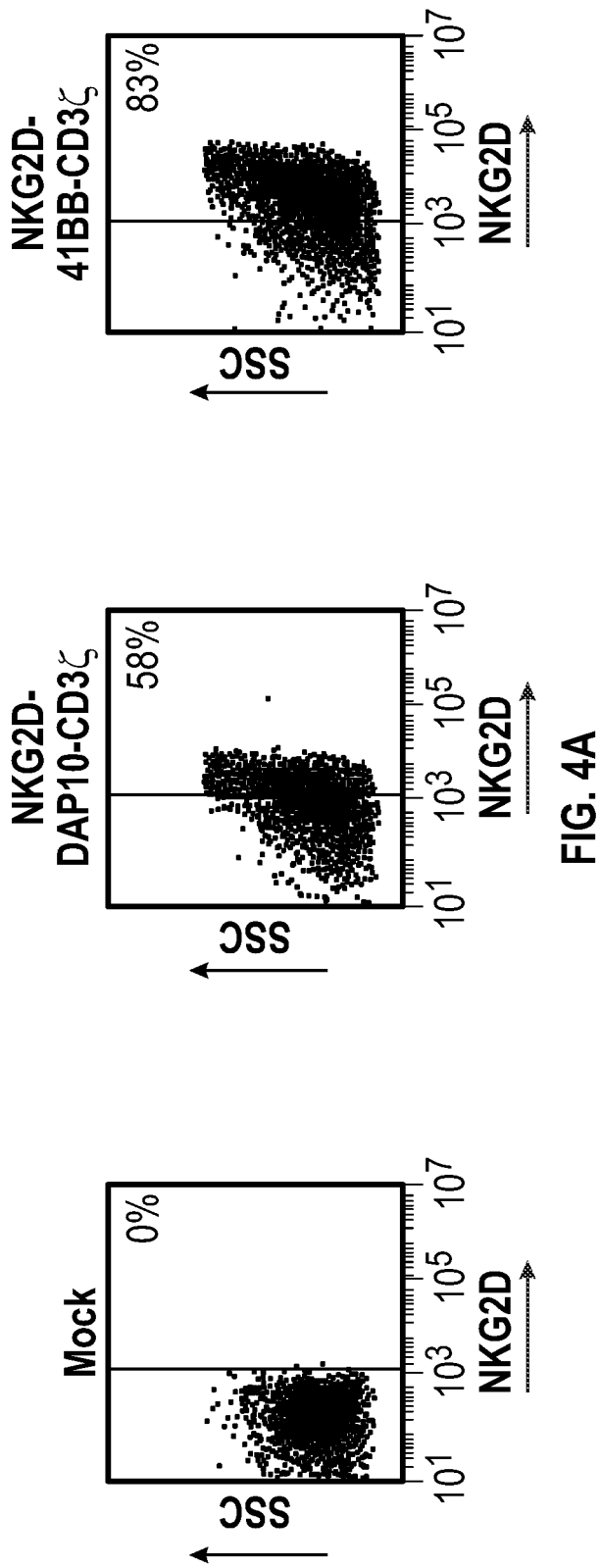

The ability of NK cells to effectively express these constructs was first assessed. NK cells expanded from PBMC of healthy adult donors were transduced with one of the two chimeric receptors. Mock-transduced NK cells were used as control (transduced with empty MSCV vector containing GFP only). The presence and relative abundance of the chimeric receptors were determined through staining the NK cells with a Per-CP conjugated anti-NKG2D antibody. FIG. 4A depicts representative flow cytometry data related to the percentage of NKG2D-positive NK cells after transduction with Mock (left panel), NKG2D-DAP10-CD3zeta (center panel) or NKG2D-41BB-CD3zeta (right panel) constructs. Mock transduced NK cell showed no NKG2D expression with the antibody used (which does not showing staining above an isotype-matched nonreactive antibody, despite the naturally high NKG2D expression on activated NK cells), while just under 60% of cells transduced with the NKG2D-DAP10-CD3zeta construct exhibited NKG2D expression above the isotype-matched non-reactive antibody control, and over 80% of NK cells transduced with the NKG2D-41BB-CD3zeta. Pooled data for the percentage of NKG2D positive NK cells from all donors is shown in FIG. 4B. Both engineered NKG2D constructs result in substantial gain in NKG2D expression compared to Mock, though there is not a significant difference between the percent expression of the two constructs. FIG. 4C depicts expression data based on Mean Fluorescence Intensity (MFI), which represents, within the population expressing the NKG2D construct, the degree to which that cell expresses the construct (e.g., multiple copies of the construct per cell would yield a greater MFI). By this measure, the expression of the NKG2D-41BB-CD3zeta is significantly greater than that of the NKG2D-DAP10-CD3zeta construct.

Collectively, these data demonstrate that, in accordance with several embodiments disclosed herein, engineered constructs can successfully be expressed on NK cells. In several embodiments, enhanced expression of the construct can be achieved by repeated transduction of the NK cells with a particular construct. In several embodiments, the components of the constructs can be delivered to a cell in a single vector, or alternatively using multiple vectors. Depending on the embodiment, the construct itself may lead to enhanced expression, for example a linear or head to tail construct may yield increased expression because of a lesser degree of in-cell assembly that a multiple subunit construct requires.

Further to successfully expressing NKG2D constructs on NK cells, effective signaling of the NK cells is required to act on target cells. To evaluate the potency of the two populations of transduced NK cells, cytotoxicity assays were performed using two cell lines that are sensitive to NK cell activity, REH (suspension cells) and U-2 OS (adherent cells). Data summarizing the percentage cytotoxicity of the different groups of NK cells against REH cells and across independent donors at two E:T ratios are shown in FIGS. 5A-5C (error bars represent standard deviation; all experiments are done in triplicates; n=3 ($P<0.001$)). As depicted in FIGS. 5A-5C, NK cells expressing either NKG2D chimeric receptor (NKG2D-DAP10-CD3zeta shown with an arrow labeled (a) and NKG2D-41BB-CD3zeta shown with an arrow labeled (b)) had a significantly higher cytotoxicity against REH for all three donors as compared to mock NK cells (shown with an arrow labeled (c)). The mean percentage cytotoxicity of NKG2D-DAP10-CD3zeta-expressing NK cells was 91.8%±5.8% (1:1 E:T ratio) and 83.9%±5.6% (1:2 E:T ratio). Those NK cells transduced with NKG2D-41BB-CD3zeta showed similar potencies—87.4%±6.1% at a 1:1 E:T ratio and 76.2%±4.8% at a 1:2 E:T ratio. Chimeric receptor-expressing NK cells also showed elevated cytotoxicity against U-2 OS when compared to mock-transduced NK cells (See FIGS. 6A-6C, FIG. 6A depicts NKG2D-DAP10-CD3zeta shown with an arrow labeled (a), FIG. 6B depicts NKG2D-41BB-CD3zeta shown with an arrow labeled (b) and FIG. 6C depicts mock NK cells shown with an arrow labeled (c)).

These data provide evidence that NK cells can not only be engineered to express chimeric receptor constructs, but those cells that express the chimeric receptors are able to be activated and successfully generate enhanced cytotoxic effects against target cells. Importantly, these data also show that there is only a slight decrease in the potency of the cells when in the presence of a greater number of target cells (doubled in this experiment). This suggests that the desired cytotoxic effects of the engineered NK cells can still be realized, even when the NK cells are present in smaller numbers vis-à-vis target cells, as would likely be the case in clinical use. Moreover, these data indicate that, according to some embodiments, a lesser density or degree of chimeric receptor expression on a given NK cell does not necessarily result in coordinately reduced cytotoxic effects, and can be associated with an unexpected efficacy of the NK cells in view of their lesser construct expression. Additionally, these data embody the unexpectedly enhanced cytotoxicity that is achieved according to several embodiments. While non-engineered NK cells are cytotoxic, and express a significant amount of NKG2D upon activation, it is unexpected that the engineered cells disclosed herein can push the cytotoxic effects significantly beyond what can be considered an already elevated ceiling (e.g., native NK cell cytotoxicity).

Further to the cytotoxicity data, the mechanism by which the NK cells are exerting these effects was examined, by evaluating the production if interferon-gamma (IFNγ) by the NK cells expressing the various NKG2D constructs. IFNγ is a key cytokine produced and released by NK cells (typically during an innate immune response) that recruits macrophages and has immunostimulatory effects. FIG. 7A shows the relative amount of IFNγ production (measured by MFI) in Mock (left panel), NKG2D-DAP10-CD3zeta-expressing NK cells (center panel), and NKG2D-41BB-CD3zeta-expressing NK cells (right panel) with or without stimulation by REH cells. NK cells were stained by APC-conjugated anti-IFNγ antibody for intracellular IFNγ. Data was analyzed by paired t test. These data show that each of the three groups of NK cells were observed to have a similar level of IFNγ production without stimulation, with an increase observed after stimulation by REH cells. As provided for in several embodiments, engineered NK cells expressing NKG2D constructs can lead to robust cytokine production. The presence of a target cell (here, REH cells) to which the engineered NK cells responds sets into motion the biochemical cascade which leads to IFNγ production and ultimately cytotoxic effects. As shown in FIG. 7A, the NKG2D-41BB-CD3zeta-expressing NK cells show a robust production of IFNγ in the presence of stimulatory REH cells. Interestingly, the NKG2D-DAP10-CD3zeta-expressing NK cells failed to show a similar degree of response. This is further demonstrated in FIG. 7B, where levels of IFNγ between different groups of NK cells after stimulation with REH cells (median values were represented; data was analyzed by unpaired t test) are evaluated. All IFNγ experiments were conducted in triplicates, with three independent donors, n=9. FIG. 7B shows that IFNγ production by NKG2D-DAP10-CD3zeta-expressing NK cells was not significantly different from mock-transduced NK cells. In contrast, the NKG2D-41BB-CD3zeta-expressing NK cells show a significant increase in IFNγ production as compared to mock-transduced NK cells. These data are interesting because they demonstrate that, as discussed herein, signaling by a chimeric receptor in response to ligand binding is an essential step in generating cytotoxic effects against a target cell of interest. However, there is not a singular pathway through which the various constructs signal, as NK cells transduced with two different chimeric receptors both exhibit relatively similar cytotoxicity, but without mirroring levels of IFNγ production. Thus, according to some embodiments, constructs are provided that achieve cytotoxic effects through an elevated production of IFNγ, or other immunostimulatory cytokine, as compared to normal NK cells. However, in several embodiments, increased production of IFNγ is not necessarily achieved or detected, rather another immunostimulatory pathway can be exploited by a given chimeric construct to achieve elevated cytotoxic effects.

Example 2—CD16 and CD16-4-1BB Containing NKG2D Constructs

Additional constructs were generated to evaluate expression, cytotoxicity and cytokine production. As provided for herein, several embodiments relate to constructs comprising a truncated NKG2D (in some embodiments codon optimized), that employ a CD16 transmembrane and/or signaling domain. The constructs generated for evaluation in this experiment are schematically shown in FIGS. 2A-2B, which show the structure of A) NKG2D-CD16 and B) NKG2D-CD16-41BB chimeric receptors. Both chimeric receptors rely on the transmembrane region of CD16 to associate with either CD3zeta or FcRγ. The plasmids used to generate these constructs are shown in FIG. 3B. As discussed above, in several embodiments, the constructs employed rely on endogenous expression of CD3zeta or FcRγ, however, in several embodiments the plasmid encoding the chimeric receptor (or a separate plasmid) is configured to elevate expression of CD3zeta and/or FcRγ by the NK cell, thereby enhancing the potency of the cells.

Figure 8C:
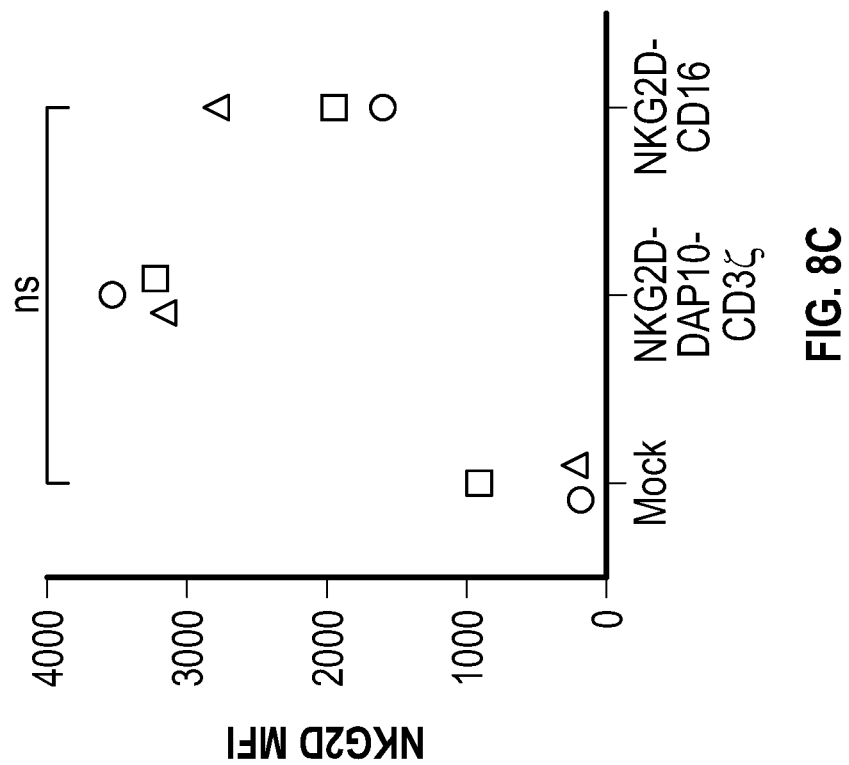
Figure 8B:
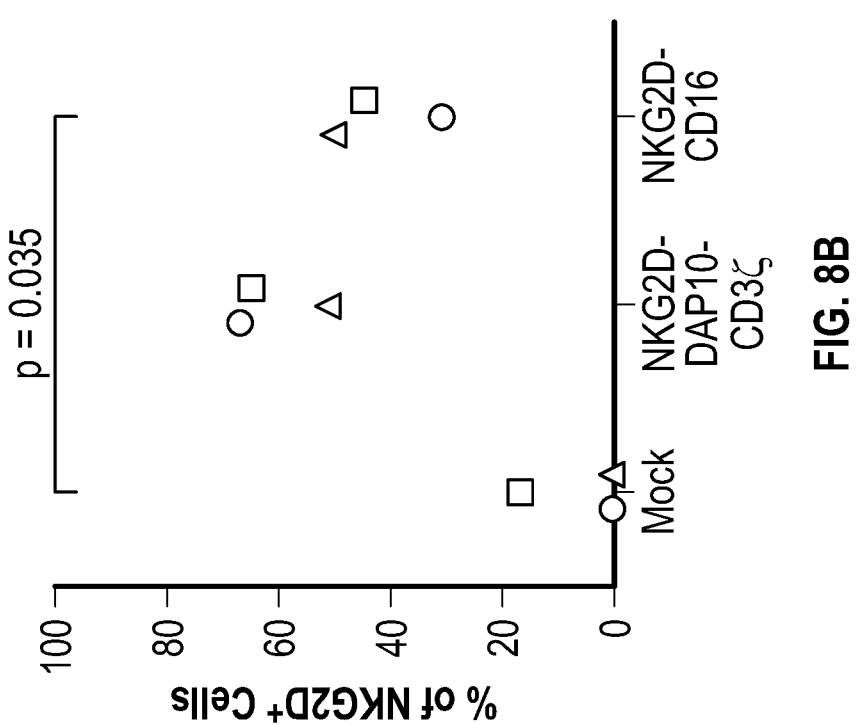

As above, expression levels of the constructs were evaluated. FIG. 8A depicts representative flow cytometry data for mock (left panel), NKG2D-DAP10-CD3zeta-expressing NK cells (center panel), and NKG2D-CD16-expressing NK cells (Experiments were conducted using cells from three independent donors represented by different symbols. Data was analyzed by paired t test). FIG. 8B shows summary data relating to the percentage of cells that that express NKG2D (and hence the constructs). As expected, mock-transfected NK cells show low levels of NKG2D expression with the antibody used. In contrast, both of the engineered constructs exhibited significantly enhanced expression, with NKG2D-CD16-transduced NK cells expressing 35.8%±6.9% greater expression as compared to mock-transduced NK cells. Additionally, as evaluated by MFI (FIG. 8C), NKG2D-CD16-transduced NK cells also exhibited increased expression of the construct. These data are important to demonstrate that the constructs can effectively be introduced into NK cells and are expressed.

Having established expression of the constructs, their ability to exhibit cytotoxic effects was evaluated. As discussed above, NK cells from three donors were tested for cytotoxic effects against REH cells and U-2 OS cells, each at three E:T ratios (all experiments were done in triplicate, n=3). Interestingly, the enhanced expression of the NKG2D-CD16 construct as compared to mock NK cells did not result in increased cytotoxicity (see FIG. 9A-9C, error bars represent standard deviations). As with the prior example, NKG2D-DAP10-CD3zeta-expressing NK cells (shown with an arrow labeled (a)) did exhibit an increased cytotoxicity. With respect to cytotoxicity against U-2 OS cells, the NKG2D-CD16 (shown with an arrow labeled (b)) did exhibit an increased cytotoxicity as compared to mock NK cells (shown with an arrow labeled (c)) (see FIGS. 10A-10C). These data indicate that the degree of cytotoxic impact on a particular given target cell type may vary with the NK construct used. In some embodiments, a particular construct may not be as effective, however, in several embodiments, combinations of populations of NK cells can be used and exhibit synergistic effects. In other words, a population of NK cells, with a portion expressing NKG2D-CD16 and a portion expressing NKG2D-DAP10-CD3zeta (or other combination of any of the constructs disclosed herein), may exhibit unexpectedly enhanced cytotoxicity as compared to either sub-population alone.

Figure 11:
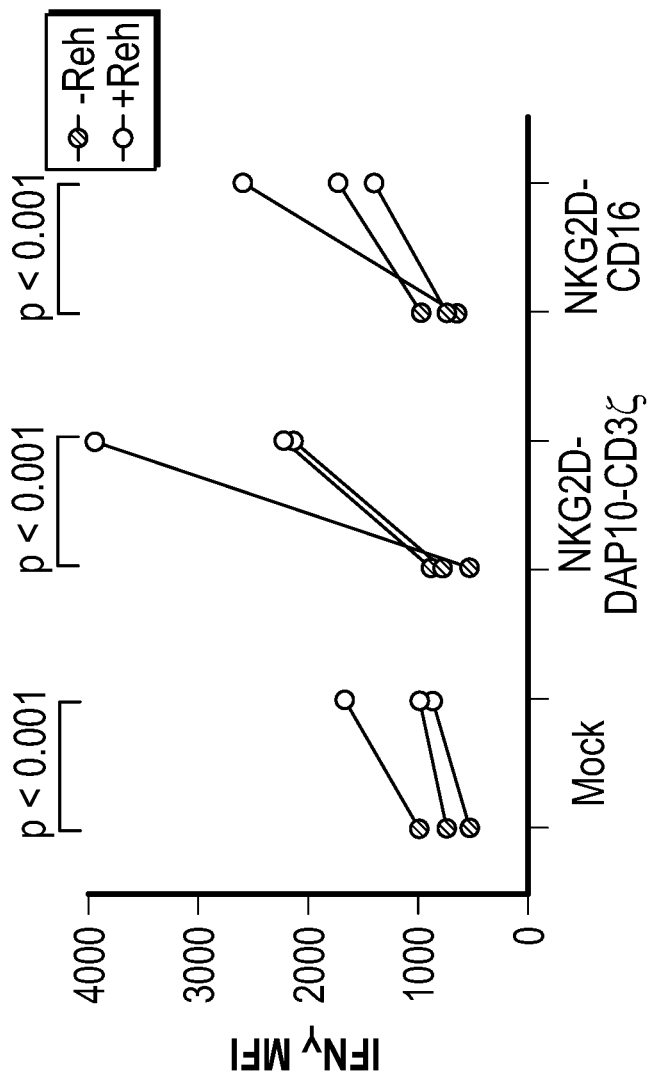
FIG. 11 depicts data related to the production of interferon-gamma by NK cells expressing various NKG2D constructs in the presence and absence of stimulation with REH cells.

Interferon-γ production was measured next, in order to confirm the mechanism of action of the transfected NK cells. The NK cells expressing the various constructs were either stimulated by REH cells, or not, and the production of IFNγ was measured. These data are shown in FIG. 11 (data was analyzed by paired t test). All groups of NK cells had similar level of IFNγ without stimulation, and an increase after incubation with REH cells. The NKG2D-CD16-expressing NK cells exhibited an increase in IFNγ production of 634±211 MFI, which was greater than the increase exhibited by the mock-transduced NK cells (423±70 MFI). However, the increase was lower than that observed for NKG2D-DAP10-CD3zeta-expressing NK cells, which increased 2041±411 MFI. In line with data, according to several embodiments the production of IFNγ is correlated with the cytotoxic effects that NK cells expressing certain constructs exhibit.

Figure 12A:
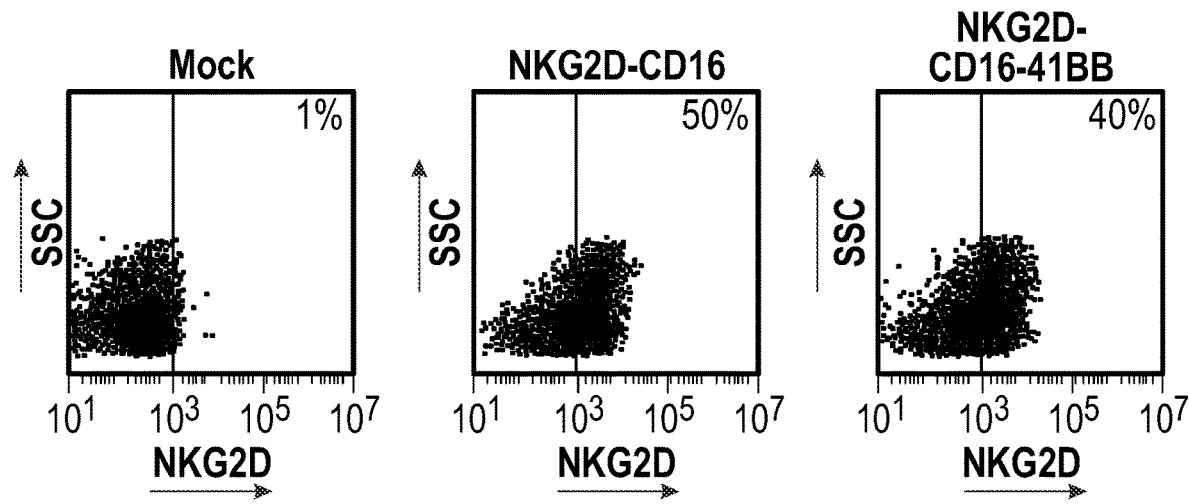
FIGS. 12A-12B depict data related to expression of NKG2D-DAP10-CD3zeta and NKG2D-CD16-41BB in NK cells.
Figure 12B:
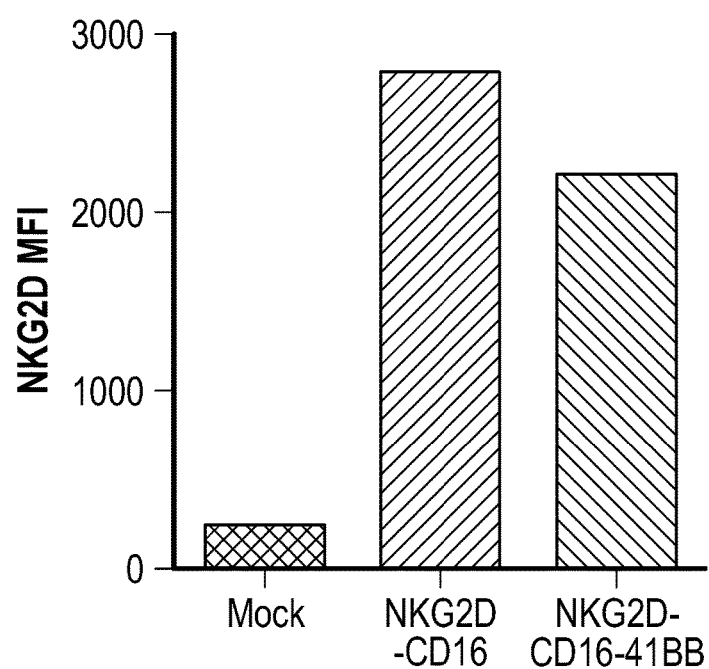

In accordance with several embodiments disclosed herein, multiple signaling regions may be used. Additional experiments were conducts to evaluate the expression of a NKG2D-CD16-41BB in expanded NK cells (experiments were conducted using cells from one donor). The expression data is shown in FIGS. 12A-12B. FIG. 12A shows raw flow cytometry data that demonstrate that the addition of the 4-1BB signaling region does not significantly impair the expression of the construct by NK cells, as compared to the NKG2D-CD16 construct. This is also reflected in the summary histogram of FIG. 12B that shows the relative amount of NKG2D receptors on the surface of each of the NK cell groups tested. The NKG2D-CD16-41BB shows slightly reduced MFI as compared to NKG2D-CD16, but both constructs show elevated expression versus mock.

Cytotoxic effects were evaluated as described above, using both REH and U-2 OS cells as targets. FIGS. 13A-13B depict the resultant data (error bars represent standard deviations; all experiments were conducted in triplicates, n=3). FIG. 13A shows the cytotoxic effects of the constructs against REH cells. Similar to the experiment above, the NKG2D-CD16-expressing cells shown with an arrow labeled (b)) did not show significantly elevated cytotoxic effects as compared to mock NK cells shown with an arrow labeled (a). In contrast, NK cells expressing NKG2D-CD16-41BB (shown with an arrow labeled (c)) showed enhanced cytotoxicity against REH cells. With respect to efficacy against U-2 OS cells, both the NKG2D-CD16 and NKG2DCD16-41BB expressing cells showed enhanced cytotoxicity, with the NKG2D-CD16-41BB expressing cells exhibiting a more robust cytotoxic effect. This demonstrates that, in accordance with several embodiments, use of a combination of signaling domains can result in unexpected enhancements in the efficacy of a transduced NK cell. Thus, as described above, several embodiments employ two or more transmembrane/signaling domains that work synergistically together to yield enhanced cytotoxicity against target cells.

Example 3—Additional NKG2D Constructs

Figure 16A:
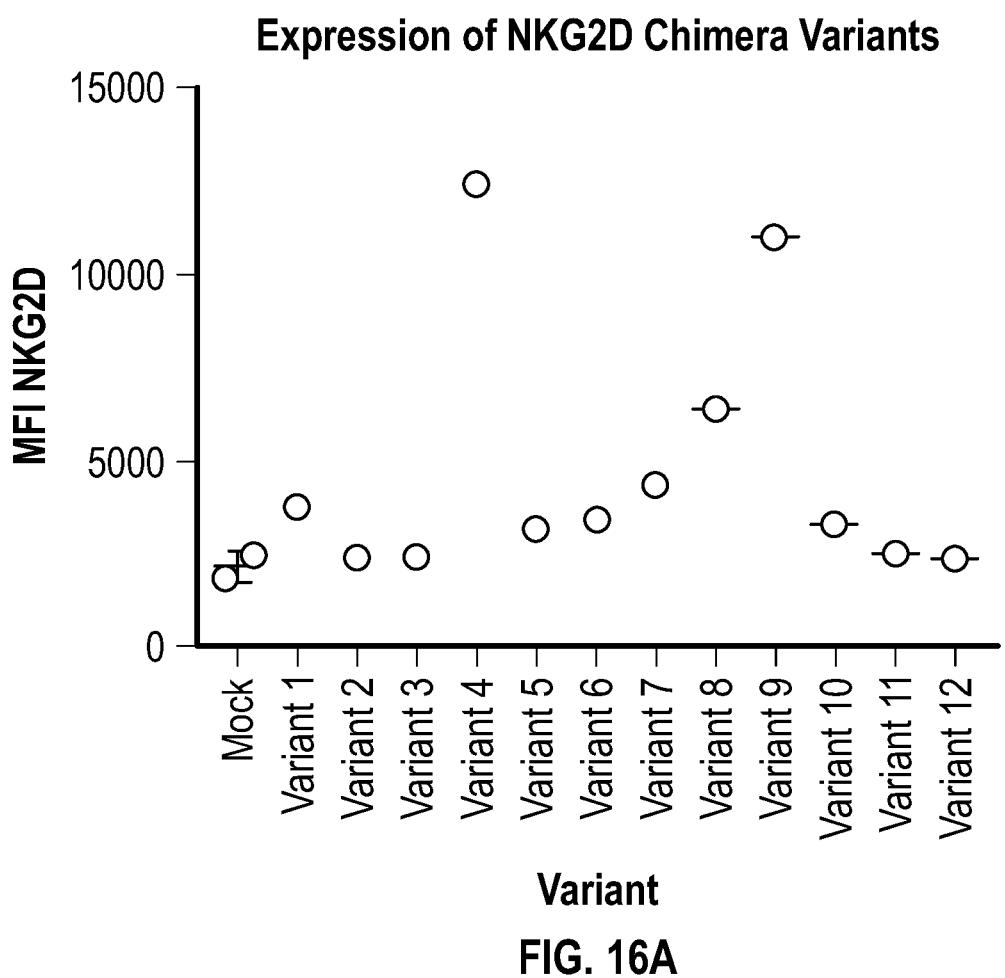
FIGS. 16A-16C depict data related to the expression of the various NKG2D constructs in NK cells.
Figure 16B:
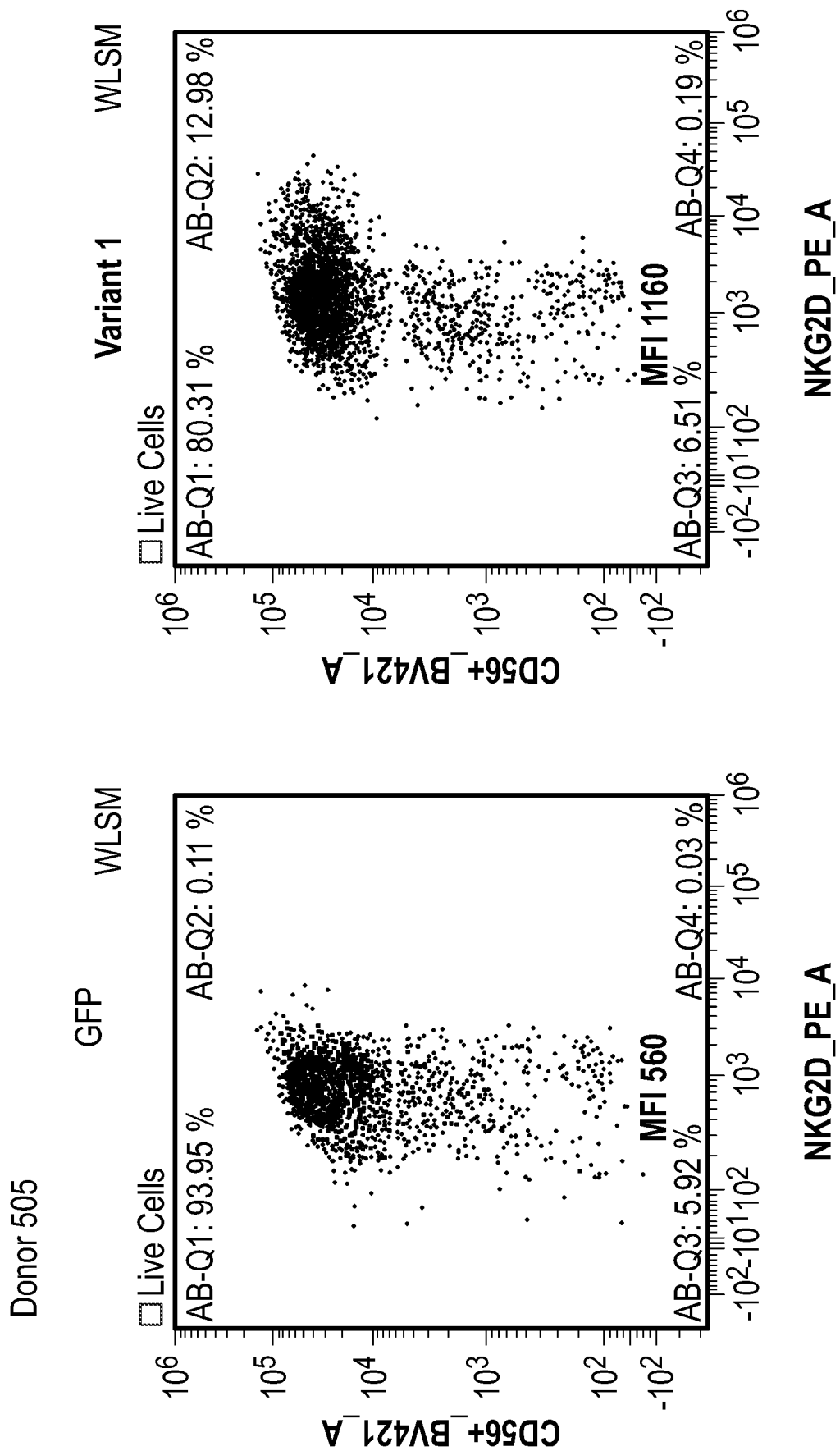
Figure 16B:
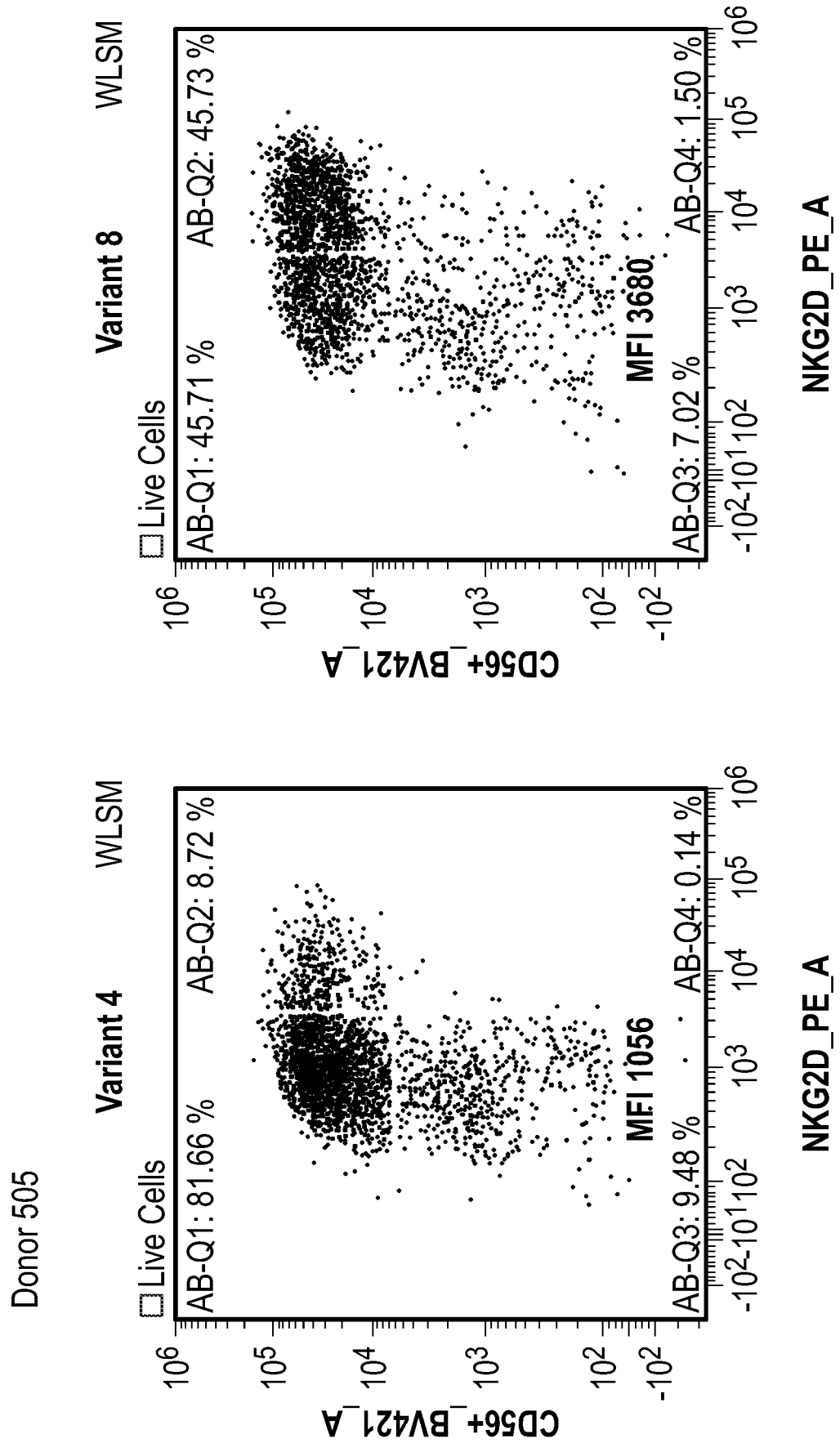
Figure 16B:
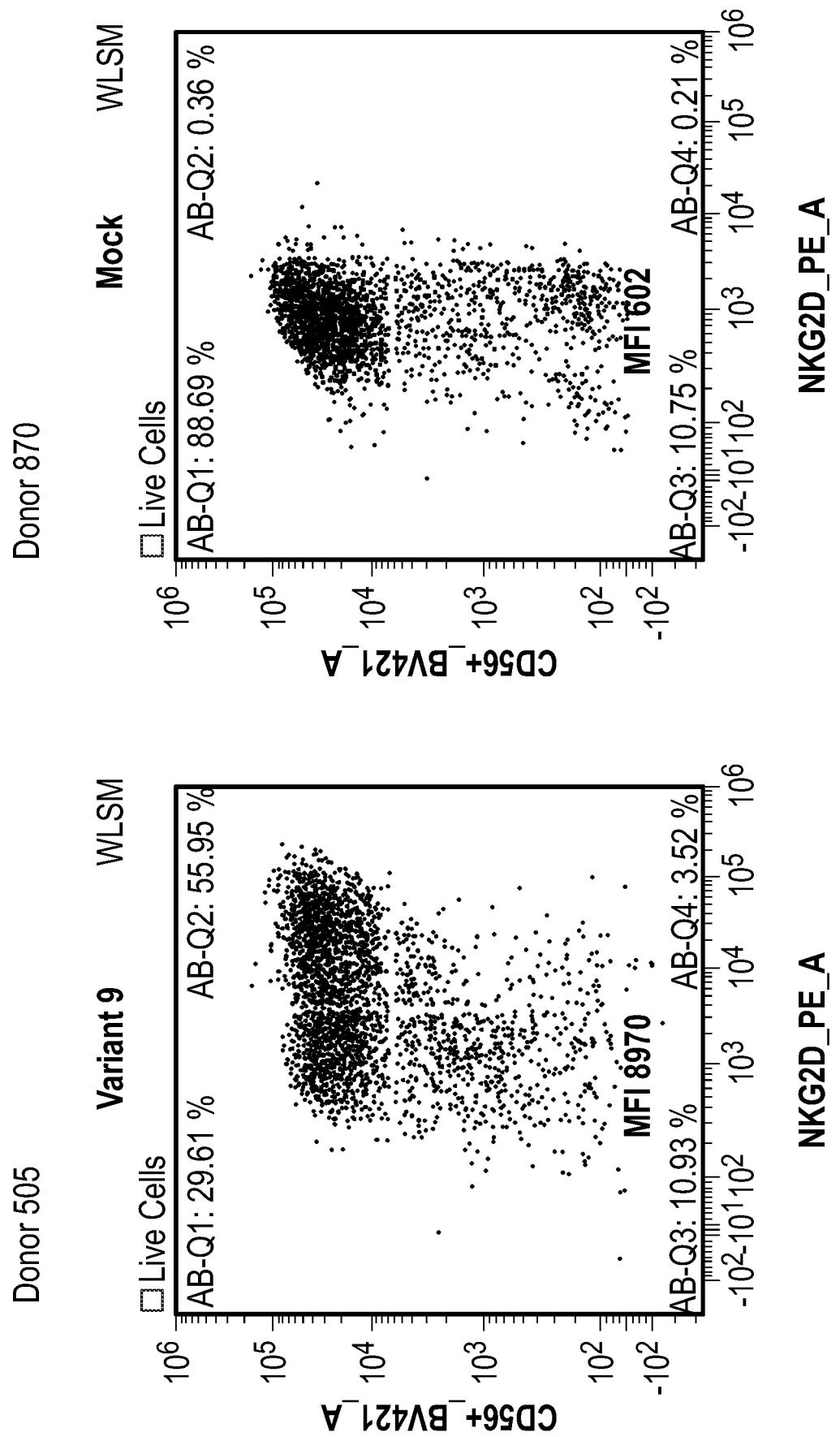
Figure 16B:
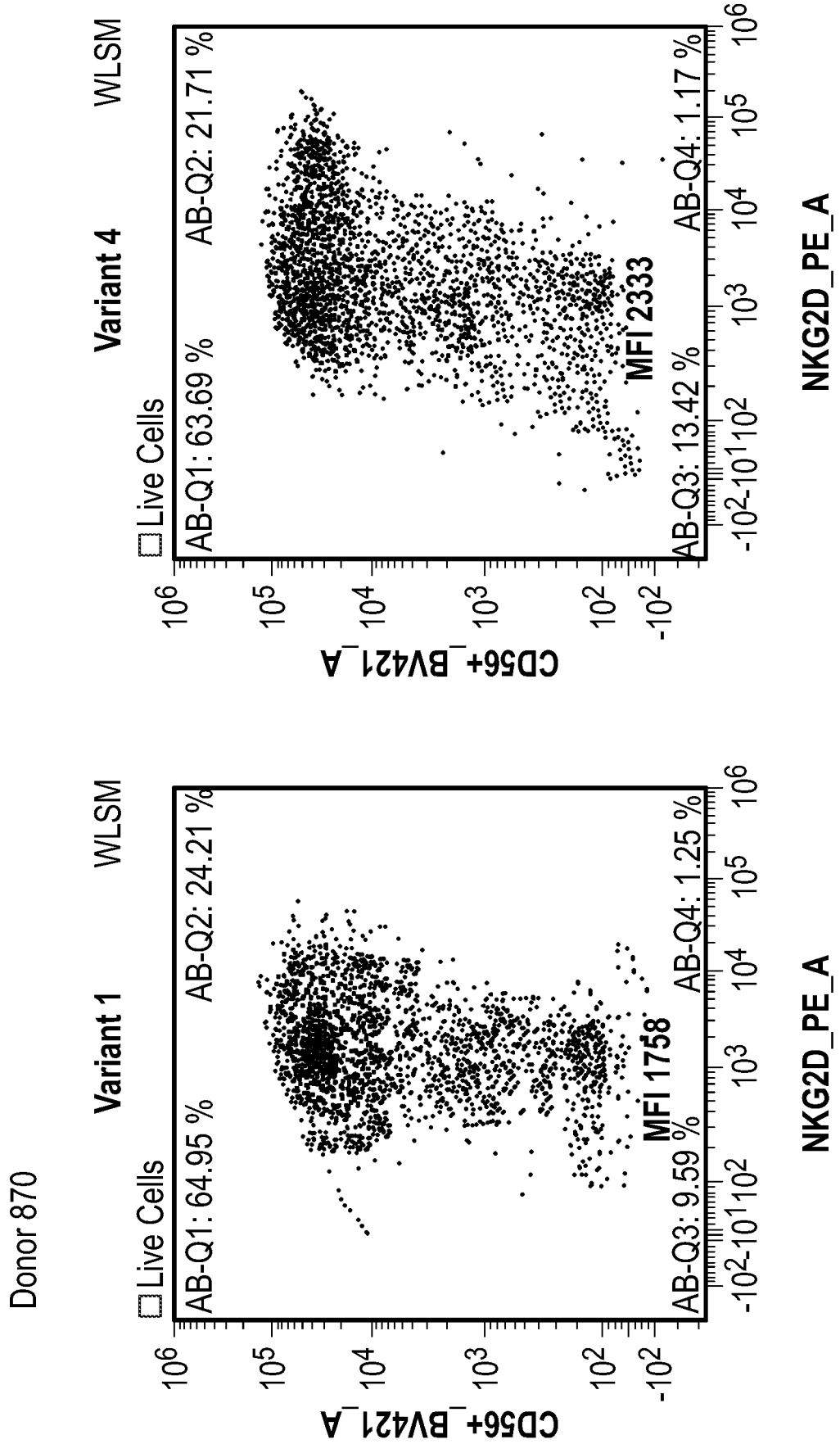
Figure 16B:
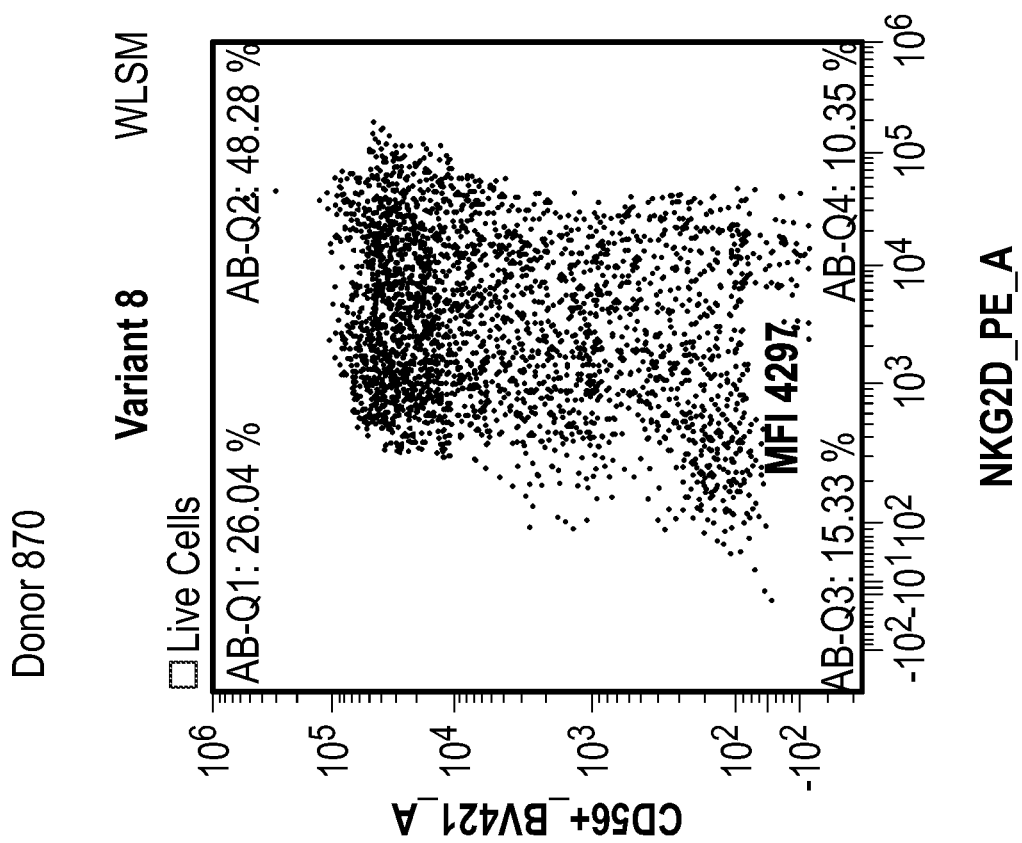
Figure 16C:
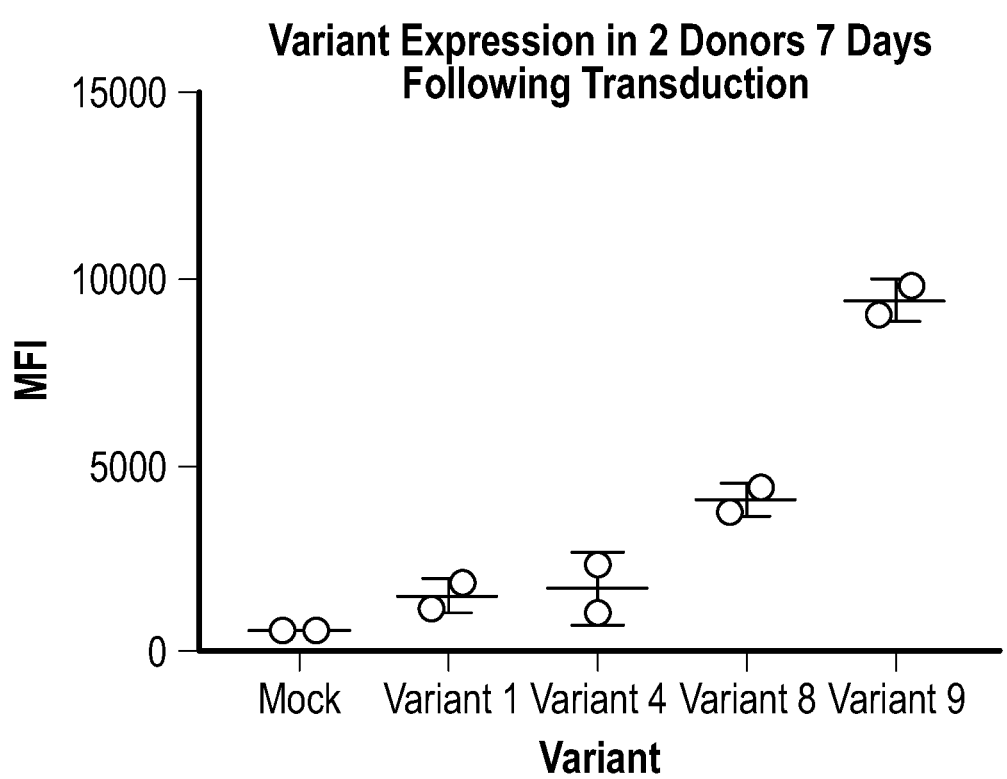
Figure 17:
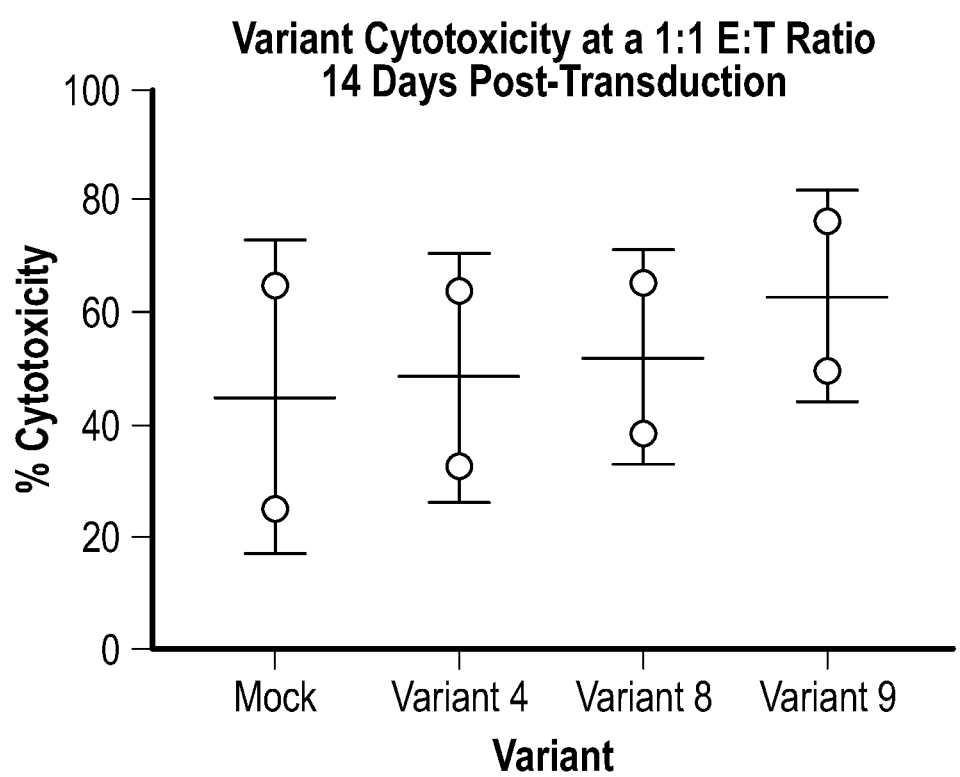
FIG. 17 depicts data related to the cytotoxicity of the various NKG2D constructs 14 days post-transduction into NK cells at a 1:1 E:T ratio.

Additional constructs with varying extracellular domains, transmembrane domains, and intracellular effector domains were generated to evaluate their expression and cytotoxicity. The 12 constructs generated for evaluation in this experiment are schematically shown in FIG. 14. Some of these variant chimeric receptors rely on a CD16 transmembrane region to associate with either CD3zeta or FcRγ. As discussed above, in several embodiments, the constructs employed rely on endogenous expression of CD3zeta or FcRγ, however, in several embodiments the plasmid encoding the chimeric receptor (or a separate plasmid) is configured to elevate expression of CD3zeta and/or FcRγ by the NK cell, thereby enhancing the potency of the cells. As above, expression levels of the constructs were evaluated. Mock-transfected NK cells show low levels of NKG2D expression as evaluated by MFI (FIG. 16A). In contrast, NK cells transduced with the variant NKG2D constructs described above showed varying levels of NKG2D expression, with engineered variant constructs 4 and 9 exhibiting significantly enhanced expression in NK cells. FIG. 16B depicts representative flow cytometry data for variant NKG2D constructs 1, 4, 8, 9 after transduction into the NK cells of two donors. Relative to mock-transduced NK cells, Variant 8- and 9-transduced NK cells showed particularly strong expression of the chimeric receptor. Variant construct expression persisted in the NK cells of two donors 7 days following transduction, with Variants 8 and 9 showing particularly elevated levels as evaluated by MFI (FIG. 16C). These data are important to demonstrate that the constructs can effectively be introduced into NK cells and are expressed. Having established expression of the constructs, their ability to deliver cytotoxic effects in transduced NK cells was also evaluated. The cytotoxicity of the NKG2D variant constructs 4, 8, and 9 were evaluated 14 days post-transduction into NK cells at a 1:1 E:T ratio (FIG. 17).

Figure 18A:
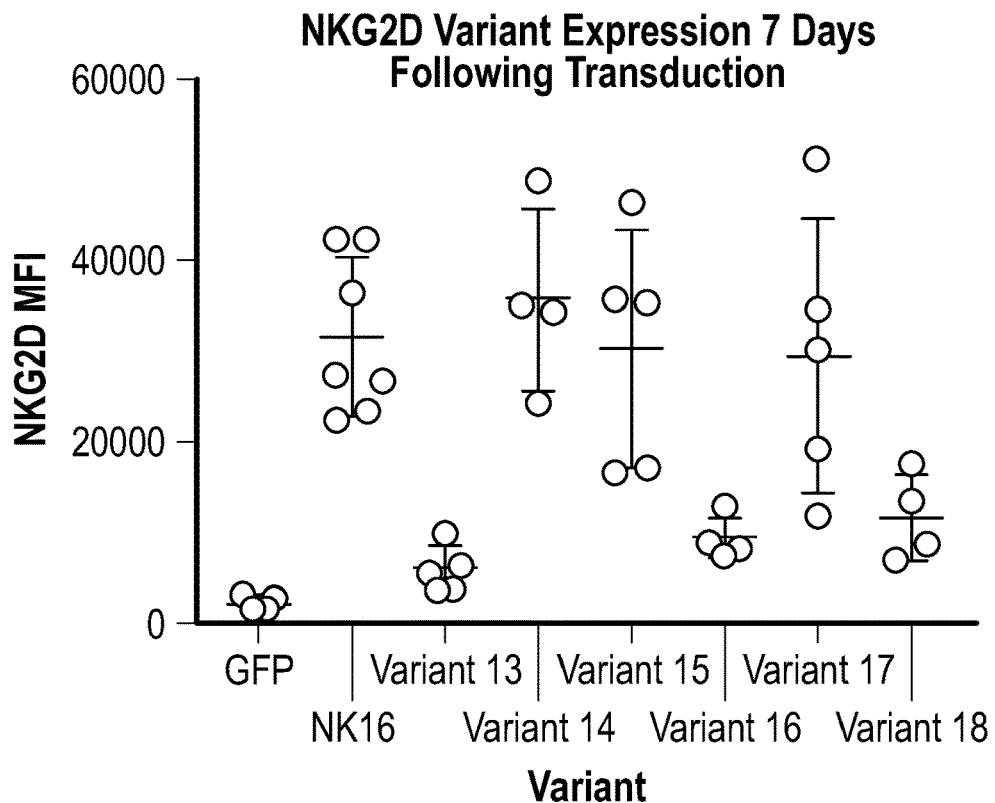
FIGS. 18A-18B depicts data related to the expression of the various NKG2D constructs following transduction into NK cells.
Figure 18B:
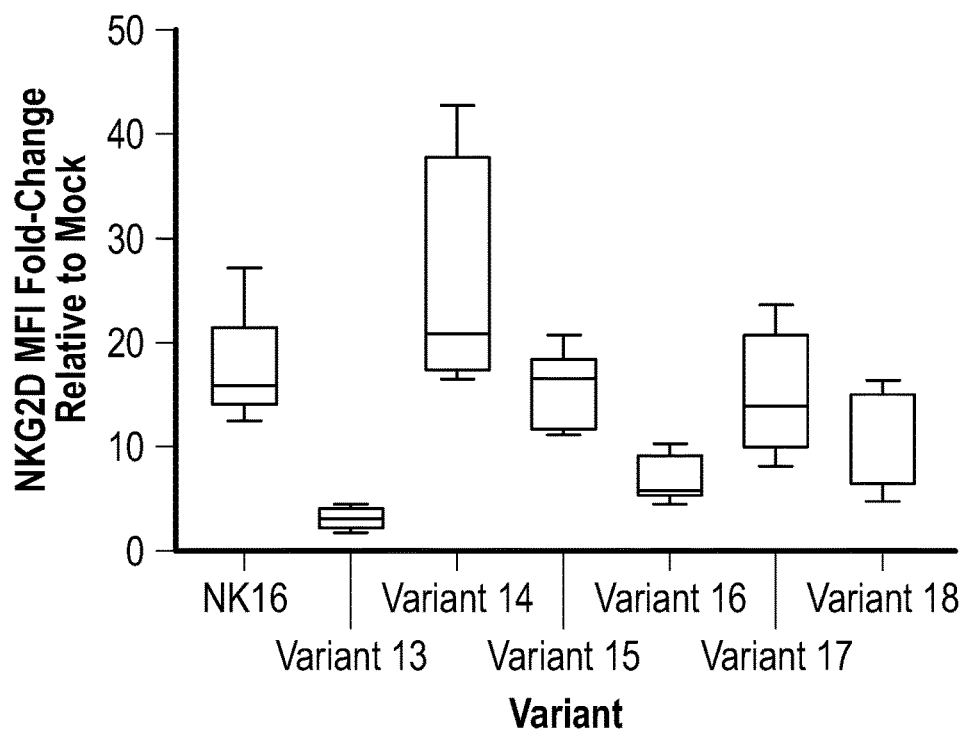
Figure 19A:
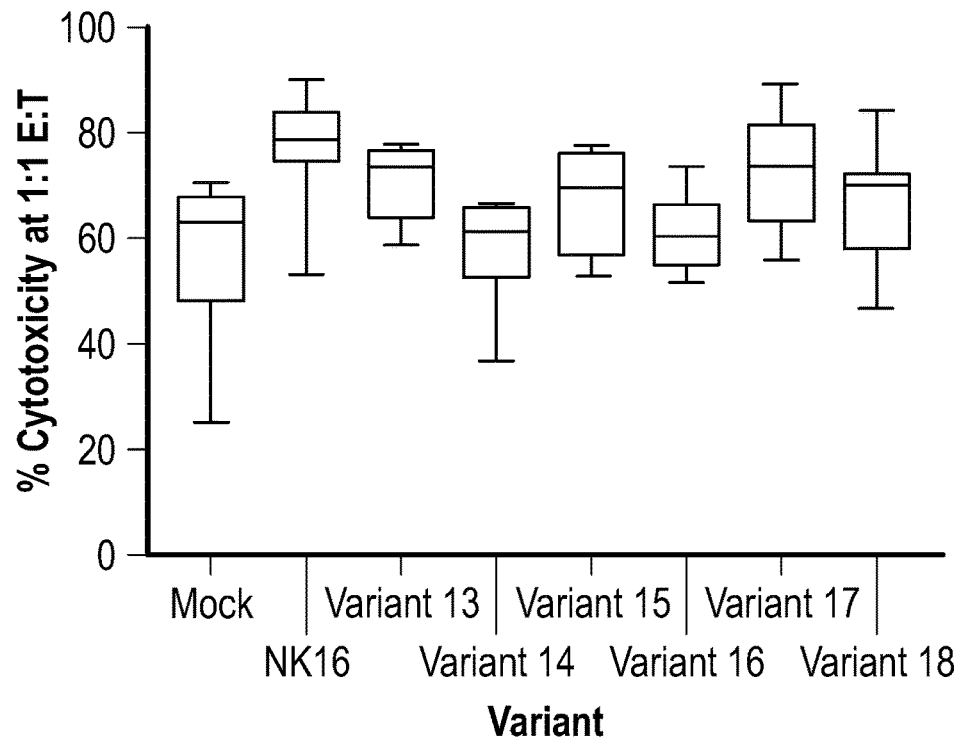
FIGS. 19A-19B depict data related to the cytotoxicity of the various NKG2D constructs.
Figure 19B:
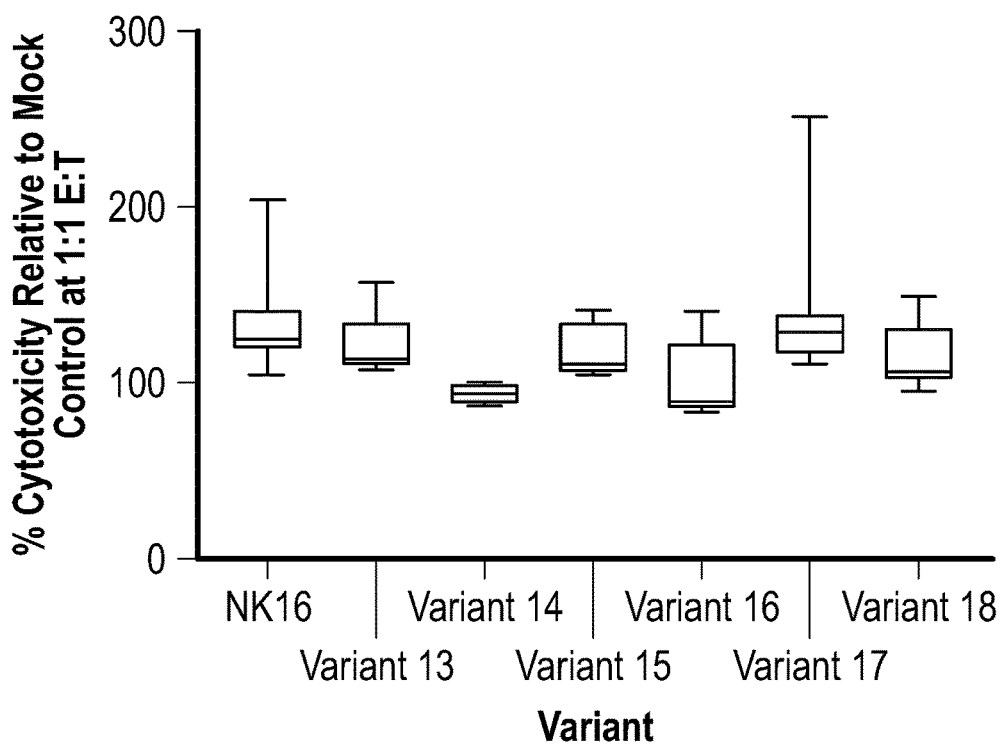
Figure 20:
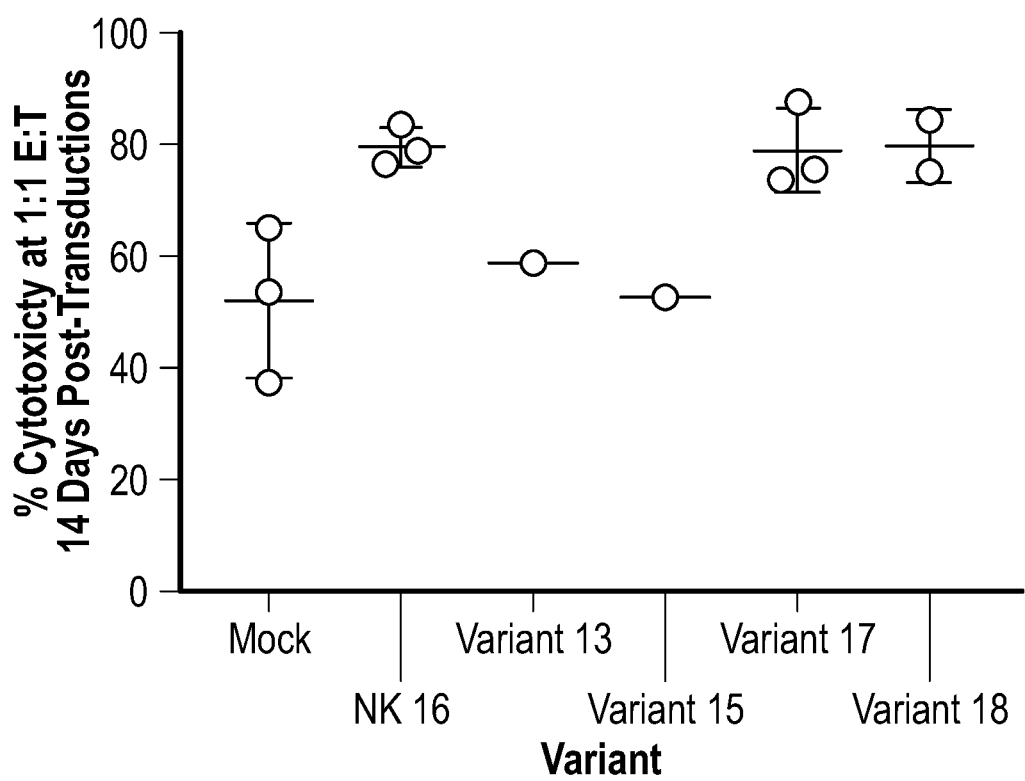
FIG. 20 depicts data related to the cytotoxicity of the various NKG2D constructs 14 days post-transduction into NK cells at a 1:1 E:T ratio. Prior to analysis NK cells were cultured in media supplemented with 40 IU of IL-2/mL.

Further variant constructs were generated and are schematically shown in FIG. 15, which show the structure of chimeric receptors comprising various extracellular domains, transmembrane domains, and intracellular effector domains. Some of these variant chimeric receptors rely on an effector domain comprising CD3zeta and/or another signaling domain to transduce signaling upon ligand binding, while other variant chimeric receptors comprise a CD3zeta transmembrane domain that recruits full-length CD3zeta molecule to the synapse via dimerization. As above, expression levels of the constructs were evaluated. As evaluated by MFI (FIGS. 18A-B), NK cells transduced with engineered constructs exhibited increased expression of the chimeric receptor relative to mock transduced cells. Cytotoxic effects were evaluated as described above using an effector:target ratio of 1:1. As depicted in FIGS. 19A-B, NK cells transduced with engineered constructs (particularly variant 18) have enhanced cytotoxicity relative to the mock control.

Figure 21:
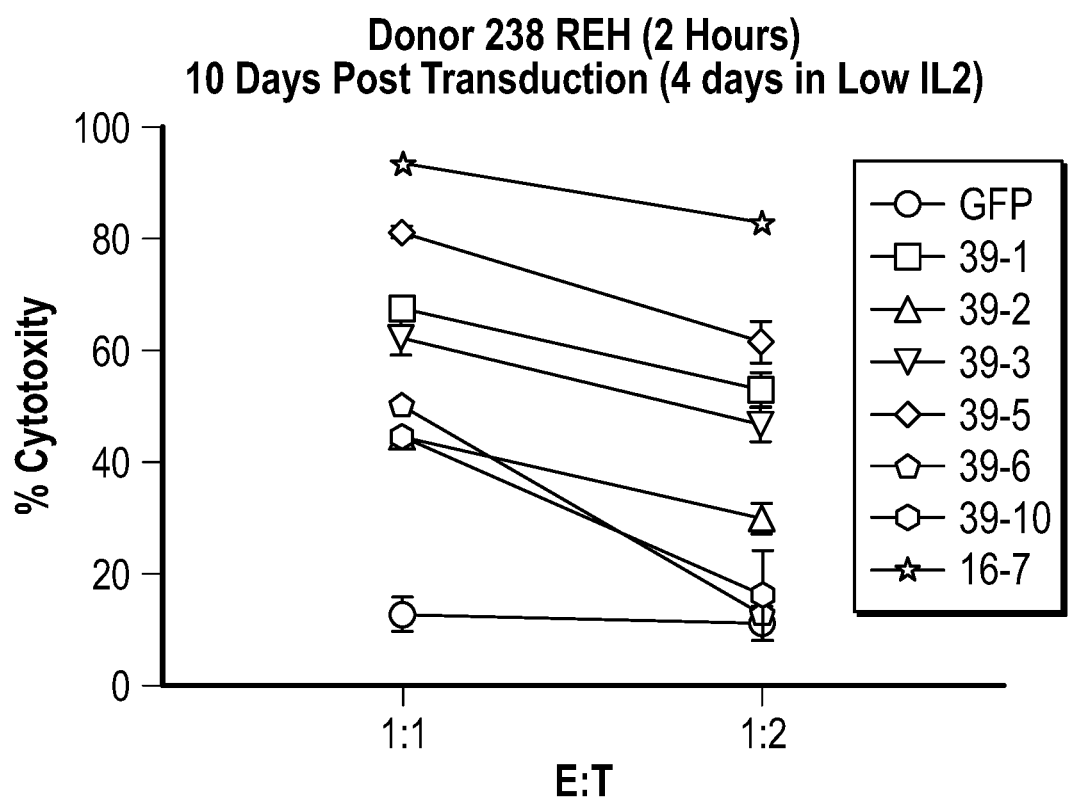
FIG. 21 depicts data related to the cytotoxicity of the various NKG2D constructs 10 days post-transduction into Donor 238 NK cells (with 4 days of culturing in media supplemented with 40 IU of TL-2/mL every two days) against cultured REH cells at 1:1 and 1:2 E:T ratios for two hours.
Figure 23A:
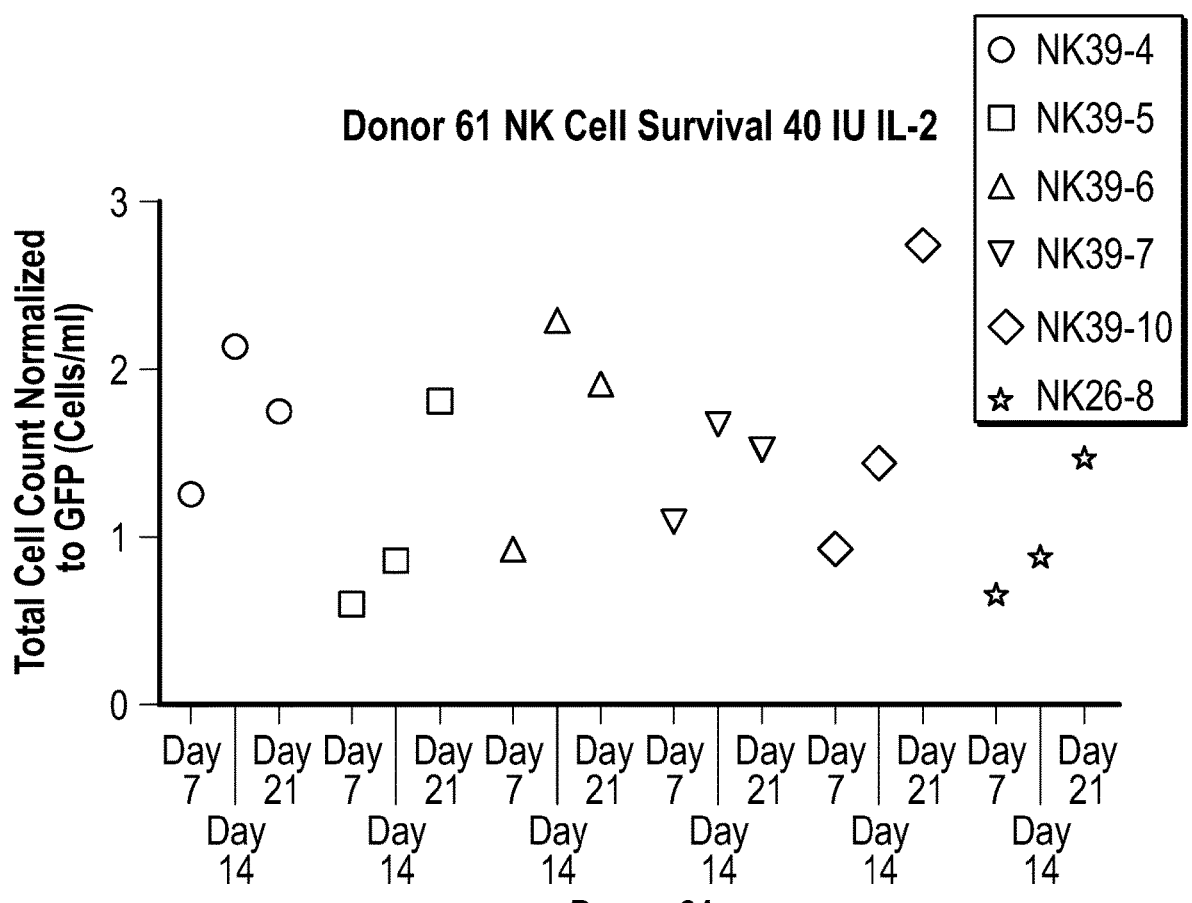
FIGS. 23A-23B depict data related to the persistence of the various NKG2D constructs generated from NK cells from two different donors (Donor 61 and Donor 103 in FIGS. 23A and 23B, respectively). NK cells were cultured in media supplemented with 40 IU of IL-2/mL.
Figure 23B:
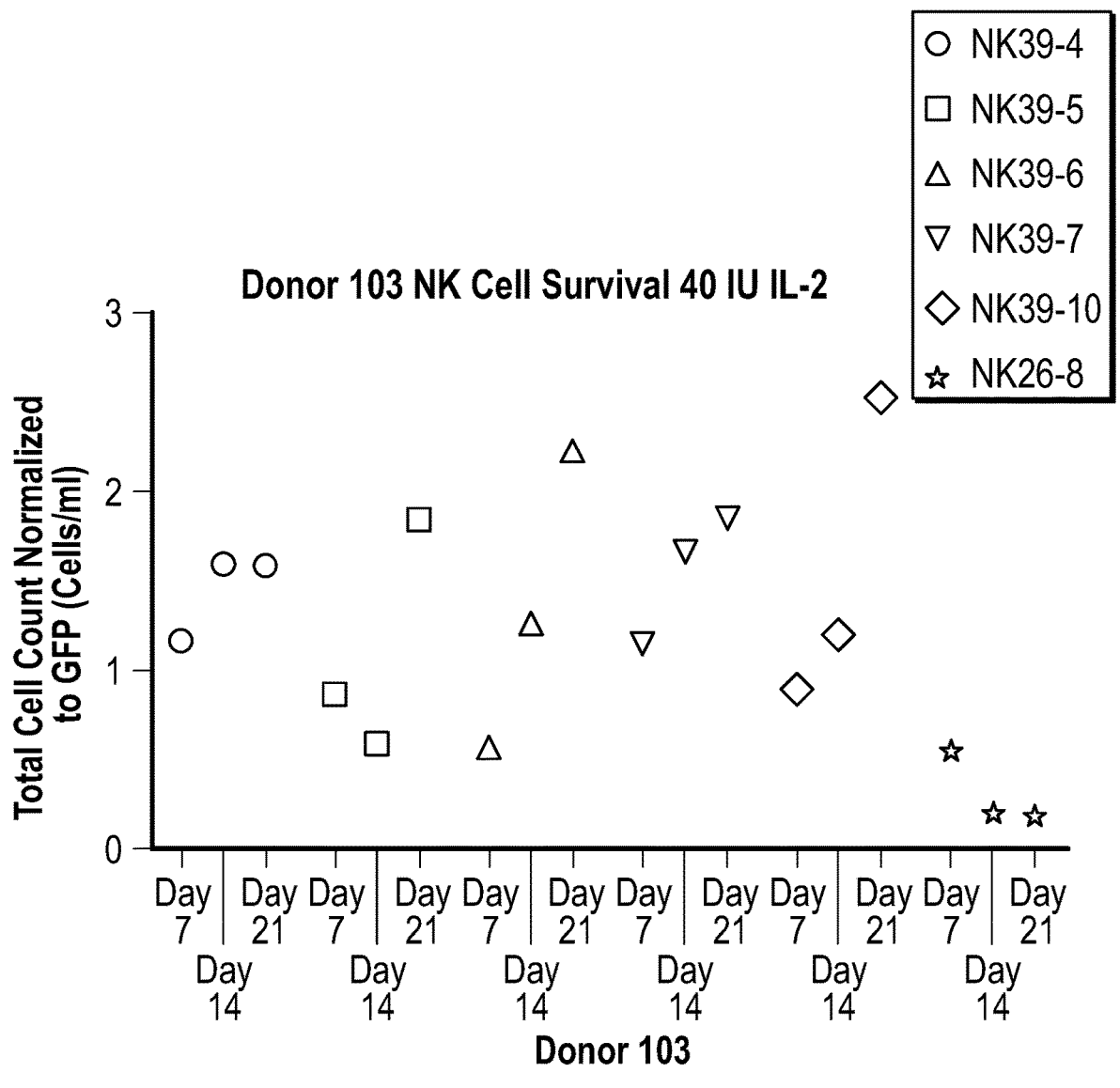

As variant 18 exhibited robust expression in NK cells that was accompanied by enhanced cytotoxic effects, a series of variant NKG2D constructs comprising a CD3zeta transmembrane domain were generated. These variants are termed "NK39" and are schematically shown in FIG. 15. Fourteen days following transfection into donor NK cells (with 4 days of culturing in low IL-2 conditions), the cytotoxicity of the transduced NK cells were evaluated. FIG. 21 shows the cytotoxic effects of the constructs against cultured REH cells at 1:1 and 1:2 E:T ratios. All the of the NK cells expressing engineered NK39 constructs showed significantly elevated cytotoxic effects as compared to control NK cells at a 1:1 E:T ratio. When evaluated at a 1:2 E:T ratio, chimeric constructs 16-7, 39-1, 39-2, 39-3, and 39-5 each enhanced the cytotoxic effects of their respective transduced NK cells relative to the mock control. As exogenous expression of activating receptors can lead to NK cell anergy and cell death, the engineered constructs were transduced into two donor NK cells and survival was evaluated after 21 days. As depicted in FIGS. 23A-B, NK39-5 and NK39-10 transduced cells show better survival than NK16 in two tested donors.

Example 4—Evaluation of NK45 NKG2D Constructs

Additional constructs with varying extracellular domains, hinges, transmembrane domains, and intracellular effector domains according to embodiments disclosed herein are schematically shown in FIG. 22. The expression, cytotoxicity, persistence, and cytokine production mediated by these 7 constructs were evaluated in this Example relative to three of the NK39 constructs described in Example 3 (NK39-5, NK39-6, NK39-10) as well as a version of NK16 that bicistronically expresses membrane-bound interleukin 15 (NK26-8). In accordance with several embodiments disclosed herein, multiple signaling regions may be used. Some of these variant chimeric receptors rely on an effector domain comprising CD3zeta and/or another signaling domain (e.g., OX40, CD28, and/or 4-1BB costimulatory domains) to transduce signaling upon ligand binding, while other variant chimeric receptors comprise a CD3zeta transmembrane domain that recruits full-length CD3zeta molecule to the synapse via dimerization. As disclosed herein, these constructs are further configured to co-express membrane-bound IL15.

Figure 24:
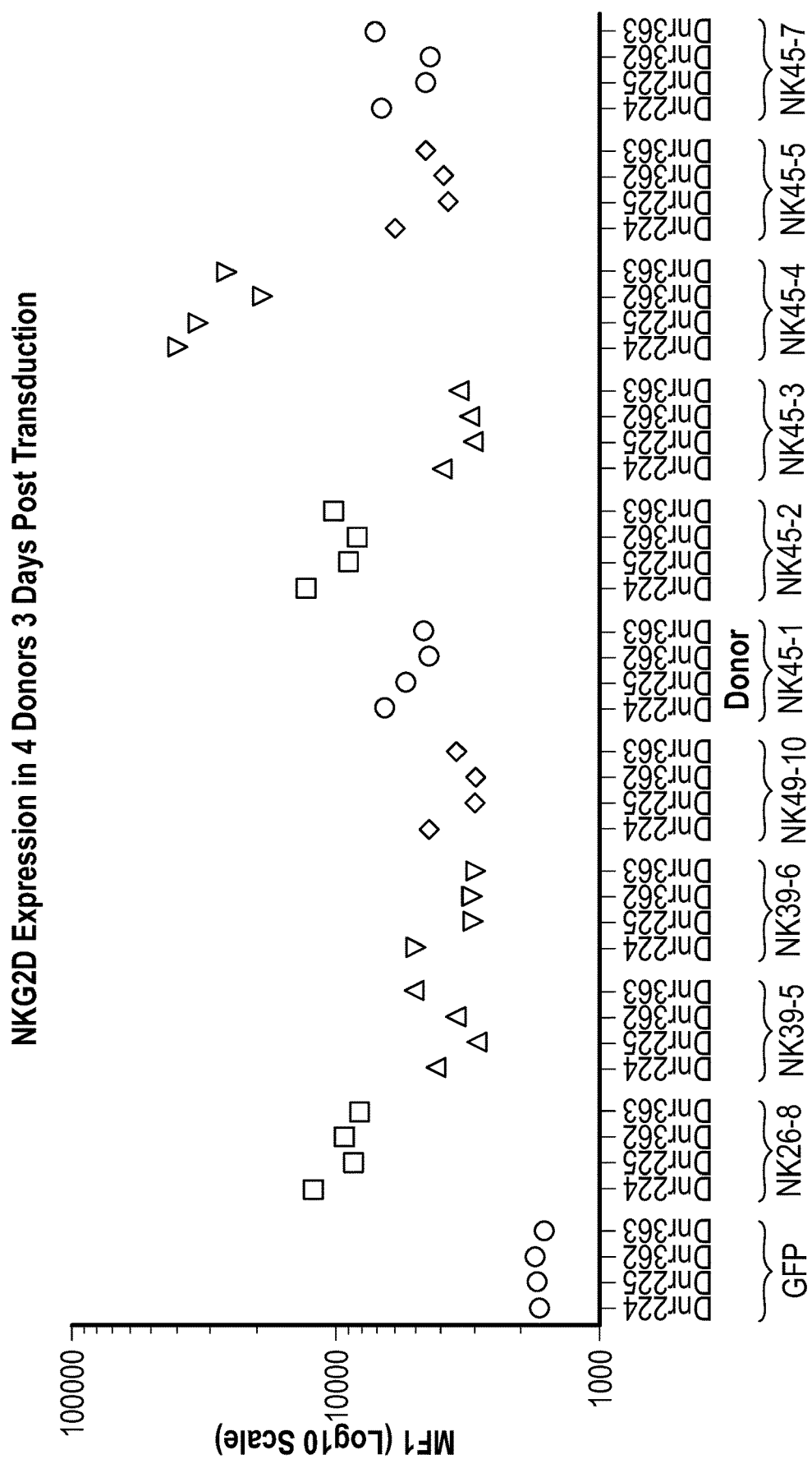
FIG. 24 depicts data related to the expression of the various NKG2D constructs. NK cells were expanded from peripheral blood mononuclear cells (PBMC) of 4 healthy donors (224, 225, 362 and 363) and transduced with viruses directing the expression of the indicated constructs. Three days following transduction, NK cells were stained with a fluorescently labelled anti-NKG2D antibody and analyzed using flow cytometry. Relative NKG2D expression was assessed by mean fluorescence intensity (MFI) of labeled cells.

As above, the ability of NK cells to effectively express these constructs was first assessed. NK cells expanded from the PBMC of four donors were transduced with the variant constructs (or an empty MSCV control vector containing GFP only) and NKG2D expression was evaluated by MFI after 3 days. As depicted in FIG. 24, mock-transfected NK cells show relatively low levels of NKG2D expression. In contrast, the engineered variant constructs exhibited significantly enhanced expression, with NK45-4 (NKG2D-OX40-CD3zeta) showing surprisingly robust expression in all donors. OX40 is expressed in activated NK cells, but its role has not been well-established. A variant chimeric receptor with an effector domain containing a CD28 costimulatory domain (NK45-2; NKG2D-CD28-CD3zeta) also demonstrated robust expression 3 days post-transduction.

Figure 25A:
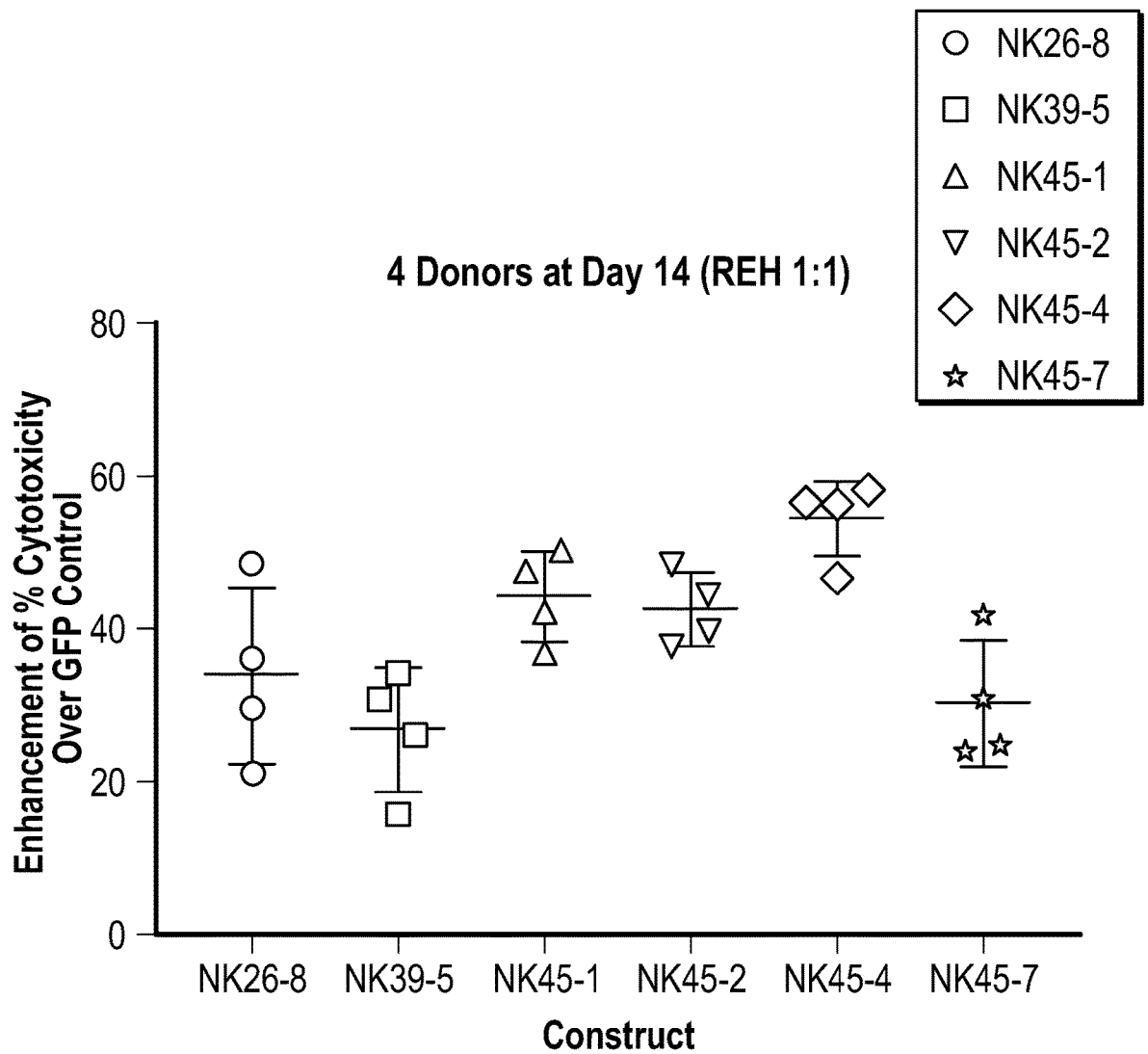
FIGS. 25A-25B depict data related to the cytotoxicity of NK cells transduced with various NKG2D constructs. NK cells were expanded from PBMC of 4 donors; Eight days after transduction, NK cytotoxicity against cultured REH and HL60 cells (FIGS. 25A and 25B, respectively) was measured at a 1:1 E:T ratio. NK cells were cultured in media supplemented with 40 IU of IL-2/mL prior to analysis.
Figure 25B:
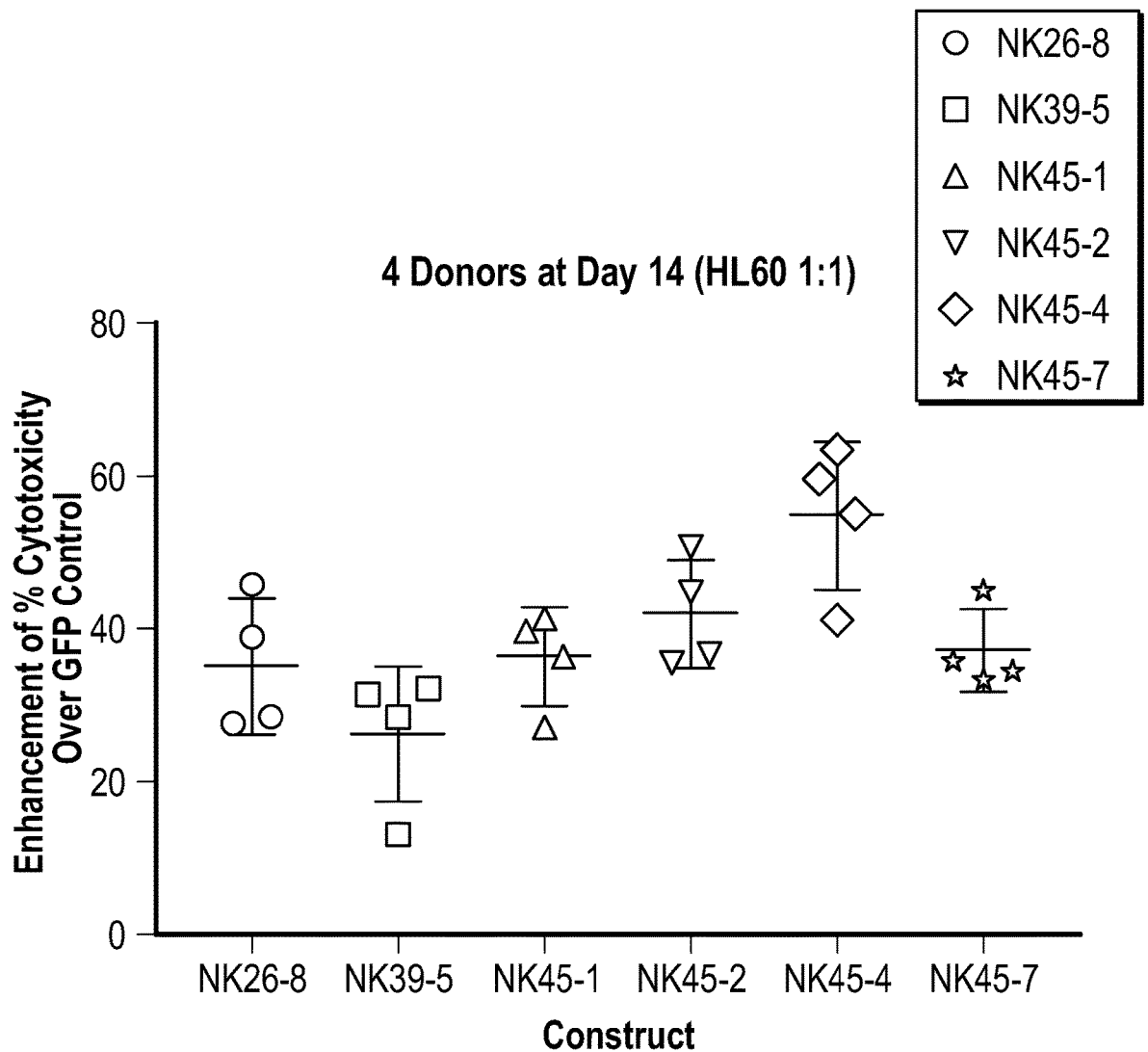
Figure 28A:
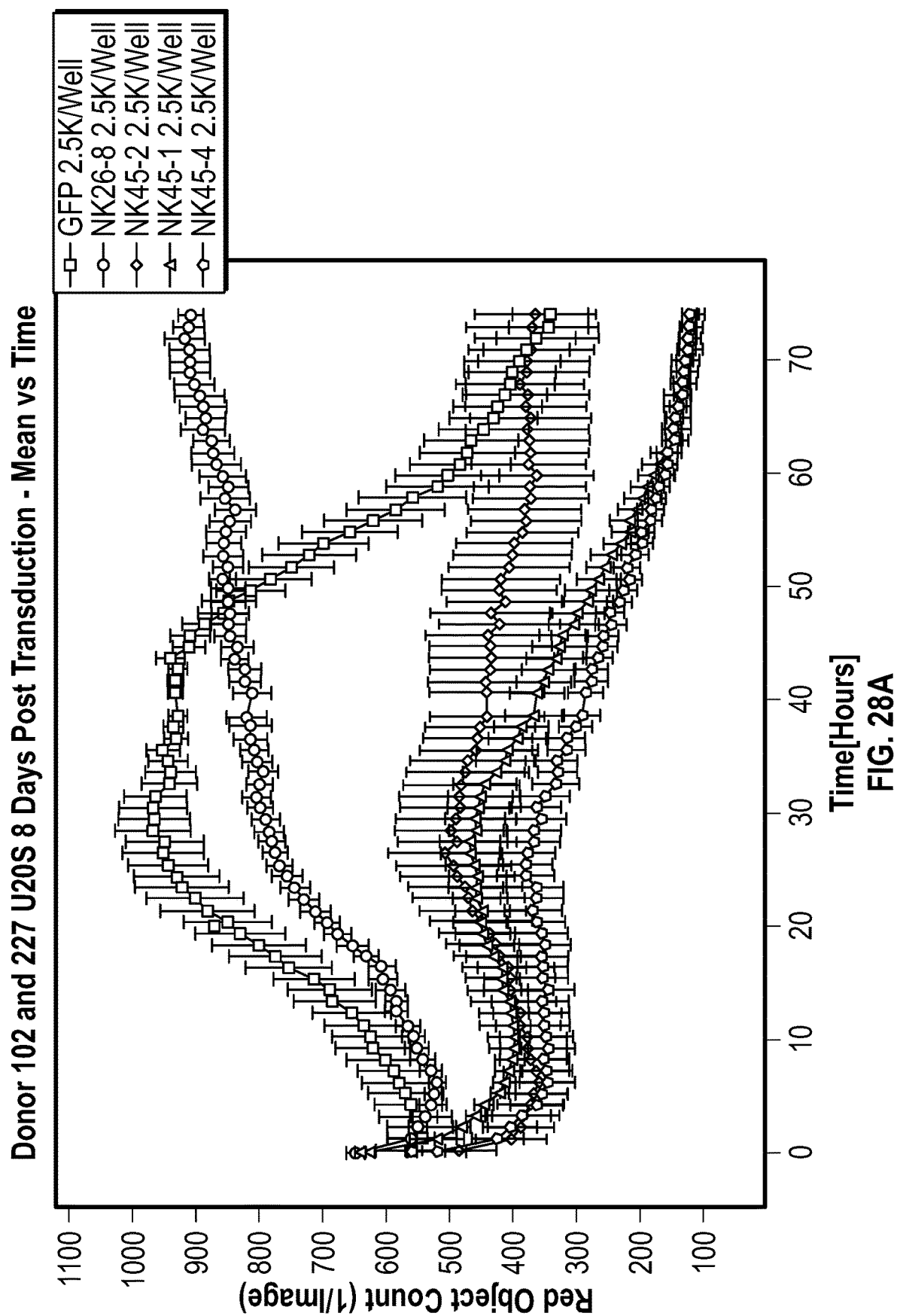
FIGS. 28A-28B depict data related to the cytotoxicity of NK cells transduced with the indicated NKG2D constructs. NK cytotoxicity was measured against U2OS cells stably transduced to express Red Fluorescent Protein; U2OS cells were cultured with NK cells at a 1:4 and 1:2 E:T ratios (FIGS. 28A and 28B, respectively). Live U2OS cells were counted every 60 minutes for 72 hours using an Incucyte S3 Live-Cell Analysis System. Prior to analysis NK cells were cultured in media supplemented with 40 IU of IL-2/mL.
Figure 28B:
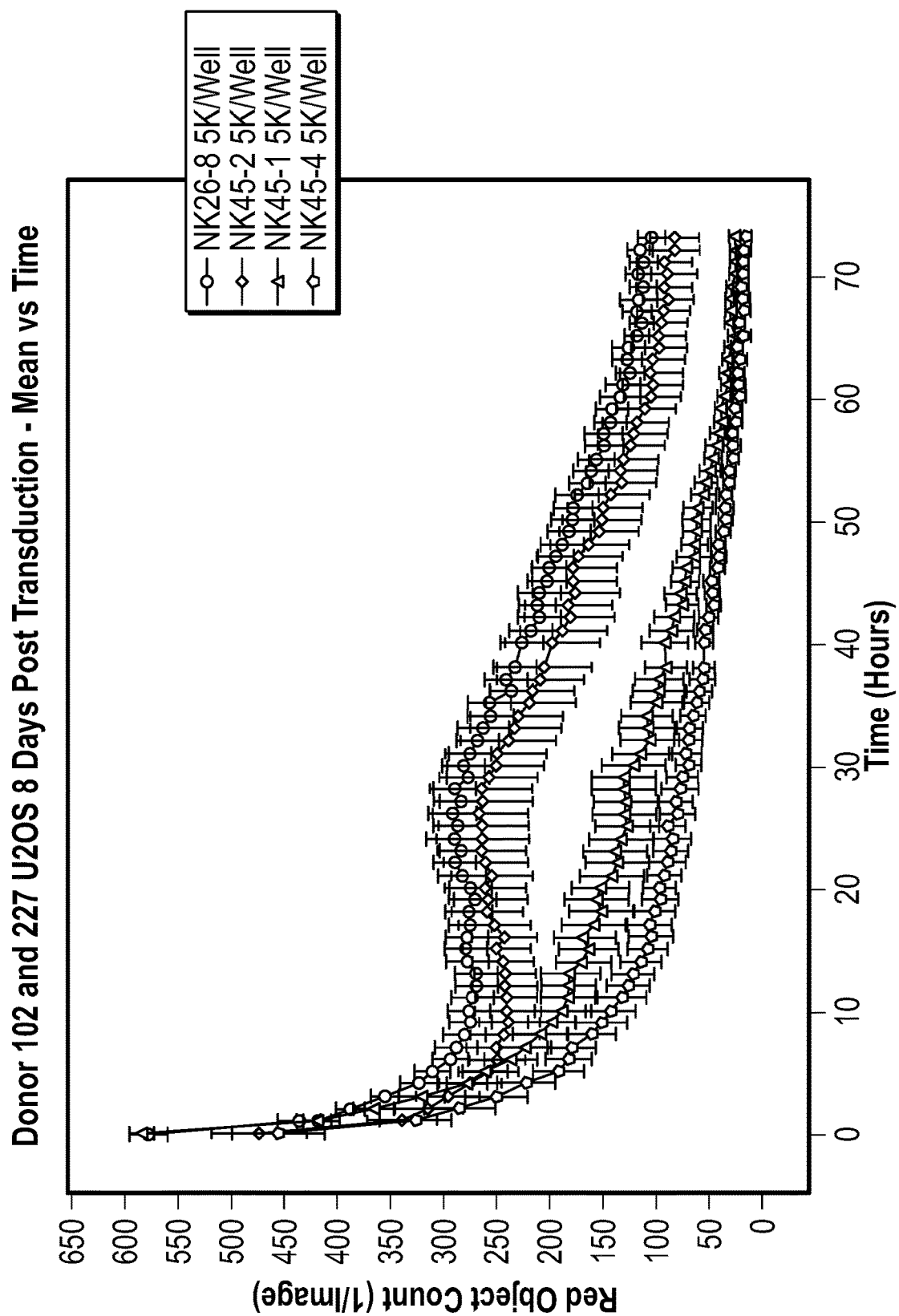

Having established expression of the variant constructs, their ability to exert cytotoxic effects was evaluated as above using REH and HL60 cells as targets. The potency of NK cells from four donors were examined against REH cells (FIG. 25A) and HL60 cells (FIG. 25B) at 1:1 E:T ratios 14 days post-transduction. As depicted in FIGS. 25A-B, the engineered constructs exerted an enhanced cytotoxicity against both REH and HL60 cells in all four donors as compared to mock NK cells. In addition to its pronounced expression profile, cells expressing NK45-4 (NKG2D-OX40-CD3zeta) also exhibited surprisingly elevated cytotoxicity relative to the mock control and the other constructs tested. NK cells expressing NK45-1 and NK45-2 also demonstrated pronounced cytotoxicity in these assays. These data demonstrate that, in accordance with several embodiments, use of a combination of signaling domains (particularly an OX40 costimulatory domain) can result in unexpected enhancements in the efficacy of a transduced NK cell. FIGS. 28A-B depict the cytotoxic activity against U2OS cells of the NK cells transduced with several of the variant constructs at various E:T ratios (1:2 and 1:4) and assessed over a more extended period of time. Surprisingly, NK cells transduced with the 45-4 construct appear to maintain cytotoxic activity through the time course. Advantageously, these experiments indicate that, according to several embodiments disclosed herein, the NKG2D variant constructs provide unexpectedly enhanced cytotoxicity over an extended period of time, which, depending on the embodiment, can range from 2-3 days, 3-5 days, 5-7, days, 7-8 days, 8-10 days, 10-14 days, 14-21 days, or 21-50 days (and any range in between those listed, including endpoints). In several embodiments, even longer durations of cytotoxic effects are achieved.

Figure 26A:
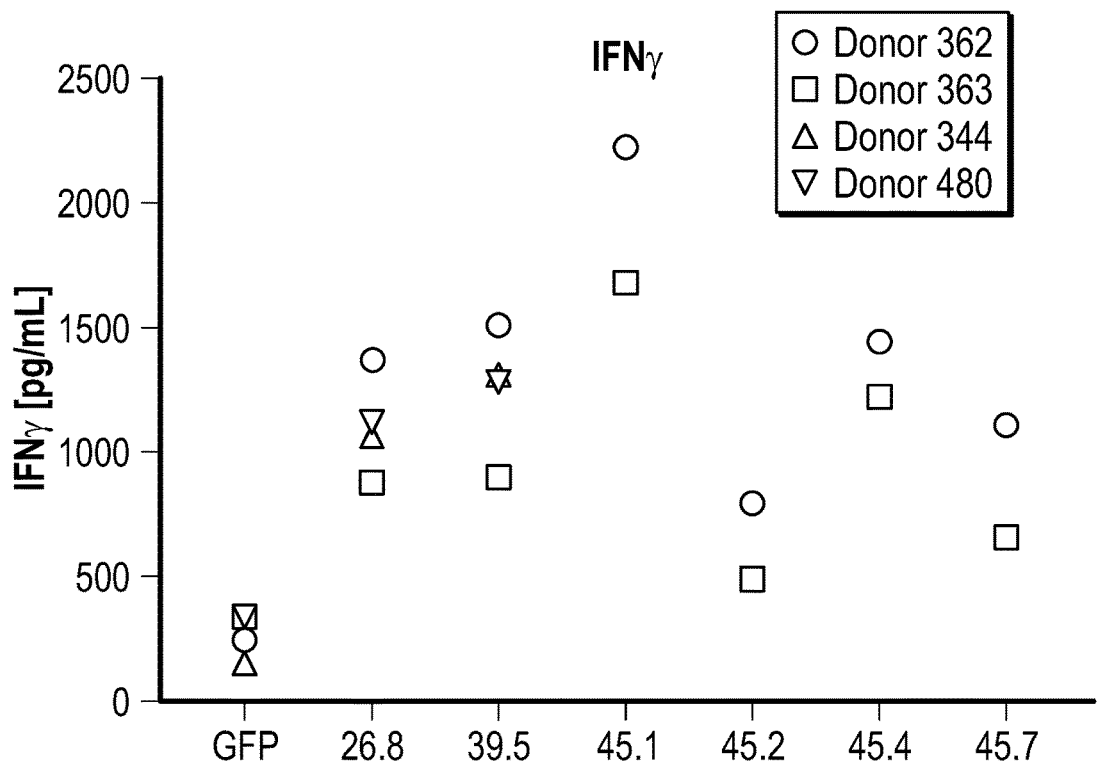
FIGS. 26A-26C depict data related to the production of interferon-gamma (IFNγ), tumor necrosis factor-alpha (TNFα), and granulocyte-macrophage colony-stimulating factor (GM-CSF) by NK cells expressing various NKG2D constructs after overnight stimulation with REH tumor cells. Eight days after transduction with the indicated constructs, $1 \times 10^5$ NK cells were stimulated with $1 \times 10^5$ REH cells in individual wells of a 96-well round bottom plate; after overnight incubation, supernatants were harvested, and cytokine levels measured against relevant standards using a Meso Scale Discovery device.
Figure 26B:
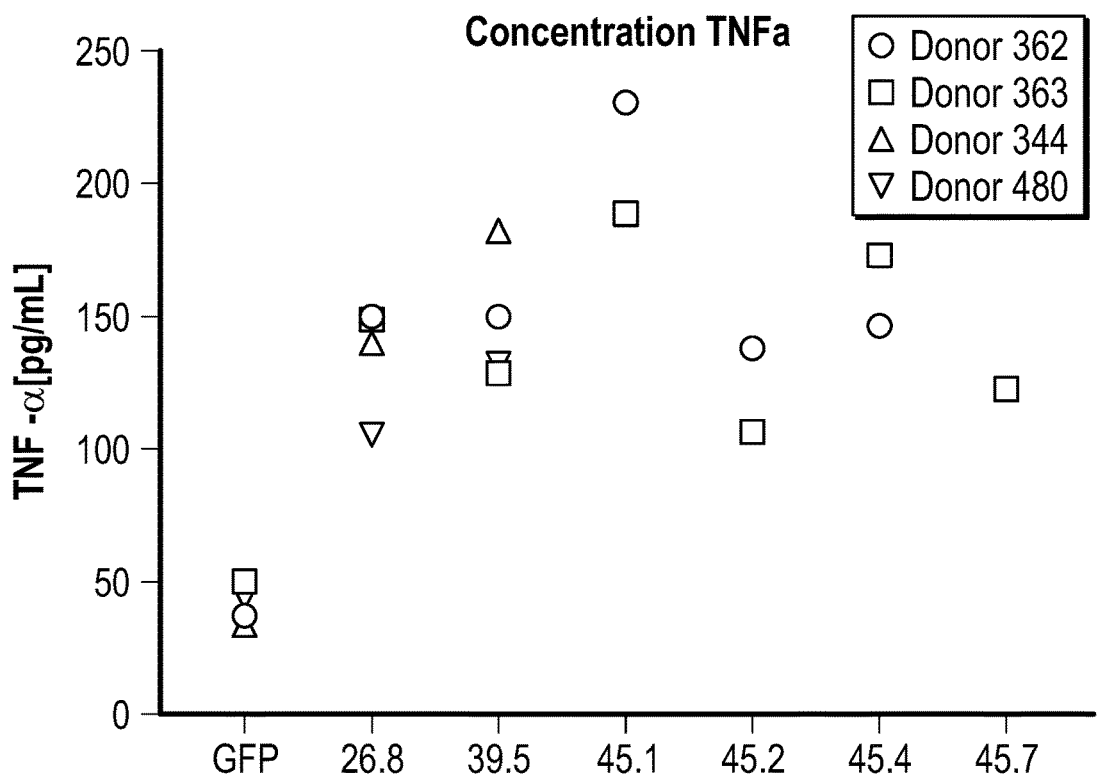
Figure 26C:
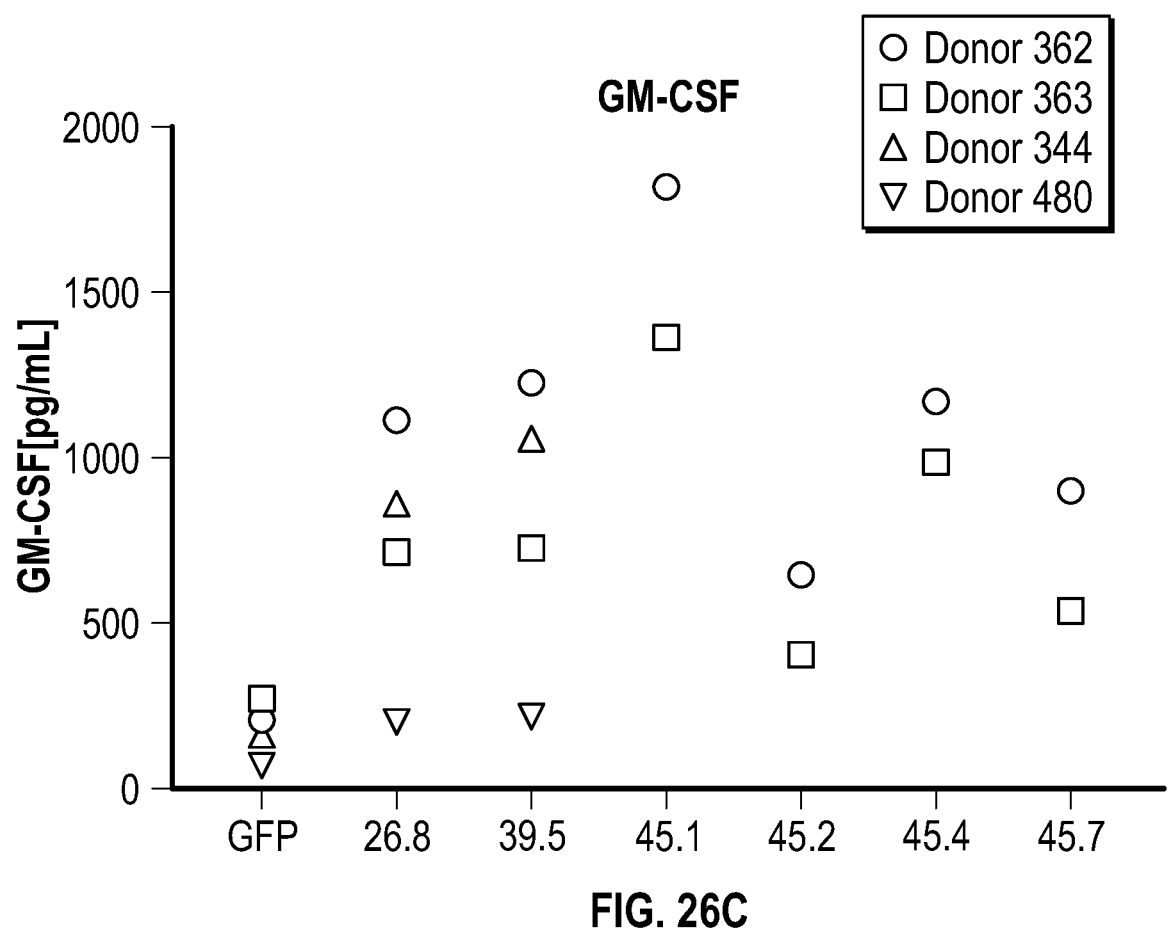

Further to the cytotoxicity data, the mechanism by which the NK cells are exerting these effects was examined by evaluating their production of IFNγ, TNFα, and GM-CSF following stimulation with REH cells. As depicted in FIGS. 26A-C, expression of each of the variant constructs yielded enhanced cytokine secretion relative to the production of IFNγ, TNFα, and GM-CSF exhibited by the GFP-expressing control NK cells. The chimeric receptor NK45-1 consistently mediated high cytokine production, which is surprising because this construct expresses at substantially lower levels than NK26-8 (from which it differs only with regards to the hinge region). Thus, these data demonstrate the unexpected importance of the hinge regions disclosed herein to mediating robust cytokine production in response to stimulation. Additionally, NKG2D-OX40-CD3zeta-expressing NK cells also showed an elevated production of IFNγ, TNFα, and GM-CSF.

Figure 27A:
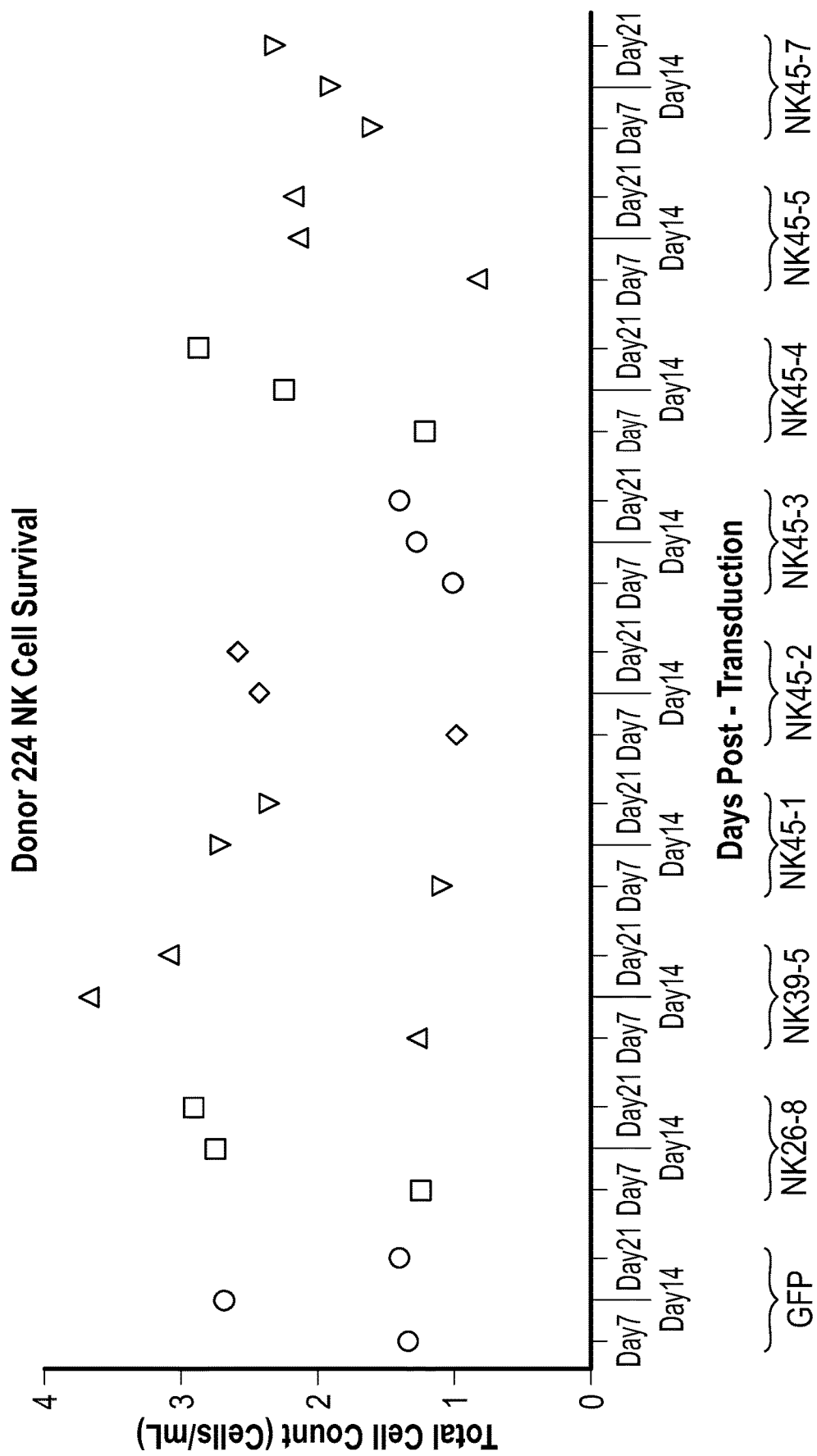
FIGS. 27A-27B depict data related to the persistence of NK cells from two donors (donors 224 and 225 in FIGS. 27A and 27B, respectively) expressing the various NKG2D constructs 7, 14, and 21 days post-transduction. Prior to analysis NK cells were cultured in media supplemented with 40 IU of IL-2/mL.
Figure 27B:
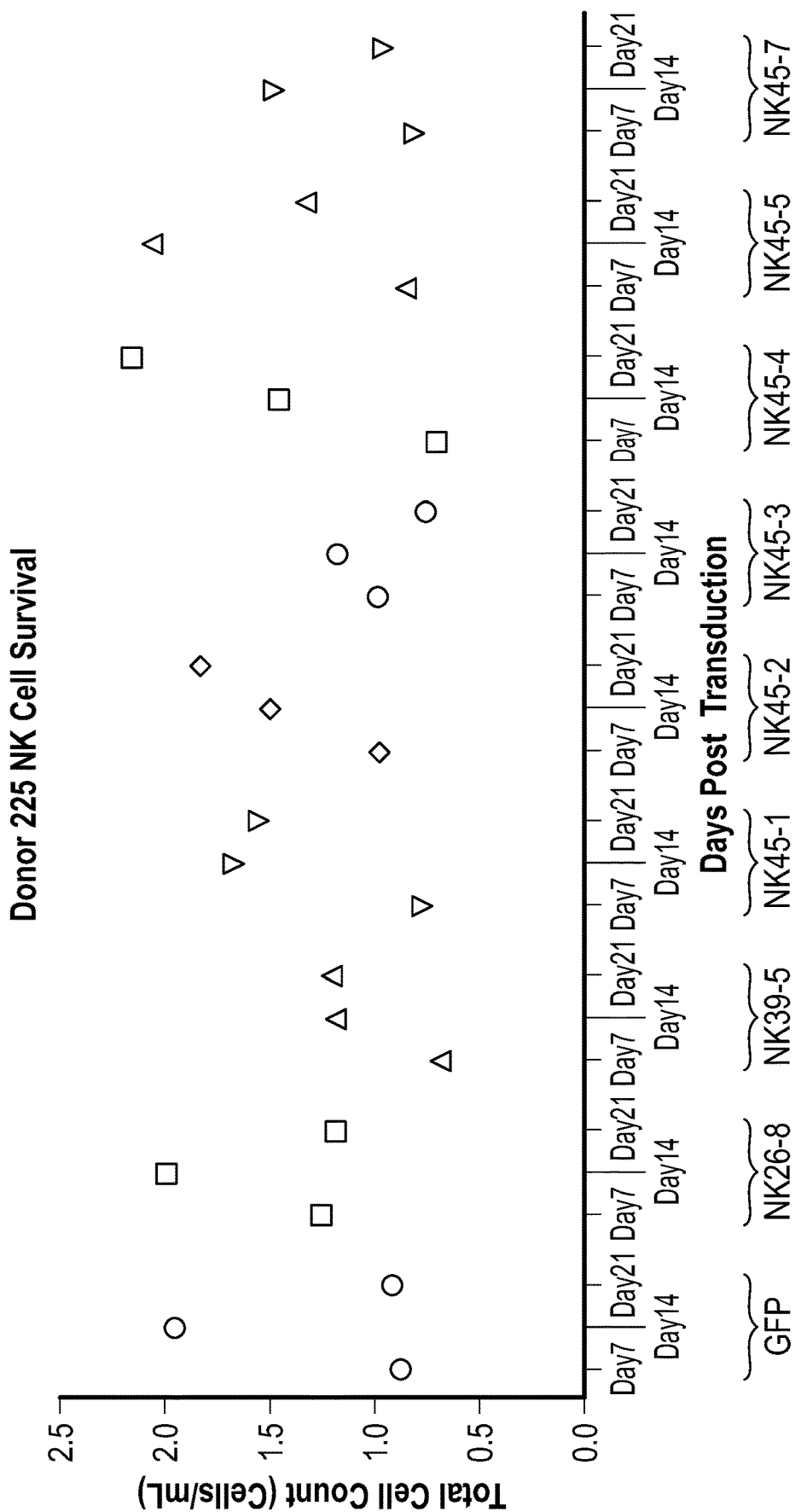

As exogenous expression of activating receptors can lead to NK cell anergy and cell death, the engineered constructs were transduced into two donor NK cells and the total cell count was evaluated 7, 14, and 21 days post-transduction. Surprisingly, the unexpectedly robust expression of NK45-4 does not come at the cost of reduced NK cell persistence in culture, as the total cell count remained at levels comparable to the GFP-expressing control cells (FIGS. 27A and 27B). Likewise, other NK cells expressing variant constructs at high levels continued to proliferate in the 2 donors for at least 3 weeks post-transduction. Collectively, these data demonstrate that, in accordance with several embodiments disclosed herein, engineered constructs can successfully be expressed at high levels in NK cells and mediate cytotoxic effects, and further, that this enhanced expression does not come at the detriment of reduced NK cell proliferation and/or survival.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "administering a population of expanded NK cells" include "instructing the administration of a population of expanded NK cells." In addition, where features or aspects of the disclosure are described in terms of Markush groups, those skilled in the art will recognize that the disclosure is also thereby described in terms of any individual member or subgroup of members of the Markush group.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 90%" includes "90%." In some embodiments, at least 95% homologous includes 96%, 97%, 98%, 99%, and 100% homologous to the reference sequence. In addition, when a sequence is disclosed as "comprising" a nucleotide or amino acid sequence, such a reference shall also include, unless otherwise indicated, that the sequence "comprises", "consists of" or "consists essentially of" the recited sequence.

What is claimed is:

1. A natural killer (NK) cell expressing a chimeric receptor, the chimeric receptor comprising:
   (a) an extracellular receptor domain comprising a fragment of Natural Killer Group 2 member D (NKG2D) that binds native ligands of NKG2D; and
   (b) an effector domain comprising a transmembrane region and an intracellular signaling domain,
      wherein the transmembrane region comprises a CD8α transmembrane domain, and the intracellular signaling domain comprises an OX-40 domain and CD3zeta, and
      wherein the chimeric receptor comprises the amino acid sequence of SEQ ID NO: 109.

2. The NK cell of claim 1, wherein the fragment of NKG2D is encoded by SEQ ID NO:2.

3. The NK cell of claim 1, wherein CD3zeta is encoded by SEQ ID NO:13.

4. The NK cell of claim 2, wherein CD3zeta is encoded by SEQ ID NO: 13.

5. The NK cell of claim 1, wherein the NK cell expresses a membrane-bound interleukin-15 (mbIL15).

6. The NK cell of claim 5, wherein the mbIL15 comprises an amino acid sequence having at least about 90% sequence identity to the amino acid sequence of SEQ ID NO: 17.

7. The NK cell of claim 5, wherein the mbIL15 comprises the amino acid sequence of SEQ ID NO:17.

8. The NK cell of claim 5, wherein the chimeric receptor and the mbIL15 are bicistronically expressed from a polynucleotide.

* * * * *